United States Patent
Wu et al.

(10) Patent No.: US 9,809,604 B2
(45) Date of Patent: Nov. 7, 2017

(54) DGAT1 INHIBITOR AND PREPARATION METHOD AND USE THEREOF

(71) Applicants: Qingdao Huanghai Pharmaceutical Co., Ltd., Qingdao (CN); Medshine Discovery Inc., Nanjing, Jiangsu (CN)

(72) Inventors: Chengde Wu, Shanghai (CN); Zhiliu Zhang, Shanghai (CN); Tao Yu, Shanghai (CN)

(73) Assignees: Qingdao Huanghai Pharmaceutical Co., Ltd., Qingdao (CN); Medshine Discovery Inc., Nanjing, Jiangsu (CN)

( * ) Notice: Subject to any disclaimer, the term of this patent is extended or adjusted under 35 U.S.C. 154(b) by 0 days.

(21) Appl. No.: 14/912,428

(22) PCT Filed: Aug. 18, 2014

(86) PCT No.: PCT/CN2014/084586
§ 371 (c)(1),
(2) Date: Feb. 17, 2016

(87) PCT Pub. No.: WO2015/024486
PCT Pub. Date: Feb. 26, 2015

(65) Prior Publication Data
US 2016/0272651 A1  Sep. 22, 2016

(30) Foreign Application Priority Data

Aug. 23, 2013 (CN) .......................... 2013 1 0371069

(51) Int. Cl.
| | | |
|---|---|---|
| *C07D 498/04* | (2006.01) | |
| *A61K 31/553* | (2006.01) | |
| *A61P 3/10* | (2006.01) | |
| *A61P 3/04* | (2006.01) | |

(52) U.S. Cl.
CPC .......... *C07D 498/04* (2013.01); *A61K 31/553* (2013.01)

(58) Field of Classification Search
CPC ... A61K 31/553; A61K 31/519; C07D 498/04
See application file for complete search history.

(56) References Cited

U.S. PATENT DOCUMENTS

| | | |
|---|---|---|
| 7,718,645 B2 | 5/2010 | Dow et al. |
| 2009/0036425 A1 | 2/2009 | Dow et al. |
| 2009/0137551 A1 | 5/2009 | Dow et al. |
| 2010/0204119 A1 | 8/2010 | Aspnes et al. |
| 2011/0251173 A1 | 10/2011 | Birch et al. |

FOREIGN PATENT DOCUMENTS

| | | |
|---|---|---|
| CN | 101772504 A | 7/2010 |
| WO | 2007126957 A1 | 11/2007 |
| WO | 2009016462 A1 | 2/2009 |
| WO | 2010086820 A1 | 8/2010 |
| WO | 2010108051 A1 | 9/2010 |
| WO | 2011121350 A1 | 10/2011 |

OTHER PUBLICATIONS

International Search Report received in PCT/CN2014/084586, dated Nov. 26, 2014.
Written Opinion received in PCT/CN2014/084586, dated Nov. 26, 2014.

*Primary Examiner* — Susanna Moore
(74) *Attorney, Agent, or Firm* — Suzannah K. Sundby, Esq.; Canady + Lortz LLP

(57) ABSTRACT

The present invention discloses a novel DGAT1 inhibitor, especially the compound of formula (I) or a pharmaceutically acceptable salt thereof, preparation and pharmaceutical composition thereof, as well as their uses in the preparation of a medicament for the prevention and treatment of Familial hyperchylomicronemia (FCS), obesity, hyperlipoproteinemia or hypertriglyceridemia.

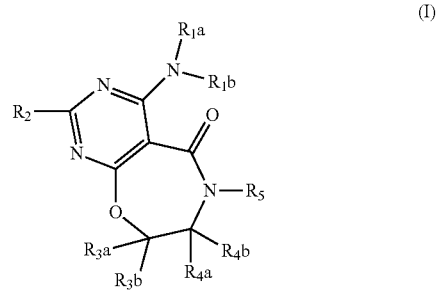

(I)

20 Claims, No Drawings

DGAT1 INHIBITOR AND PREPARATION METHOD AND USE THEREOF

This application claims priority to Chinese Patent Application Number CN201310371069.0 filed Aug. 23, 2013. The Chinese Patent Application is cited in this text.

FIELD OF THE INVENTION

The present invention relates to a novel DGAT1 inhibitor, especially the compound of formula (I) or a pharmaceutically acceptable salt thereof, preparation and pharmaceutical composition thereof, as well as their uses in the preparation of a medicament for the prevention and treatment of familial hyperchylomicronemia (FCS), obesity, hyperlipoproteinemia or hypertriglyceridemia.

BACKGROUND OF THE INVENTION

Diacylglycerol acyltransferase (DGAT) is a microsomal enzyme that plays a central role in the metabolism of cellular glycerolipids. DGAT catalyzes the final step in triacylglycerol (TAG) biosynthesis by converting diacylgycerol and fatty acyl-coenzyme A into triacylglycerol. DGAT plays a fundamental role in the metabolism of cellular diacylglycerol and is important in higher eukaryotes for physiologic processes involving triacylglycerol metabolism such as intestinal absorption, lipoprotein assembly, adipose tissue formation, and lactation.

Triacylglycerol (TAG) is the essential material for mammal to maintain normal physiological function, however, too much triacylglycerol (TAG) reserve will lead to genetic obesity.

Currently, there is only one class of new drugs, (polypeptidase-4 inhibitor) was approved in the field of controlling blood sugar in people with type II diabetes. CPDs targeting lipid partitioning and lipid biosynthetic enzymes also have emerged; including inhibitors of the enzymes DGAT1 and SCD1. DGATs are the key enzymes which catalyze the final step of the triglyceride synthesis. DGAT1 gene defect and inhibition of DGAT1 can prevent obesity induced by high-fat diet and increase the sensitivity of organisms to insulin without side effect.

Hypertriglyceridemia has been identified as a major independent cardiovascular disease risk factors in the future. Diacylglycerol acyltransferase is a key enzyme in the final step of biochemical synthesis of triglycerides and therefore it has been identified as a potential therapeutic target against humanity hyperlipidemia and cardiovascular disease.

DGAT1 is an essential host factor for viral assembly, and is required for the trafficking of HCV core from endoplasmic reticulum membranes to the surface of lipid droplets (LDs) to produce infectious particle. Selective inhibition or silencing of DGAT1, but not of DGAT2, dramatically impaired the product and secretion of infectious virus, while leaving HCV RNA replication unaffected.

The global diabetes equipment and drug market reached $50.8 billion in 2011, and in accordance with market expectations, this figure will reach $98.4 billion in 2018, from 2011 to 2018, the annual growth rate of 9.9%. Chinese diabetes market reached S15 billion, the number of patients reached 39.8 million, with an annual growth rate of over 40%. The cost for treating diabetes per capita is $451, and cost for treating patients with diabetic complications is as high as $1,694. By 2025, the total number of diabetes patients in China will reach 59.3 million.

The diabetes drug market may reach $2 billion in 2017 from $1.1 billion at the end of 2009. By 2015 the diabetes and obesity market could reach $6.7 billion in China. The obesity population is 70 million in China. 14.6% of the total adult, national weight loss market capacity should be 67.7 billion yuan, however, the current weight loss products market with annual sales is less than 10 billion yuan.

Novartis is developing Pradigastat (LCQ-908, Novartis), its indications include FCS, diabetes, obesity, hyperlipoproteinemia, hypertriglyceridemia, angiocardiopathy, renal function damage or liver function damage, and it is currently in clinical trials.

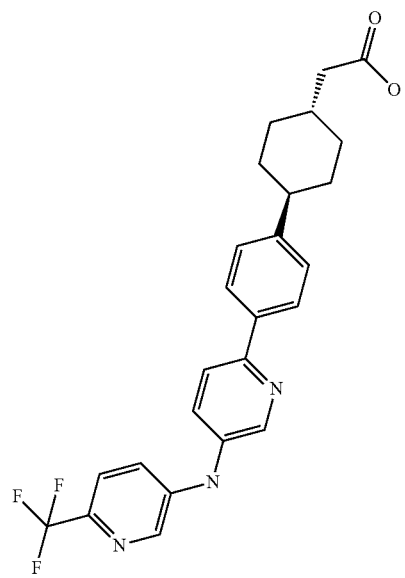

Pradigastat (LCQ-908, Novartis)

Pfizer's international Patent Application WO2009016462A1, WO2010086820A1 disclosed, a series compounds, and literature "Discovery of PF-04620110: A Potent, Orally-Bioavailable Inhibitor of DGAT1, ACS Med. Chem. Lett 2011, 2, 407-412" described the compound as followed.

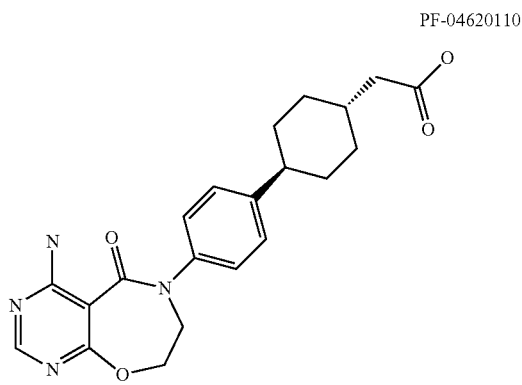 [SMILES: Nc1ncnc2c1C(=O)N(c1ccc([C@H]3CC[C@H](CC(=O)O)CC3)cc1)CCO2]

PF-04620110

The activity, half-life period, solubility, pharmacokinetics and other aspects of performance of the aforesaid compounds could be improved.

SUMMARY OF INVENTION

The present invention provides compounds of the general formula (I) or a pharmaceutically acceptable salt thereof,

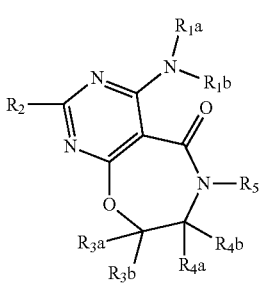

(I)

wherein, $R_{1a}$, $R_{1b}$, $R_2$, $R_{3a}$, $R_{3b}$, $R_{4a}$ or $R_{4b}$ is independently selected from the group consisting of H, $C_{1-10}$alkyl, $C_{1-10}$ alkoxy, $C_{3-10}$ cycloalkyl or $C_{3-10}$ cycloalkoxy, wherein each of the $C_{1-10}$ alkyl, $C_{1-10}$ alkoxy, $C_{3-10}$ cycloalkyl or $C_{3-10}$ cycloalkoxy is optionally substituted by the substituent selected from the group consisting of halogen, OH, SH, $NH_2$ or $PH_2$, and the number of substituent is 1 or more;

$R_5$ represents

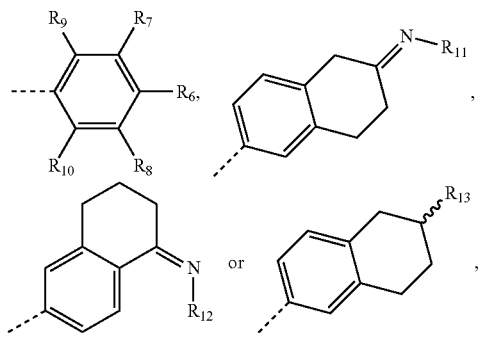

wherein, $R_6$ represents optionally substituted benzoheterocycle, optionally substituted single heterocycle, optionally substituted cycloalkyl aldehyde and optionally substituted cycloalkylformyl, and aryl optionally substituted by substituents, said aryl connected with benzoheterocyclic optionally substituted by subtituents, wherein, the foresaid heterocycle is saturated or unsaturated, the number of heteroatom or heteroradical is 1~8, which is independently selected from the group consisting of N, S, F, O, SO and $SO_2$;

the number of substituent is 1 or more, which is independently selected from the group consisting of halogen, OH, SH, $NH_2$, $PH_2$, =O, $C_{1-10}$alkyl, $C_{1-10}$ alkoxy, $C_{3-10}$ cycloalkoxy, —$C_{1-10}$OH, —$C_{1-10}$COOH, —$C_{1-10}$COOH, —$C_{1-10}$OC$_{1-10}$, —$C_{1-10}$COOC$_{1-10}$, —$C_{1-10}$CN or —$C_{1-10}$CONH$_2$, wherein, the foresaid $C_{1-10}$ alkyl, $C_{3-10}$ cycloalkyl, $C_{3-10}$ cycloalkoxy, —$C_{1-10}$OH, —$C_{1-10}$COOH, —OC$_{1-10}$COOH, —$C_{1-10}$OC$_{1-10}$, —$C_{1-10}$COOC$_{1-10}$, —$C_{1-10}$CN or $C_{1-10}$CONH$_2$ is optionally substituted by 1 or more substituents that selected from the group consisting of halogen, OH, SH, $NH_2$, $PH_2$, CN, $CF_3$, —$OCF_3$, —$OCH_3$, $C_{1-6}$ alkyl, $C_{1-6}$ cycloalkyl and $C_{1-6}$ alkoxy;

the carbon atoms, located on both sides or on the same side of each oxygen or carbonyl in said —$C_{1-10}$OC$_{1-10}$ or —$C_{1-10}$COOC$_{1-10}$, are optionally joined together to form a ring; and the H atom, connected with the N atom of —$C_{1-10}$CONH$_2$ is optionally substituted by $C_{1-6}$ alkyl singly or bothly;

$R_{7-10}$ independently represents $C_{1-10}$ alkyl, $C_{1-10}$ alkoxy, $C_{3-10}$ cycloalkyl, $C_{3-10}$ cycloalkoxy, H, halogen, OH, SH, $NH_2$, $PH_2$ and CN, wherein each of the $C_{1-10}$alkyl, $C_{1-10}$alkoxy, $C_{3-10}$cycloalkyl, $C_{3-10}$ cycloalkoxy is optionally substituted by the substituent selected from the group consisting of halogen, OH, SH, $NH_2$, $PH_2$, CN, $CH_3$ or $CF_3$, the number of substituent is 1 or more;

$R_{11-13}$ independently represents $C_{1-10}$alkyl, $C_{1-10}$alkoxy, $C_{3-10}$cycloalkyl, $C_{3-10}$cycloalkoxy, wherein each of the $C_{1-10}$alkyl, $C_{1-10}$alkoxy, $C_{3-10}$cycloalkyl, $C_{3-10}$ cycloalkoxy is optionally substituted by the substituent selected from the group consisting of halogen, OH, SH, $NH_2$, $PH_2$, CN, $CF_3$, —$OCF_3$ or —$OCH_3$, the number of substituent is 1~3.

Preference is given to compounds of the general formula (I), wherein $R_{1a}$, $R_{1b}$ or $R_2$ is selected from H.

Preference is given to compounds of the general formula (I), wherein $R_{3a}$, $R_{3b}$, $R_{4a}$ or $R_{4b}$ or is independently selected from the group consisting of H or methyl.

Preference is given to compounds of the general formula (I), wherein $R_6$ is selected from the group consisting of optionally substituted 9~10 membered benzoheterocyclic, optionally substituted 5~6 membered single heterocyclic, optionally substituted $C_{3-10}$ cycloalkylformyl, phenyl optionally substituted by subtituents, said phenyl connected with a 9-10 membered benzoheterocyclic optionally substituted by subtituents, wherein, the aforesaid heterocycle is saturated of unsaturated, the number of heteroatom or heteroradical is 1~8, which is independently selected from the group consisting of N, S, F, O, SO and $SO_2$;

the number of substituent is 1~3, which is independently selected from the group consisting of halogen, OH, SH, $NH_2$, $PH_2$, =O, $C_{1-10}$ alkyl, $C_{1-10}$alkoxy, $C_{3-10}$ cycloalkyoxy, —$C_{1-10}$OH, —$C_{1-10}$COOH, —OC$_{1-10}$COOH, —$C_{1-10}$OC$_{1-10}$, —$C_{1-10}$COOC$_{1-10}$, —$C_{1-10}$CN or —$C_{1-10}$CONH$_2$, wherein, the aforesaid $C_{1-10}$ alkyl, $C_{3-10}$ cycloalkyl, $C_{3-10}$ cycloalkoxy, —$C_{1-10}$OH, —$C_{1-10}$COOH, —OC$_{1-10}$COOH, —$C_{1-10}$OC$_{1-10}$, —$C_{1-10}$COOC$_{1-10}$, —$C_{1-10}$CN or —$C_{1-10}$CONH$_2$ is optionally substituted by 1 or more substituents that selected from the group consisting of halogen, OH, SH, $NH_2$, $PH_2$, CN, $CF_3$, —$OCF_3$, —$OCH_3$, $C_{1-6}$ alkyl, $C_{1-6}$cycloalkyl and $C_{1-6}$alkoxy;

the carbon atoms, located on both sides or on the same side of each oxygen or carbonyl in said —$C_{1-10}$OC$_{1-10}$ or —$C_{1-10}$COOC$_{1-10}$, are optionally joined together to form a ring;

the H atom, connected with the N atom of —$C_{1-10}$CONH$_2$, is optionally substituted by $C_{1-6}$alkyl singly or bothly.

Preference is given to compounds of the general formula (I), $R_6$ is selected from the group consisting of

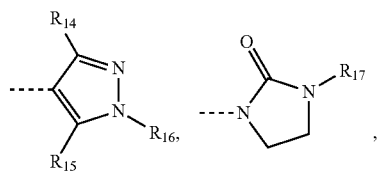

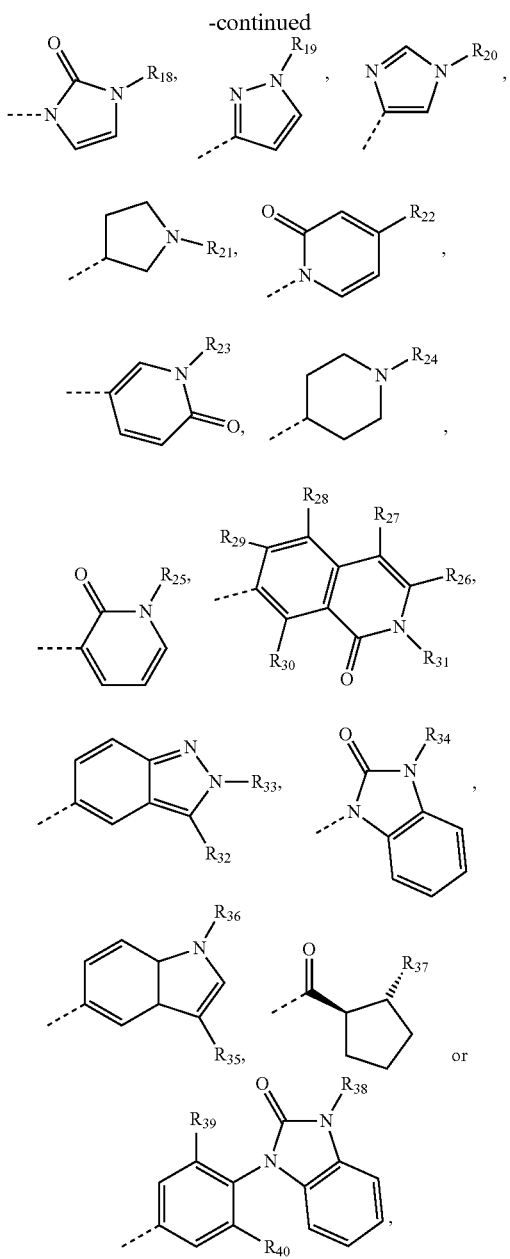

wherein,

R$_{14}$ and R$_{15}$ are independently selected from the group consisting of H, C$_{1-6}$alkyl or C$_{1-6}$ alkoxy, wherein each of the C$_{1-6}$ alkyl or C$_{1-6}$ alkoxy is optionally substituted by the substituent selected from the group consisting of halogen, OH, SH, NH$_2$ or PH$_2$, the number of substituent is 1~3; and R$_{16-40}$ are independently selected from the group consisting of H, halogen, OH, SH, NH$_2$, PH$_2$, C$_{1-6}$alkyl, C$_{1-6}$ alkoxy, —C$_{1-6}$OH, —C$_{1-6}$COOH, —OC$_{1-6}$COOH, —C$_{1-6}$OC$_{1-6}$, —C$_{1-6}$ COOC$_{1-6}$, —C$_{1-6}$CN, and —C$_{1-6}$CONH$_2$, wherein, the aforesaid C$_{1-6}$alkyl, C$_{1-6}$ alkoxy, —C$_{1-6}$OH, —C$_{1-6}$COOH, —OC$_{1-6}$COOH, —C$_{1-6}$OC$_{1-6}$, —C$_{1-6}$ COOC$_{1-6}$, —C$_{1-6}$CN, —C$_{1-6}$CONH$_2$ are optionally substituted by the substituent selected from the group consisting of halogen, OH, SH, NH$_2$, PH$_2$ or C$_{1-6}$ cycloalkyl, the number of substituent is 1~3;

the carbon atoms, located on both sides or on the same side of each oxygen or carbonyl in said —C$_{1-6}$OC$_{1-6}$ or —C$_{1-6}$COOC$_{1-6}$, are optionally joined together to form a ring; and the H atom, connected with the N atom of —C$_{1-6}$NH$_2$, is optionally substituted by C$_{1-6}$alkyl singly or bothly.

Preference is given to compounds of the general formula (I), the aforesaid R$_{14}$, R$_{15}$ are selected from the group consisting of H, methyl and CF$_3$.

Preference is given to compounds of the general formula (I), the aforesaid R$_{26-30}$ are selected from H.

Preference is given to compounds of the general formula (I), the aforesaid R$_{16-40}$ are selected from the group consisting of 1) halogen;
2) —CH$_3$, —CH$_2$CH(CH$_3$)$_2$, —C(CH$_3$)$_3$, —CH$_2$CH(CH$_3$)$_2$, —CH(CH$_3$)$_2$,

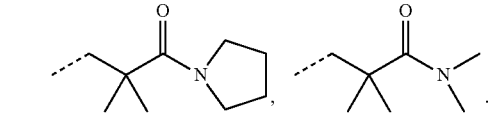

3) —CH$_2$CF$_3$, —CH$_2$C(CH$_3$)$_2$F, —CH$_2$C(CH$_3$)F$_2$, —CH$_2$CHF$_2$, —OCH$_2$CF$_3$;
4) —CH$_2$CH$_2$OH, —CH$_2$C(CH$_3$)$_2$CH$_2$OH, —CH$_2$C(CH$_3$)$_2$OH;
5) —COOH, —CH$_2$COOH, —CH$_2$CH$_2$COOH, —CH$_2$C(CH$_3$)$_2$COOH, —CH$_2$CH(CH$_3$)COOH, —CH(CH$_3$)COOH, —C(CH$_3$)$_2$)COOH, —CH(CH$_2$CH$_3$)COOH, —C(CH$_3$)$_2$COOH, —CH$_2$CH$_2$COOH, —CH(CH$_3$)COOH, —CH(CH$_2$CH$_3$)COOH,

<br>

—OCH(CH$_3$)COOH;
6) —CH$_2$C(CH$_3$)$_2$OCH$_3$,

<br>

7) —CH$_2$COOC$_2$H$_5$;
8) —CH$_2$CN; and
9) —CH$_2$CONH$_2$,

<br>

Preference is given to compounds of the general formula (I), the aforesaid R$_7$ and R$_8$ are independently selected from the group consisting —CH$_3$, —CH$_2$CH$_3$, —CF$_3$, —OCH$_3$, —OCF$_3$, halogen, OH or H.

Preference is given to compounds of the general formula (I), the aforesaid R$_9$ and R$_{10}$ are selected from H.

Preference is given to compounds of the general formula (I), the aforesaid $R_{11-13}$ are independently selected from the group consisting of —$OCH_3$, —$OCF_3$, —$CH_2CF_3$ or —$CF_3$.

Preference is further given here to compounds of the general formula (I), 1) 2-(3-(4-(4-amino-5-oxo-7,8-dihydropyrimido[5,4-f][1,4]oxazepin-6(5H)-yl)-2-chlorophenyl)-2-oxoimidazolidin-1-yl)acetic acid
2-(3-(4-(4-amino-5-oxo-7,8-dihydropyrimido[5,4-f][1,4]oxazepin-6(5H)-yl)-2-fluorophenyl)-2-oxoimidazolidin-1-yl)acetic acid
3) 2-(3-(4-(4-amino-5-oxo-7,8-dihydropyrimido[5,4-f][1,4]oxazepin-6(5H)-yl)-2-methylphenyl)-2-oxoimidazolidin-1-yl)acetic acid
4) 2-(3-(4-(4-amino-5-oxo-7,8-dihydropyrimido[5,4-f][1,4]oxazepin-6(5H)-yl)-2-ethyl-6-methylphenyl)-2-oxoimidazolidin-1-yl)acetic acid
5) 2-(3-(4-(4-amino-5-oxo-7,8-dihydropyrimido[5,4-f][1,4]oxazepin-6(5H)-yl)-2-ethylphenyl)-2-oxoimidazolidin-1-yl)acetic acid
6) 3-(3-(4-(4-amino-5-oxo-7,8-dihydropyrimido[5,4-f][1,4]oxazepin-6(5H)-yl)-2-chlorophenyl)-2-oxoimidazolidin-1-yl)propanoic acid
7) 2-(3-(4-(4-amino-5-oxo-7,8-dihydropyrimido[5,4-f][1,4]oxazepin-6(5H)-yl)-2-trifluoromethoxy)phenyl)-2-oxoimidazolidin-1-yl)acetic acid
8) 4-amino-6-(3-chloro-4-(2-oxo-3-(2,2,2-trifluoroethyl)imidazolidin-1-yl)phenyl)-7,8-dihydropyrimido[5,4-f][1,4]oxazepin-5(6H)-one
9) 4-amino-6-(3,5-dimethyl-4-(2-oxo-3-(2,2,2-trifluoroethyl)-2,3-dihydro-1H-benzo[d]imidazol-1-yl)phenyl)-7,8-dihydropyrimido[5,4-f][1,4]oxazepin-5(6H)-one
10) 2-(3-(4-(4-amino-5-oxo-7,8-dihydropyrimido[5,4-f][1,4]oxazepin-6(5H)-yl)phenyl)-2-oxo-2,3-dihydro-1H)-2-imidazol-1-yl)acetic acid
11) 2-(3-(4-(4-amino-5-oxo-7,8-dihydropyrimido[5,4-f][1,4]oxazepin-6(5H)-yl)-2-oxoimidazolidin)-1-yl)acetic acid
12) Ethyl-2-(3-(4-(4-amino-5-oxo-7,8-dihydropyrimido[5,4-f][1,4]oxazepin-6(5H)-yl)phenyl)-2-oxoimidazolidin)-1-yl)acetate
13) 3-(3-(4-(4-amino-5-oxo-7,8-dihydropyrimido[5,4-f][1,4]oxazepin-6(5H)-yl)phenyl)-2-oxoimidazolidin)-1-yl)propanoic acid
14) 2-(3-(4-(4-amino-5-oxo-7,8-dihydropyrimido[5,4-f][1,4]oxazepin-6(5H)-yl)-2-methoxyphenyl)-2-oxoimidazolidin-1-yl)acetic acid
15) 2-(3-(4-(4-amino-5-oxo-7,8-dihydropyrimido[5,4-f][1,4]oxazepin-6(5H)-yl)phenyl)-2-oxoimidazolidin-1-yl)propanoic acid
16) 2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)acetic acid
17) 2-(3-(4-(4-amino-5-oxo-7,8-dihydropyrimido[5,4-f][1,4]oxazepin-6(5H)-yl)phenyl)-2-oxoimidazolidin-1-yl)-3-methylbutanoic acid
18) 2-(3-(4-(4-amino-5-oxo-7,8-dihydropyrimido[5,4-f][1,4]oxazepin-6(5H)-yl)-2,6-dimethylphenyl)-2-oxoimidazolidin-1-yl)acetic acid
19) 2-(3-(4-(4-amino-5-oxo-7,8-dihydropyrimido[5,4-f][1,4]oxazepin-6(5H)-yl)-2,6-diethylphenyl)-2-oxoimidazolidin-1-yl)acetic acid
20) 3-(3-(4-(4-amino-5-oxo-7,8-dihydropyrimido[5,4-f][1,4]oxazepin-6(5H)-yl)phenyl-2-oxo-2,3-dihydro-1H-imidazol-1-yl)propanoic acid
21) 2-(3-(4-(4-amino-5-oxo-7,8-dihydropyrimido[5,4-f][1,4]oxazepin-6(5H)-yl)-2-(trifluoromethyl)phenyl)-2-oxo-2,3-dihydro-1H-imidazol-1-yl)acetic acid
22) 2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)propanoic acid
23) 2-(3-(4-(4-amino-5-oxo-7,8-dihydropyrimido[5,4-f][1,4]oxazepin-6(5H)-yl)phenyl)-2-oxoimidazolidin-1-yl)butanoic acid
24) 3-(3-(4-(4-amino-5-oxo-7,8-dihydropyrimido[5,4-f][1,4]oxazepin-6(5H)-yl)phenyl)-2-oxoimidazolidin-1-yl)-2-methylpropanoic acid
25) 2-(3-(4-(4-amino-5-oxo-7,8-dihydropyrimido[5,4-f][1,4]oxazepin-6(5H)-yl)-2-trifluoromethyl)phenyl)-2-oxoimidazolidin-1-yl)acetic acid
26) 2-(3-(4-(4-amino-5-oxo-7,8-dihydropyrimido[5,4-f][1,4]oxazepin-6(5H)-yl)-2-fluoro-6-methylphenyl)-2-oxoimidazolidin-1-yl)acetic acid
27) 2-(3-(4-(4-amino-5-oxo-7,8-dihydropyrimido[5,4-f][1,4]oxazepin-6(5H)-yl)-2-chloro-6-methylphenyl)-2-oxoimidazolidin-1-yl)acetic acid
28) 2-(3-(4-(4-amino-5-oxo-7,8-dihydropyrimido[5,4-f][1,4]oxazepin-6(5H)-yl)-2-chlorophenyl)-2-oxo-2,3-dihydro-1H-imidazol-1-yl)acetic acid
29) 4-amino-6-(3-chloro-4-(3-isobutyl-2-oxoimidazolidin-1-yl)phenyl-7,8-dihydropyrimido[5,4-f][1,4]oxazepin-5(6H)-one
30) 4-amino-6-(3-chloro-4-(3-(cyclopropylmethyl)-2-oxoimidazolidin-1-yl)phenyl-7,8-dihydropyrimido[5,4-f][1,4]oxazepin-5(6H)-one
31) 4-amino-6-(3-chloro-4-(3-(2-fluoro-2-methylpropyl-2-oxoimidazolidin-1-yl)phenyl-7,8-dihydropyrimido[5,4-f][1,4]oxazepin-5(6H)-one
32) 2-(4-(4-(4-amino-5-oxo-7,8-dihydropyrimido[5,4-f][1,4]oxazepin-6(5H)-yl)phenyl)-3,5-dimethyl-1H-pyrazol-1-yl)acetic acid
33) 2-(4-(4-(4-amino-5-oxo-7,8-dihydropyrimido[5,4-f][1,4]oxazepin-6(5H)-yl)-2-chlorophenyl)-1H-pyrazol-1-yl)-2-methylpropanoic acid
34) 2-(4-(4-(4-amino-5-oxo-7,8-dihydropyrimido[5,4-f][1,4]oxazepin-6(5H)-yl)-2-chlorophenyl)-1H-pyrazol-1-yl)propanoic acid
35) 3-(4-(4-(4-amino-5-oxo-7,8-dihydropyrimido[5,4-f][1,4]oxazepin-6(5H)-yl)-2-chlorophenyl)-1H-pyrazol-1-yl)propanoic acid
36) 2-(4-(4-(4-amino-5-oxo-7,8-dihydropyrimido[5,4-f][1,4]oxazepin-6(5H)-yl)-2-chlorophenyl)-3-methyl-1H-pyrazol-1-yl)acetic acid
37) 3-(4-(4-(4-amino-5-oxo-7,8-dihydropyrimido[5,4-f][1,4]oxazepin-6(5H)-yl)-2-fluorophenyl)-1H-pyrazol-1-yl)propanoic acid
38) 3-(4-(4-(4-amino-5-oxo-7,8-dihydropyrimido[5,4-f][1,4]oxazepin-6(5H)-yl)-2-chlorophenyl)-3,5-dimethyl-1H-pyrazol-1-yl)propanoic acid
39) 2-(4-(4-(4-amino-5-oxo-7,8-dihydropyrimido[5,4-f][1,4]oxazepin-6(5H)-yl)phenyl)-3-trifluoromethyl-1H-pyrazol-1-yl)acetic acid
40) 4-amino-6-(3-chloro-4-(3-methyl-1-(2,2,2-trifluoroethyl)-1H-pyrazol-4-yl)phenyl)-7,8-dihydropyrimido[5,4-f][1,4]oxazepin-5(6H)-one
41) 4-amino-6-(3,5-dimethyl-4-(3-methyl-1-(2,2,2-trifluoroethyl)-1H-pyrazol-4-yl)phenyl)-7,8-dihydropyrimido[5,4-f][1,4]oxazepin-5(6H)-one
42) 4-amino-6-(3-chloro-4-(1-(2-hydroxy-2-methylpropyl)-1H-pyrazol-4-yl)phenyl)-7,8-dihydropyrimido[5,4-f][1,4]oxazepin-5(6H)-one 43) 4-amino-6-(4-(1-(2,2-difluoroethyl)-3-methyl-1H-pyrazol-4-yl)-3,5-dimethylphenyl)-7,8-dihydropyrimido[5,4-f][1,4]oxazepin-5(6H)-one
44) 4-amino-6-(3-chloro-4-(1-(3-hydroxy-2,2-dimethylpropyl)-1H-pyrazol-4-yl)phenyl)-7,8-dihydropyrimido[5,4-f][1,4]oxazepin-5(6H)-one
45) (R)-4-amino-6-(3-chloro-4-(1-isobutyl-1H-pyrazol-4-yl)phenyl)-8-methyl-7,8-dihydropyrimido[5,4-f][1,4]oxazepin-5(6H)-one
46) 2-(4-(4-(4-amino-5-oxo-7,8-dihydropyrimido[5,4-f][1,4]oxazepin-6(5H)-yl)-2-chlorophenyl)-1H-pyrazol-1-yl)acetamide
47) 4-amino-6-(3,5-dimethyl-4-(3-methyl-1-((3-methyloxetan-3-yl)methyl)-1H-pyrazol-4-yl)phenyl-7,8-dihydropyrimido[5,4-f][1,4]oxazepin-5(6H)-one
48) 4-amino-6-(4-(1-(2,2-difluoropropyl)-3-methyl-1H-pyrazol-4-yl)-3,5-dimethylphenyl)-7,8-dihydropyrimido[5,4-f][1,4]oxazepin-5(6H)-one
49) 2-(4-(4-(4-amino-5-oxo-7,8-dihydropyrimido[5,4-f][1,4]oxazepin-6(5H)-yl)phenyl)-1H-pyrazol-1-yl)acetic acid
50) 3-(4-(4-(4-amino-5-oxo-7,8-dihydropyrimido[5,4-f][1,4]oxazepin-6(5H)-yl)phenyl)-1H-pyrazol-1-yl)propanoic acid
51) 2-(4-(4-(4-amino-5-oxo-7,8-dihydropyrimido[5,4-f][1,4]oxazepin-6(5H)-yl)phenyl)-1H-pyrazol-1-yl)propanoic acid
52) 2-(4-(4-(4-amino-5-oxo-7,8-dihydropyrimido[5,4-f][1,4]oxazepin-6(5H)-yl)phenyl)-1H-pyrazol-1-yl)butanoic acid
53) 2-(4-(4-(4-amino-5-oxo-7,8-dihydropyrimido[5,4-f][1,4]oxazepin-6(5H)-yl)phenyl)-1H-pyrazol-1-yl)-3-methylbutanoic acid
54) 2-(4-(4-(4-amino-5-oxo-7,8-dihydropyrimido[5,4-f][1,4]oxazepin-6(5H)-yl)phenyl)-1H-pyrazol-1-yl)-2-methylpropanoic acid
55) 2-(4-(4-(4-amino-5-oxo-7,8-dihydropyrimido[5,4-f][1,4]oxazepin-6(5H)-yl)phenyl)-3-methyl-1H-pyrazol-1-yl)acetic acid
56) 2-(4-(4-(4-amino-5-oxo-7,8-dihydropyrimido[5,4-f][1,4]oxazepin-6(5H)-yl)-2-chlorophenyl)-1H-pyrazol-1-yl)acetic acid
57) 2-(4-(4-(4-amino-5-oxo-7,8-dihydropyrimido[5,4-f][1,4]oxazepin-6(5H)-yl)-2-methylphenyl)-1H-pyrazol-1-yl)acetic acid
58) 2-(4-(4-(4-amino-5-oxo-7,8-dihydropyrimido[5,4-f][1,4]oxazepin-6(5H)-yl)-2-methylphenyl)-1H-pyrazol-1-yl)propanoic acid
59) 2-(4-(4-(4-amino-5-oxo-7,8-dihydropyrimido[5,4-f][1,4]oxazepin-6(5H)-yl)-2-methylphenyl)-1H-pyrazol-1-yl)-3-methylbutanoic acid
60) 3-(4-(4-(4-amino-5-oxo-7,8-dihydropyrimido[5,4-f][1,4]oxazepin-6(5H)-yl)-2-methylphenyl)-1H-pyrazol-1-yl)propanoic acid
61) 2-(4-(4-(4-amino-5-oxo-7,8-dihydropyrimido[5,4-f][1,4]oxazepin-6(5H)-yl)-2-chlorophenyl)-1H-pyrazol-1-yl)butanoic acid
62) 3-(4-(4-(4-amino-5-oxo-7,8-dihydropyrimido[5,4-f][1,4]oxazepin-6(5H)-yl)phenyl)-3-(trifluoromethyl)-1H-pyrazol-1-yl)propanoic acid
63) 2-(4-(4-(4-amino-5-oxo-7,8-dihydropyrimido[5,4-f][1,4]oxazepin-6(5H)-yl)-2-methylphenyl)-1H-pyrazol-1-yl)-2-methylpropanoic acid
64) 2-(4-(4-(4-amino-5-oxo-7,8-dihydropyrimido[5,4-f][1,4]oxazepin-6(5H)-yl)-2-methylphenyl)-1H-pyrazol-1-yl)butanoic acid
65) 2-(4-(4-(4-amino-5-oxo-7,8-dihydropyrimido[5,4-f][1,4]oxazepin-6(5H)-yl)-2-chlorophenyl)-1H-pyrazol-1-yl)-3-methylbutanoic acid
66) 2-(4-(4-(4-amino-5-oxo-7,8-dihydropyrimido[5,4-f][1,4]oxazepin-6(5H)-yl)-2,6-dimethylphenyl)-1H-pyrazol-1-yl)-2-methylpropanoic acid
67) 2-(4-(4-(4-amino-5-oxo-7,8-dihydropyrimido[5,4-f][1,4]oxazepin-6(5H)-yl)-2,6-dimethylphenyl)-1H-pyrazol-1-yl)acetic acid
68) 4-amino-6-(3-chloro-4-(1-(2,2,2-trifluoroethyl)-1H-pyrazol-4-yl)phenyl-7,8-dihydropyrimido[5,4-f][1,4]oxazepin-5(6H)-one
69) 2-(4-(4-(4-amino-5-oxo-7,8-dihydropyrimido[5,4-f][1,4]oxazepin-6(5H)-yl)-2-methoxyphenyl)-1H-pyrazol-1-yl)acetic acid
70) 3-(4-(4-(4-amino-5-oxo-7,8-dihydropyrimido[5,4-f][1,4]oxazepin-6(5H)-yl)-2,6-dimethylphenyl)-1H-pyrazol-1-yl)propanoic acid
71) 3-(4-(4-(4-amino-5-oxo-7,8-dihydropyrimido[5,4-f][1,4]oxazepin-6(5H)-yl)-2-chlorophenyl)-1H-pyrazol-1-yl)-2,2-dimethylpropanoic acid
72) 2-(4-(4-(4-amino-5-oxo-7,8-dihydropyrimido[5,4-f][1,4]oxazepin-6(5H)-yl)-2-chlorophenyl)-3,5-dimethyl-1H-pyrazol-1-yl)acetic acid
73) 2-(4-(4-(4-amino-5-oxo-7,8-dihydropyrimido[5,4-f][1,4]oxazepin-6(5H)-yl)-2,6-dimethylphenyl)-3-methyl-1H-pyrazol-1-yl)acetic acid
74) 3-(4-(4-(4-amino-5-oxo-7,8-dihydropyrimido[5,4-f][1,4]oxazepin-6(5H)-yl)-2-methoxyphenyl)-1H-pyrazol-1-yl)propanoic acid
75) 2-(4-(4-(4-amino-5-oxo-7,8-dihydropyrimido[5,4-f][1,4]oxazepin-6(5H)-yl)-2-fluorophenyl)-1H-pyrazol-1-yl)acetic acid
76) 3-(4-(4-(4-amino-5-oxo-7,8-dihydropyrimido[5,4-f][1,4]oxazepin-6(5H)-yl)phenyl)-3,5-dimethyl-1H-pyrazol-1-yl)propanoic acid
77) 3-(4-(4-(4-amino-5-oxo-7,8-dihydropyrimido[5,4-f][1,4]oxazepin-6(5H)-yl)-2-methylphenyl)-3,5-dimethyl-1H-pyrazol-1-yl)propanoic acid
78) 3-(4-(4-(4-amino-5-oxo-7,8-dihydropyrimido[5,4-f][1,4]oxazepin-6(5H)-yl)-2-chlorophenyl)-3-methyl-1H-pyrazol-1-yl)propanoic acid
79) 4-amino-6-(3-chloro-4-(1-ethyl-1H-pyrazol-4-yl)phenyl-7,8-dihydropyrimido[5,4-f][1,4]oxazepin-5(6H)-one
80) 4-amino-6-(3-chloro-4-(1-isobutyl-1H-pyrazol-4-yl)phenyl-7,8-dihydropyrimido[5,4-f][1,4]oxazepin-5(6H)-one
81) 4-amino-6-(3-chloro-4-(1-isopropyl-1H-pyrazol-4-yl)phenyl-7,8-dihydropyrimido[5,4-f][1,4]oxazepin-5(6H)-one
82) 4-amino-6-(3-chloro-4-(1-(2-hydroxyethyl)-1H-pyrazol-4-yl)phenyl-7,8-dihydropyrimido[5,4-f][1,4]oxazepin-5(6H)-one
83) 3-(4-(4-(4-amino-5-oxo-7,8-dihydropyrimido[5,4-f][1,4]oxazepin-6(5H)-yl)-2,6-dimethylphenyl)-3-methyl-1H-pyrazol-1-yl)propanoic acid
84) 2-(4-(4-(4-amino-5-oxo-7,8-dihydropyrimido[5,4-f][1,4]oxazepin-6(5H)-yl)-2-chlorophenyl)-1H-pyrazol-1-yl)acetonitrile
85) 4-amino-6-(3-chloro-4-(1-(2,2-dimethyl-3-oxo-3-(pyrrolidin-1-yl)propyl-1H-pyrazol-4-yl)phenyl)-7,8-dihydropyrimido[5,4-f][1,4]oxazepin-5(6H)-one
86) 4-amino-6-(3-chloro-4-(1-isobutyl-1H-pyrazol-4-yl)phenyl)-8,8-dimethyl-7,8-dihydropyrimido[5,4-f][1,4]oxazepin-6(5H)-one 87) 4-amino-6-(3-chloro-4-(1-(cyclopropylmethyl)-1H-pyrazol-4-yl)phenyl)-7,8-dihydropyrimido[5,4-f][1,4]oxazepin-6(5H)-one
88) 4-amino-6-(3-chloro-4-(1-neopentyl-1H-pyrazol-4-yl)phenyl)-7,8-dihydropyrimido[5,4-f][1,4]oxazepin-5(6H)-one
89) 3-(4-(4-(4-amino-5-oxo-7,8-dihydropyrimido[5,4-f][1,4]oxazepin-6(5H)-yl)-2-chlorophenyl)-1H-pyrazol-1-yl)-N,N,2,2-tetramethylpropanamide
90) 4-amino-6-(3-ethyl-4-(1-(isobutyl-1H-pyrazol-4-yl)phenyl)-7,8-dihydropyrimido[5,4-f][1,4]oxazepin-5(6H)-one
91) 4-amino-6-(3-chloro-4-(1-(2-fluoro-2-methylpropyl)-1H-pyrazol-4-yl)phenyl)-7,8-dihydropyrimido[5,4-f][1,4]oxazepin-5(6H)-one
92) 4-amino-6-(3-chloro-4-(1-isobutyl-1H-pyrazol-4-yl)phenyl)-7,7-dimethyl-7,8-dihydropyrimido[5,4-f][1,4]oxazepin-5(6H)-one
93) 4-amino-6-(4-(3,5-dimethyl-1-(2,2,2-trifluoroethyl)-1H-pyrazol-4-yl)phenyl)-3,5-dimethylphenyl)-7,8-dihydropyrimido[5,4-f][1,4]oxazepin-5(6H)-one
94) 4-amino-6-(3-chloro-4-(1-(2-methoxy-2-methylpropyl)-1H-pyrazol-4-yl)phenyl)-7,8-dihydropyrimido[5,4-f][1,4]oxazepin-5(6H)-one
95) 4-amino-6-(3-chloro-4-(1-(2-fluoro-2-methylpropyl)-1H-pyrazol-3-yl)phenyl)-7,8-dihydropyrimido[5,4-f][1,4]oxazepin-5(6H)-one
96) (R)-4-amino-6-(3-chloro-4-(1-isobutyl-1H-pyrazol-4-yl)phenyl)-7-methyl-7,8-dihydropyrimido[5,4-f][1,4]oxazepin-5(6H)-one
97) 4-amino-6-(4-(1-(2-fluoro-2-methylpropyl)-3-methyl-1H-pyrazol-4-yl)-3,5-dimethylphenyl)-7,8-dihydropyrimido[5,4-f][1,4]oxazepin-5(6H)-one
98) 4-amino-6-(4-(1-(2-hydroxy-2-methylpropyl)-3-methyl-1H-pyrazol-4-yl)-3,5-dimethylphenyl)-7,8-dihydropyrimido[5,4-f][1,4]oxazepin-5(6H)-one
99) 4-amino-6-(4-(1-(2-methoxy-2-methylpropyl)-3-methyl-1H-pyrazol-4-yl)-3,5-dimethylphenyl)-7,8-dihydropyrimido[5,4-f][1,4]oxazepin-5(6H)-one
100) 4-amino-6-(4-(2-oxo-1-(2,2,2-trifluoroethyl)-1,2-dihydropyridin-3-yl)phenyl)-7,8-dihydropyrimido[5,4-f][1,4]oxazepin-5(6H)-one
101) 4-amino-6-(3,5-dimethyl-4-(6-oxo-1-(2,2,2-trifluoroethyl)-1,6-dihydropyridin-3-yl)phenyl)-7,8-dihydropyrimido[5,4-f][1,4]oxazepin-5(6H)-one
102) 4-amino-6-(3-chloro-4-(1-(2-fluoro-2-methylpropyl)-1H-imidazol-4-yl)phenyl)-7,8-dihydropyrimido[5,4-f][1,4]oxazepin-5(6H)-one
103) 2-(4-(4-(4-amino-5-oxo-7,8-dihydropyrimidine[5,4-f][1,4]oxazepin-6(5H)-yl)phenyl)piperidinyl)acetic acid
104) 2-(3-(4-(4-amino-5-oxo-7,8-dihydropyrimidine[5,4-f][1,4]oxazepin-6(5H)-yl)phenyl)pyrrole-1-yl)acetic acid
105) 4-amino-6-(3,5-dimethyl-4-(1-oxo-2-(2,2,2-trifluoroethyl)-1,2-dihydroiosquinolin-7-yl)phenyl)-7,8-dihydropyrimido[5,4-f][1,4]oxazepin-5(6H)-one
106) (E)-4-amino-6-(6-((2,2,2-trifluoroethoxy)imino)-5,6,7,8-tetrahydronaphthalen-2-yl)-7,8-dihydropyrimido[5,4-f][1,4]oxazepin-5(6H)-one
107) (Z)-4-amino-6-(5-((2,2,2-trifluoroethoxy)imino)-5,6,7,8-tetrahydronaphthalen-2-yl)-7,8-dihydropyrimido[5,4-f][1,4]oxazepin-5(6H)-one
108) 4-amino-6-(6-((2,2,2-trifluoroethoxy)-5,6,7,8-tetrahydronaphthalen-2-yl)-7,8-dihydropyrimido[5,4-f][1,4]oxazepin-5(6H)-one
109) 4-amino-6-(3,5-dimethyl-4-(3-(methyl-2-(2,2,2-trifluoroethyl)-2H-indazol-5-yl)phenyl)-7,8-dihydropyrimido[5,4-f][1,4]oxazepin-5(6H)-one The aforesaid compounds in the present invention are named compound 1 to 109, their structural formula and preparation methods detailed in example 1 to 109.

The present invention also provides a process for preparing the compound of formula (I), wherein $R_5$ represents

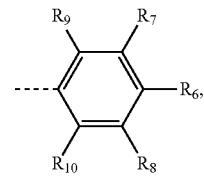

includes the following step,

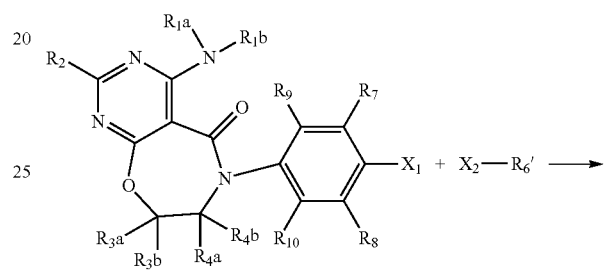

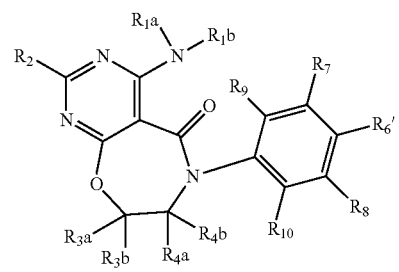

wherein, $X_1$, $X_2$ are independently selected from the group consisting of $CF_3$,

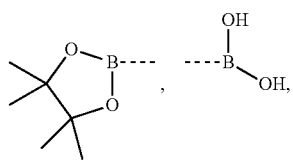

halogen, OH, SH, $NH_2$, $PH_2$ and $C_{1-6}$alkyl, wherein the $C_{1-6}$alkyl is optionally substituted by halogen, OH, SH, $NH_2$ or $PH_2$, the number of substituent is 1 or more;

$R_6{}'$ represents $R_6$, or $R_6$ optionally protected by the protecting group;

$R_{1a}$, $R_{1b}$, $R_2$, $R_{3a}$, $R_{3b}$, $R_{4a}$, $R_{4b}$, $R_{6-10}$ are the same as defined in claims 1-10.

The present invention also provides another process for preparing the compound of formula (I), wherein $R_5$ represents

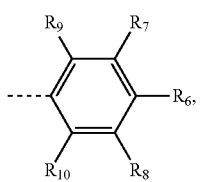

which includes the following step,

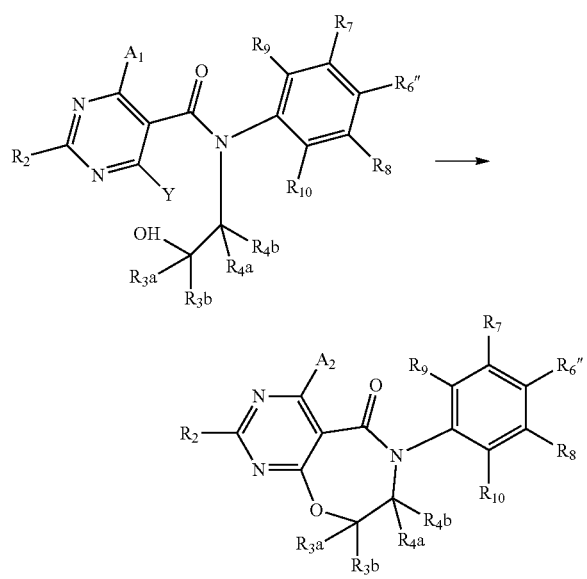

wherein, $A_1$, $A_2$ and Y are independently selected from the group consisting of $CF_3$, halogen, OH, SH, $NH_2$, $PH_2$ and $C_{1-6}$alkyl, wherein the $C_{1-6}$alkyl is optionally substituted by halogen, OH, SH, $NH_2$ or $PH_2$, the number of substituent is 1 or more;

$R_6'$ represents $R_6$, or $R_6$ optionally protected by the protecting group;

$R_2$, $R_{3a}$, $R_{3b}$, $R_{4a}$, $R_{4b}$, $R_{6-10}$ are the same as defined in claims 1-10.

Preference is given to the process for preparing the compound of formula (I), the aforesaid protecting group represents amino-protecting group or hydroxy-protecting group.

Preference is given to the process for preparing the compound of formula (I), the aforesaid amino-protecting group is selected from the group consisting of BOC, Cbz, Fmoc, Bn, PMB, Pht, Ac, Trt, $CF_3CO$, Alloc, methyl ester, Troc or PMP; the hydroxy-protecting group is selected from the group consisting of ethyl, TBS, TBDPS, TMS, Ac, Me, MOM, MEM, THP, Bn, PMB, MTM or Piv.

The present invention also provides a pharmaceutical composition comprising therapeutically effective amount of the compound of formula (I) or a pharmaceutically acceptable salt thereof and pharmaceutical acceptable carriers.

The present invention also provides a use of the compound of formula (I) or a pharmaceutically acceptable salt thereof, or the pharmaceutical composition in the preparation of a medicament for the prevention or treatment of FCS, obesity, hyperlipoproteinemia or hypertriglyceridemia.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

Definitions

Halogen is selected from the group consisting of fluorine, chlorine, bromine and iodine; $C_{1-6}$ is selected from the group consisting of $C_1$, $C_2$, $C_3$, $C_4$, $C_5$ and $C_6$; $C_{4-10}$ is selected from the group consisting of $C_4$, $C_5$, $C_6$, $C_7$, $C_8$, $C_9$ and $C_{10}$; $C_{1-10}$ is selected from the group consisting of $C_1$, $C_2$, $C_3$, $C_4$, $C_5$, $C_6$, $C_7$, $C_8$, $C_9$ and $C_{10}$; 5-10 membered heterocycle is selected from the group consisting of 5, 6, 7, 8, 9 and 10-membered heterocycle.

The compounds herein described may have asymmetric centers. Compounds of the present invention containing an asymmetrically substituted atom may be isolated in optically active or racemic forms. It is well known, in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Both cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated. All processes used to prepare compounds of the present invention and intermediates made therein are considered to be part of the present invention. All tautomers of shown or described compounds are also considered to be part of the present invention.

The term "substituted", as used herein, means that any one or more hydrogens on the designated atom is replaced with a selection from the indicated group, including deuterium "D" atom, a variant of hydrogen, provided that the designated atom's normal valency is not exceeded, and that the substitution results in a stable compound. When a substituent is keto (i.e., =O), then 2 hydrogens on the atom are replaced. Keto substituents are not present on aromatic moieties. Ring double bonds, as used herein, are double bonds that are formed between two adjacent ring atoms (e.g., C=C, C=N, or N=N). The present invention, in general, does not cover groups such as N-halo, S(O)H, and $SO_2H$.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

When any variable (e.g., $R_6$) occurs more than one time in any constituent or formula for a compound, its definition at each occurrence is independent of its definition at every other occurrence. Thus, for example, if a group is shown to be substituted with 0-2 $R_6$, then said group may optionally be substituted with up to two $R_6$ groups and $R_6$ at each occurrence is selected independently from the definition of $R_6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. C1-C10 means one to ten carbons). In some embodiments, the term "alkyl" means a straight or branched chain, or combinations thereof, which may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom. In some embodiments, the term "heteroalkyl," by itself or in combination with another term, means a stable straight or branched chain, or combinations thereof, consisting of the stated number of carbon atoms and at least one heteroatom. In an exemplary embodiment, the heteroatoms can be selected from the group consisting of B, O, N and S, and wherein, the nitrogen and sulfur atoms may optionally be oxidized and the nitrogen heteroatom may optionally be quaternized. The heteroatom(s) B, O, N and S may be placed at any interior position of the heteroalkyl group or at the position at which the alkyl group is attached to the remainder of the molecule. Examples include, but are not limited to, —CH$_2$—CH$_2$—O—CH$_3$—, —CH$_2$—CH$_2$—NH—CH$_3$, —CH$_2$—CH$_2$N(—CH$_3$)—CH$_3$, —CH$_2$—S—CH$_2$—CH$_3$, —CH$_2$—CH$_2$, —S(O)—CH$_3$, —CH$_2$—CH$_2$—S(O)$_2$—CH$_3$, —CH=CH—O—CH$_3$, —CH$_2$—CH=N—OCH$_3$, and —CH=CH—N(CH$_3$)—CH$_3$. Up to two heteroatoms may be consecutive, such as, for example, —CH$_2$—NH—OCH$_3$.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl and the like. Non-limiting examples of heterocycloalkyl moieties include 1-(1,2,5,6-tetrahydropyridyl), 1-piperidinyl, 2-piperidinyl, 3-piperdinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo(C1-C4)alkyl" is mean to include, but not be limited to, trifluoromethyl, 2,2,2-trifluoroethyl, 4-chlorobutyl, 3-bromopropyl, and the like.

The term "aryl" means, unless otherwise stated, a polyunsaturated, aromatic, substituent that can be a single ring or multiple rings (preferably from 1 to 3 rings), which are fused together or linked covalently. The term "heteroaryl" refers to aryl groups (or rings) that contain from one to four heteroatoms. In an exemplary embodiment, the heteroatom is selected, from B, N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthio, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are genetically referred to as "alkyl group substituents," and they can be one or more of a variety of groups selected from, but not limited to: —R', —OR', =O, =NR', =N—OR', —NR'R",
—SR', -halogen, —SiR'R"R"', OC(O)R', —(O)R', —CO$_2$R', —CONR'R",
—OC(O)NR'R", —N"C(O)R', NR'C(O)NR'R"', —NR"C(O)$_2$R', —NR''''—C(NR'R''R''')=NR'''', NR''''C(NR'R'')=N''', —S(O)R', —S(O)₂R',
—S(O)₂NR'R'', NR''SO₂R', —CN, —NO₂, —N₃, —CH(Ph)₂, fluoro(C1-C4)alkoxy, and fluoro(C1-C4)alkyl, in a number ranging from zero to (2m'+1), where m' is the total number of carbon atoms in such radical, R', R'', R''', R'''' and R'''''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R'', R''', R'''' and R'''''' groups when more than one of these groups is present. When R' and R'' are attached to the same nitrogen atom, they can be combined with the nitrogen atom to form a 5-, 6-, or 7-membered ring. For example, —NR'R'' meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF₃ and —CH₂CF₃) and acyl (e.g., —C(O)CH₃, —C(O)CF₃, —C(O)CH₂OCH₃, and the like).

Similar to the substituents described for the alkyl radical, substituents for the aryl and heteroaryl groups are genetically referred to as "aryl group substituents." The substituents are selected from, for example: —R', —OR', —NR'R'', —SR', -halogen, —SiR'R''R''', OC(O)R', —C(O)R', —CO2R', —CONR'R'', —OC(O)NR'R'', —NR''C(O)R', NR' C(O)NR''R''', —NR''C(O)₂R', —NR''''—C(NR'R''R''')=R'''', NR'''' C(NR'R'')=NR''', —S(O)R', —S(O)₂R', —S(O)₂R'R'', NR''SO₂R', —CN, —NO₂, —CH(Ph)₂, fluoro(C1-C4)alkoxy, and fluoro(C1-C4)alkyl, in a number ranging from zero to the total number of open valences on the aromatic ring system; and where R', R'', R''', R'''' and R'''''' are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R'', R''', R'''' and R'''''' groups when more than one of these groups is present. Two of the substituents on adjacent atoms of the aryl or heteroaryl ring may optionally be replaced with a substituent of the formula -T-C(O)—(CRR')q-U-, wherein T and U are independently —NR—, —O—, —CRR'— or a single bond, and q is an integer of from 0 to 3.

Alternatively, two of the substituents on adjacent atoms of the aryl or heteroaryl ring may optionally be replaced with a substituent of the formula -A(CH₂)rB—, wherein A and B are independently —CRR'—, —O—, —NR—, —S—, —S(O)—, S(O)₂—, —S(O)₂NR'— or a single bond, and r is an integer of from 1 to 4. One of the single bonds of the new ring so formed may optionally be replaced with a double bond.

Alternatively, two of the substituents on adjacent atoms of the aryl or heteroaryl ring may optionally be replaced with a substituent of the formula —(CRR')s-X—(CR''R''')_d—, where s and d are independently integers of from 0 to 3, and X is —O—, —NR'—, —S—, —S(O)—, —S(O)₂—, or —S(O)₂NR'—. The substituents R, R', R'' and R''' are preferably independently selected from hydrogen or substituted or unsubstituted (C1-C6)alkyl.

"Ring" as used herein, means a substituted or unsubstituted cycloalkyl, substituted or unsubstituted heterocycloalkyl, substituted or unsubstituted aryl, or substituted or unsubstituted heteroaryl. A ring includes fused ring moieties. The number of atoms in a ring is typically defined by the number of members in the ring. For example, a "5- to 7-membered ring" means there are 5 to 7 atoms in the encircling arrangement. Unless otherwise specified, the ring optionally includes one to three heteroatoms. Thus, the term "5- to 7-membered ring" includes, for example phenyl, pyridinyl and piperidinyl. The term "5- to 7-membered heterocycloalkyl ring", on the other hand, would include pyridinyl and piperidinyl, but not phenyl. The term "ring" further includes a ring system comprising more than one "ring", wherein each "ring" is independently defined as above.

As used herein, the term "heteroatom" includes atoms other than carbon (C) and hydrogen (H). Examples include oxygen (O), nitrogen (N), sulfur (S), silicon (Si), germanium (Ge), aluminum (Al) and boron (B).

The term "leaving group" means a functional group or atom which, can be displaced by another functional group or atom in a substitution reaction, such as a nucleophilic substitution reaction. By way of example, representative leaving groups include triflate, chloro, bromo and iodo groups; sulfonic ester groups, such as mesylate, tosylate, brosylate, nosylate and the like; and acyloxy groups, such as acetoxy, trifluoroacetoxy and the like.

The symbol "R" is a general abbreviation that represents a substituent group that is selected from substituted or unsubstituted alkyl, substituted or unsubstituted heteroalkyl, substituted or unsubstituted aryl, substituted or unsubstituted heteroaryl, substituted or unsubstituted cycloalkyl and substituted or unsubstituted heterocycloalkyl groups.

By "effective" amount of a drug, formulation, or permeant is meant a sufficient amount of an active agent to provide the desired local or systemic effect. A "Topically effective," "Cosmetically effective," "pharmaceutically effective" or "therapeutically effective" amount refers to the amount of drug needed to effect the desired therapeutic result.

The term "pharmaceutically acceptable salt" is meant to include a salt of a compound of the invention which is prepared with relatively nontoxic acids or bases, depending on the particular substituents found on the compounds described herein. When compounds of the invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", Journal of Pharmaceutical Science 66: 1-19 (1977)). Certain specific compounds of the invention contain both basic and acidic functionalities that allow the compounds to be converted into either base or acid addition salts.

The neutral forms of the compounds are preferably regenerated by contacting the salt with a base or acid and isolating the parent compounds in the conventional manner. The parent form of the compound differs from the various salt forms in certain physical properties, such as solubility in polar solvents.

In addition to salt forms, the present invention provides compounds which are in a prodrug form. Prodrugs of the compounds described herein readily undergo chemical changes under physiological conditions to provide the compounds of the invention. Additionally, prodrugs can be converted to the compounds of the invention by chemical or biochemical methods in an ex vivo environment.

Certain compounds of the invention can exist in unsolvated forms as well as solvated forms, including hydrated forms. In general, the solvated forms are equivalent to unsolvated forms and are encompassed within the scope of the present invention. Certain compounds of the invention may exist in multiple crystalline or amorphous forms.

Certain compounds of the invention possess asymmetric carbon atoms (optical centers) or double bonds; the racemates, diastereomers, geometric isomers and individual isomers are encompassed within the scope of the present invention. The graphic representations of racemic, ambiscalemic and scalemic or enantiomerically pure compounds used herein are taken from Maehr, J. Chem. Ed. 1985, 62: 114-120. Solid and broken wedges are used to denote the absolute configuration of a stereocenter unless otherwise noted. When the compounds described herein contain olefinic double bonds or other centers of geometric asymmetry, and unless specified otherwise, it is intended that the compounds include both E and Z geometric isomers. Likewise, all tautomeric forms are included.

Compounds of the invention can exist in particular geometric or stereoisomeric forms. The invention contemplates all such compounds, including cis- and trans-isomers. (−)- and (+)-enantiomers. (R)- and (S)-enantiomers, diastereomers, (D)-isomers, (L)-isomers, the racemic mixtures thereof, and other mixtures thereof, such us enanitomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

Optically active (R)- and (S)-isomers and d and l isomers can be prepared using chiral synthons or chiral reagents, or resolved using conventional techniques. If, for instance, a particular enantiomer of a compound of the present invention is desired, it can be prepared by asymmetric synthesis, or by derivatization with a chiral auxiliary, where the resulting diastereomeric mixture is separated and the auxiliary group cleaved to provide the pure desired enantiomers. Alternatively, where the molecule contains a basic functional group, such as an amino group, of an acidic functional group, such as a carboxyl group, diastereomeric salts can be formed with an appropriate optically active acid or base, followed by resolution of the diastereomers thus formed by fractional crystallization or chromatographic means known in the art, and subsequent recovery of the pure enantiomers. In addition, separation of enantiomers and diastereomers is frequently accomplished using chromatography employing chiral, stationary phases, optionally in combination with chemical derivatization (e.g., formation of carbamates from amines).

The compounds of the invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I) or carbon-14 ($^{14}$C). All isotopic variations of the compounds of the invention, whether radioactive or not, are intended to be encompassed within the scope of the present invention.

The term "pharmaceutically acceptable carrier" or "pharmaceutically acceptable vehicle" refers to any formulation or carrier medium that provides the appropriate delivery of an effective amount of an active agent as defined herein, does not interfere with the effectiveness of the biological activity of the active agent, and that is sufficiently non-toxic to the host or patient. Representative carriers include water, oils, both vegetable and mineral, cream bases, lotion bases, ointment bases and the like. These bases include suspending agents, thickeners, penetration enhancers, and the like. Their formulation is well known to those in the art of cosmetics and topical pharmaceuticals. Additional information concerning carriers can be found in Remington: The Science and Practice of Pharmacy, 21st Ed., Lippincott, Williams & Wilkins (2005) which, is incorporated herein by reference.

The term "excipients" is conventionally known to mean carriers, diluents and/or vehicles used in formulating drug compositions effective for the desired use.

The terms "effective amount" or a "therapeutically effective amount" of a drug or pharmacologically active agent refers to a nontoxic but sufficient amount of the drug or agent to provide the desired effect. In the oral dosage forms of the present disclosure, an "effective amount" of one active of the combination is the amount of that active that is effective to provide the desired effect when used in combination with the other active of the combination. The amount that is "effective" will vary from subject to subject, depending on the age and general condition of the individual, the particular active agent or agents, and the appropriate "effective" amount in any individual case may be determined by one of ordinary skill in the art using routine experimentation.

The phrases "active ingredient", "therapeutic agent", "active", or "active agent" mean a chemical entity which can be effective in treating a targeted disorder, disease or condition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in Remington's Pharmaceutical Sciences, 18th ed., Mack Publishing Company, Easton, Pa., 1990, p. 1445, the disclosure of which is hereby incorporated by reference.

Since prodrugs are known to enhance numerous desirable qualities of pharmaceuticals (e.g., solubility, bioavailability, manufacturing, etc.) the compounds of the present invention may be delivered in prodrug form. Thus, the present invention is intended cover prodrugs of the presently claimed compounds, methods of delivering the same and compositions containing the same. "Prodrugs" are intended to include any covalently bonded carriers that release an active parent drug of the present invention in vivo when such prodrug is administered to a mammalian subject. Prodrugs the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug of the present invention is administered to a mammalian subject, it cleaves to form a free hydroxyl, free amino, or free sulfhydryl group, respectively. Examples of prodrugs include, but are not limited to, acetate, formate, and benzoate derivatives of alcohol and amine functional groups in the compounds of the present invention.

The phrase "oral dosage form" means any pharmaceutical composition administered to a subject via the oral cavity. Exemplary oral dosage forms include tablets, capsules, films, powders, sachets, granules, solutions, solids, suspensions or as more than one distinct unit (e.g., granules, tablets, and/or capsules containing different actives) packaged together for co-administration, and other formulations known in the art. An oral dosage form can be one, two, three, four, five or six units. When the oral dosage form has multiple units, all of the units are contained within a single package, (e.g. a bottle or other form of packaging such as a blister pack). When the oral dosage form is a single unit, it may or may not be in a single package, in a preferred embodiment, the oral dosage form is one, two or three units. In a particularly preferred embodiment, the oral dosage form is one unit.

"Inhibiting" and "blocking," are used interchangeably herein to refer to the partial or full blockade of an enzyme, such as a serine protease.

The term "leaving group" means a functional group or atom which can be displaced by another functional group or atom in a substitution reaction, such as a nucleophilic substitution reaction. By way of example, representative leaving groups include inflate, chloro, bromo and iodo groups; sulfonic ester groups, such as mesylate, tosylate, brosylate, nosylate and the like; and acyloxy groups, such as acetoxy, trifluoroacetoxy and the like.

The term, "amino-protecting group" means a protecting group suitable for preventing undesired reactions at an amino nitrogen. Representative amino-protecting groups include, but are not limited to, formyl; acyl groups, for example alkanoyl groups, such as acetyl, trichloroacetyl or trifluoroacetyl; alkoxycarbonyl groups, such as tert-butoxycarbonyl (Boc); arylmethoxycarbonyl groups, such as benzyloxycarbonyl (Cbz) and 9-fluorenylmethoxycarbonyl (Fmoc); arylmethyl groups, such as benzyl (Bn), trityl (Tr), and 1,1-di-(4'-methoxyphenyl)methyl; silyl groups, such as trimethylsilyl (TMS) and tert-butyldimethylsilyl (TBS); and the like.

The term "hydroxy-protecting group" means a protecting group suitable for preventing undesired reactions at a hydroxy group. Representative hydroxy-protecting groups include, but are not limited to, alkyl groups, such as methyl, ethyl, and tert-butyl; acyl groups, for example alkanoyl groups, such as acetyl; arylmethyl groups, such as benzyl (Bn), p-methoxybenzyl (PMB), 9-fluorenylmethyl (Fm), and diphenylmethyl (benzhydryl, DPM); silyl groups, such as trimethylsilyol (TMS) and tert-butyldimethylsilyl (TBS); and the like.

Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-6}$alkoxy is intended to include $C_1$, $C_2$, $C_3$, $C_4$, $C_5$ and $C_6$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. 3-7 cycloalkyl is intended to include $C_3$, $C_4$, $C_5$, $C_6$, and $C_7$ cycloalkyl groups. "Alkenyl" is intended to include hydrocarbon chains of either straight or branched configuration and one or more unsaturated carbon-carbon bonds that may occur in any stable point along the chain, such as ethenyl and propenyl.

$C_{2-6}$alkenyl is intended to include $C_2$, $C_3$, $C_4$, $C_5$, and $C_6$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-6}$Alkynyl is intended to include $C_2$, $C_3$, $C_4$, $C_5$, and $C_6$ alkynyl groups.

"Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic of 7, 8, 9, 10, 11, 12, or 13-membered bicyclic or tricyclic ring, any of which may be saturated, partially unsaturated, or unsaturated (aromatic). Examples of such carbocycles include, but are not limited to cyclopropyl, cyclobutyl, cyclobutenyl, cyclopentyl, cyclopentenyl, cyclohexyl, cycloheptenyl, cycloheptyl, cycloheptenyl, adamantyl, cyclooctyl, cyclooctenyl, cyclooctadienyl, [3.3.0]bicyclooctane, [4.3.0]bicyclononane, [4.4.0]bicyclodecane, [2.2.2]bicyclooctane, fluorenyl, phenyl, naphthyl, indanyl adamantyl, and tetrahydronaphthyl. As shown above, bridged rings are also included in the definition of carbocyclo (e.g., [2.2.2]bicyclooctane). A bridged ring occurs when one or more carbon atoms link two non-adjacent carbon atoms. Preferred bridges are one or two carbon atoms. It is noted that a bridge always converts a monocyclic ring into a trycyclic ring. When a ring is bridged, the substituents recited for the ring may also be present on the bridge.

As used herein, the term "heterocyclo" or "heterocyclic group" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 ring heteroatoms independently selected from the group consisting of N, O and S and including any bicyclic group in which any of the above-defined heterocyclic rings is fused to a benzene ring. The nitrogen and sulfur heteroatoms may optionally be oxidized (i. e., NO and S (O) p). The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocyclo exceeds 1, then these heteroatoms are not adjacent to one another. It is preferred that the total number of S and O atoms in the heterocyclo is not more than 1. As used herein, the term "aromatic heterocyclic group" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O and S. The nitrogen atom may be substituted or unsubstituted (i.e., N or NR wherein R is H or another substituent, if defined). The nitrogen and sulfur heteroatoms may optionally be oxidized (i.e., NO and S (O) p). It is to be noted that total number of S and O atoms in the aromatic heterocycle is not more than 1.

Bridged rings are also included in the definition of heterocycle. A bridged ring occurs when one or more atoms (i.e., C, O, N, or S) link two non-adjacent carbon or nitrogen atoms. Preferred bridges include, but are not limited to, one carbon atom, two carbon atoms, one nitrogen atom, two nitrogen atoms, and a carbon-nitrogen group. It is noted that a bridge always converts a monocyclic ring into a trycyclic ring. When a ring is bridged, the substituents recited for the ring may also be present on the bridge.

Examples of heterocycles include, but are not limited to, acridinyl, azocinyl, benizmidazolyl, benzofuranyl, benzothiofuranyl, benzothiophenyl, benzoxazolyl, benzoxazolinyl, benzothiazolyl, benzotriazolyl, benzotetrazolyl benzoisoxazolyl, benzoisothiazolyl, benzoimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthryidinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclindinyl, tetrahydrofuranyl, tetrahydroisoquinolinyl, tetrajhydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4p-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

"Stable compound" and "stable structure" are meant to indicate a compound that is sufficiently robust to survive isolation to a useful degree of purity from a reaction mixture, and formulation into an efficacious therapeutic agent.

"Substituted" is intended to indicate that one or more hydrogens on the atom indicated in the expression using "substituted" is replaced with a selection from the indicated group (s), provided that the indicated atom's normal valency is not exceeded, and that the substitution results in a stable compound. When a substituent is keto (i.e., =O) group, then 2 hydrogens on the atom are replaced.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Therapeutically effective amount" is intended to include an amount of a compound of the present invention that is effective when administered alone or in combination to inhibit factor Xa. "Therapeutically effective amount" is also intended to include an amount of the combination of compounds claimed that is effective to inhibit factor Xa. The combination of compounds is preferably a synergistic combination. Synergy, as described, for example, by Chou and Talaly, Adv. Enzyme Regul. 1984, 22: 27-55, occurs when the effect (in this case, inhibition of factor Xa) of the compounds when administered in combination is greater than the additive effect of the compounds when administered alone as a single agent. In general, a synergistic effect is most clearly demonstrated at sub-optimal concentrations of the compounds. Synergy can be in terms of lower cytotoxicity, increased antithrombotic effect, or some other beneficial effect of the combination compared with the individual components.

Synthesis

The compounds of the present invention can be prepared in a number of ways known to one skilled in the art of organic synthesis. The compounds of the present invention can be synthesized using the methods described below, together with synthetic methods known in the art of synthetic organic chemistry, or by variations thereon as appreciated by those skilled in the art. Preferred methods include, but are not limited to, those described below.

The structures of all compounds disclosed herein were identified by nuclear magnetic resonance (NMR) or/and liquid chromatograph-mass spectrometer (LCMS). NMR chemical shifts were recorded as ppm ($10^{-6}$). NMR were performed on Bruker AVANCE-400 spectrometer. The appropriate solvent used was deuterated-chloroform ($CDCl_3$), deuterated-methanol ($CD_3OD$-$d_4$). The internal standard was etramethylsilane (TMS).

LCMS was determined on Agilent 1200 (Xtimate C18 2.1*30 mm chromatographic column) and Agilent 6110 (ion source: ESI).

HPLC was determined on Shimadzu LC10AD high pressure liquid chromatography spectrometer (Xtimate C18 2.1*30 mm chromatographic column).

For thin-layer silica gel chromatography (TLC) Yantai Huanghai HSGF254 or Qingdao GF254 silica gel plate was used. The dimension of the plates used in TLC was 0.15 mm to 0.2 mm, and the dimension of the plates used in product purification was 0.4 mm to 0.5 mm.

Column chromatography generally used was Qingdao Huanghai Factory 200 to 300 mesh silica gel as a stationary phase.

The staring materials of the present invention were prepared by the conventional synthesis methods in the prior art, or purchased from ABCR GmbH & Co. KG, Acros Organics, Aldrich Chemical Company, TCI, Alfa, Accela Chem-Bio Inc, Beijing coupling and other companies.

Unless otherwise stated, reactions disclosed herein were carried out in a argon or nitrogen atmosphere. The term "argon atmosphere" or "nitrogen stmosphere" refers to an atmosphere in a reaction flask equipped with a balloon filled with about 1 L argon or nitrogen.

"Hydrogen atmosphere" refers to an atmosphere in a reaction flask equipped with a balloon filled with about 1 L hydrogen or nitrogen.

Pressured hydrogenation reactions were performed with a Parr 3916EKX hydrogenation spectrometer and a QL-500 hydrogen generator or HC2-SS hydrogenation apparatus. In hydrogenation reactions, the reaction system was generally vacuumed and filled with hydrogen, with the above operation repeated three times.

Microwave reactions were performed with a GEM Discover-S 908860 or Biotage Initiator 60 microwave reactor.

Unless otherwise stated, the solution used in example refers to an aqueous solution.

Unless otherwise stated, the reaction temperature was room temperature, and the room temperature was 20° C. to 30° C.

The reaction process in the examples was monitored by thin layer cheromatography (TLC), the solvent system for development of a TLC plate comprises: A: dichloromethane and methanol, B: n-hexane and ethyl acetate, C: petroleum ether and ethyl acetate, D: acetone. The volume ratio of the solvents in the solvent system was adjusted according to the polarity of the compounds.

The elution system for purification of the compounds bu column chromatography and thin layer chromatography included: A: dichloromethane and methanol system, B: petroleum ether and ethyl acetate system, C: dichloromethane and acetone system. The volume of the colvent was adjusted according to the polarity of the compounds and sometimes a little alkaline reagent, such as triethylamine, or acidic reagent, such as acetic acid, was also added.

The invention is further illustrated by the Examples that follow for clarity. The examples are illustrative, not intended to define or limit the scope of the invention.

All solvents used are commercially available and are used without further purification.

The following abbreviations are used: aq is aqueous; HATU is O-(7-azabenzotriazol-1-yl)-N,N,N',N'-tetramethjyluronium hexafluorophosphate; EDC is N-(3-dimethylaminopropyl)-N'-ethylcarbodiimide hydrochloride, m-CPBA is 3-chloroperoxybenzoic acid; equivalent is eq.; CDI is carbonyl diimidaole; DCM is dichloromethane; PE is petroleum ether; DIAD is diisoprapyi azodicarboxylate; DMF is N,N-dlmethylformamide; DMSO is dimethylsulfoxide; EtOAc is ethyl acetate; EtOH is ethanol; MeOH is methanol; CBz is benzyloxycarbonyl, a amine protecting group; BOC is tert-butylcarbonyl, amine protecting group; HOAc is acetic acid; NaCNBH$_3$ is sodium cyanoborohydride; r.t. is room temperature; O/N is overnight; THF is tetrahydrofuran; Boc$_2$O is di-tert-butyl dicarbonate; TFA is trifluoroacetic acid; DIPEA is diisopropylethylamine is; SOCl$_2$ is sulfurous dichloride; CS$_2$ is carbon disulfide; TsOH is 4-methylbenzenesulfonic acid; NFSI is N-fluoro-N-(phenylsulfonyl)benzenesulfonamide; NCS is N-chlorosuccinimide; n-Bu$_4$NF is tetrabutylammmmonium fluoride; i-PrQH is 2-propanol and mp is melting point.

Compounds are named either manually or by using ChemDraw®, or using vendors catalogue name if commercially available.

Compared with the prior art, the compounds of the present invention have better effect, lower toxic than the compounds in the prior art, and make great progress in activity, T1/2, solubility and DMPK and etc., which are more suitable to be pharmaceuticals.

EMBODIMENTS

The following illustrative examples have been prepared, isolated and characterized using the methods disclosed herein. The following examples demonstrate a partial scope of the invention and are not meant to be limiting of the scope of the invention. While the invention has been described in detail and with reference to specific embodiments thereof, it will be apparent to one skilled in the art that various changes and modifications can be made therein without departing from the spirit and scope thereof.

Example 1

2-(3-(4-(4-amino-5-oxo-7,8-dihydropyrimido[5,4-f][1,4]oxazepin-6(5H)-yl)-2-chlorophenyl)-2-oxoimidazolidin-1-yl)acetic acid

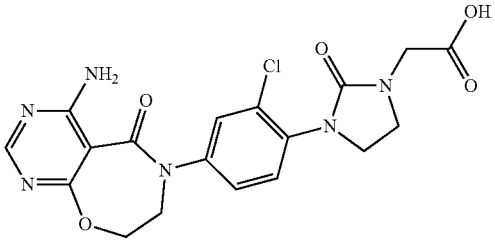

27
28
-continued
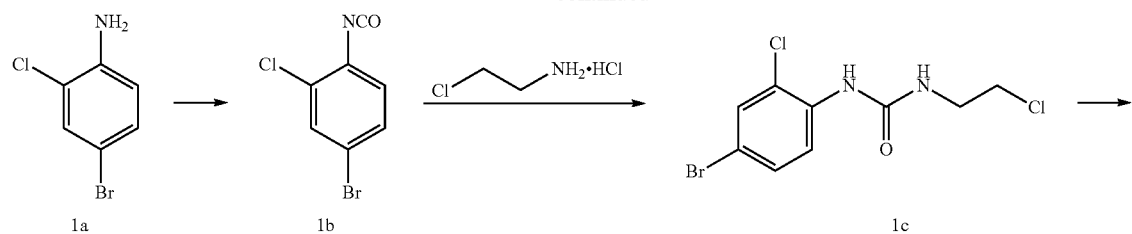
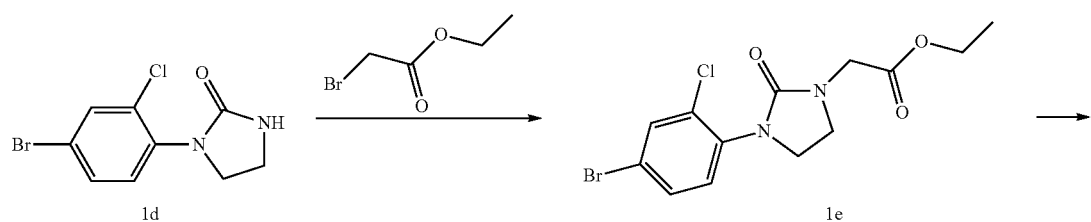
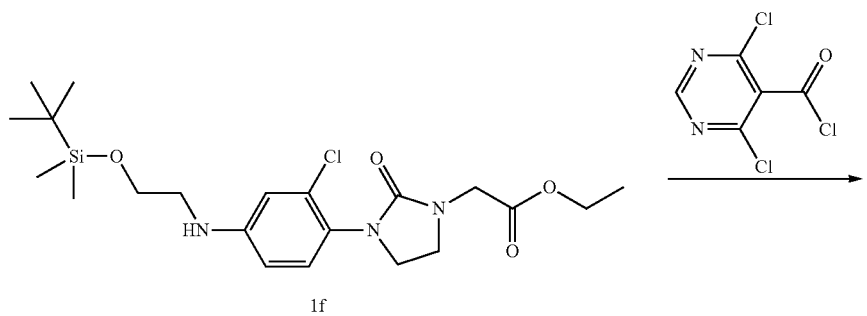
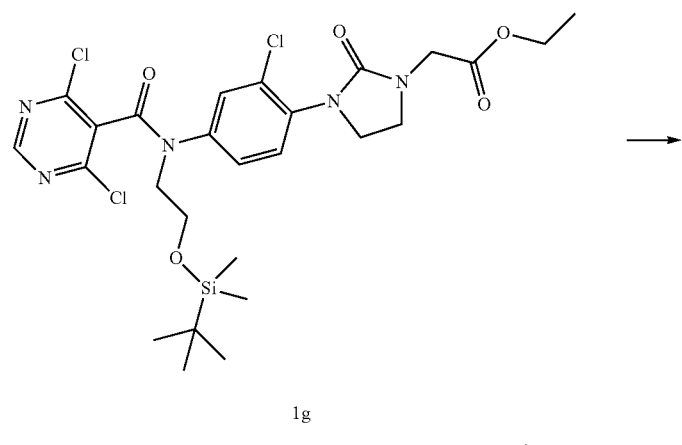
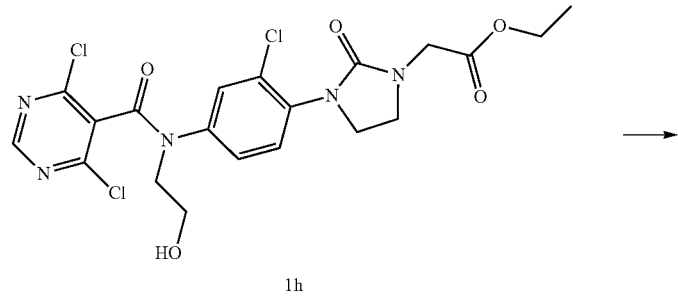

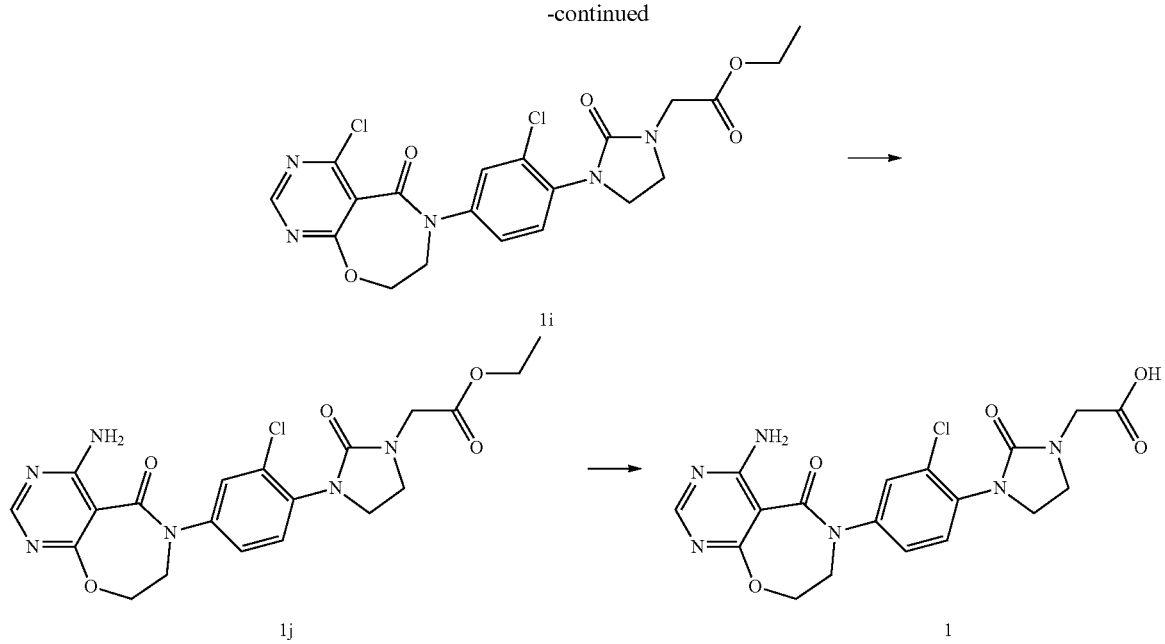

Step 1

4-bromo-2-chloro-1-isocyanatobenzene

To a solution of 4-bromo-2-chloroaniline 1a (1.0 g, 4.88 mmol) in THF (20 mL, dry) was added triphosgen (478 mg, 1.63 mmol). The mixture was stirred for 3 h. The reaction mixture was evaporated to afford 4-bromo-2-chloro-1-isocyanatobenze 1b (1.12 g, white solid) which was used in the next step directly.

Step 2

1-(4-bromo-2-chlorophenyl)-3-(2-chloroethyl)urea

To a solution of 4-bromo-2-chloro-1-isocyanatobenzene 1b (1.12 g, 4.85 mmol) and TEA (2.1 mL, 14.55 mmol) in THF (100 mL, dry) was added 2-chloroethanamine hydrochloride (844 mg, 7.27 mmol). The mixture was stirred for 2 h. The reaction mixture was added water (200 mL), extracted with DCM (200 mL*3), the combined organic layers were washed with water (100 mL*2) and brine (100 mL*2), dried over $Na_2SO_4$, filtered and evaporated to afford 1-(4-bromo-2-chlorophenyl)-3-(2-chloroethyl)urea 1c (1.12 g, white solid) which was used in the next step directly.

$^1$H NMR (400 MHz, CDCl$_3$) δ8.03 (d, 1H), 7.36 (dd, 1H), 6.63 (d, 1H), 3.69-3.66 (m, 2H), 3.64-3.60 (m, 2H)

Step 3

1-(4-bromo-2-chlorophenyl)imidazolidin-2-one

To a solution of 1-(4-bromo-2-chlorophenyl)-3-(2-chloroethyl)urea 1c (1.12 g, 3.6 mmol) in DMF (20 mL, dry) was added NaH (433 mg, 10.8 mmol). The mixture was stirred for 12 h. The reaction mixture was quenched with water (50 mL), extracted with EA (50 mL*3). The combined organic layers were washed with water (50 mL*2) and brine (50 mL*2), dried over $Na_2SO_4$, filtered and concentrated to afford crude 1-(4-bromo-2-chlorophenyl)imidazolidin-2-one 1d (986 mg, white solid) which was used in the next step directly.

Step 4 ethyl 2-(3-(4-bromo-2-chlorophenyl)-2-oxoimidazolidin-1-yl)acetate

To a solution of 1-(4-bromo-2-chlorophenyl)imidazolidin-2-one 1d (986 mg, 3.6 mmol) in DMF (20 mL, dry) was added NaH (215 mg, 5.39 mmol) at 0° C. The mixture was stirred for 0.5 h; ethyl 2-bromoacetate (596 mg, 5.37 mmol) was added. The mixture was stirred for 12 h. The reaction mixture was quenched by water (50 mL), extracted with EA (50 mL*3). The combined organic layers were washed with water (50 mL*2) and brine (50 mL*2), dried over $Na_2SO_4$, filtered and concentrated to afford the crude product. The residue was purified by silica column to afford ethyl 2-(3-(4-bromo-2-chlorophenyl)-2-oxoimidazolidin-1-yl)acetate 1e (750 mg, white solid).

$^1$H NMR (400 MHz, CDCl$_3$) δ 7.58 (d, 1H), 7.40 (dd, 1H), 7.25 (d, 1H), 4.20 (q, 2H), 4.04 (s, 2H), 3.84-3.80 (m, 2H), 3.67-3.62 (m, 2H), 1.28 (t, 3H)

Step 5

Ethyl 2-(3-(4-((2-((tert-butyldimethylsilyl)oxy)ethyl)amino)-2-chlorophenyl)-2-oxoimidazolidin-1-yl)acetate To a solution of 2-(3-(4-bromo-2-chlorophenyl)-2-oxoimidazolidin-1-yl)acetate 1e (750 mg, 2.1 mmol) in toluene (15 mL, dry) was added 2-((tert-butyldimethylsilyl)oxy)ethanamine (549 mg, 3.1 mmol), Cs$_2$CO$_3$ (2.03 g, 6.2 mmol), Pd$_2$(dba)$_3$ (50 mg, 0.05 mmol), x-phos (40 mg, 0.07 mmol). The mixture was stirred at 100° C. for 12 h. The reaction mixture was cooled to RT, added water (50 mL), extracted with EA (50 mL*3), the combined organic layers were washed with water (50 ml*2) and brine (50 mL*2), dried over Na₂SO₄, filtered and concentrated to afford the crude product. The residue was purified by silica column to afford ethyl 2-(3-(4-((2-((tert-butyldimethylsilyl)oxy)ethyl) amino)-2-chlorophenyl)-2-oxoimidazolidin-1-yl)acetate 1f (550 mg, yellow oil).

¹H NMR (400 MHz, CDCl₃) δ 7.05 (d, 1H), 6.58 (d, 1H), 6.43 (dd, 1H), 4.14 (q, 2H), 3.98 (s, 2H), 3.74-3.66 (m, 4H), 3.56-3.52 (m, 2H), 3.11 (q, 2H), 1.22 (t, 3H), 0.83 (s, 9H), 0.00 (s, 6H)

Step 6

Ethyl-2-(3-(4-(N-(2-((tert-butyldimethylsilyl)oxy) ethyl)-4,6-dichloropyrimidine-5-carboxamido)-2-chlorophenyl)-2-oxoimidazolidin-1-yl)acetate To a solution of ethyl 2-(3-(4-((2-((tert-butyldimethylsilyl)oxy)ethyl)amino)-2-chlorophenyl)-2-oxoimidazolidin-1-yl)acetate 1f (550 mg, 1.2 mmol) in DCM (5 mL) was added TEA (519 uL, 3.6 mmol) and 4,6-dichloropyrimidine-5-carbonyl chloride (378 mg, 1.8 mmol). Reaction mixture was stirred for 12 h. The mixture was added water (10 mL), extracted with DCM (10 mL*3), the combined organic layers were washed with water (10 mL*2) and brine (10 mL*2), dried over Na₂SO₄ filtered and concentrated to afford the crude product ethyl 2-(3-(4-(N-(2-((tert-butyldimethylsilyl)oxy)ethyl)-4,6-dichloropyrimidine-5-carboxamido)-2-chlorophenyl)-2-oxoimidazolidin-1-yl)acetate 1g (756 mg, yellow solid) which was used in the next step directly.

Step 7 ethyl-2-(3-(2-chloro-4-(4,6-dichloro-N-(2-hydroxyethyl)pyrimidine-5-carboxamido)phenyl)-2-oxoimidazolidin-1-yl)acetate To a solution of ethyl 2-(3-(4-(N-(2-((tert-butyldimethylsilyl)oxy)ethyl)-4,6-dichloropyrimidine-5-carboxamido)-2-chlorophenyl)-2-oxoimidazolidin-1-yl)acetate 1g (756 mg, 1.2 mmol) in EtOH (10 mL) was added HCl (con, 0.3 ml). The reaction mixture was stirred for 1 h. The mixture was added water (10 mL), extracted with EA (10 mL*3), the combined organic layers were washed with water (10 mL*2) and brine (10 mL*2), dried over Na₂SO₄, filtered and concentrated to afford the crude product ethyl 2-(3-(2-chloro-4-(4,6-dichloro-N-(2-hydroxyethyl)pyrimidine-5-carboxamido)phenyl)-2-oxoimidazolidin-1-yl)acetate 1H (618 mg, yellow solid) which was used in the next step directly.

Step 8 ethyl-2-(3-(2-chloro-4-(4-chloro-5-oxo-7,8-dihydropyrimido[5,4-f][1,4]oxazepin-6(5H)-yl)phenyl)-2-oximidazolidin-1-yl)acetate A mixture of ethyl-2-(3-(2-chloro-4-(4,6-dichloro-N-(2-hydroxyethyl)pyrimidine-5-carboxamido)phenyl)-2-oxoimidazolidin-1-yl)acetate 1h (618 mg, 1.2 mmol) and TEA (519 uL, 3.6 mmol) in MeCN (5 mL) was stirred for at 80° C. 18 h. The reaction mixture was cooled to RT, added water (20 mL), extracted with EA (30 mL*3), the combined organic layers were washed with water (30 mL*2) and brine (30 mL*2), dried over Na₂SO₄ filtered and concentrated to afford the crude product ethyl 2-(3-(2-chloro-4-(4-chloro-5-oxo-7,8-dihydropyrimido[5,4-f][1,4]oxazepin-6(5H)-yl) phenyl)-2-oximidazolidin-1-yl)acetate 1i (260 mg, yellow solid) which was used in the next step directly.

¹H NMR (400 MHz, DMSO-d6) δ 8.83 (s, 1H), 7.70 (d, 1H), 7.52-7.46 (m, 2H), 4.75 (t, 2H), 4.21 (t, 2H), 4.15 (q, 2H), 4.03 (s, 2H), 3.80-3.76 (m, 3H), 3.62-3.58 (m, 2H), 1.23 (t, 3H)

Step 9

Ethyl-2-(3-(4-(4-amino-5-oxo-7,8-dihydropyrimido [5,4-f][1,4]oxazepin-6(5H)-yl)phenyl)-2-chlorophenyl)-2-oximidazolidin-1-yl)acetate A mixture of ethyl-2-(3-(2-chloro-4-(4-chloro-5-oxo-7,8-dihydropyrimido[5,4-f][1,4]oxazepin-6(5H)-yl)phenyl)-2-oximidazolidin-1-yl)acetate 1i (260 mg, 543 umol) in 0.5 M ammonia in dioxane (10 mL) was stirred for 12 h. The reaction mixture was concentrated in vacuo to remove dioxane. The residue was added DCM (30 mL), washed with water (30 mL*2) and brine (30 mL*2), dried over Na₂SO₄ filtered and concentrated to afford the crude product ethyl 2-(3-(4-(4-amino-5-oxo-7,8-dihydropyrimido[5,4-f][1,4] oxazepin-6(5H)-yl)-2-chlorophenyl)-2-oximidazolidin-1-yl)acetate 1j (260 mg, yellow solid) which was used in the next step directly.

¹H NMR (400 MHz, DMSO-d6) δ 8.18 (s, 1H), 7.67 (d, 1H), 7.66 (br, s, 2H), 7.47 (d, 1H), 7.41 (dd, 1H), 4.63 (t, 2H), 4.15 (q, 2H), 4.03 (s, 3H), 3.79-3.75 (m, 2H), 3.65 (s, 2H), 3.62-3.58 (m, 2H), 1.23 (t, 3H)

Step 10

2-(3-(4-(4-amino-5-oxo-7,8-dihydropyrimido[5,4-f] [1,4]oxazepin-6(5H)-yl)-2-chlorophenyl)-2-oximidazolidin-1-yl)acetate acid A mixture of ethyl 2-(3-(4-(4-amino-5-oxo-7,8-dihydropyrimido[5,4-f][1,4]oxazepin-6(5H)-yl)-2-chlorophenyl)-2-oximidazolidin-1-yl)acetate acid 1j (250 mg, 543 umol) and LiOH.H₂O (68 mg, 1.6 mmol) in dioxane/H₂O (3/1, 8 mL) was stirred for 12 h. The mixture was adjusted to pH=5~6 with 1N aq HCl slowly. The solid that formed was collected by filtration, dried in vacuo to afford 2-(3-(4-(4-amino-5-oxo-7,8-dihydropyrimido[5,4-f][1,4]oxazepin-6(5H)-yl)-2-chlorophenyl)-2-oximidazolidin-1-yl)acetate acid 1 (74 mg, white solid).

MS m/z (ESI): 433.1 [M+1]

¹H NMR (400 MHz, DMSO-d6) δ 12.81 (s, 1H), 8.17 (s, 1H), 7.67-7.66 (m, 3H), 7.47-7.36 (m, 2H), 4.62 (t, 2H), 4.02 (t, 2H), 3.93 (s, 2H), 3.78-3.74 (m, 2H), 3.61-3.58 (m, 2H)

Example 2

2-(3-(4-(4-amino-5-oxo-7,8-dihydropyrimido[5,4-f] [1,4]oxazepin-6(5H)-yl)-2-fluorophenyl)-2-oximidazolidin-1-yl)acetate acid

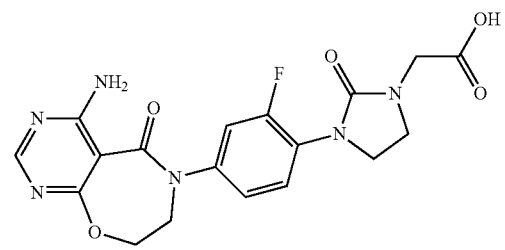

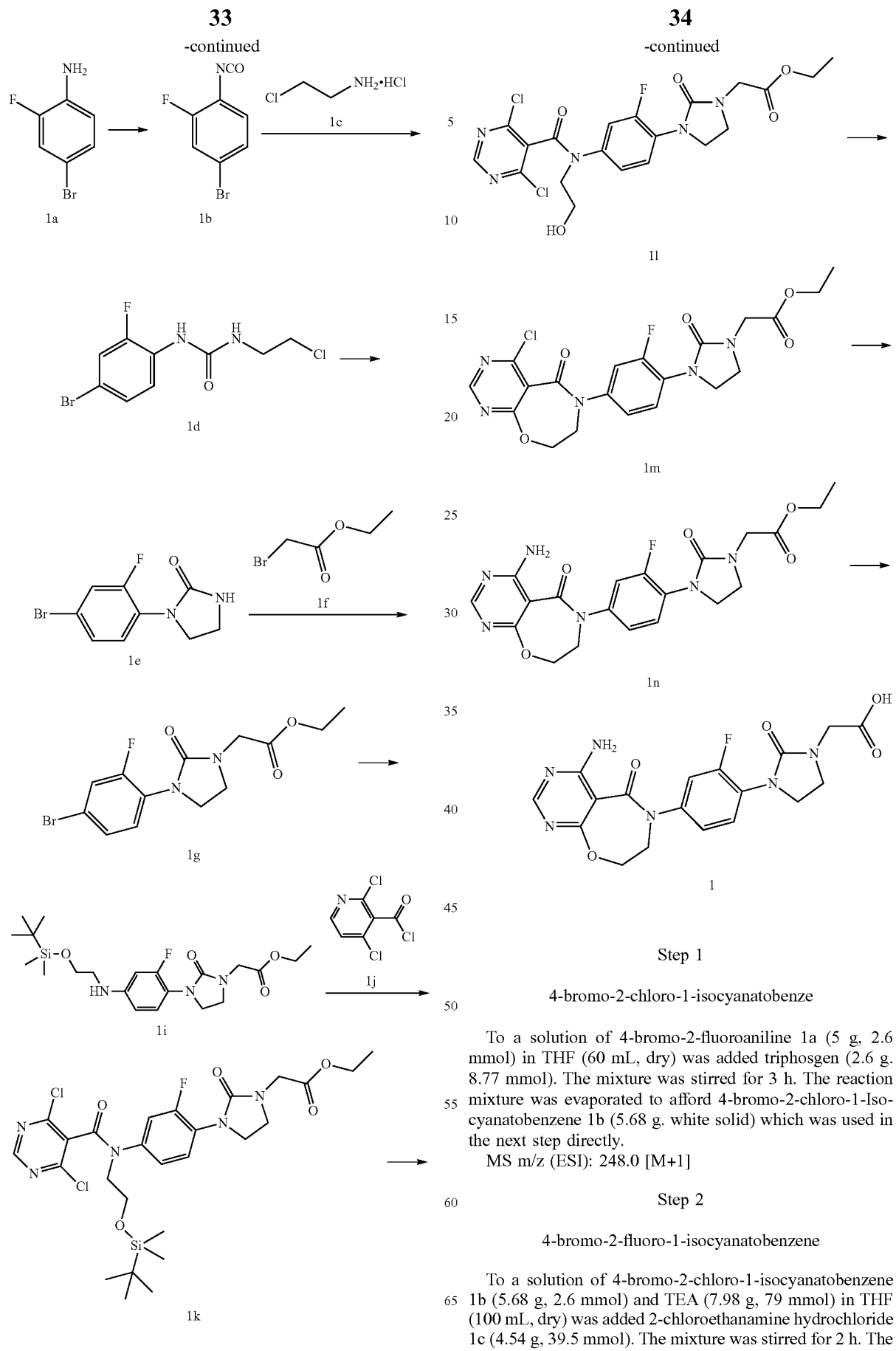

Step 1

4-bromo-2-chloro-1-isocyanatobenze

To a solution of 4-bromo-2-fluoroaniline 1a (5 g, 2.6 mmol) in THF (60 mL, dry) was added triphosgen (2.6 g. 8.77 mmol). The mixture was stirred for 3 h. The reaction mixture was evaporated to afford 4-bromo-2-chloro-1-Isocyanatobenzene 1b (5.68 g. white solid) which was used in the next step directly.

MS m/z (ESI): 248.0 [M+1]

Step 2

4-bromo-2-fluoro-1-isocyanatobenzene

To a solution of 4-bromo-2-chloro-1-isocyanatobenzene 1b (5.68 g, 2.6 mmol) and TEA (7.98 g, 79 mmol) in THF (100 mL, dry) was added 2-chloroethanamine hydrochloride 1c (4.54 g, 39.5 mmol). The mixture was stirred for 2 h. The reaction mixture was added water (200 mL, extracted with DCM (200 mL*3), the combined organic layers were washed with water (100 mL*2) and brine (100 mL*2), dried $Na_2SO_4$, filtered and evaporated to afford 4-bromo-2-fluoro-1-isocyanatobenzene 1d (7.67 g, white solid) which was used in the next step directly.

$^1$H NMR (400 MHz, $CDCl_3$) δ 8.15-8.05 (m, 1H), 7.2-7.1 (m, 2H), 3.75-3.70 (m, 2H), 3.65-3.60 (m, 2H)

Step 3

1-(4-bromo-2-fluorophenyl)imidazolidin-2-one

To a solution of 4-bromo-2-fluoro-1-isocyanatobenzene 1d (2 g, 6.78 mmol) in DMF (60 mL, dry) was added NaH (411 mg, 10.2 mmol). The mixture was stirred for 12 h. The reaction mixture was quenched with water (100 mL), extracted with EA (200 mL*3). The combined organic layers were washed with water (300 mL*3) and brine (300 mL*2), dried over $Na_2SO_4$, filtered and concentrated to afford crude 1-(4-bromo-2-fluorophenyl)imidazolidin-2-one 1e (2.2 g, white solid) which was used in the next step directly.

MS m/z (ESI): 425.0 [M+1]

$^1$H NMR (400 MHz, $CDCl_3$) δ 7.45 (t, 1H), 7.30-7.20 (m, 2H), 4.00-3.90 (m, 2H), 3.60-3.50 (m, 2H)

Step 4

Ethyl 2-(3-(4-bromo-2-chlorophenyl)-2-oxoimidazolidin-1-yl)acetate

To solution of 1-(4-bromo-2-fluorophenyl)imidazolidin-2-one 1e (1.96 g, 7.6 mmol) in DMF (40 mL, dry) was added NaH (456 mg, 11.4 mmol). The mixture was stirred for 0.5 h. ethyl 2-bromoacetate 1f (1.9 g, 11.4 mmol) was added. The mixture was stirred for 12 h. The mixture was quenched water (50 mL), extracted with EA (100 mL*3). The combined organic layers were washed with water (200 mL*3) and brine (200 mL*2), dried over $Na_2SO_4$, filtered and concentrated to afford the crude product. The residue was purified by silica column to afford ethyl 2-(3-(4-bromo-2-chlorophenyl)-2-oxoimidazolidin-1-yl)acetate 1g (1.61 g, white solid).

MS m/z (ESI): 345.1 [M+1]

$^1$H NMR (400 MHz, $CDCl_3$) δ 7.50-7.40 (m, 1H), 7.30-7.20 (m, 2H), 4.22 (q, 2H), 4.06 (s, 2H), 3.9 (t, 2H), 3.65-3.55 (m, 2H), 1.30-1.25 (m, 3H)

Step 5 ethyl 2-(3-(4-((2-((tert-butyldimethylsilyl)oxy)ethyl)amino-2-fluorophenyl)-2-oxoimidazolidin-1-yl)acetate To a solution of ethyl 2-(3-(4-bromo-2-chlorophenyl)-2-oxoimidazolidin-1-yl)acetate 1g (1.67 g, 7.84 mmol) in toluene (30 mL, dry) was added 2-((tert-butyldimethylsilyl)oxy)ethanamide 1h (1.72 g, 9.68 mmol), $Cs_2CO_3$ (3.15 g, 9.68 mmol), $Pd_2(dba)_3$ (225.4 mg, 0.4 mmol), x-phos (450 mg, 0.8 mmol). The mixture was stirred at 100° C. for 12 h. The reaction mixture was cooled to RT, added water (50 mL), extracted with EA (50 mL*3), the combined organic layers were washed with water (50 mL*2) and brine (50 mL*2), dried over $Na_2SO_4$, filtered and concentrated to afford the crude product. The residue was purified by silica column to afford ethyl 2-(3-(4-((2-tert-butyldimethylsilyl)oxy)ethyl amino)-2-fluorophenyl)-2-oxoimidazolidin-1-yl) acetate 1i (1.1 g, yellow oil), yield: 51.6%

$^1$H NMR (400 MHz, $CDCl_3$) δ 7.19-7.15 (m, 1H), 6.39-6.33 (m, 2H), 4.22-4.18 (m, 2H), 4.05 (s, 2H), 3.8-3.75 (m, 4H), 3.63-3.57 (m, 2H), 3.17 (q, 2H), 1.27 (t, 3H), 0.90 (s, 9H)

Step 6

Ethyl 2-(3-(4-(N-(2-((tert-butyldimethylsilyl)oxy)ethyl)-4,6-dichloropyrimidine-5-carboxamido)-2-fluorophenyl)-2-oxoimidazolidin-1-yl)acetate To a solution of ethyl 2-(3-(4-((2-((tert-butyldimethylsilyl)oxy)ethyl)amino)-2-fluorophenyl)-2-oxoimidazolidin-1-yl)acetate 1i (1.1 g, 2.5 mmol) in DCM (20 mL) was added TEA (1 mL, 7.5 mmol) and 4,6-dichloropyrimidine-5-carbonyl chloride 1j (1.05 g, 5.0 mmol). Reaction mixture was stirred for 12 h. The mixture was added water (50 mL), extracted with DCM (50 mL*2), the combined organic layers were washed with water (50 mL*2) and brine (50 mL*2), dried over $Na_2SO_4$, filtered and concentrated to afford the crude product ethyl 2-(3-(4-(N-(2-((tert-butyldimethylsilyl)oxy)ethyl-4,6-dichloropyrimidine-5-carboxamido)-2-fluorophenyl)-2-oxoimidazolidin-1-yl)acetate 1k (1.9 g, yellow solid) which was used in the next step directly.

$^1$H NMR (400 MHz, $CDCl_3$) δ 8.59 (s, 1H), 7.05-7.03 (m, 2H), 4.51-3.91 (m, 4H), 3.90-3.91 (m, 2H), 2.6 (s, 2H), 1.61 (s, 6H), 1.47-1.41 (m, 3H)

Step 7 ethyl 2-(3-(4-(4,6-dichloro-N-(2-hydroxyethyl)pyrimidine-5-carboxamido)-2-fluorophenyl)-2-oxoimidazolidin-1-yl)acetate To a solution of ethyl 2-(3-(4-N-(2-((tert-butyldimethylsilyl)oxy)ethyl)-4,6-dichloropyrimidine-5-carboxamido)-2-fluorophenyl)-2-oxoimidazolidin-1-yl)acetate 1k (1 g, 1.63 mmol) in EtOH (10 mL) was added HCl (con. 0.3 ml). The reaction mixture was stirred for 1 h. The mixture was added water (10 mL), adjusted to Ph=6~7 with saturated $NaHCO_3$ solution, extracted with DCM (30 mL*3), the combined organic layers were washed with brine (50 mL*2), dried over $Na_2SO_4$, filtered and concentrated to afford the crude product ethyl 2-(3-(4-(4,6-dichloro-N-(2-hydroxyethyl)pyrimidine-5-carboxamido)-2-fluorophenyl)-2-oxoimidazolidin-1-yl)acetate 1l (600 mg, yellow oil) which was used in the next step directly.

Step 8

Ethyl 2-(3-(4-(4-chloro-5-oxo-7,8-dihydropyrimido[5,4-f][1,4]oxazepin-6(5H)-yl)-2-fluorophenyl)-2-oxoimidazolidin-1-yl)acetate A mixture of ethyl 2-(3-(4-(4,6-dichloro-N-(2-hydroxyethyl)pyrimidine-5-carboxamido)-2-fluorophenyl)-2-oxoimidazolidin-1-yl)acetate 1l (600 mg, 1.09 mmol) in MeCN (20 mL) was added TEA (0.5 mL, 3.3 mmol) stirred for at 80° C. 18 h. The reaction mixture was added water (30 mL), extracted with DCM (50 mL*3), the combined organic layers were washed with water (50 mL*2) and brine (50 mL*2), dried over $Na_2SO_4$, filtered and concentrated to afford the crude product ethyl 2-(3-(4-(4-chloro-5-oxo-7,8-dihydropyrimido[5,4-f][1,4]oxazepin-6(5H)-yl)-2-fluorophenyl)-2-oxoimidazolidin-1-yl)acetate 1m (490 mg, yellow solid) which was used in the next step directly.

$^1$H NMR (400 MHz, CDCl$_3$) δ 8.77 (s, 1H), 7.75-7.76 (m, 2H), 7.30-7.26 (m, 1H), 7.18-7.10 (m, 1H), 4.75 (t, 2H), 4.24 (q, 2H), 4.13 (t, 2H), 4.10-4.02 (m, 2H), 3.95 (t, 2H), 3.66 (q, 2H), 1.30-1.20 (m, 3H)

Step 9

Ethyl 2-(3-(4-(4-amino-5-oxo-7,8-dihydropyrimido[5,4-f][1,4]oxazepin-6(5H)-yl)-2-fluorophenyl)-2-oxoimidazolidin-1-yl)acetate A mixture of ethyl 2-(3-(4-(4-chloro-5-oxo-7,8-dihydropyrimido[5,4-f][1,4]oxazepin-6(5H)-yl)-2-fluorophenyl)-2-oxoimidazolidin-1-yl)acetate 1m (490 mg, 1.05 mmol) in 0.5 M ammonia in dioxane (10 mL) was stirred for 12 h. The reaction mixture was concentrated in vacuo to remove dioxane. The residue was added DCM (30 mL), washed with water (30 mL*2) and brine (30 mL*2), dried over Na$_2$SO$_4$, filtered and concentrated to afford the crude product Ethyl 2-(3-(4-(4-amino-5-oxo-7,8-dihydropyrimido[5,4-f][1,4]oxazepin-6(5H)-yl)-2-fluorophenyl)-2-oxoimidazolidin-1-yl)acetate 1n (460 mg, yellow oil) which was used in the next step directly.

$^1$H NMR (400 MHz, CDCl3) δ 8.30 (s, 1H), 7.67 (t, 1H), 7.10-7.02 (m, 2H), 4.69 (s, 2H), 4.23 (q, 2H), 4.07 (s, 2H), 4.0 (t, 2H), 3.98-3.92 (m, 2H), 3.70-3.60 (m, 2H), 1.30-1.20 (m, 3H)

Step 10

2-(3-(4-(4-amino-5-oxo-7,8-dihydropyrimido[5,4-f][1,4]oxazepin-6(5H)-yl)-2-fluorophenyl)-2-oxoimidazolidin-1-yl)acetate acid A mixture of ethyl 2-(3-(4-(4-amino-5-oxo-7,8-dihydropyrimido[5,4-f][1,4]oxazepin-6(5H)-yl)-2-fluorophenyl)-2-oxoimidazolidin-1-yl)acetate 1n (230 mg, 0.5 mmol) in dioxane/H$_2$O (v/v=3/1, 6 mL) was added LiOH.H$_2$O (61 mg, 2.5 mmol) was stirred for 12 h. The mixture was adjusted to pH=5~6 with 1N aq HCl slowly. The solid that formed was collected by filtration, dried in vacuo to afford 2-(3-(4-(4-amino-5-oxo-7,8-dihydropyrimido[5,4-f][1,4]oxazepin-6(5H)-yl)-2-fluorophenyl)-2-oxoimidazolidin-1-yl)acetate acid 1 (20 mg, yellow solid), yield: 9.7%.

MS m/z (ESI): 417.1 [M+1]

$^1$H NMR (400 MHz, CD$_3$OD) δ 12.80 (s, 1H), 7.60 (m, 2H), 7.46 (t, 1H), 7.40 (dd, 1H), 7.23-7.21 (m, 1H), 4.58 (t, 2H), 3.98-3.95 (m, 2H), 3.89 (s, 2H), 3.78 (t, 2H), 3.53 (t, 2H)

Example 3

2-(3-(4-(4-amino-5-oxo-7,8-dihydropyrimido[5,4-f][1,4]oxazepin-6(5H)-yl)-2-methylphenyl)-2-oxoimidazolidin-1-yl)acetate acid

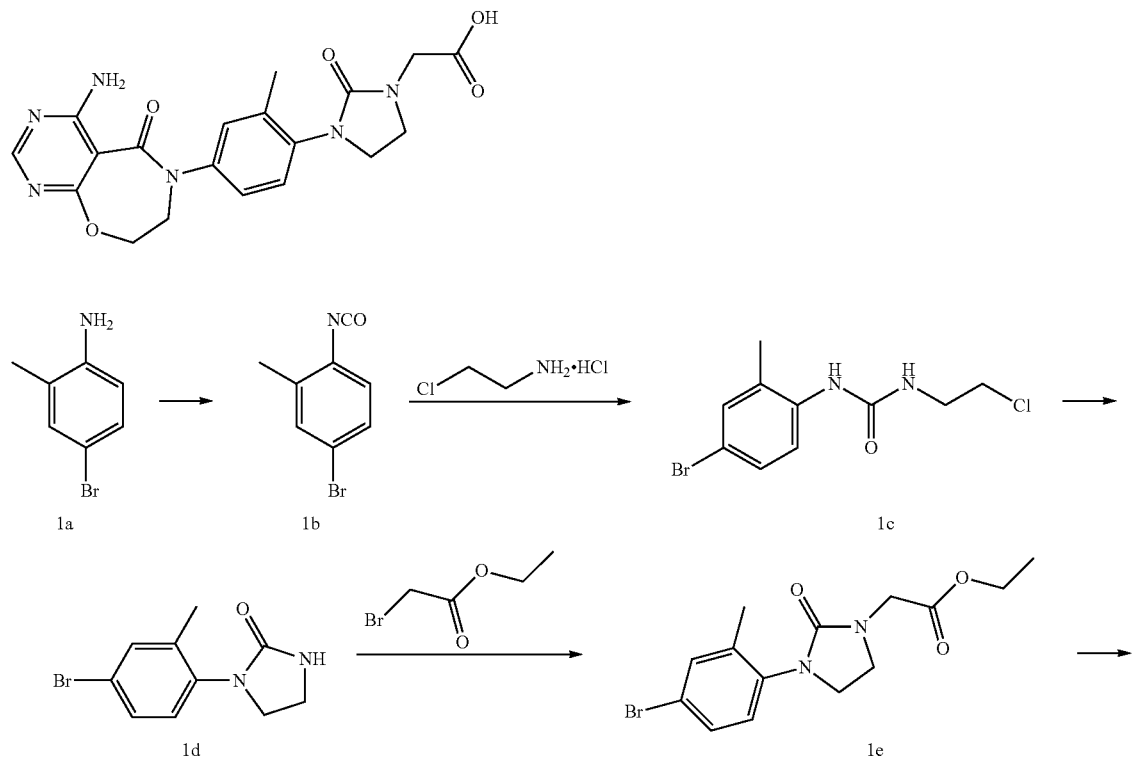

-continued
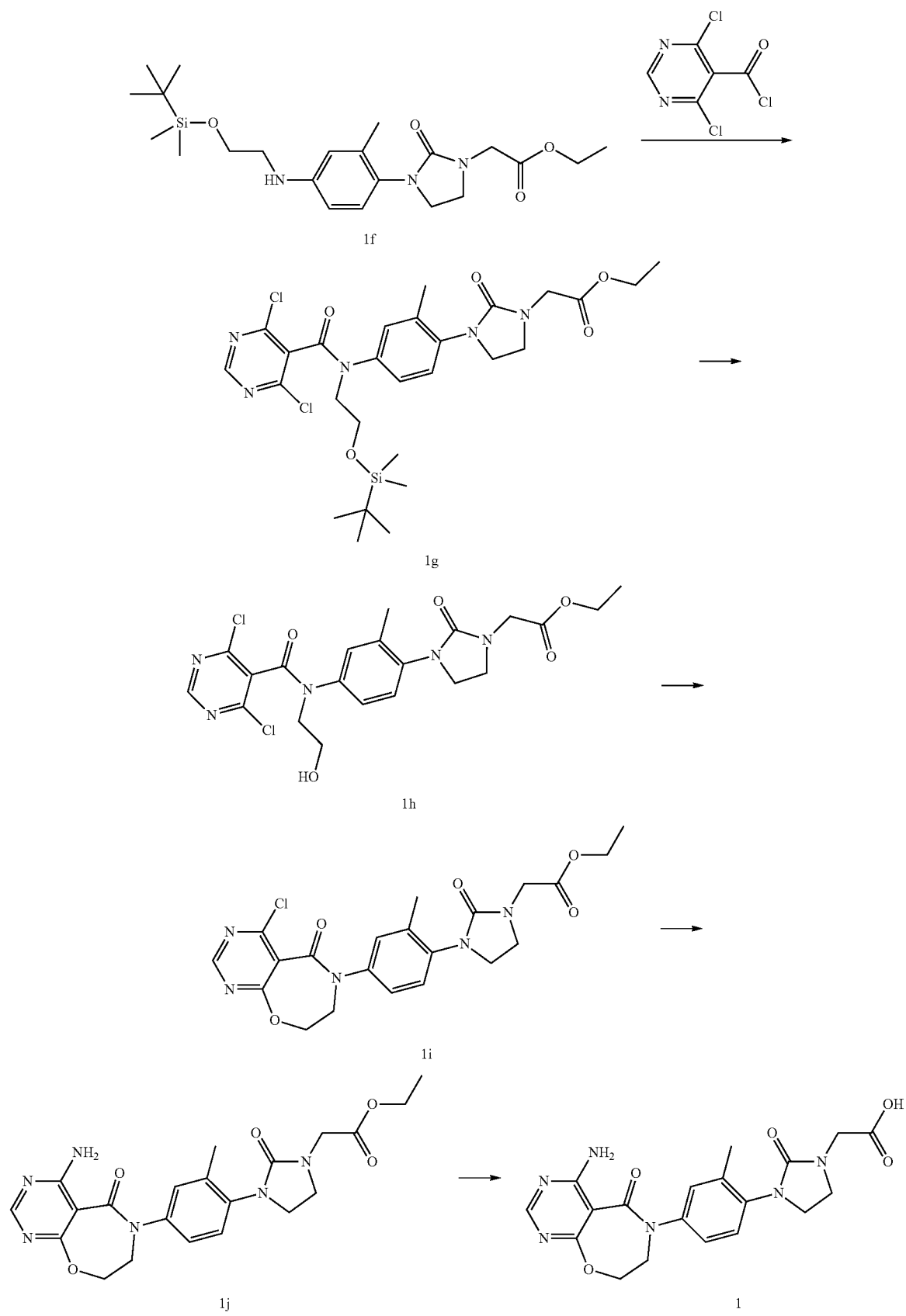

Step 1

4-bromo-1-isocyanato-2-methylbenzene

To a solution of 4-bromo-2-methylaniline 1a (10.0 g, 53.76 mmol) in THF (200 mL, dry) was added triphosgen (5.32 g, 17.92 mmol). The mixture was stirred for 3 h. The reaction mixture was evaporated to afford 4-bromo-1-isocyanato-2-methylbenzene 1b (11.4 g, white solid) which was used in the next step directly.

Step 2

1-(4-bromo-2-methylphenyl)-3-(2-chloroethyl)urea

To a solution of 1-(4-bromo-1-isocyanato-2-methylphenyl) 1b (11.4 g, 53.76 mmol) and TEA (22.6 mL, 161.29 mmol) in THF (350 mL) was added 2-chloroethanamine hydrochloride (9.35 g, 80.65 mmol). The mixture was stirred for 2 h. The reaction mixture was added water (200 mL), extracted with EA (200 mL*3), the combined organic layers were washed with water (100 mL*2) and brine (100 mL*2), dried over $Na_2SO_4$, filtered and evaporated to afford 1-(4-bromo-2-methylphenyl)-3-(2-chloroethyl)urea 1c (14.3 g, white solid) which was used in the next step directly.

$^1$H NMR (400 MHz, $CDCl_3$) δ 7.37 (br.s, 1H), 7.33 (d, 1H), 7.25 (d, 1H), 6.08 (br, 1H), 5.07 (br.s, 1H), 3.64-3.61 (m, 2H), 3.57-3.54 (m, 2H), 2.25 (s, 3H)

Step 3

1-(4-bromo-2-methylphenyl)imidazolidin-2-one

To a solution 1-(4-bromo-2-methylphenyl)-3-(2-chloroethyl)urea 1c (9.00 g, 30.87 mmol) in DMF (90 mL, dry) was added NaH (1.86 g, 46.55 mmol) under an ice-bath. The mixture was stirred for 12 h. The reaction mixture was quenched with saturated $NH_4Cl$ solution (100 mL), extracted with EA (100 mL*3). The combined organic layers were washed with water (100 mL*2) and brine (100 mL*2), dried over $Na_2SO_4$, filtered and concentrated to afford crude 1-(4-bromo-2-methylphenyl)imidazolidin-2-on 1d (6.3 g, white solid) which was used in the next step directly.

$^1$H NMR (400 MHz, DMSO-d6) δ 7.44-7.43 (m, 1H), 7.36-7.33 (m, 1H), 7.14 (d, 1H), 6.70 (br.s., 1H), 3.69-3.65 (m, 2H), 3.40-3.36 (m, 2H), 2.17 (m, 3H)

Step 4

Ethyl 2-(3-(4-bromo-2-methylphenyl)-2-oxoimidazolidin-1-yl)acetate

To a solution of 1-(4-bromo-2-methylphenyl)imidazolidin-2-on 1d (2.00 g, 7.84 mmol) in DMF (20 mL, dry) was added NaH (470 mg, 11.76 mmol). The mixture was stirred at RT for 0.5 h, ethyl 2-bromoacetate (1.96 g, 11.76 mmol) was added. The mixture was stirred for 12 h. The reaction mixture was quenched by saturated $NH_4Cl$ solution (50 mL), extracted with EA (50 mL*3). The combined organic layers were washed with water (50 mL*2) and brine (50 mL*2), dried over $Na_2SO_4$, filtered and concentrated to afford the crude product. The residue was purified by silica column to afford ethyl 2-(3-(4-bromo-2-methylphenyl)-2-oxoimidazolidin-1-yl)acetate 1e (0.9 g, white solid), yield: 33.7%.

$^1$H NMR (400 MHz, $CDCl_3$) δ 7.39-7.38 (m, 1H), 7.32-7.29 (m, 1H), 7.05 (d, 1H), 4.20 (q, 1H), 4.03 (s, 2H), 3.64-3.60 (m, 2H), 2.26 (s, 3H) 1.28 (t, 1H)

Step 5

Ethyl 2-(3-(4-((2-((tert-butyldimethylsilyl)oxy)-ethyl)amino-2-methylphenyl)-2-oxoimidazolidin-1-yl)acetate To a solution of ethyl 2-(3-(4-bromo-2-methylphenyl)-2-oxoimidazolidin-1-yl)acetate 1e (900 mg, 2.64 mmol) in toluene (30 mL, dry) was added 2-((tert-butyldimethylsilyl)oxy)ethanamine 699 mg, 3.96 mmol), $Cs_2CO_3$ (2.58 g, 7.92 mmol), $Pd_2(dba)_3$ (242 mg, 0.26 mmol), x-phos (253 mg, 0.53 mmol). The mixture was stirred at 100° C. for 12 h. The reaction mixture was cooled to RT, added water (50 mL), extracted with EA (50 mL*3), the combined organic layers were washed with water (50 mL*2) and brine (50 mL*2), dried over $Na_2SO_4$, filtered and concentrated to afford the crude product. The residue was purified by silica column to afford ethyl 2-(3-(4-((2-((tert-butyldimethylsilyl)oxy)ethyl)amino-2-methylphenyl)-2-oxoimidazolidin-1-yl)acetate 1f (800 mg, yellow oil), yield: 70.2%.

$^1$H NMR (400 MHz, $CDCl_3$) δ 6.92 (d, 1H), 6.42-6.37 (m, 2H), 4.14 (q, 1H), 3.96 (s, 2H), 3.74-3.71 (m, 2H), 3.63-3.58 (m, 2H), 3.54-3.50 (m, 2H), 3.13-3.09 (m, 2H), 2.14 (s, 3H), 1.22 (t, 1H), 0.83 (s, 9H), 0.00 (s, 6H)

Step 6

Ethyl 2-(3-(4-(N-(2-((tert-butyldimethylsilyl)oxy)ethyl)-4,6-dichloropyrimidine-5-carboxamido)-2-methylphenyl)-2-oxoimidazolidin-1-yl)acetate To a solution of ethyl 2-(3-(4-((2-((tert-butyldimethylsilyl)oxy)ethyl)amino-2-methylphenyl)-2-oxoimidazolidin-1-yl)acetate 1f (800 mg, 1.84 mmol) in DCM (10 mL) was added TEA (558 mg, 5.52 mmol) and 4,6-dichloropyrimidine-5-carbonyl chloride (446 mg, 2.20 mmol). Reaction mixture was stirred for 12 h. The mixture was added water (10 mL), extracted with DCM (10 mL*3), the combined organic layers were washed with water (10 mL*2) and brine (10 mL*2), dried over $Na_2SO_4$, filtered and concentrated to afford the crude product ethyl 2-(3-(4-(N-(2-((tert-butyldimethylsilyl)oxy)ethyl)-4,6-dichloropyrimidine-5-carboxamido)-2-methylphenyl)-2-oxoimidazolidin-1-yl)acetate 1g (1.1 g, yellow solid) which was used in the next step directly.

$^1$H NMR (400 MHz, $CDCl_3$) δ 8.52 (s, 1H), 7.26 (d, 1H), 7.16 (dd, 1H), 6.99 (d, 1H), 4.14 (q, 1H), 3.94 (s, 2H), 3.92-3.89 (m, 2H), 3.85-3.82 (m, 2H), 3.62-3.51 (m, 4H), 2.13 (s, 3H), 1.21 (t, 1H), 0.81 (s, 9H), 0.00 (s, 6H)

Step 7

Ethyl 2-(3-(4-(4,6-dichloro-N-(2-hydroxyethyl)pyrimidine-5-carboxamido)-2-methylphenyl)-2-oxoimidazolidin-1-yl)acetate To a solution of ethyl 2-(3-(4-N-(2-((tert-butyldimethylsilyl)oxy)ethyl)-4,6-dichloropyrimidine-5-carboxamido)-2-methylphenyl)-2-oxoimidazolidin-1-yl)acetate 1g (1.10 g, 18.01 mmol) in EtOH (10 mL) was added HCl (con, 0.3 ml). The reaction mixture was stirred for 1 h. The mixture was added water (10 mL), extracted with EA (10 mL*3), the combined organic layers were washed with water (10 mL*2), saturated $NaHCO_3$ solution (10 mL*2) and brine (10 mL*2), dried over Na₂SO₄, filtered and concentrated to afford the crude product ethyl 2-(3-(4-(4,6-dichloro-N-(2-hydroxyethyl)pyrimidine-5-carboxamido)-2-methylphenyl)-2-oxoimidazolidin-1-yl)acetate 1h (720 mg, yellow solid) which was used in the next step directly.

¹H NMR (400 MHz, CDCl₃) δ 8.51 (s, 1H), 7.21 (d, 1H), 7.16-7.13 (m, 1H), 7.00 (d, 1H), 4.11 (q, 1H), 3.97-3.95 (m, 2H), 3.92 (s, 2H), 3.82-3.79 (m, 2H), 3.61-3.49 (m, 4H), 2.13 (s, 3H), 1.19 (t, 1H)

Step 8

Ethyl 2-(3-(4-(4-chloro-5-oxo-7,8-dihydropyrimido[5,4-f][1,4]oxazepin-6(5H)-yl)-2-methylphenyl)-2-oxoimidazolidin-1-yl)acetate A mixture of ethyl 2-(3-(4-(4,6-dichloro-N-(2-hydroxyethyl)pyrimidine-5-carboxamido)-2-methyl phenyl)-2-oxoimidazolidin-1-yl)acetate 1h (720 mg, 1.45 mmol) in MeCN (10 mL) was added TEA (440 mg, 4.35 mmol) stirred for 80° C. 12 h. The reaction mixture was cooled to RT and added water (20 mL), extracted with EA (20 mL*3), the combined organic layers were washed with brine (20 mL*2), dried over Na₂SO₄, filtered and concentrated to afford the crude product ethyl 2-(3-(4-(4-chloro-5-oxo-7,8-dihydropyrimido[5,4-f][1,4]oxazepin-6(5H)-yl)-2-methylphenyl)-2-oxoimidazolidin-1-yl)acetate 1i (450 mg, yellow solid) which was used in the next step directly.

¹H NMR (400 MHz, CDCl₃) δ 8.75 (s, 1H), 7.29 (d, 1H), 7.28-7.24 (m, 1H), 7.22-7.19 (m, 1H), 4.74-4.72 (m, 2H), 4.21 (q, 1H), 4.05 (s, 2H) 4.02-4.00 (m, 2H), 3.78-3.62 (m, 4H), 2.33 (s, 3H), 1.29 (t, 1H).

Step 9

Ethyl 2-(3-(4-(4-amino-5-oxo-7,8-dihydropyrimido[5,4-f][1,4]oxazepin-6(5H)-yl)-2-methylphenyl)-2-oxoimidazolidin-1-yl)acetate A mixture of ethyl 2-(3-(4-(4-chloro-5-oxo-7,8-dihydropyrimido[5,4-f][1,4]oxazepin-6(5H)-yl)-2-methylphenyl)-2-oxoimidazolidin-1-yl)acetate 11 (450 mg, 0.98 mmol) in 0.5 M ammonia in dioxane (10 mL) was stirred for 12 h. The reaction mixture was concentrated in vacuo to remove dioxane. The residue was added EA (30 mL), washed with water (30 mL*2) and brine (30 mL*2), dried over Na₂SO₄, filtered and concentrated to afford the crude product ethyl 2-(3-(4-(4-amino-5-oxo-7,8-dihydropyrimido[5,4-f][1,4]oxazepin-6(5H)-yl)-2-methylphenyl)-2-oxoimidazolidin-1-yl)acetate 1j (230 mg, yellow solid) which was used in the next step directly.

Step 10

2-(3-(4-(4-amino-5-oxo-7,8-dihydropyrimido[5,4-f][1,4]oxazepin-6(5H)-yl)-2-methylphenyl)-2-oxoimidazolidin-1-yl)acetate acid A mixture of ethyl 2-(3-(4-(4-amino-5-oxo-7,8-dihydropyrimido[5,4-f][1,4]oxazepin-6(5H)-yl)-2-fluorophenyl)-2-oxoimidazolidin-1-yl)acetate 1j (230 mg, 0.52 mol) in dioxane/H₂O (v/v=3/1, 8 mL) was added LiOH.H₂O (109 mg, 2.61 mmol) was stirred for 12 h. The mixture was adjusted to pH=5~6 with 1 N aq HCl slowly. The mixture was concentrated and the residue was purified by prepare HPLC to afford 2-(3-(4-(4-amino-5-oxo-7,8-dihydropyrimido[5,4-f][1,4]oxazepin-6(5H)-yl)-2-methylphenyl)-2-oxoimidazolidin-1-yl)acetic acid 1 (25 mg, white solid), yield: 11.8%.

MS m/z (ESI): 413.1 [M+1]

¹H NMR (400 MHz, DMSO-d₆) δ 9.02 (br, s, 2H), 8.47 (s, 1H), 7.28-7.20 (m, 3H), 4.84-4.82 (m, 2H), 4.13-4.11 (m, 2H), 3.87 (m, 2H), 3.71-3.67 (m, 2H), 3.55-3.51 (m, 2H), 2.18 (s, 3H)

Example 4

2-(3-(4-(4-amino-5-oxo-7,8-dihydropyrimido[5,4-f][1,4]oxazepin-6(5H)-yl)-2-ethyl-6-methylphenyl)-2-oxoimidazolidin-1-yl)acetic acid

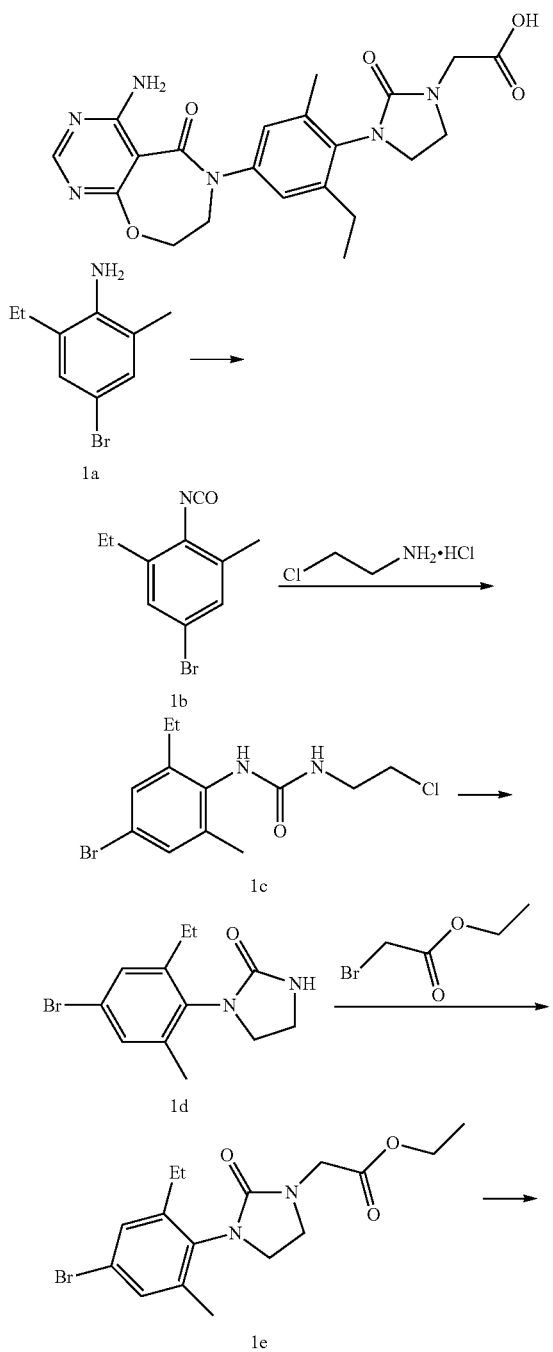

-continued

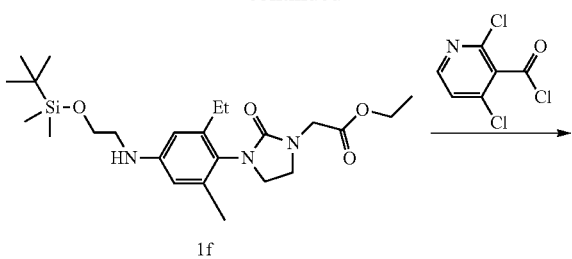

1f

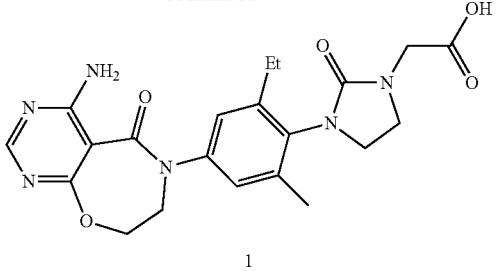

-continued

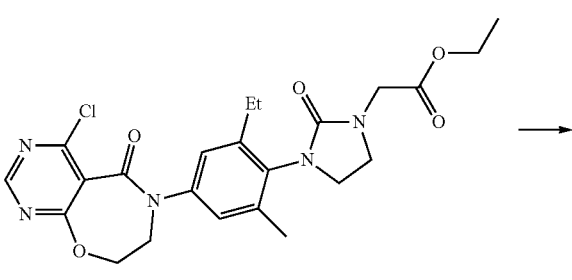

1g

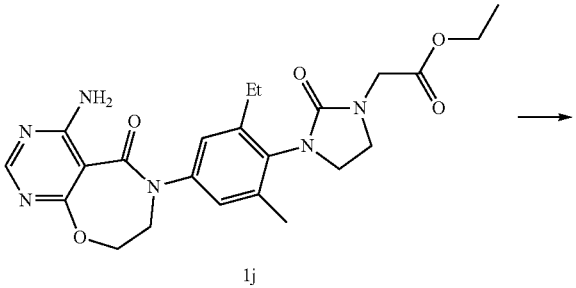

1

Step 1

5-bromo-1-ethyl-2-isocyanato-3-methylbenzene

To a solution, of 4-bromo-2-ethyl-6-methylaniline 1a (2.00 g, 9.40 mmol) in THF (20 mL) was added triphosgen (941 mg, 3.10 mmol). The mixture was stirred at RT for 3 h. The reaction mixture was evaporated to afford 5-bromo-1-ethyl-2-isocyanato-3-methylbenzene 1b (2.2 g, white solid) which was used in the next step directly.

Step 2

1-(4-bromo-2-ethyl-6-methylphenyl)-3-(2-chloroethyl)urea

To a solution of 5-bromo-1-ethyl-2-isocyanato-3-methylbenzene 1b (2.20 g, 9.40 mol) and TEA (4.0 mL, 28.20 mmol) in THF (350 mL) was added 2-chloroethanamine hydrochloride (1.60 g, 14.10 mmol). The mixture was stirred for 2 h at RT. The reaction mixture was added water (200 mL), extracted with DCM (200 mL*3), the combined organic layers were washed with water (100 mL*2) and brine (100 mL*2), dried over Na$_2$SO$_4$, filtered and evaporated to afford 1-(4-bromo-2-ethyl-6-methylphenyl)-3-(2-chloroethyl)urea 1c (2.87 g, white solid) which was used in the next step directly.

$^1$H NMR (400 MHz, CDCl$_3$) δ 7.63 (s, 1H), 7.23 (dd, 2H), 6.33 (br. s, 1H), 3.58 (t, 2H), 3.55 (s, 2H), 2.51 (s, 2H), 2.10 (s, 3H) 1.05 (t, 3H)

Step 3

1-(4-bromo-2-ethyl-6-methylphenyl)imidazolidin-2-one

To a solution of 1-(4-bromo-2-ethyl-6-methylphenyl)-3-(2-chloroethyl)urea 1c (2.86 g, 9.00 mmol) in DMF (20 mL, dry) was added NaH (540 mg, 13.60 mmol). The mixture was stirred for 12 h. The reaction mixture was quenched with water (50 mL), extracted with EA (50 mL*3). The combined organic layers were washed with water (50 mL*2) and brine (50 mL*2), dried over Na$_2$SO$_4$, filtered and concentrated to afford crude 1-(4-bromo-2-ethyl-6-methylphenyl)imidazolidin-2-one 1d (2.15 g, white solid) which was used in the next step directly.

$^1$H NMR (400 MHz, CDCl$_3$) δ 7.25-7.24 (m, 2H), 3.70-3.58 (m, 4H), 2.69-2.48 (m, 2H), 2.24 (s, 3H), 1.24-1.20 (m, 3H)

Step 4

Ethyl 2-(3-(4-bromo-2-ethyl-6-methylphenyl)-2-oxoimidazolidin-1-yl)acetate

To a solution of 1-(4-bromo-2-ethyl-6-methylphenyl)imidazolidin-2-one 1d (1.00 g, 3.50 mol) in DMF (20 mL, dry) was added NaH (210 mg, 5.20 mmol). The mixture was stirred for 0.5 h; ethyl 2-bromoacetate (871 mg, 5.20 mmol) was added. The mixture was stirred for 12 h. The reaction mixture was quenched with water (50 mL), extracted with EA (50 mL*3). The combined organic layers were washed with water (50 mL*2) and brine (50 mL*2), dried over $Na_2SO_4$, filtered and concentrated to afford the crude product. The residue was purified by silica column to afford ethyl 2-(3-(4-bromo-2-ethyl-6-methylphenyl)-2-oxoimidazolidin-1-yl)acetate 1e (0.65 g, white solid), yield: 50.0%.

$^1$H NMR (400 MHz, $CDCl_3$) δ 7.23 (s, 2H), 4.20 (q, 2H), 4.02 (s, 2H), 3.69-3.59 (m, 4H), 2.67-2.48 (m, 2H), 2.22 (s, 3H), 1.28 (t, 3H), 1.21 (t, 3H)

Step 5

Ethyl 2-(3-(4-((2-((tert-butyldimethylsilyl)oxy)ethyl)amino)-2-ethyl-6-methylphenyl)-2-oxoimidazolidin-1-yl)acetate To a solution of ethyl 2-(3-(4-bromo-2-ethyl-6-methylphenyl)-2-oxoimidazolidin-1-yl)acetate 1e (650 mg, 1.77 mol) in toluene (15 mL, dry) was added 2-((tert-butyldimethylsilyl)oxy)ethanamine (467 mg, 2.66 mol), $Cs_2CO_3$ (1.73 g, 5.31 mmol), $Pd_2(dba)_3$ (50 mg, 0.05 mmol), x-phos (40 mg, 0.07 mmol). The mixture was stirred at 100° C. for 12 h. The reaction mixture was cooled to RT, added water (50 mL), extracted with EA (50 mL*3), the combined organic layers were washed with water (50 mL*2) and brine (50 mL*2), dried over $Na_2SO_4$, filtered and concentrated to afford the crude product. The residue was purified by silica column to afford ethyl 2-(3-(4-((2-((tert-butyldimethylsilyl)oxy)ethyl)amino)-2-ethyl-6-methylphenyl)-2-oxoimidazolidin-1-yl)acetate 1f (480 mg, yellow oil), yield: 58.0%.

$^1$H NMR (400 MHz, $CDCl_3$) δ 6.35 (dd, 1H), 4.19 (q, 2H), 4.03 (s, 2H), 3.78 (t, 2H), 3.61 (s, 4H), 3.18 (t, 2H), 2.61-2.42 (m, 2H), 2.16 (s, 3H), 1.28 (t, 3H), 1.19 (t, 3H), 0.89 (s, 9H), 0.06 (s, 6H)

Step 6

Ethyl 2-(3-(4-(N-(2-((tert-butyldimethylsilyl)oxy)ethyl)-4,6-dichloropyrimidine-5-carboxamido-2-ethyl-6-methylphenyl)-2-oxoimidazolidin-1-yl)acetate To a solution of ethyl 2-(3-(4-((2-((tert-butyldimethylsilyl)oxy)ethyl)amino)-2-ethyl-6-methylphenyl-2-oxoimidazolidin-1-yl)acetate 1f (480 mg, 1.04 mmol) in DCM (5 mL) was added TEA (449 uL, 3.11 mmol) and 4,6-dichloropyrimidine-5-carbonyl chloride (653 mg, 3.11 mol). Reaction mixture was stirred for 12 h. The mixture was added water (10 mL), extracted with DCM (10 mL*3), the combined organic layers were washed with water (10 mL*2) and brine (10 mL*2), dried over $Na_2SO_4$, filtered and concentrated to afford the crude product ethyl 2-(3-(4-(N-(2-((tert-butyldimethylsilyl)oxy)ethyl)-4,6-dichloropyrimidine-5-carboxamido)-2-ethyl-6-methylphenyl)-2-oxoimidazolidin-1-yl)acetate 1g (662 mg, yellow solid) which was used in the next step directly.

Step 7 ethyl 2-(3-(4-(4,6-dichloro-N-(2-hydroxyethyl)pyrimidine-5-carboxamido)-2-ethyl-6-methylphenyl)-2-oxoimidazolidin-1-yl)acetate To a solution of ethyl 2-(3-(4-(N-(2-((tert-butyldimethylsilyl)oxy)ethyl)-4,6-dichloropyrimidine-5-carboxamido)-2-ethyl-6-methylphenyl)-2-oxoimidazolidin-1-yl)acetate 1g (662 mg, 1.04 mol) in EtOH (10 mL) was added HCl (con, 0.3 ml). The reaction mixture was stirred for 1 h. The mixture was added water (10 mL), extracted with EA (10 mL*3), the combined organic layers were washed with water (10 mL*2) and brine (10 mL*2), dried over $Na_2SO_4$, filtered and concentrated to afford the crude product ethyl 2-(3-(4-(4,6-dichloro-N-(2-hydroxyethyl)pyrimidine-5-carboxamido)-2-ethyl-6-methylphenyl)-2-oxoimidazolidin-1-yl)acetate 1h (440 mg, yellow solid) which was used in the next step directly.

Step 8

Ethyl 2-(3-(4-(4-chloro-5-oxo-7,8-dihydropyrimido[5,4-f][1,4]oxazepin-6(5H)-yl)-2-ethyl-6-methylphenyl-2-oxoimidazolidin-1-yl)acetate A mixture of ethyl 2-(3-(4-(4,6-dichloro-N-(2-hydroxyethyl)pyrimidine-5-carboxamido)-2-ethyl-6-methylphenyl)-2-oxoimidazolidin-1-yl)acetate 1h (440 mg, 841 umol) in MeCN (5 mL) was added TEA (364 μL, 2.52 mmol) stirred at 80° C. for 12 h. The reaction mixture was cooled to RT, extracted with EA (30 mL*3), the combined organic layers were washed with brine (30 mL*2), dried over $Na_2SO_4$, filtered and concentrated to afford the crude product ethyl 2-(3-(4-(4-chloro-5-oxo-7,8-dihydropyrimido[5,4-f][1,4]oxazepin-6(5H)-yl)-2-ethyl-6-methylphenyl-2-oxoimidazolidin-1-yl)acetate 1i (250 mg, yellow solid) which was used in the next step directly.

$^1$H NMR (400 MHz, DMSO-d6) δ 8.80 (s, 1H), 7.17 (d, 2H), 4.70 (t, 2H), 4.14-4.08 (m, 4H), 3.96 (s, 2H), 3.59 (s, 4H), 2.59-2.52 (m, 2H), 2.17 (s, 3H), 1.21-1.17 (m, 3H), 1.15-1.11 (m, 3H)

Step 9

Ethyl 2-(3-(4-(4-amino-5-oxo-7,8-dihydropyrimido[5,4-f][1,4]oxazepin-6(5H)-yl)-2-ethyl-6-methylphenyl-2-oxoimidazolidin-1-yl)acetate A mixture of ethyl 2-(3-(4-(4-chloro-5-oxo-7,8-dihydropyrimido[5,4-f][1,4]oxazepin-6(5H)-yl)-2-ethyl-6-methylphenyl-2-oxoimidazolidin-1-yl)acetate 1i (250 mg, 513 umol) in 0.5 M ammonia in dioxane (10 mL) was stirred for 12 h. The reaction mixture was concentrated in vacuo to remove dioxane. The residue was added DCM (30 mL), washed with water (30 mL*2) and brine (30 mL*2), dried over $Na_2SO_4$, filtered and concentrated to afford the crude product ethyl 2-(3-(4-(4-amino-5-oxo-7,8-dihydropyrimido[5,4-f][1,4]oxazepin-6(5H)-yl)-2-ethyl-6-methylphenyl-2-oxoimidazolidin-1-yl)acetate 1j (240 mg, yellow solid) which was used in the next step directly.

$^1$H NMR (400 MHz, DMSO-$d_6$) δ 8.17 (s, 1H), 7.63 (br. s, 2H), 7.14 (s, 2H), 4.60 (t, 2H), 4.12 (q, 2H), 4.03 (q, 2H), 3.98 (s, 2H), 3.61 (s, 4H), 2.59-2.52 (m, 2H), 2.19 (s, 3H), 1.24-1.13 (m, 6H).

Step 10

2-(3-(4-(4-amino-5-oxo-7,8-dihydropyrimido[5,4-f][1,4]oxazepin-6(5H)-yl)-2-ethyl-6-methylphenyl-2-oxoimidazolidin-1-yl)acetic acid A mixture of ethyl 2-(3-(4-(4-amino-5-oxo-7,8-dihydropyrimido[5,4-f][1,4]oxazepin-6(5H)-yl)-2-ethyl-6-methylphenyl-2-oxoimidazolidin-1-yl)acetate 1j (240 mg, 513 umol) in dioxane/$H_2O$ (v/v=3/1, 8 mL) was added LiOH.$H_2O$ (64 mg, 1.52 mmol) was stirred for 12 h. The reaction mixture was adjusted to pH=5~6 with 1 N aq HCl slowly. The solid that formed was collected by filtration, dried in vacuo to afford 2-(3-(4-(4-amino-5-oxo-7,8-dihydropyrimido[5,4-f][1,4]oxazepin-6(5H)-yl)-2-ethyl-6-methylphenyl-2-oxoimidazolidin-1-yl)acetic acid 1 (108 mg, white solid), yield: 47.0%.

MS m/z (ESI): 441.1 [M+1]

$^1$H NMR (400 MHz, DMSO-$d_6$) δ 8.19 (s, 1H), 7.70 (br. s, 2H), 7.14 (s, 2H), 4.60 (s, 2H), 3.99 (s, 2H), 3.88 (s, 2H), 3.60 (s, 4H), 2.61-2.52 (m, 2H), 2.17 (s, 3H), 1.14 (t, 3H)

Example 5

2-(3-(4-(4-amino-5-oxo-7,8-dihydropyrimido[5,4-f][1,4]oxazepin-6(5H)-yl)-2-ethylphenyl)-2-oxoimidazolidin-1-yl)acetic acid

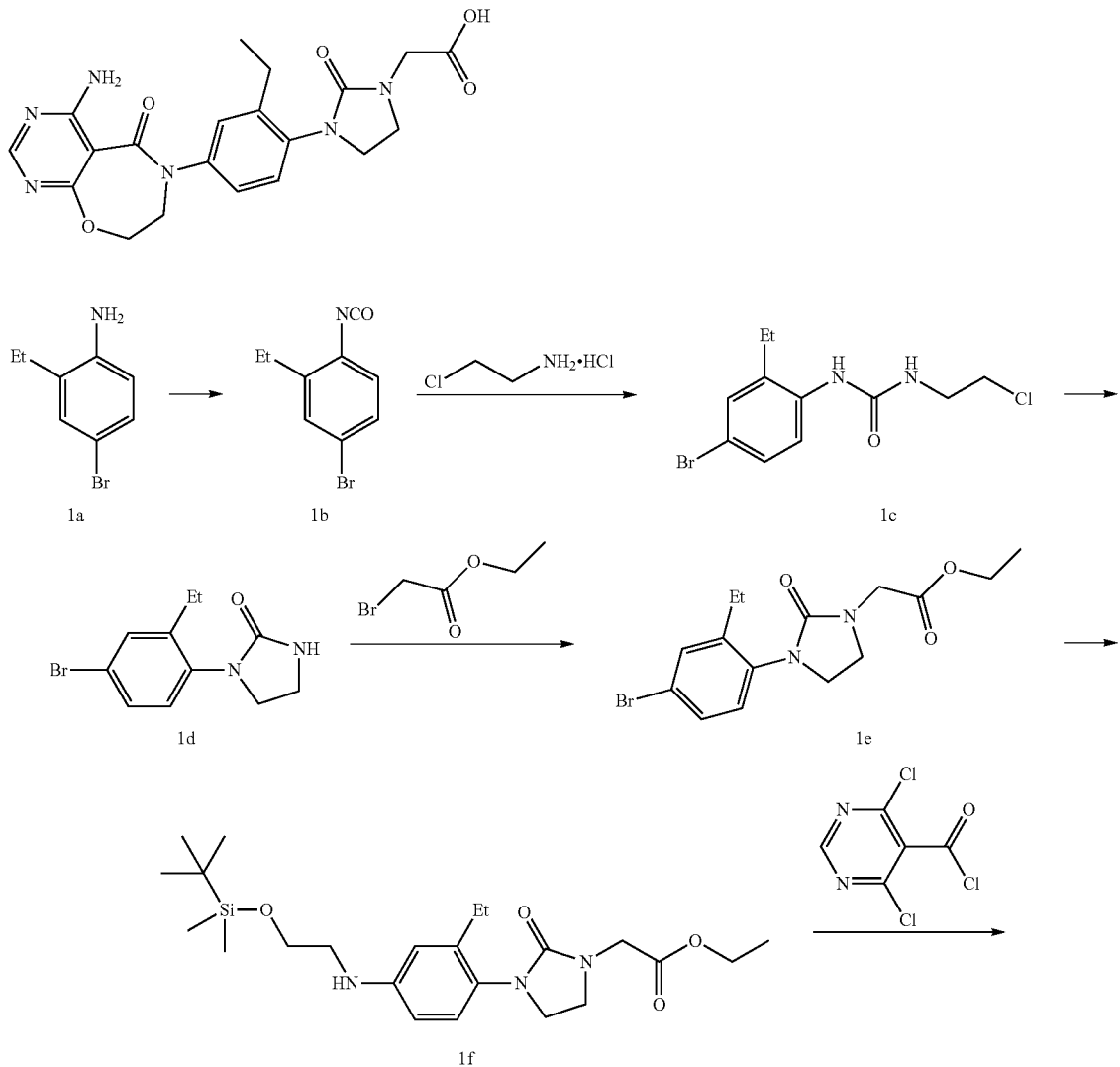

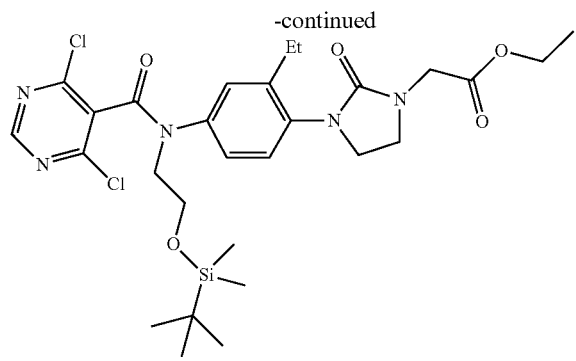

1g

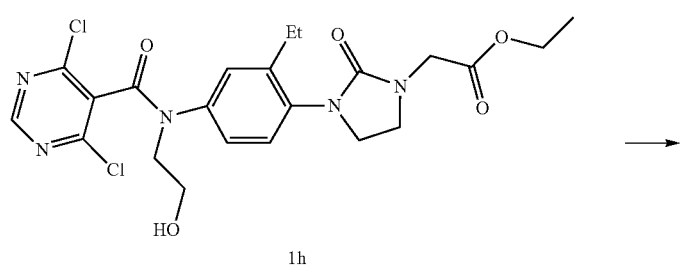

1h

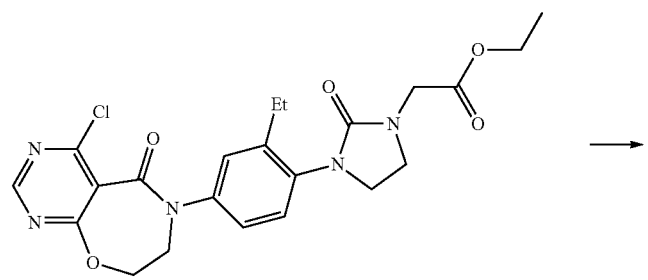

1i

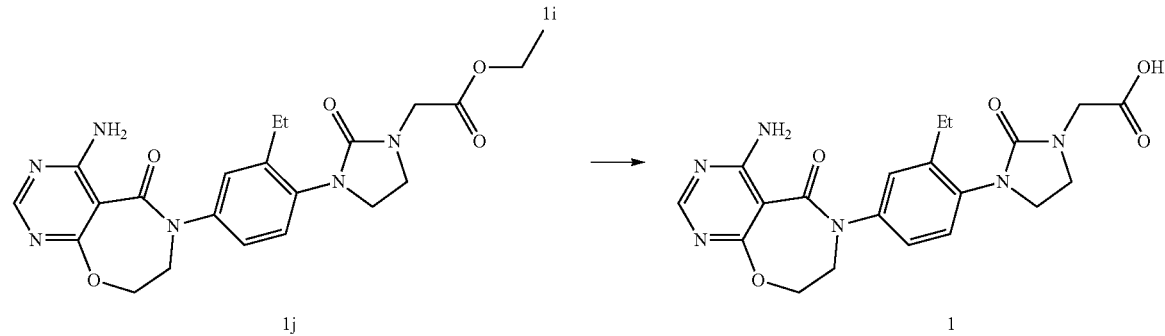

1j                                              1

Step 1

4-bromo-2-ethyl-1-isocyanatobenzene

To a solution of 4-bromo-2-ethylaniline 1a (3.00 g, 14.99 mmol) in THF (30 mL) was added triphosgen (1.48 g, 5.00 mmol). The mixture was stirred for 3 h. The reaction mixture was evaporated to afford 4-bromo-2-ethyl-1-isocyanatobenzene 1b (3.39 g, white solid) which was used in the next step directly.

Step 2

1-(4-bromo-2-ethylphenyl)-3-(2-chloroethyl)urea

To a solution of 4-bromo-2-ethyl-1-isocyanatobenzene 1b (3.39 g, 14.99 mmol) in TEA (6.3 mL, 45.00 mmol) in THF (100 mL) was added 2-chloroethanamine hydrochloride (2.61 g, 22.50 mmol). The mixture was stirred for 2 h. The reaction mixture was added water (200 mL), extracted with EA (200 mL*3), the combined organic layers were washed with water (100 mL*2) and brine (100 mL*2), dried over Na$_2$SO$_4$, filtered and concentrated to afford the 1-(4-bromo-2-ethylphenyl)-3-(2-chloroethyl)urea 1c (4 g, white solid) which was used in the next step directly.

$^1$H NMR (400 MHz, DMSO-d6) δ 7.84 (s, 1H), 7.75 (d, 1H), 7.28-7.23 (m, 2H), 6.91-6.88 (m, 1H), 3.64 (t, 2H), 3.40 (t, 2H), 2.53-2.49 (m, 2H), 1.09 (t, 3H)

Step 3

1-(4-bromo-2-ethylphenyl)imidazolidin-2-one

To a solution of 1-(4-bromo-2-ethylphenyl)-3-(2-chloroethyl)urea 1c (3.39 g, 15.00 mmol) in DMF (30 mL, dry) was added NaH (792 mg, 19.80 mmol) under an ice-bath. The mixture was stirred for 12 h. The reaction mixture was quenched with saturate NH$_4$Cl solution (120 mL), extracted with EA (100 mL*3). The combined organic layers were washed with (100 mL*2) and brine (100 mL*2), dried over Na$_2$SO$_4$, filtered and concentrated to afford the crude 1-(4-bromo-2-ethylphenyl)imidazolidin-2-one 1d (2.2 g, white solid) which was used in the next step directly.

$^1$H NMR (400 MHz, DMSO-d6) δ 7.46 (d, 1H), 7.41-7.38 (m, 1H), 7.17 (d, 1H), 6.72 (s, 1H), 3.70 (t, 2H), 3.41 (t, 2H), 2.60-2.51 (m, 2H), 1.14 (t, 3H)

Step 4

Ethyl 2-(3-(4-bromo-2-ethylphenyl)-2-oxoimidazolidin-1-yl)acetate

To a solution of 1-(4-bromo-2-ethylphenyl)imidaxolidin-2-one 1d (1.00 g, 3.72 mmol) in DMF (20 mL, dry) was added NaH (223 mg, 5.58 mmol). The mixture was stirred for 0.5 h; ethyl 2-bromoacetate (802 mg, 4.84 mmol) was added. The mixture was stirred for 12 h. The reaction mixture was quenched with saturate NH$_4$Cl solution (50 mL), extracted with EA (50 mL*3). The combined organic layers were washed with water (50 mL*2) and brine (50 mL*2), dried over Na$_2$SO$_4$, filtered and concentrated to afford the crude product. The residue was purified by silica column to afford ethyl 2-(3-(4-bromo-2-ethylphenyl)-2-oxoimidazolidin-1-yl)acetate 1e (0.8 g, white solid), yield: 60.6%.

$^1$H NMR (400 MHz, CDCl$_3$) δ 7.43 (d, 1H), 7.35-7.33 (m, 1H), 7.07 (d, 1H), 4.25-4.20 (q, 2H), 4.05 (s, 2H), 3.75-3.70 (m, 2H), 3.66-3.62 (m, 2H), 2.68-2.62 (q, 2H), 1.30 (t, 3H), 1.23 (t, 3H)

Step 5 ethyl 2-(3-(4-((2-tert-butyldimethylsilyl)oxy)ethyl)amino)-2-ethylphenyl)-2-oxoimidazolidin-1-yl)acetate To a solution of 2-(3-(4-bromo-2-ethylphenyl)-2-oxoimidazolidin-1-yl)acetate 1e (800 mg, 2.25 mmol) in toluene (15 mL, dry) was added 2-((tert-butyldimethylsilyl)oxy)ethanamine (467 mg, 2.66 mmol), Cs$_2$CO$_3$ (2.20 g, 6.75 mmol), Pd$_2$(dba)$_3$ (54 mg, 0.11 mmol), x-phos (101 mg, 0.11 mmol). The mixture was stirred at 100° C. for 12 h. The reaction mixture was cooled to RT, added water (50 mL), extracted with EA (50 mL*3), the combined organic layers were washed with water (50 mL*2) and brine (50 mL*2), dried over Na$_2$SO$_4$, filtered and concentrated to afford the crude product. The residue was purified by silica column to afford ethyl 2-(3-(4-((2-((tert-butyldimethylsilyl)oxy)ethyl)amino)-2-ethylphenyl)-2-oxoimidazolidin-1-yl)acetate 1f (600 mg, yellow oil).

$^1$H NMR (400 MHz, CDCl$_3$) δ 7.99 (d, 1H), 6.52 (d, 1H), 6.49-6.46 (dd, 1H), 4.24-4.19 (q, 2H), 4.05 (s, 2H), 3.82-3.79 (m, 2H), 3.69-3.57 (m, 4H), 3.22 (t, 2H), 2.61-2.55 (q, 2H), 1.30 (t, 3H), 1.21 (t, 3H), 0.91 (s, 9H), 0.07 (s, 6H)

Step 6

Ethyl 2-(3-(4-(N-(2-((tert-butyldimethylsilyl)oxy)ethyl)-4,6-dichloropyrimidine-5-carboxamido)-2-ethylphenyl)-2-oxoimidazolidin-1-yl)acetate To a solution of ethyl 2-(3-(4-((2-((tert-butyldimethylsilyl)oxy)ethyl)amino)-2-ethylphenyl)-2-oxoimidazolidin-1-yl)acetate 1f (600 mg, 1.33 mmol) in DCM (10 mL) was added TEA (0.56 mL, 3.99 mmol) and 4,6-dichloropyrimidine-5-carbonyl chloride (423 mg, 2.00 mmol). Reaction mixture was stirred for 12 h. The mixture was added water (10 mL), extracted with DCM (10 mL*3), the combined organic layers were washed with water (10 mL*2) and brine (10 mL*2), dried over Na$_2$SO$_4$, filtered and concentrated to afford the crude product ethyl 2-(3-(4-(N-(2-((tert-butyldimethylsilyl)oxy)ethyl)-4,6-dichloropyrimidine-5-carboxamido)-2-ethylphenyl)-2-oxoimidazolidin-1-yl)acetate 1g (800 mg, yellow solid) which was used in the next step directly.

$^1$H NMR (400 MHz, CDCl$_3$) δ 8.58 (s, 1H), 7.33-7.27 (m, 2H), 7.08 (d, 1H), 4.24-4.18 (q, 2H), 4.02-3.99 (m, 2H), 3.92-3.91 (m, 2H), 3.66-3.61 (m, 3H), 3.13-3.09 (m, 3H), 2.59-2.54 (q, 2H), 1.29 (t, 3H), 1.11 (t, 3H), 0.89 (s, 9H), 0.07 (s, 6H)

Step 7

Ethyl 2-(3-(4-(4,6-dichloro-N-(2-hydroxyethyl)pyrimidine-5-carboxamido)-2-ethylphenyl)-2-oxoimidazolidin-1-yl)acetate To a solution of ethyl 2-(3-(4-(N-(2-((tert-butyldimethylsilyl)oxy)ethyl)-4,6-dichloropyrimidine-5-carboxamido)-2-ethylphenyl)-2-oxoimidazolidin-1-yl)acetate 1g (800 mg, 1.28 mmol) in EtOH (10 mL) was added HCl (con, 0.3 ml). The reaction mixture was stirred for 1 h. The mixture was added water (10 mL), extracted with EA (10 mL*3), the combined organic layers were washed with water (10 mL*2) and brine (10 mL*2), dried over Na$_2$SO$_4$, filtered and concentrated to afford the crude product ethyl 2-(3-(4-(4,6-dichloro-N-(2-hydroxyethyl)pyrimidine-5-carboxamido)-2-ethylphenyl)-2-oxoimidazolidin-1-yl)acetate 1 h (600 mg, yellow solid) which was used in the next step directly.

Step 8 ethyl 2-(3-(4-(4-chloro-5-oxo-7,8-dihydropyrimido[5,4-f][1,4]oxazepin-6(5H)-yl)-2-ethylphenyl)-2-oxoimidazolidin-1-yl)acetate A mixture of ethyl 2-(3-(4-(4,6-dichloro-N-(2-hydroxyethyl)pyrimidine-5-carboxamido)-2-ethylphenyl)-2-oxoimidazolidin-1-yl)acetate 1h (600 mg, 1.18 mol) in MeCN (10 mL) was added TEA (0.49 mL, 3.54 mmol) stirred at 80° C. for 12 h. The reaction mixture was cooled to RT and added water (20 mL), extracted with EA (20 mL*3), the combined organic layers were washed with brine (20 mL*2), dried over Na$_2$SO$_4$, filtered and concentrated to afford the crude product ethyl 2-(3-(4-(4-chloro-5-oxo-7,8-dihydropyrimido[5,4-f][1,4]oxazepin-6(5H)-yl)-2-ethylphenyl)-2-oxoimidazolidin-1-yl)acetate 1i (500 mg, yellow solid) which was used in the next step directly.

$^1$H NMR (400 MHz, CDCl$_3$) δ 8.77 (s, 1H), 7.31-7.23 (m, 3H), 4.75 (t, 2H), 4.26-4.21 (q, 2H), 4.07-4.04 (m, 2H), 3.79-3.75 (m, 2H), 3.69-3.65 (m, 3H), 2.75-2.69 (q, 3H), 1.33-1.25 (m, 6H)

Step 9 ethyl 2-(3-(4-(4-amino-5-oxo-7,8-dihydropyrimido[5,4-f][1,4]oxazepin-6(5H)-yl)-2-ethylphenyl)-2-oxoimidazolidin-1-yl)acetate A mixture of ethyl 2-(3-(4-(4-chloro-5-oxo-7,8-dihydropyrimido[5,4-f][1,4]oxazepin-6(5H)-yl)-2-ethylphenyl-2-oxoimidazolidin-1-yl)acetate 1i (500 mg, 1.06 mmol) in 0.5 M ammonia in dioxane (10 mL) was for 12 h. The reaction mixture was concentrated in vacuo to remove dioxane. The residue was added EA (30 mL), washed with water (30 mL*2) and brine (30 mL*2), dried over Na$_2$SO$_4$, filtered and concentrated to afford the crude product ethyl 2-(3-(4-(4-amino-5-oxo-7,8-dihydropyrimido[5,4-f][1,4]oxazepin-6(5H)-yl)-2-ethylphenyl-2-oxoimidazolidin-1-yl)acetate 1j (300 mg, yellow solid) which was used in the next step directly.

$^1$H NMR (400 MHz, CDCl$_3$) δ 8.29 (s, 1H), 8.16 (br.s, 1H), 7.30-7.13 (m, 3H), 5.66 (brs, 1H), 4.69 (t, 2H), 4.26-4.20 (q, 2H), 4.07-4.01 (m, 2H), 3.79-3.71 (m, 2H), 3.68-3.64 (m, 3H), 2.74-2.68 (q, 3H), 1.33-1.24 (m, 6H)

Step 10

2-(3-(4-(4-amino-5-oxo-7,8-dihydropyrimido[5,4-f][1,4]oxazepin-6(5H)-yl)-2-ethylphenyl-2-oxoimidazolidin-1-yl)acetic acid A mixture of ethyl 2-(3-(4-(4-amino-5-oxo-7,8-dihydropyrimido[5,4-f][1,4]oxazepin-6(5H)-yl)-2-ethylphenyl-2-oxoimidazolidin-1-yl)acetate 1j (300 mg, 0.66 mmol) in dioxane/H$_2$O (v/v=3/1.8 mL) was added LiOH.H$_2$O (139 mg, 3.30 mmol) was stirred for 12 h. The mixture was adjusted to pH=5~6 with 1 N aq HCl slowly. The mixture was concentrated and the residue was purified by prepare HPLC to afford 2-(3-(4-(4-amino-5-oxo-7,8-dihydropyrimido[5,4-f][1,4]oxazepin-6(5H)-yl)-2-ethylphenyl-2-oxoimidazolidin-1-yl)acetic acid 1 (24.7 mg, white solid), yield: 8.8%.

MS m/z (ESI): 427.2 [M+1]

$^1$H NMR (400 MHz, DMSO-d$_6$) δ 8.37-8.18 (m, 2H), 7.31-7.23 (m, 2H), 4.73 (t, 2H), 4.08 (s, 3H), 3.89 (s, 3H), 3.71 (t, 2H), 3.45-3.43 (m, 4H), 2.59 (q, 2H), 1.16 (t, 3H)

Example 6

3-(3-(4-(4-amino-5-oxo-7,8-dihydropyrimido[5,4-f][1,4]oxazepin-6(5H)-yl)-2-chlorophenyl-2-oxoimidazolidin-1-yl)propanoic acid

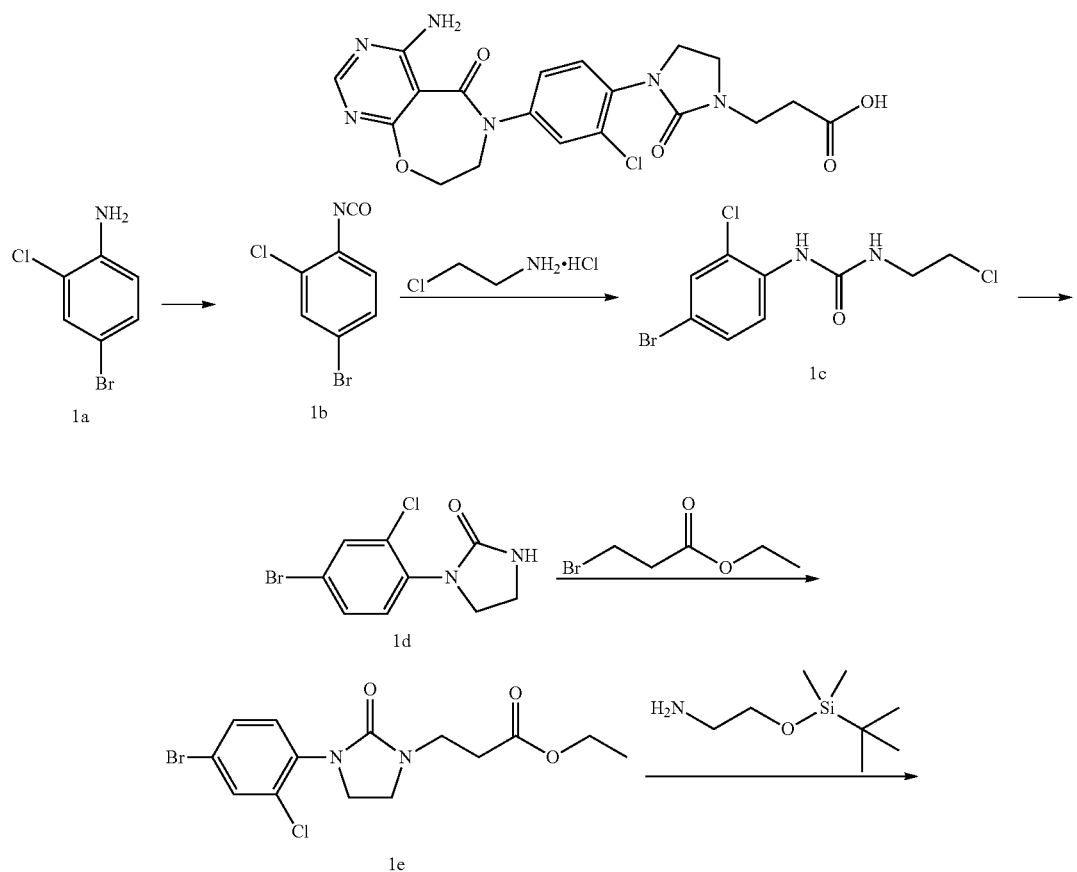

-continued
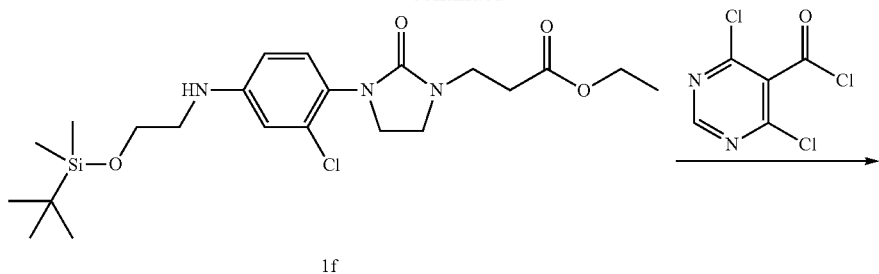
1f
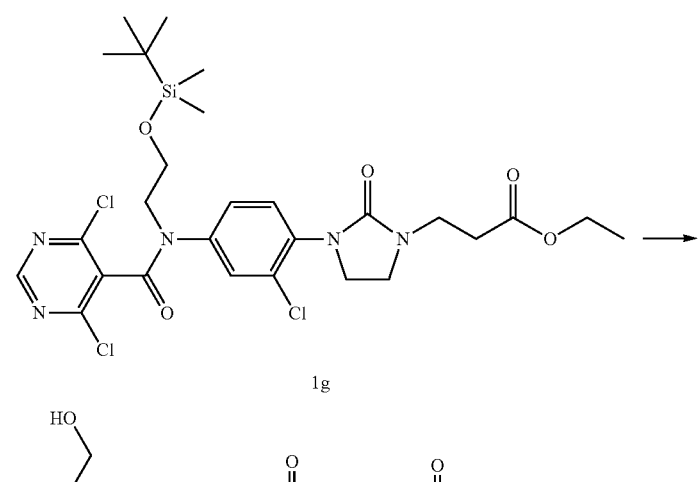
1g
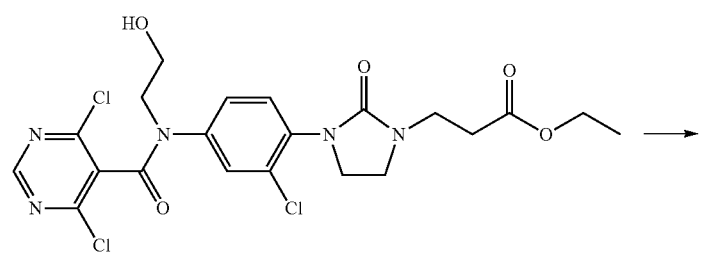
1h
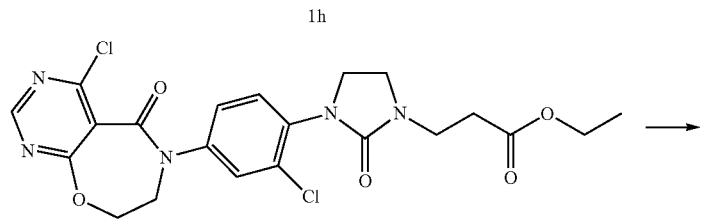
1i
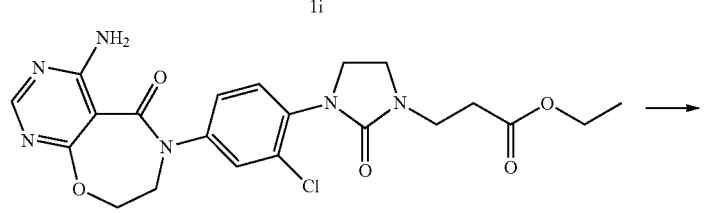
1j
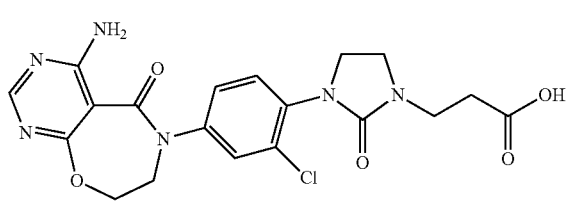
1

Step 1

4-bromo-2-ethyl-1-isocyanatobenzene

To a solution of 4-bromo-2-chloro-1-isocyanatobenzene 1b (7.00 g, 34 mmol) in THF (250 mL) was added triphosgen (3.30 g, 11.20 mmol). The mixture was stirred for 3 h. The reaction mixture was evaporated to afford 4-bromo-2-chloro-1-isocyanatobenzene 1b (7.0 g, white solid) which was used in the next step directly.

Step 2

1-(4-bromo-2-chlorophenyl)-3-(2-chloroethyl)urea

To a solution of 4-bromo-2-chloro-1-isocyanatobenzene 1b (3.00 g, 12.90 mmol) and TEA (1.96 g, 19.30 mmol) in THF (100 mL) was added 2-chloroethanamine hydrochloride (2.25 g, 19.30 mmol). The mixture was stirred for 2 h. The reaction mixture was added water (200 mL), extracted with DCM (200 mL*3), the combined organic layers were washed with water (100 mL*2) and brine (100 mL*2), dried over $Na_2SO_4$, filtered and evaporated to afford 1-(4-bromo-2-chlorophenyl)-3-(2-chloroethyl) urea 1c (3.1 g, white solid) which was used in the next step directly.

Step 3

1-(4-bromo-2-chlorophenyl)imidazolidin-2-one

To a solution of 1-(4-bromo-2-chlorophenyl)-3-(2-chloroethyl)urea 1c (3.30 g, 10.80 mmol) in DMF (100 mL, dry) was added NaH (634 mg, 15.80 mmol). The mixture was stirred for 12 h. The reaction mixture was quenched with water (70 mL), extracted with EA (70 mL*3). The combined organic layers were washed with water (70 mL*2) and brine (70 mL*2), dried over $Na_2SO_4$, filtered and concentrated to afford crude 1-(4-bromo-2-chlorophenyl)imidazolidin-2-one 1d (3.1 g, white solid) which was used in the next step directly.

$^1$H NMR (400 MHz, DMSO-$d_6$) δ 7.76 (d, 1H), 7.54 (dd, 1H), 7.31-7.36 (m, 1H), 6.85 (br. s, 3H), 3.72 (t, 2H), 3.39 (t, 2H)

Step 4

Ethyl 3-(3-(4-bromo-2-chlorophenyl)-2-oxoimidazolidin-1-yl)propanoate

To a solution of 1-(4-bromo-2-chlorophenyl)imidazolidin-2-one 1d (3.10 g, 7.80 mmol) in DMF (50 mL, dry) was added NaH (472 mg, 11.80 mmol). The mixture was stirred at RT for 0.5 h; ethyl 2-bromoacetate (1.21 mL, 9.45 mmol) was added. The mixture was stirred for 12 h. The reaction mixture was quenched with water (20 mL), extracted with EA (20 mL*3). The combined organic layers were washed with water (20 mL*2) and brine (20 mL*2), dried over $Na_2SO_4$, filtered and concentrated to afford the crude product. The residue was purified by silica column to afford ethyl 3-(3-(4-bromo-2-chlorophenyl)-2-oxoimidazolidin-1-yl) propanoate 1e 11.4 g, white solid), yield: 47.0%.

$^1$H NMR (400 MHz, DMSO-$d_6$) δ 7.56 (d, 1H), 7.40-7.37 (m, 1H), 7.24 (d, 1H), 4.15 (q, 2H), 3.75-3.71 (m, 2H), 3.59-3.52 (m, 4H), 2.60 (t, 2H), 1.26 (t, 3H)

Step 5 ethyl 3-(3-(4-((2-((tert-butyldimethylsilyl)oxy)ethyl)amino)-2-chlorophenyl)-2-oxoimidazolidin-1-yl)propanoate To a solution of ethyl 3-(3-(4-bromo-2-chlorophenyl)-2-oxoimidazolidin-1-yl)propanoate 1e (700 mg, 1.86 mol) in toluene (15 mL, dry) was added 2-((tert-butyldimethylsilyl)oxy)ethanamine (490 mg, 2.80 mmol), $Cs_2CO_3$ (1.82 g, 5.59 mmol), $Pd_2(dba)_3$ (50 mg, 0.0 mmol), x-phos (40 mg, 0.07 mmol). The mixture was stirred as 100° C. for 12 h. The reaction mixture way cooled to RT, added water (50 mL), extracted with EA (50 mL*3), the combined organic layers were washed with water (50 mL*2) and brine (50 mL*2), dried over $Na_2SO_4$, filtered and concentrated to afford the crude product. The residue was purified by silica column to afford ethyl 3-(3-(4-((2-((tert-butyldimethylsilyl)oxy)ethyl) amino)-2-chlorophenyl)-2-oxoimidazolidin-1-yl)propanoate 1f (650 mg, yellow oil).

$^1$H NMR (400 MHz, CDCl$_3$) δ 7.01 (d, 1H), 6.58 (d, 1H), 6.43 (dd, 1H), 4.09 (q, 2H), 3.72 (d, 2H), 3.61-3.57 (m, 2H), 3.50 (t, 2H), 3.43-3.41 (m, 2H), 3.10 (q, 2H), 2.54 (t, 2H), 1.20 (t, 3H), 0.83 (s, 9H), 0.00 (s, 6H)

Step 6

Ethyl 3-(3-(4-(N-(2-((tert-butyldimethylsilyl)oxy)ethyl)-4,6-dichloropyrimidine-5-carboxamido)-2-chlorophenyl)-2-oxoimidazolidin-1-yl)propanoate To a solution of ethyl 3-(3-(4-((2-((tert-butyldimethylsilyl)oxy)ethyl)amino)-2-chlorophenyl)-2-oxoimidazolidin-1-yl)propanoate 1f (650 mg, 1.38 mmol) in DCM (5 mL) was added TEA (877 mg, 4.15 mmol) and 4,6-dichloropyrimidine-5-carbonyl chloride (420 mg, 4.15 mmol). Reaction mixture was stirred for 12 h. The mixture was added water (10 mL), extracted with DCM (10 mL*3), the combined organic layers were washed with water (10 mL*2) and brine (10 mL*2), dried over $Na_2SO_4$, filtered and concentrated to afford the crude product ethyl 3-(3-(4-(N-(2-((tert-butyldimethylsilyl)oxy)ethyl-4,6-dichloropyrimidine-5-carboxamido)-2-chlorophenyl)-2-oxoimidazolidin-1-yl) propanoate 1g (887 mg, yellow solid) which was used in the next step directly.

Step 7 ethyl 3-(3-(2-chloro-4-(4,6-dichloro-N-(2-hydroxyethyl)pyrimidine-5-carboxamido)phenyl)-2-oxoimidazolidin-1-yl)propanoate To a solution of ethyl 3-(3-(4-(N-(2-((tert-butyldimethylsilyl)oxy)ethyl)-4,6-dichloropyrimidine-5-carboxamido)-2-chlorophenyl)-2-oxoimidazolidin-1-yl)propanoate 1g (887 mg, 1.38 mmol) in EtOH (10 mL) was added HCl (con, 0.3 ml). The reaction mixture was stirred for 1 h. The mixture was added water (10 mL), extracted with DCM (10 mL*3), the combined organic layers were washed with water (10 mL*2) and brine (10 mL*2), dried over $Na_2SO_4$, filtered and concentrated to afford the crude product ethyl 3-(3-(2-chloro-4-(4,6-dichloro-N-(2-hydroxyethyl)pyrimidine-5-carboxamido)phenyl)-2-oxoimidazolidin-1-yl)propanoate 1h (732 mg, yellow solid) which was used in the next step directly.

¹H NMR (400 MHz, CDCl₃) δ 8.63 (s, 1H), 7.52 (d, 1H), 7.33-7.29 (m, 2H), 4.15 (q, 2H), 4.03 (t, 2H), 3.91 (t, 2H), 3.71 (t, 2H), 3.59-3.51 (m, 4H), 2.59 (t, 2H), 1.26 (t, 3H)

Step 8 ethyl 3-(3-(2-chloro-4-(4-chloro-5-oxo-7,8-dihydropyrimido[5,4-f][1,4]oxazepin-6(5H)-yl)phenyl)-2-oxoimidazolidin-1-yl)propanoate A mixture of ethyl 3-(3-(2-chloro-4-(4,6-dichloro-N-(2-hydroxyethyl)pyrimidine-5-carboxamido)phenyl)-2-oxoimidazolidin-1-yl)propanoate 1h (732 mg, 1.38 mmol) in MeCN (5 mL) was added TEA (600 uL, 4.14 mmol) stirred at 80° C. for 12 h. The reaction mixture was cooled to RT and added water (20 mL), extracted with EA (30 mL*3), the combined organic layers were washed with water (30 mL) and brine (30 ml*2), dried over Na₂SO₄, filtered and concentrated to afford the crude product ethyl 3-(3-(2-chloro-4-(4-chloro-5-oxo-7,8-dihydropyrimido[5,4-f][1,4]-oxazepin-6(5H)-yl)phenyl)-2-oxoimidazolidin-1-yl)propanoate 1i (240 mg, yellow solid) which was used in the next step directly.

¹H NMR (400 MHz, CDCl₃) δ 8.76 (s, 1H), 7.48-7.45 (m, 2H), 7.30 (dd, 1H), 4.74-4.72 (m, 2H), 4.16 (q, 2H), 4.03 (t, 2H), 3.79-3.76 (m, 2H), 3.61-3.55 (m, 4H), 2.62 (t, 2H), 1.27 (t, 3H)

Step 9 ethyl 3-(3-(4-(4-amino-5-oxo-7,8-dihydropyrimido[5,4-f][1,4]oxazepin-6(5H)-yl)phenyl)-2-oxoimidazolidin-1-yl)propanoate A mixture of ethyl 3-(3-(2-chloro-4-(4-chloro-5-oxo-7,8-dihydropyrimido[5,4-f][1,4]oxazepin-6(5H)-yl)phenyl)-2-oxoimidazolidin-1-yl)propanoate 1i (240 mg, 253 umol) in 0.5 M ammonia in dioxane (10 mL) was stirred for 12 h. The reaction mixture was concentrated in vacuo to remove dioxane. The residue was added DCM (30 mL), washed with water (30 mL*2) and brine (30 mL*2), dried over Na₂SO₄, filtered and concentrated to afford the crude product ethyl 3-(3-(4-(4-amino-5-oxo-7,8-dihydropyrimido[5,4-f][1,4]oxazepin-6(5H)-yl)phenyl)-2-chlorophenyl)-2-oxoimidazolidin-1-yl)propanoate (170 mg, yellow solid) which was used in the next step directly.

¹H NMR (400 MHz, CDCl₃) δ 8.28 (s, 1H), 7.45 (d, 1H), 7.38 (d, 1H), 7.30 (dd, 1H), 4.68-4.66 (m, 2H), 4.16 (q, 2H), 3.99 (t, 2H), 3.77 (s, 2H), 3.69 (s, 2H), 3.61-3.55 (m, 4H), 2.62 (t, 2H), 1.27 (t, 3H)

Step 10

3-(3-(4-(4-amino-5-oxo-7,8-dihydropyrimido[5,4-f][1,4]oxazepin-6(5H)-yl)-2-chlorophenyl)-2-oxoimidazolidin-1-yl)propanoic acid A mixture of ethyl 3-(3-(4-(4-amino-5-oxo-7,8-dihydropyrimido[5,4-f][1,4]oxazepin-6(5H)-yl)-2-chlorophenyl)-2-oxoimidazolidin-1-yl)propanoate 1j (170 mg, 358 umol) in dioxane/H₂O (v/v=3/1.8 mL) was added LiOH.H₂O (45 mg, 1.07 mmol) was stirred for 12 h. The mixture was adjusted to pH=5~7 with 1 N aq HCl slowly. The mixture was concentrated and the residue was purified by prepare HPLC to afford 3-(3-(4-(4-amino-5-oxo-7,8-dihydropyrimido[5,4-f][1,4]oxazepin-6(5H)-yl)-2-chlorophenyl)-2-oxoimidazolidin-1-yl)propanoic acid 1 (120 mg, white solid), yield: 75.0%.

MS m/z (ESI): 477.0 [M+1]

¹H NMR (400 MHz, DMSO-d₆) δ 8.17 (s, 1H), 7.65-7.64 (br. s, 3H), 7.45 (d, 1H), 7.39 (dd, 1H), 4.63-4.60 (m, 2H), 4.01 (t, 2H), 3.72-3.68 (m, 2H), 3.52-3.48 (m, 2H), 3.40 (t, 2H) 2.49-2.78 (m, 2H)

Example 7

2-(3-(4-(4-amino-5-oxo-7,8-dihydropyrimido[5,4-f][1,4]oxazepin-6(5H)-yl)-2-(trifluoromethoxy)phenyl)-2-oxoimidazolidin-1-yl)acetic acid

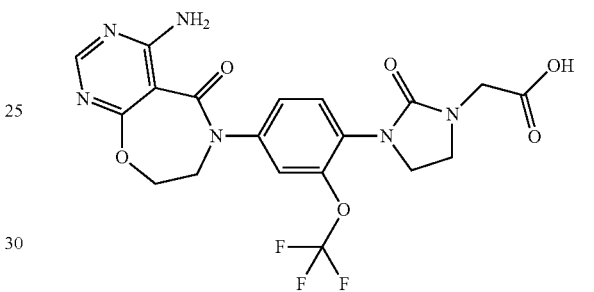

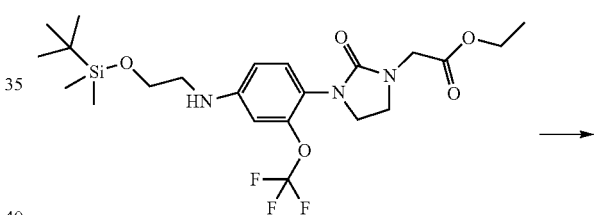

1a

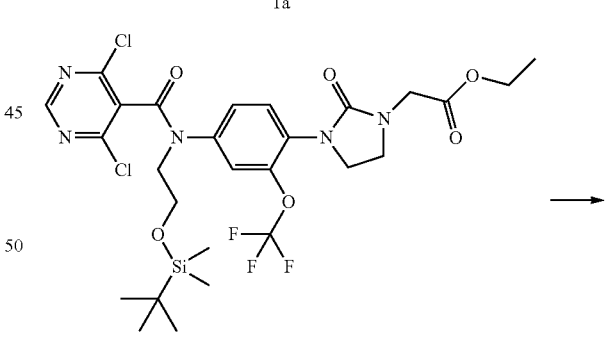

1b

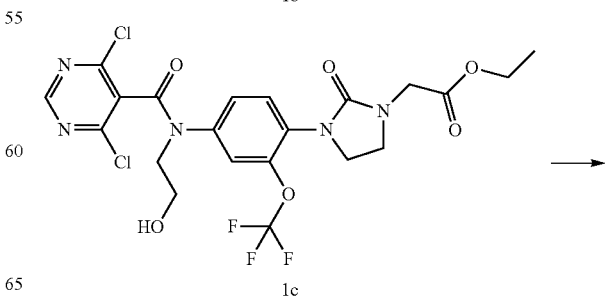

1c

-continued

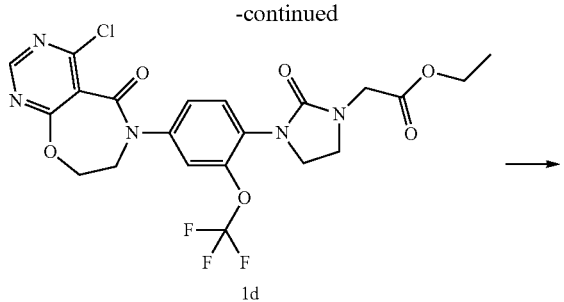

1d

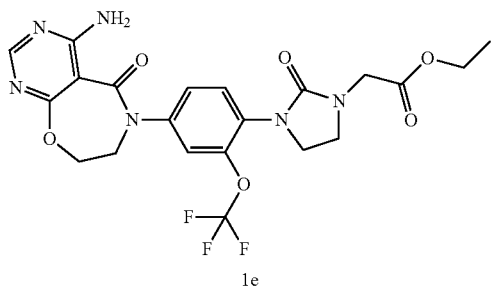

1e

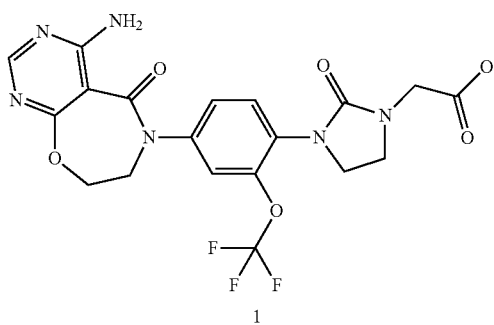

1

Step 1 ethyl 2-(3-(4-(N-(2-((tert-butyldimethylsilyl)oxy)ethyl)-4,6-dichloropyrimidine-5-carboxamido)-2-(trifluoromethoxy)phenyl)-2-oxoimidazolidin-1-yl)acetate To a solution ethyl 2-(3-(4-((2-((tert-butyldimethylsilyl)oxy)ethyl)amino)-2-(trifluoromethoxy)phenyl)-2-oxoimidazolidin-1-yl)acetate 1a (350 mg, 0.7 mmol) in DCM (10 mL) was added TEA (140 mg, 1.4 mmol) and 4,6-dichloropyrimidine-5-carbonyl chloride (220 mg, 1.5 mmol). Reaction mixture was stirred for 12 h. The mixture was added water (20 mL), extracted with DCM (20 mL*3), the combined organic layers were washed with brine (50 mL), dried over $Na_2SO_4$, filtered and concentrated to afford the crude product ethyl 2-(3-(4-(N-(2-((tert-butyldimethylsilyl)oxy)ethyl)-4,6-dichloropyrimidine-5-carboxamido)-2-(trifluoromethoxy)phenyl-2-oxoimidazolidin-1-yl)acetate 1b (170 mg, white solid) which was used in the next step directly.

$^1$H NMR (400 MHz, $CDCl_3$) δ 8.56 (s, 1H), 7.48 (d, 1H), 7.31-7.33 (m, 2H), 4.16 (q, 2H), 3.97 (s, 2H), 3.92-3.94 (m, 2H), 3.85-3.87 (m, 2H), 3.76 (t, 2H), 3.55 (t, 2H), 1.21 (t, 3H), 0.81 (s, 9H), 0.00 (s, 6H)

Step 2 ethyl 2-(3-(4-(4,6-dichloro-N-(2-hydroxyethyl)pyrimidine-5-carboxamido)-2-(trifluoromethoxy)phenyl)-2-oxoimidazolidin-1-yl)acetate To a solution of ethyl 2-(3-(4-(N-(2-((tert-butyldimethylsilyl)oxy)ethyl)-4,6-dichloropyrimidine-5-carboxamido)-2-(trifluoromethoxy)phenyl)-2-oxoimidazolidin-1-yl)acetate 1b (170 mg, 0.28 mmol) in EtOH (10 mL) was added HCl (con, 0.3 ml). The reaction mixture was stirred for 2 h. The mixture was added saturated $NaHCO_3$ solution to adjusted pH>7, extracted with DCM (10 mL*3), the combined organic layers were washed with water (5 mL*2) and brine (5 mL*2), dried over $Na_2SO_4$, filtered and concentrated to afford the crude product ethyl 2-(3-(4-(4,6-dichloro-N-(2-hydroxyethyl)pryimidine-5-carboxamido)-2-(trifluoromethyl)phenyl)-2-oxoimidazolidin-1-yl)acetate 1c (140 mg, yellow solid) which was used in the next step directly.

$^1$H NMR (400 MHz, $CDCl_3$) δ 8.65 (s, 1H), 7.57 (d, 1H), 7.37-7.42 (m, 2H), 4.22 (q, 2H), 4.06-4.09 (m, 2H), 4.04 (s, 2H), 3.93-3.96 (m, 2H), 3.85 (t, 2H), 3.61 (t, 2H) 1.27 (t, 3H)

Step 3 ethyl 2-(3-(4-(4-chloro-5-oxo-7,8-dihydropyrimido[5,4-f][1,4]oxazepin-6(5H)-yl)phenyl)-2-(trifluoromethoxy)phenyl)-2-oxoimidazolidin-1-yl)acetate A mixture of ethyl 2-(3-(4-(4,6-dichloro-N-(2-hydroxyethyl)pryimidine-5-carboxamido)-2-(trifluoromethoxy)phenyl)-2-oxoimidazolidin-1-yl-acetate 1c (140 mg, 0.25 mmol) in MeCN (10 mL) was added TEA (75 mg, 0.75 mmol) stirred for at 80° C. 12 h. The reaction mixture was added water (40 mL), extracted with EA (20 mL*3), the combined organic layers were washed with brine (100 mL), dried over $Na_2SO_4$, filtered and concentrated to afford the crude product ethyl 2-(3-(4-(4-chloro-5-oxo-7,8-dihydropyrimido[5,4-f][1,4]oxazepin-6(5H)-yl)-2-(trifluoromethoxy)phenyl)-2-oxoimidazolidin-1-yl)acetate 1d (130 mg, yellow oil) which was used in the next step directly.

$^1$H NMR (400 MHz, $CDCl_3$) δ 8.79 (s, 1H), 7.67 (d, 1H), 7.31-7.39 (m, 2H), 4.76 (t, 2H), 4.25 (q, 2H), 4.04-4.21 (m, 5H), 3.91 (t, 2H), 3.68 (t, 2H), 1.27 (t, 3H)

Step 4 ethyl 2-(3-(4-(4-amino-5-oxo-7,8-dihydropyrimido[5,4-f][1,4]oxazepin-6(5H)-yl)-2-(trifluoromethoxy)phenyl)-2-oxoimidazolidin-1-yl)acetate A mixture of ethyl 2-(3-(4-(4-chloro-5-oxo-7,8-dihydropyrimido[5,4-f][1,4]oxazepin-6(5H)-yl)-2-(trifluoromethoxy)phenyl)-2-oxoimidazolidin-1-yl)acetate 1d (130 mg, 0.25 mmol) in saturated in ammonia in dioxane (5 mL) was stirred for 12 h. The reaction mixture was added water (20 mL), extracted with EA (20 mL*3), the combined organic layers were washed with brine (100 mL), dried over Na$_2$SO$_4$, filtered and concentrated. The residue was purified by prepare TLC to afford the crude product ethyl 2-(3-(4-(4-amino-5-oxo-7,8-dihydropyrimido[5,4-f][1,4]oxazepin-6(5H)-yl)-2-trifluoromethoxy)phenyl)-2-oxoimidazolidin-1-yl)acetate 1e (80 mg, yellow solid), yield: 64.0%.

$^1$H NMR (400 MHz, CD$_3$OD) δ 8.15 (s, 1H), 7.57 (d, 1H), 7.49 (s, 1H), 7.41 (dd, 1H), 4.70-4.72 (m, 2H), 4.22 (q, 2H), 4.07-4.09 (m, 2H), 3.86-3.91 (m, 2H), 3.69-3.71 (m, 2H) 3.30 (s, 2H), 1.28 (t, 3H)

Step 5

2-(3-(4-(4-amino-5-oxo-7,8-dihydropyrimido[5,4-f][1,4]oxazepin-6(5H)-yl)-2-(trifluoromethoxy)phenyl)-2-oxoimidazolidin-1-yl)acetic acid A mixture of ethyl 3-(3-(4-(4-amino-5-oxo-7,8-dihydropyrimido[5,4-f][1,4]oxazepin-6(5H)-yl-2-(trifluoromethoxy)phenyl)-2-oxoimidazolidin-1-yl)acetate 1e (80 mg, 0.15 mmol) in dioxane/H$_2$O (v/v=3/1, 4 mL) was added LiOH.H$_2$O (50 mg, 1.25 mmol) was stirred for 12 h. The mixture was adjusted to pH<5 with 1 N aq HCl slowly, extracted with EA (10 mL*3), the combined organic layers were washed with water (5 mL*2) and brine (5 mL*2), dried over Na$_2$SO$_4$, filtered and concentrated. The residue was purified by prepare HPLC to afford 2-(3-(4-(4-amino-5-oxo-7,8-dihydropyrimido[5,4-f][1,4]oxazepin-6(5H)-yl)-2-(trifluoromethoxy)phenyl)-2-oxoimidazolidin-1-yl)acetic acid 1 (28 mg, white solid), yield: 37.3%.

$^1$H NMR (400 MHz, CD$_3$OD) δ 8.55 (s, 2H), 8.34 (s, 1H), 7.40-7.55 (m, 3H), 4.75 (t, 2H), 4.10 (t, 2H), 3.89 (s, 2H), 3.72-3.77 (m, 4H)

Example 8

4-amino-6-(3-chloro-4-(2-oxo-3-(2,2,2-trifluoroethyl)imidazolidin-1-yl)phenyl)-7,8-dihydropyrimido[5,4-f][1,4]oxazepin-5(6H)one

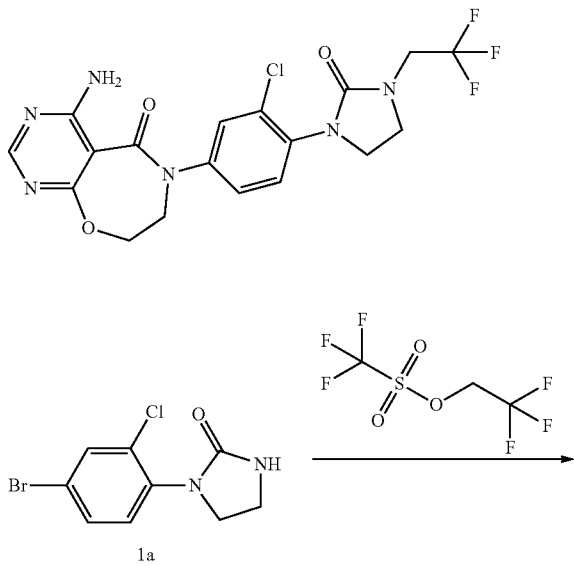

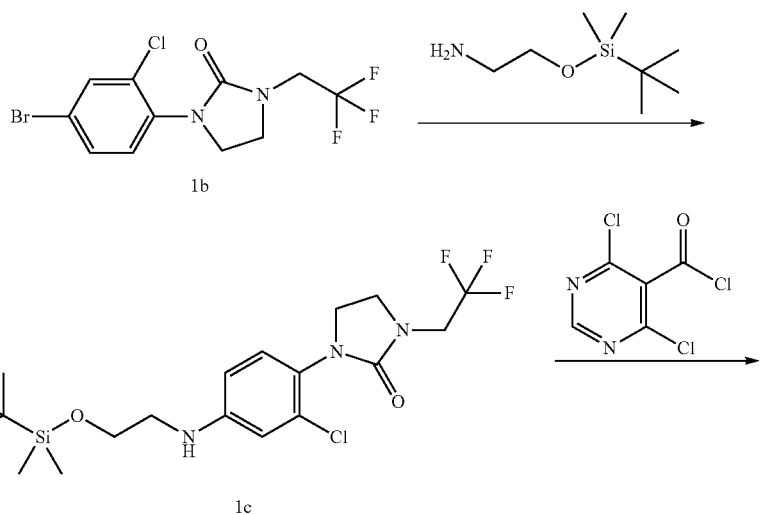

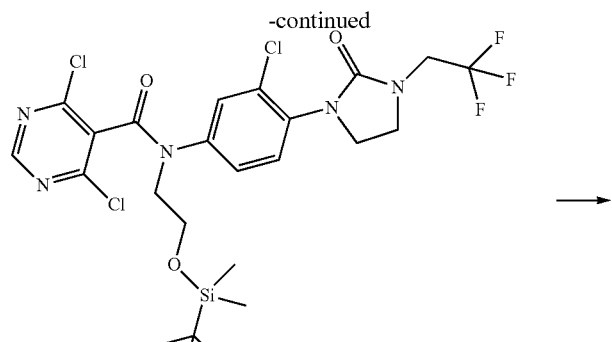

1d

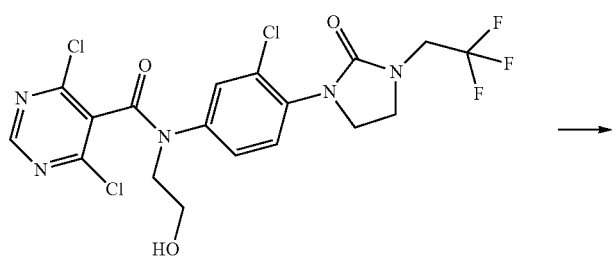

1e

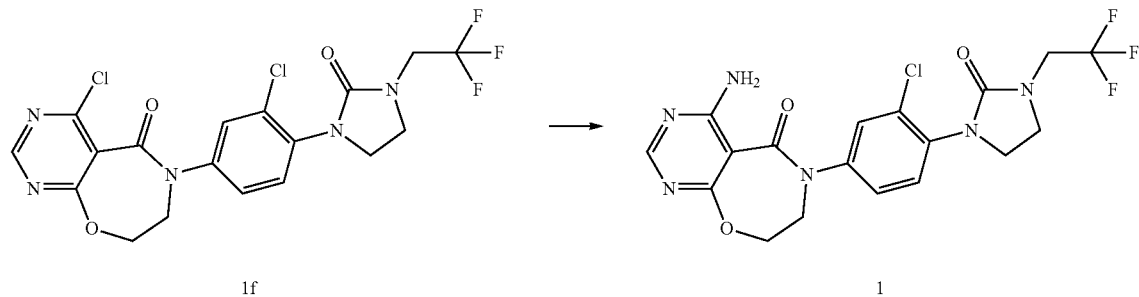

1f                                    1

Step 1

1-(4-bromo-2-chlorophenyl)-3-(2,2,2-trifluoroethyl)imidazolidin-2-one

To a solution of 1-(4-bromo-2-chlorophenyl)imidazolidin-2-one (1.00 g, 3.63 mmol) in DMF (20 mL, dry) was added NaH (217 mg, 5.44 mmol). The mixture was stirred for 30 min. 2,2,2-trifluoroethyl trifluoromethanesulfonate (1.26 g, 5.44 mmol) was added to such above solution. Reaction mixture was stirred for 12 h. The mixture was added H₂O (20 mL*2) extracted with EA (20 mL*2), the organic layers were combined. The mixture was washed with H₂O (50 mL), sat aq NaCl (20 mL*2), dried over Na₂SO₄. Filtered and filtrate was concentrated to give the crude product. The residue was purified by silica column (Eluent C) to afford 1-(4-bromo-2-chlorophenyl)-3-(2,2,2-trifluoroethyl)imidazolidin-2-one (500 mg, 38.5%) as a white solid, yield: 38.5%.

$^{1}$H NMR (400 MHz, CDCl₃) δ 7.60 (d, 1H), 7.42 (dd, 1H), 7.24 (d, 1H), 3.90-3.80 (m, 4H), 3.69-3.65 (m, 2H)

Step 2

1-(4-((2-((tert-butyldimethylsilyl)oxy)ethyl)amino-2-chlorophenyl)-3-(2,2,2-trifluoroethyl)imidazolidin-2-one To a solution of 1-(4-bromo-2-chlorophenyl)-3-(2,2,2-trifluoroethyl)imidazolidin-2-one (500 mg, 1.40 mmol) in toluene (10 mL, dry) was added (2-((tert-butyldimethylsilyl)oxy)ethanamine (367 mg, 2.10 mmol), Cs₂CO₃ (1.30 g, 4.20 mmol), x-phos (40 mg, 0.07 mmol), Pd₂(dba)₃ (50 mg, 0.07 mmol). Reaction mixture was stirred at 100° C. for 12 h. The mixture cooled to room temperature. Then the mixture was diluted with water (30 mL), extracted with DCM (30 mL*3), the organic layers were combined. The mixture was washed with H2O (30 mL*2), sat aq NaCl (30 mL*2), dried over Na₂SO₄, filtered and filtrate was concentrated. Crude product was purified by silica column (Eluent C) to afford 1-(4-((2-((tert-butyldimethylsilyl)oxy)ethyl)amino)-2-chlorophenyl)-3-(2,2,2-trifluoroethyl)imidazolidin-2-one (420 mg) as a yellow oil, yield: 64.0%.

¹H NMR (400 MHz, CDCl₃) δ 7.08 (d, 1H), 6.64 (d, 1H), 6.43 (dd, 1H), 3.84 (q, J=9.2 Hz, 2H), 3.78 (t, 2H), 3.75-3.71 (m, 2H), 3.62-3.58 (m, 2H), 3.16 (q, 2H), 0.88 (s, 9H), 0.05 (s, 6H)

Step 3

N-(2-((tert-butyldimethylsilyl)oxy)ethyl)-4,6-dichloro-N-(3-chloro-4-(2-oxo-3-(2,2,2-trifluoroethyl)imidazolidin-1-yl)phenyl)pyrimidine-5-carboxamide To a solution of 1-(4-((2-((tert-butyldimethylsilyl)oxy)ethyl)amino)-2-chlorophenyl)-3-(2,2,2-trifluoroethyl)imidazolidin-2-one (420 mg, 929 umol) in DCM (5 mL) was added TEA (400 uL, 2.80 mmol), compound of 4,6-dichloropyrimidine-5-carbonyl chloride (393 mg, 1.80 mmol) was added to above solution. Reaction mixture was stirred for 12 h. The mixture was added water (20 mL), and extracted with DCM (30 mL*3), the organic layers were combined and washed with H2O (20 mL*2), sat aq NaCl (20 mL*2), dried over Na₂SO₄. Filtered and filtrate was concentrated to afford N-(2-((tert-butyldimethylsilyl)oxy)ethyl)-4,6-dichloro-N-(3-chloro-4-(2-oxo-3-(2,2,2-trifluoroethyl)imidazolidin-1-yl)phenyl)pyrimidine-5-carboxamide (582 mg) as a crude product which used in the next step directly.

Step 4

4,6-dichloro-N-(3-chloro-4-(2-oxo-3-(2,2,2-trifluoroethyl)imidazolidin-1-yl)phenyl)-N-(2-hydroxyethyl)pyrimidine-5-carboxamide To a solution of N-(2-((tert-butyldimethylsilyl)oxy)ethyl)-4,6-dichloro-N-(3-chloro-4-(2-oxo-3-(2,2,2-trifluoroethyl)imidazolidin-1-yl)phenyl)pyrimidine-5-carboxamide (582 mg, 928 umol) in EtOH (10 mL, dry) was added HCl (con. 0.3 ml). Reaction mixture was stirred for 1 h. The mixture was diluted with water (10 mL), extracted with DCM (10 mL*3), Combined organic layers and washed with H₂O (10 mL*2), sat aq NaCl (10 mL*2), dried over Na₂SO₄. Filtered and filtrate was concentrated to afford 4,6-dichloro-N-(3-chloro-4-(2-oxo-3-(2,2,2-trifluoroethyl)imidazolidin-1-yl)phenyl)-N-(2-hydroxyethyl)pyrimidine-5-carboxamide (475 mg, yellow solid) a crude product which used in the next step directly.

Step 5

4-chloro-6-(3-chloro-4-(2-oxo-3-(2,2,2-trifluoroethyl)imidazolidin-1-yl)phenyl)-7,8-dihydropyrimido[5,4-f][1,4]oxazepin-5(6H)-yl)one A mixture of 4,6-dichloro-N-(3-chloro-4-(2-oxo-3-(2,2,2-trifluoroethyl)imidazolidin-1-yl)phenyl-N-(2-hydroxyethyl)pyrimidine-5-carboxamide (475 mg, 926 umol) and TEA (40 uL, 2.80 mmol) in MeCN (5 mL) was stirred for at 80° C. 12 h. The mixture was cooled to room temperature and extracted with DCM (10 mL*3). Combined organic layers and washed with water (10 mL*2) sat aq NaCl (10 mL*2), dried over Na₂SO₄. Filtered and filtrate concentrated to afford (410 mg, yellow solid) as a crude product winch used in the next step directly.

¹H NMR (400 MHz, CDCl₃) δ 8.77 (s, 1H), 7.51 (d, 1H), 7.48 (d, 1H), 7.32 (dd, J=8.4 Hz, 1H), 4.75 (t, 2H), 4.04 (t, 2H), 3.90-3.84 (m, 4H), 3.72-3.68 (m, 2H)

Step 6

4-amino-6-(3-chloro-4-(2-oxo-3-(2,2,2-trifluoroethyl)imidazolidin-1-yl)phenyl)-7,8-dihydropyrimido[5,4-f][1,4]oxazepin-5(6H)-one A solution of 4-chloro-6-(3-chloro-4-(2-oxo-3-(2,2,2-trifluoroethyl)imidazolidin-1-yl)phenyl)-7,8-dihydropyrimido[5,4-f][1,4]oxazepin-5(6H)-one (410 mg, 860 umol) in 0.5 M ammonia in dioxane (10 mL) was stirred for 12 h. The reaction mixture was concentrated in vacuo to remove dioxane. The residue was purified by prep HPLC to give 4-amino-6-(3-chloro-4-(2-oxo-3-(2,2,2-trifluoroethyl)imidazolidin-1-yl)phenyl)-7,8-dihydropyrimido[5,4-f][1,4]oxazepin-5(6H)-one (135 mg, white solid), yield: 34.3%.

MS m/z (ESI): 456.9 [M+1]

¹H NMR (400 MHz, DMSO-d6) δ 8.59 (br, 1H), 8.42 (br.s, 1H), 8.36 (s, 1H), 7.68 (d, 1H), 7.49 (d, 1H), 7.41 (dd, 1H), 4.77 (t, 2H), 4.11 (t, 2H), 4.00 (q, 2H), 3.79-3.75 (m, 2H), 3.64-3.60 (m, 2H)

Example 9

4-amino-6-(3,5-dimethyl-4-(2-oxo-3-(2,2,2-trifluoroethyl)-2,3-dihydro-1H-benzo[d]imidazol-1-yl)phenyl)-7,8-dihydropyrimido[5,4-f][1,4]oxazepin-5(6H)-one

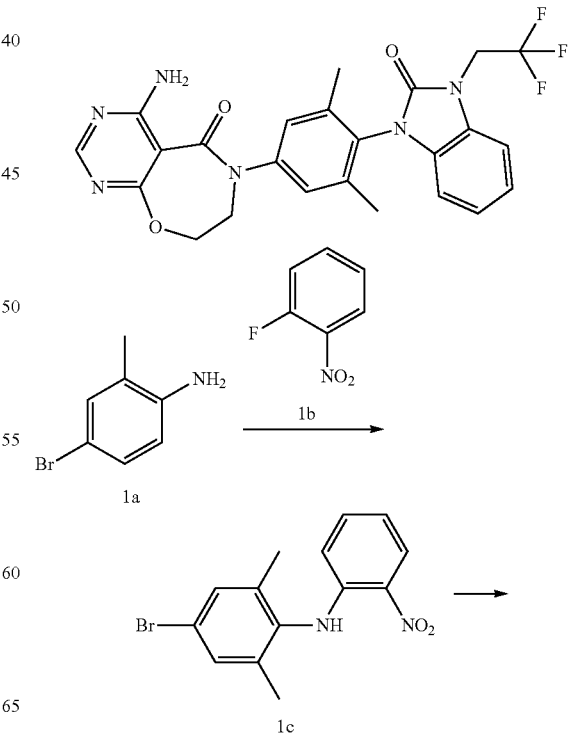

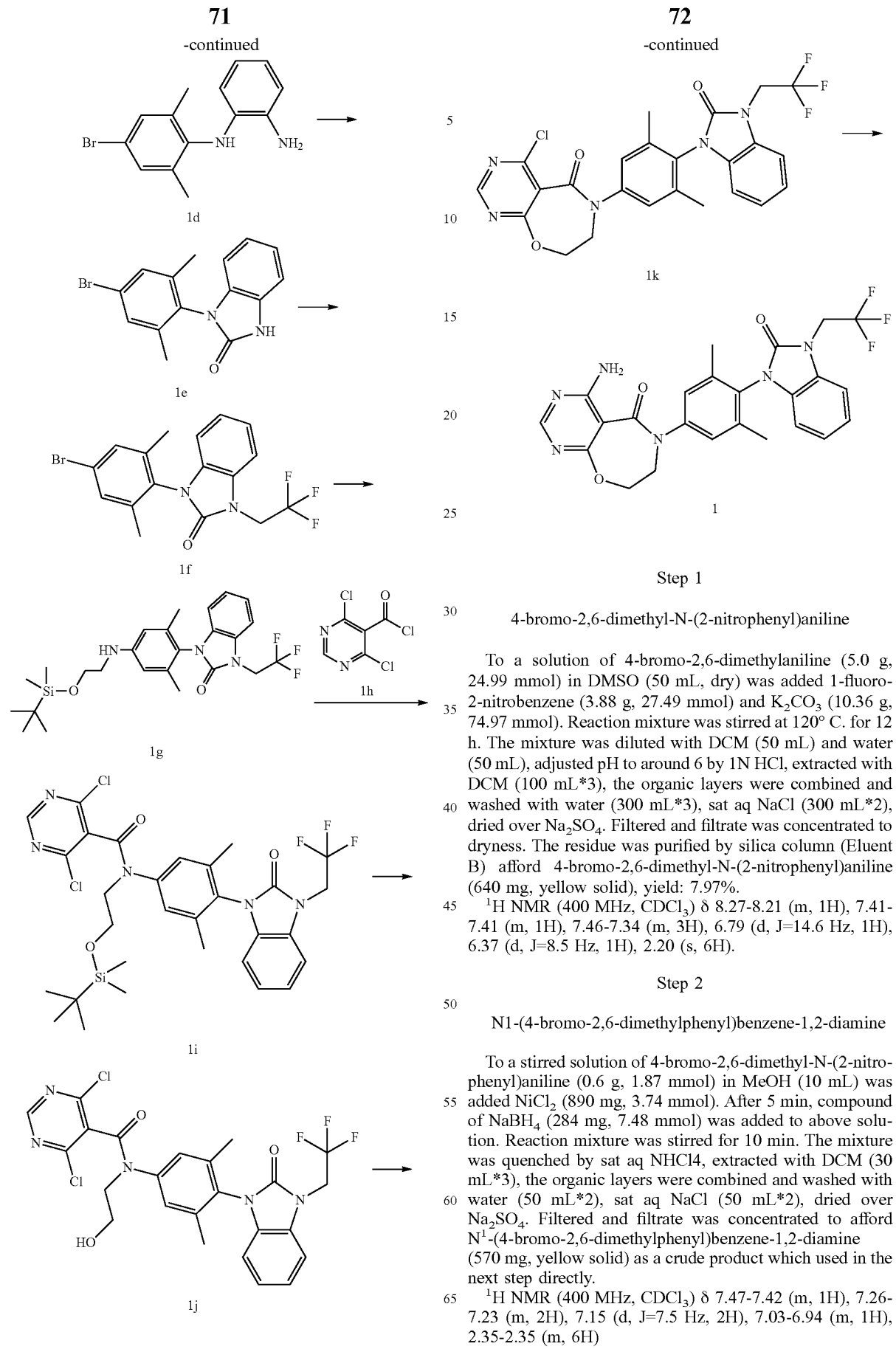

Step 1

4-bromo-2,6-dimethyl-N-(2-nitrophenyl)aniline

To a solution of 4-bromo-2,6-dimethylaniline (5.0 g, 24.99 mmol) in DMSO (50 mL, dry) was added 1-fluoro-2-nitrobenzene (3.88 g, 27.49 mmol) and $K_2CO_3$ (10.36 g, 74.97 mmol). Reaction mixture was stirred at 120° C. for 12 h. The mixture was diluted with DCM (50 mL) and water (50 mL), adjusted pH to around 6 by 1N HCl, extracted with DCM (100 mL*3), the organic layers were combined and washed with water (300 mL*3), sat aq NaCl (300 mL*2), dried over $Na_2SO_4$. Filtered and filtrate was concentrated to dryness. The residue was purified by silica column (Eluent B) afford 4-bromo-2,6-dimethyl-N-(2-nitrophenyl)aniline (640 mg, yellow solid), yield: 7.97%.

$^1$H NMR (400 MHz, $CDCl_3$) δ 8.27-8.21 (m, 1H), 7.41-7.41 (m, 1H), 7.46-7.34 (m, 3H), 6.79 (d, J=14.6 Hz, 1H), 6.37 (d, J=8.5 Hz, 1H), 2.20 (s, 6H).

Step 2

N1-(4-bromo-2,6-dimethylphenyl)benzene-1,2-diamine

To a stirred solution of 4-bromo-2,6-dimethyl-N-(2-nitrophenyl)aniline (0.6 g, 1.87 mmol) in MeOH (10 mL) was added $NiCl_2$ (890 mg, 3.74 mmol). After 5 min, compound of $NaBH_4$ (284 mg, 7.48 mmol) was added to above solution. Reaction mixture was stirred for 10 min. The mixture was quenched by sat aq NHCl4, extracted with DCM (30 mL*3), the organic layers were combined and washed with water (50 mL*2), sat aq NaCl (50 mL*2), dried over $Na_2SO_4$. Filtered and filtrate was concentrated to afford $N^1$-(4-bromo-2,6-dimethylphenyl)benzene-1,2-diamine (570 mg, yellow solid) as a crude product which used in the next step directly.

$^1$H NMR (400 MHz, $CDCl_3$) δ 7.47-7.42 (m, 1H), 7.26-7.23 (m, 2H), 7.15 (d, J=7.5 Hz, 2H), 7.03-6.94 (m, 1H), 2.35-2.35 (m, 6H)

Step 3

1-(4-bromo-2,6-dimethylphenyl)-1H-benzo[d]imidazol-2(3H)-one

To a solution of $N^1$-(4-bromo-2,6-dimethylphenyl)benzene-1,2-diamine (400 mg, 1.38 mmol) in THF (10 mL) was added TEA (400 mg, 1.38 mmol) and CDI (894 g, 5.52 mmol). Reaction mixture was stirred at 80° C. for 12 h. The mixture was diluted with water (30 mL), extracted with DCM (30 mL*3), the organic layers were combined and washed with water (50 mL*2), sat aq NaCl (300 mL*2), dried over $Na_2SO_4$. Filtered and filtrate evaporated to dryness. The residue was purified by silica column (Eluent B) to afford 1-(4-bromo-2,6-dimethylphenyl)-1H-benzo[d]imidazol-2-(3H)-one (360 mg, yellow solid).

$^1$H NMR (400 MHz, $CDCl_3$) δ 7.72 (d, J=2.0 Hz, 1H), 7.70 (m, 1H), 7.48-7.45 (m, 1H), 7.16-7.10 (m, 2H), 7.06-7.03 (m, 1H), 6.70-6.07 (m, 1H)

Step 4

1-(4-bromo-2,6-dimethylphenyl)-3-(2,2,2-trifluoroethyl)-1H-benzo[d]imidazol-2(3H)-one To a solution of 1-(4-bromo-2,6-dimethylphenyl)-1H-benzo[d]imidazol-2(3H)-one (360 mg, 1.1 mmol) in DMF (5 mL) was added $Cs_2CO_3$ (715 mg, 2.2 mmol) and 2,2,2-trifluoroethyltrifluoromethanesulfonate (528.6 mg, 2.2 mmol). Reaction mixture was stirred for 12 h. The mixture was quenched by water (20 mL) and extracted with EtOAc (20 mL*3). The organic layers were combined and washed with water (60 ml*3), sat aq NaCl (60 mL*2) and dried over $Na_2SO_4$. Filtered and filtrate was concentrated and purified by prep TLC (Eluent B) to give 1-(4-bromo-2,6-dimethylphenyl)-3-(2,2,2-trifluoroethyl)-1H-benzo[d]imidazol-2(3H)-one (420 mg, yellow solid), yield: 95.9%.

$^1$H NMR (400 MHz, $CDCl_3$) δ 7.39 (s, 2H), 7.14-7.24 (m, 4H), 4.55-4.61 (m, 2H), 2.05-2.08 (m, 6H).

Step 5

1-(4-((2-((tert-butyldimethylsilyl)oxy)ethyl)amino)-2,6-dimethylphenyl)-3-(2,2,2-trifluoroethyl)-1H-benzo[d]imidazol-2(3H)-one A mixture of 1-(4-bromo-2,6-dimethylphenyl)-3-(2,2,2-trifluoroethyl)-1H-benzo[d]imidazol-2(3H)-one (0.4 g, 1.01 mmol), 2-((tert-butyldimethylsilyl)oxy)ethanamine (299 mg, 1.71 mmol), $Cs_2CO_3$ (656.5 g, 2.02 mmol), x-phos (15 mg) and $Pd_2(dba)_3$ (15 mg) in toluene (10 ml) was stirred for 12 h at 100° C. The mixture was cooled to room temperature. The mixture was added $H_2O$ (30 mL), and extracted with EtOAc (50 mL*3) The organic layers were combined and washed with water (50 mL*2), sat aq NaCl (50 mL*2), and dried over $Na_2SO_4$. Filtered and filtrate was concentrated. The crude product was purified by silica column (Eluent C) to give 1-(4-((2-((tert-butyldimethylsilyl)oxy)ethyl)amino)-2,6-dimethylphenyl)-3-(2,2,2-trifluoroethyl)-1H-benzo[d]imidazol-2(3H)-one (30 mg, pale yellow oil), yield: 6.06%.

MS m/z: (ESI): 494.2 [M+1]

Step 6

N-(2-((tert-butyldimethylsilyl)oxy)ethyl)-4,6-dichloro-N-(3,5-dimethyl-4-(2-oxo-3-(2,2,2-trifluoroethyl)-2,3-dihydro-1H-benzo[d]imidazol-1-yl)phenyl)pyrimidine-5-carboxamide To a solution of 1-(4-((2-(((tert-butyldimethylsilyl)oxy)ethyl)amino-2,6-dimethylphenyl)-3-(2,2,2-trifluoroethyl)-1H-benzo[d]imidazol-2(3H)-one (20 mg, 0.04 mmol) and TEA (8.08 g, 0.08 mmol) in DCM (2 ml, dry) was added 4,6-dichloropyrimidine-5-carbonyl chloride (17 mg, 0.08 mmol). The mixture was stirred for 3 h. The reaction was diluted with water (20 ml), extracted with DCM (30 mL*3), the organic layers were combined and washed with water (30 mL*2), sat aq NaCl (30 mL*2), dried over $Na_2SO_4$ and evaporated to afford N-(2-((tert-butyldimethylsilyl)oxy)ethyl)-4,6-dichloro-N-(3,5-dimethyl-4-(2-oxo-3-(2,2,2-trifluoroethyl)-2,3-dihydro-1H-benzo[d]imidazol-1-yl)phenyl)pyrimidine-5-carboxamide (40 mg, yellow solid) as a crude product used for next step reaction.

$^1$H NMR (400 MHz, $CDCl_3$) δ 8.85 (s, 12H), 7.30 (s, 2H), 7.13-7.22 (m, 3H), 7.07 (t, 1H), 4.54 (q, 2H), 4.10-4.18 (m, 2H), 3.96-4.05 (m, 2H), 2.01 (s, 6H), 0.87-0.96 (m, 9H), 0.08-0.08 (m, 1H), 0.07 (s, 6H).

Step 7

4,6-dichloro-N-(3,5-dimethyl-4-(2-oxo-3-(2,2,2-trifluoroethyl)-2,3-dihydro-1H-benzo[d]imidazol-1-yl)phenyl)-N-(2-hydroxyethyl)pyrimidine-5-carboxamide To a solution of N-(2-((tert-butyldimethylsilyl)oxy)ethyl)-4,6-dichloro-N-(3,5-dimethyl-4-(2-oxo-3-(2,2,2-trifluoroethyl)-2,3-dihydro-1H-benzo[d]imidazol-1-yl)phenyl)pyrimidine-5-carboxamide (40 mg, 0.06 mmol) in EtOH (3 ml) was added HCl (con, 0.09 ml). The mixture was stirred for 1 h. The reaction was diluted with water (10 ml), adjusted pH to around 6-7, extracted with DCM (20 mL*3), the organic layers were combined and washed with sat aq NaCl (50 ml*2), dried over $Na_2SO_4$ and evaporated to afford 4,6-dichloro-N-(3,5-dimethyl-4-(2-oxo-3-(2,2,2-trifluoroethyl)-2,3-dihydro-1H-benzo[d]imidazol-1-yl)phenyl)-N-(2-hydroxyethyl)pyrimidine-5-carboxamide (30 mg, yellow solid) as a crude product used for next step reaction directly.

$^1$H NMR (400 MHz, $CDCl_3$) δ 8.87-8.83 (m, 1H), 8.68 (s, 1H), 7.30 (s, 5H), 7.22-7.02 (m, 1H), 4.58-4.49 (m, 2H), 4.16-4.10 (m, 2H), 4.02-3.97 (m, 2H), 2.01 (s, 6H).

Step 8

4-chloro-6-(3,5-dimethyl-4-(2-oxo-3-(2,2,2-trifluoroethyl)-2,3-dihydro-1H-benzo[d]imidazol-1-yl)phenyl)-7,8-dihydropyrimido[5,4-f][1,4]oxazepin-5(6H)-yl)-one A mixture of 4,6-dichloro-N-(3,5-dimethyl-4-(2-oxo-3-(2,2,2-trifluoroethyl)-2,3-dihydro-1H-benzo[d]imidazol-1-yl)phenyl)-N-(2-hydroxyethyl)pyrimidine-5-carboxamide (30 mg, 0.05 mmol) and TEA (15 mg, 0.15 mmol) in MeCN (3 ml) was stirred for 12 h at 80° C. The mixture was adjusted pH to 7-8 with sat aq $NaHCO_3$, extracted with DCM (20 mL*3), combined organic layers and washed with H₂O (50 mL*2), sat aq NaCl (50 mL*2) dried over Na₂SO₄. Filtered and filtrate was concentrated to afford 4-chloro-6-(3,5-dimethyl-4-(2-oxo-3-(2,2,2-trifluoroethyl)-2,3-dihydro-1H-benzo[d]imidazol-1-yl)phenyl)-7,8-dihydropyrimido[5,4-f][1,4]oxazepin-5(6H)-one (30 mg, yellow solid) as a crude product which used in the next step directly.

MS m/z (ESI): 518.0 [M+1]

Step 9

4-amino-6-(3,5-dimethyl-4-(2-oxo-3-(2,2,2-trifluoroethyl)-2,3-dihydro-1H-benzo[d]imidazol-1-yl)phenyl)-7,8-dihydropyrimido[5,4-f][1,4]oxazepin-5(6H)-one A solution of 4-chloro-6-(3,5-dimethyl-4-(2,2,2-trifluoroethyl)-2,3-dihydro-1H-benzo [d]imidazol-1-yl)phenyl-7,8-dihydropyrimido[5,4-f][1,4]oxazepin-5(6H)-one (30 mg, 0.058 mmol) in 0.5 M ammonia in dioxane (5 mL) was stirred for 12 h. The reaction mixture was concentrated in vacuum to remove dioxane. The residue was extracted with DCM (20 mL*3), Combined organic layers and washed with water (30 mL*2), dried over Na₂SO₄, Filtered and filtrate was concentrated. The residue was purified by prep HPLC to give 4-amino-6-(3,5-dimethyl-4-(2-oxo-3-(2,2,2-trifluoroethyl)-2,3-dihydro-1H-benzo[d]imidazol-yl)phenyl)-7,8-dihydropyrimido[5,4-f][1,4]oxazepin-5(6H)-one (2.3 mg, white solid), yield 7.9%.

MS m/z (ESI): 499.2 [M+1]

¹H NMR (400 MHz, MeOD) δ 8.42 (s, 1H), 7.40 (m, 1H), 7.35 (s, 21H), 7.25 (m, 1H), 7.15 (m, 1H), 6.70 (m, 1H), 5.15 (m, 2H), 4.70 (m, 2H), 4.28 (m, 2H) 2.13 (s, 6H).

Example 10

2-(3-(4-(4-amino-5-oxo-7,8-dihydropyrimido[5,4-f][1,4]oxazepin-6(5H)-yl)phenyl)-2-oxo-2,3-dihydro-1H-imidazolidin-1-yl)acetic acid

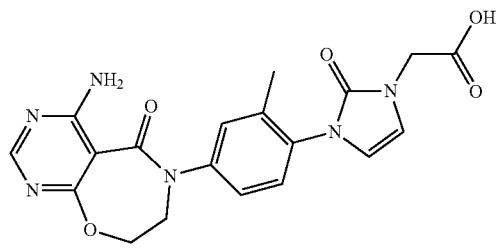 [SMILES: Nc1ncnc2c1C(=O)N(c1ccc(-n3ccn(CC(=O)O)c3=O)cc1)CCO2]

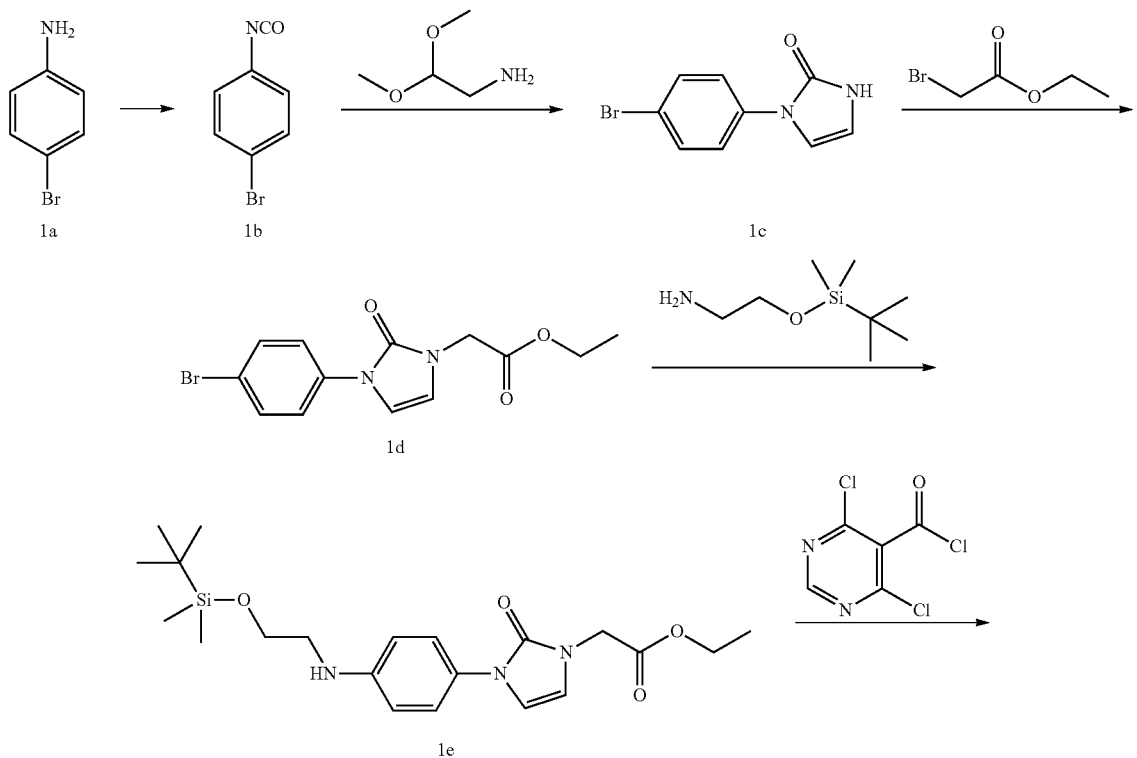

-continued

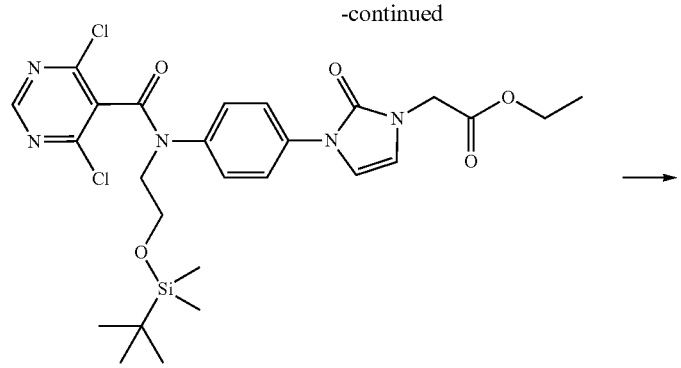

1f

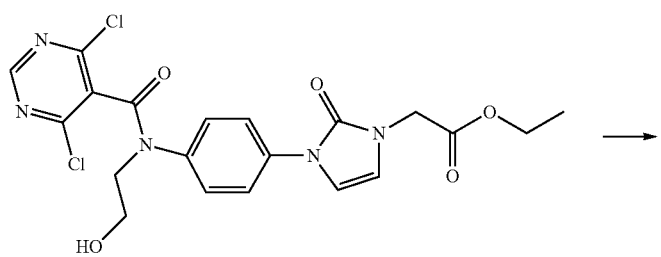

1g

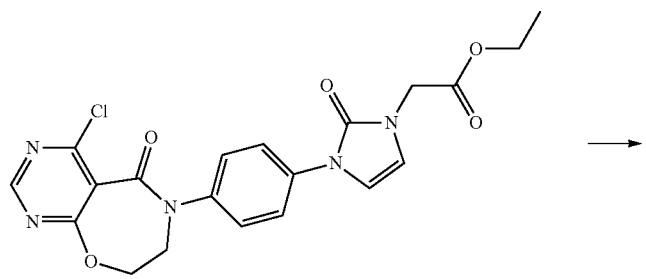

1h

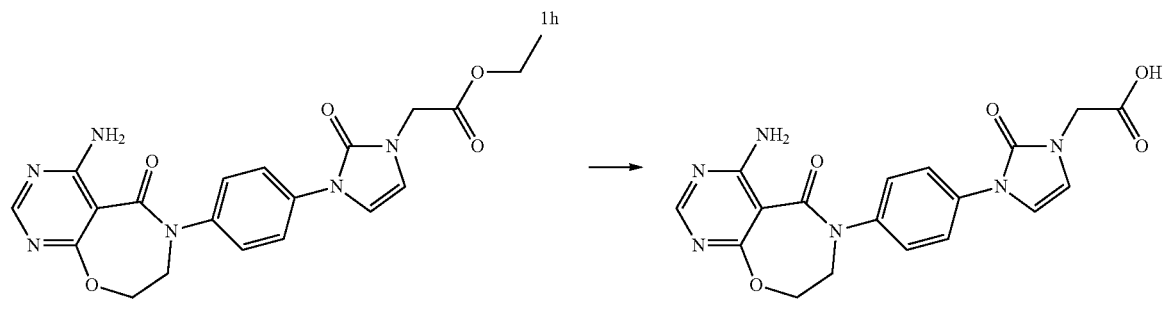

1i                                                                 1

Step 1

1-bromo-4-isocyanatobenzene

To a solution of 4-bromoaniline (5.0 g, 29.07 mmol) in THF (200 mL) was added triphosgene (2.90 g, 9.69 mmol). The mixture was stirred for 3 h. The reaction mixture was evaporated to afford 1-bromo-4-isocyanatobenzene (5.70 g, white solid). Used in the next step directly.

Step 2

1-(4-bromophenyl)-1H-imidazol-2(3H)-one

To a solution of 1-bromo-4-isocyanatobenzene (5.70 g, 28.79 mmol) in THF (150 mL) was added 2,2-dimethoxy-ethanamine (4.54 g, 42.80 mmol). The mixture was stirred for 12 h. Then reaction mixture was diluted with water (200 mL), extracted with EA (200 mL*3), the organic layers were combined and washed with water (100 mL*2), sat aq NaCl ((100 mL*2), dried over Na$_2$SO$_4$. Filtered and filtrate was concentrated. The residue was purified by silica column (Eluent C) to afford 1-(4-bromophenyl)-1H-imidazol-2(3H)-one (2.20 g, white solid), yield: 31.9%.

$^1$H NMR (400 MHz, CDCl$_3$) δ 7.72-7.68 (m, 2H), 7.59-7.55 (m, 2H), 6.98-6.96 (m, 1H), 6.60-6.58 (m, 1H)

Step 3

Ethyl 2-(3-(4-bromophenyl)-2-oxo-2,3-dihydro-1H-imidazol-1-yl)acetate

To a solution of 1-(4-bromophenyl)-1H-imidazol-2(3H)-one (1.10 g, 4.60 mmol) in DMF (25 mL, dry) was added NaH (1.92 g, 6.9 mmol). The mixture was stirred for 0.5 h. Compound of ethyl 2-bromoacetate (220 mg, 9.20 mmol) was added to such above solution. Reaction mixture was stirred for 12 h. The mixture was quenched by water (50 mL), extracted with EA (50 mL*3), the organic layers were combined wand washed with water (50 mL*2), sat aq NaCl (50 mL*2), dried over Na$_2$SO$_4$. Filtered and filtrate was concentrated. The residue was purified by silica column (Eluent C) to afford ethyl 2-(3-(4-bromophenyl)-2-oxo-2,3-dihydro-1H-imidazol-1-yl)acetate (1.05 g, white solid), yield: 70.1%.

$^1$H NMR (400 MHz, CDCl$_3$) δ 7.54-7.48 (m, 4H), 6.59 (d, 1H), 6.42 (d, 1H), 4.43 (s, 2H), 4.24 (q, 2H), 1.29 (t, 3H)

Step 4

Ethyl 2-(3-(4-((2-((tert-butyldimethylsilyl)oxy)ethyl)amino)phenyl)-2-oxo-2,3-dihydro-1H-imidazol-1-yl)acetate To a solution of ethyl 2-(3-(4-bromophenyl)-2-oxo-2,3-dihydro-1H-imidazol-1-yl)acetate (1.05 g, 3.23 mmol) in toluene (15 mL, dry) was added 2-((tert-butyldimethylsilyl)oxy)ethanamine (844 mg, 4.8 mmol), Cs$_2$CO$_3$ (3.10 g, 9.60 mmol), x-phos (100 mg, 0.17 mmol), Pd$_2$(dba)$_3$ (100 mg, 0.10 mmol). Reaction mixture was stirred at 100° C. for 12 h. The mixture was cooled to room temperature. Then the mixture was diluted with water (50 mL), extracted with DCM (30 mL*3), the organic layers were combined and washed with water (30 mL*2), sat aq NaCl (30 mL*2), dried over Na$_2$SO$_4$. Filtered and filtrate was concentrated. The residue was purified by silica column (Eluent C) to afford to afford ethyl 2-(3-(4-((2-((tert-butyldimethylsilyl)oxy)ethyl)amino)phenyl)-2-oxo-2,3-dihydro-1H-imidazol-1-yl)acetate (210 mg), yield: 15.5%.

$^1$H NMR (400 MHz, CDCl$_3$) δ 7.37-7.33 (m, 2H), 6.69-6.65 (m, 2H), 6.53 (d, 1H), 6.38 (d, 1H), 4.47 (s, 2H), 4.26 (q, 2H), 3.84 (t, 2H), 3.70 (t, 2H), 3.38 (t, 1H) 1.32 (t, 3H), 0.93 (s, 9H), 0.09 (s, 6H)

Step 5 ethyl 2-(3-(4-(N-(2-((tert-butyldimethylsilyl)oxy)ethyl)-4,6-dichloropyrimidine-5-carboxamido)phenyl)-2-oxo-2,3-dihydro-1H-imidazol-1-yl)acetate To a solution of ethyl 2-(3-(4-((2-((tert-butyldimethylsilyl)oxy)ethyl)amino)phenyl)-2-oxo-2,3-dihydro-1H-imidazol-1-yl)acetate (210 mg, 50 umol) in DCM (5 mL) was added TEA (216 uL, 1.5 mmol), compound of 4,6-dichloropyrimidine-5-carbonyl chloride (316 mg, 1.50 mmol) was added to above solution. Reaction mixture was stirred for 12 h. The mixture was diluted with water (20 mL), extracted with DCM (20 mL*3), the organic layers were combined and washed with water (20 mL*2), sat aq NaCl (20 mL*2), dried over Na$_2$SO$_4$, Filtered and filtrate was concentrated to afford ethyl 2-(3-(4-(N-(2-((tert-butyldimethylsilyl)oxy)ethyl)-4,6-dichloropyrimidine-5-carboxamido)phenyl)-2-oxo-2,3-dihydro-1H-imidazol-1-yl)acetate (297 mg, yellow solid), as a crude product which used in the next step directly.

Step 6

2-(3-(4-(4,6-dichloro-N-(2-hydroxyethyl)pyrimidine-5-carboxamido)phenyl)-2-oxo-2,3-dihydro-1H-imidazol-1-yl)acetate To a solution of ethyl 2-(3-(4-(N-(2-((tert-butyldimethylsilyl)oxy)ethyl-4,6-dichloropyrimidine-5-carboxamido)phenyl)-2-oxo-2,3-dihydro-1H-imidazol-1-yl)acetate (297 mg, 50 umol) in EtOH (10 mL, dry) was added HCl (con, 0.3 ml). Reaction mixture was stirred for 1 h. The mixture was diluted with water (20 mL), extracted with DCM (10 mL*3), the organic layers were combined and washed with water (10 mL*2), sat aq NaCl (10 mL*2), dried over Na$_2$SO$_4$, Filtered and filtrate was concentrated to afford ethyl 2-(3-(4-(4,6-dichloro-N-(2-hydroxyethyl)pyrimidine-5-carboxamido)phenyl)-2-oxo-2,3-dihydro-1H-imidazol-1-yl)acetate (240 mg, yellow solid) as a crude product which used in the next step directly.

Step 7 ethyl 2-(3-(4-(4-chloro-5-oxo-7,8-dihydropyrimido[5,4-f][1,4]oxazepin-6(5H)-yl)phenyl)-2-oxo-2,3-dihydro-1H-imidazol-1-yl)acetate A mixture of ethyl 2-(3-(4-(4,6-dichloro-N-(2-hydroxyethyl)pyrimidine-5-carboxamido)phenyl)-2-oxo-2,3-dihydro-1H-imidazol-1-yl)acetate (240 mg, 50 umol) and TEA (216 uL, 1.5 mmol) in MeCN (5 mL) was stirred for at 80° C. 12 h. The mixture was cooled to room temperature and extracted with DCM (30 mL*3), the organic layers were combined and washed with water (30 mL*2), sat aq NaCl (30 mL*2), dried over Na$_2$SO$_4$, Filtered and filtrate was concentrated. The residue was purified by silica column (Eluent C) to afford to afford ethyl 2-(3-(4-(4-chloro-5-oxo-7,8-dihydropyrimido[5,4-f][1,4]oxazepin-6(5H)-yl)phenyl)-2-oxo-2,3-dihydro-1H-imidazol-1-yl)acetate (40 mg, yellow solid), yield: 18.0%.

¹H NMR (400 MHz, CDCl₃) δ 8.76 (s, 1H), 7.73-7.70 (m, 2H), 7.46-7.42 (m, 2H), 6.63 (d, 1H), 6.44 (d, 1H), 4.77-4.74 (m, 2H), 4.45 (s, 2H), 4.25 (q, 2H), 4.05 (t, 2H) 1.30 (t, 3H)

Step 8 ethyl-2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)acetate A solution of ethyl 2-(3-(4-(4-chloro-5-oxo-7,8-dihydropyrimido[5,4-f][1,4]oxazepin-6(5H)-yl)phenyl)-2-oxo-2,3-dihydro-1H-imidazol-1-yl)acetate (40 mg, 90 umol) in 0.5 M ammonia in dioxane (10 mL) was stirred for 12 h. The reaction mixture was concentrated in vacuo to remove dioxane. The residue was added water (30 mL), extracted with DCM (30 mL*3). Combined organic layers and washed with water (10 mL), saturated aqueous brine (30 mL*2), dried over Na₂SO₄. Filtered and filtrate was concentrated in vacuo to give ethyl 2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)acetate (38 mg, yellow solid), as a crude product which used in the next step directly.

Step 9

2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)acetic acid A mixture of ethyl 2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)acetate (38 mg, 89 umol) and LiOH.H₂O (11 mg, 270 umol) in dioxane/H₂O (3/1, 8 mL) was stirred for 12 h. The mixture was adjusted pH to 5-6 with 1M HCl. The solid that formed was collected by filtration, dried in vacuo to afford 2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)acetic acid (22 mg, white solid), yield 61.9%.

MS m/z (ESI): 397.2 [M+1]

¹H NMR (400 MHz, DMSO-d6) δ 8.15 (s, 1H), 7.76-7.73 (m, 2H), 7.61 (br.s, 2H), 7.45-7.41 (m, 2H), 7.06 (d, 1H), 6.75 (d, 1H), 4.60-4.58 (m, 2H), 4.33 (m, 2H), 3.98-3.96 (m, 2H)

Following compounds were prepared referring to the preparation of examples 1~10:

| No | Structure | property | MS | HNMR |
|---|---|---|---|---|
| 11 | 2-(3-(4-(4-amino-5-oxo-7,8-dihydropyrimido-[5,4-f][1,4]oxazepin-6(5H)-yl)phenyl)-2-oxoimidazolidin-1-yl)acetic acid | white solid | 399.1 [M + 1] | ¹H NMR (400 MHz, DMSO-d₆) 8.17 (s, 1H), 7.61 (d, 4H), 7.34 (d, 2H), 4.61 (t, 2H), 3.97-3.95 (m, 4H), 3.87 (q, 2H), 3.58-3.54 (m, 2H) |
| 12 | Ethyl-2-(3-(4-(4-amino-5-oxo-7,8-dihydropyrimido[5,4-f][1,4]oxazepin-6(5H)-yl)phenyl)-2-oxoimidazolidin-1-yl)acetate | white solid | 427.2 [M + 1] | ¹H NMR (400 MHz, CDCl₃) 8.17 (s, 1H), 7.61 (d, 4H), 7.34 (d, 2H), 4.61 (t, 2H), 4.15 (q, 2H), 4.05 (s, 2H), 3.96 (t, 2H), 3.88 (t, 2H), 3.56 (t, 2H), 1.23 (t, 3H) |
| 13 | 3-(3-(4-(4-amino-5-oxo-7,8-dihydropyrimido[5,4-f][1,4]oxazepin-6(5H)-yl)phenyl)-2-oxoimidazolidin-1-yl)propanoic acid | white solid | 413.1 [M + 1] | ¹H NMR (400 MHz, DMSO-d₆) 8.17 (s, 1H), 7.61-7.58 (m, 4H), 7.32 (d, 2H), 4.60 (t, 2H), 3.95 (t, 2H), 3.80 (t, 2H), 3.49 (t, 2H), 3.42 (t, 2H), 2.51 (m, 2H) |

-continued

| No | Structure | property | MS | HNMR |
|---|---|---|---|---|
| 14 | 2-(3-(4-(4-amino-5-oxo-7,8-dihydropyrimido [5,4-f][1,4]oxazepin-6(5H)-yl)-2-methoxyphenyl)-2-oxoimidazolidin-1-yl) acetic acid | white solid | 429.2 [M + 1] | $^1$H NMR (400 MHz, DMSO-d$_6$) 8.14 (s, 1H), 7.62 (br. s, 2H), 7.24 (d, 1H) 7.09 (d, 1H), 6.92 (dd, 1H), 4.59 (t, 2H), 3.97 (t, 2H), 3,87 (s, 2H), 3.78 (s, 3H), 3.69-3.65 (m, 2H), 3.52-3.48 (m, 2H) |
| 15 | 2-(3-(4-(4-amino-5-oxo-7,8-dihydropyrimido [5,4-f][1,4]oxazipin-6(5H)-yl)phenyl)-2-oxoimidazolidin-1-yl)propanoic acid | white solid | 413.1 [M + 1] | $^1$H NMR(400 MHz, DMSO-d$_6$) δ 8.18 (s, 1H), 7.67 (d, 2H), 7.34 (d, 2H), 4.89-4.73 (m, 2H), 4.49-4.45 (m, 1H), 4.08-4.05 (m, 2H), 3.97-3.89 (m, 2H), 3.79-3.32 (m, 5H), 1.47 (d, 3H) |
| 16 | 2-(3-(4-(4-amino-5-oxo-7,8-dihydropyrimido [5,4-f][1,4]oxazepin-6(5H)-yl)phenyl)-2-oxo-2,3-dihydro-1H-imidazol-1-yl)acetic acid | white solid | 397.2 [M + 1] | $^1$H NMR (400 MHz, DMSO-d$_6$) 8.15 (s, 1H), 7.76-7.73 (m, 2H), 7.61 (br. s, 2H), 7.45-7.41 (m, 2H), 7.06 (d, 1H), 6.75 (d, 1H), 4.60-4.58 (m, 2H), 4.33 (s, 2H), 3.98-3.96 (m, 2H) |
| 17 | 2-(3-(4-(4-amino-5-oxo-7,8-dihydropyrimido [5,4-f][1,4]oxazepin-6(5H)-yl)phenyl)-2-oxoimidazolidin-1-yl)-3-methylbutanoic acid | yellow solid | 441.3 [M + 1] | $^1$H NMR (400 MHz, CD$_3$OD) 8.16 (s, 1H), 7.63 (d, 2H), 7.3 (dd, 2H), 4.70 (t, 2H), 4.05 (q, 3H), 3.90 (d, 2H), 3.85 (s, 2H), 3.14 (t, 1H), 2.22 (s, 1H), 1.05 (t, 3H), 0.95 (t, 3H) |

| No | Structure | property | MS | HNMR |
|---|---|---|---|---|
| 18 | 2-(3-(4-4-amino-5-oxo-7,8-dihydropyrimido[5,4-f][1,4]oxazepin-6(5H)-yl)-2,6-dimethyl phenyl)-2-oxoimidazolidin-1-yl)acetic acid | white solid | 427.1 [M + 1] | ¹H NMR (400 MHz, DMSO-d₆) δ 8.84 (br, 1H), 8.61 (br, 1H), 8.43 (s, 1H), 7.12 (d, 2H), 4.79 (t, 2H ),4.09 (t, 2H), 3.58 (s, 4H), 2.16 (s, 6H) |
| 19 | 2-(3-(4-(4-amino-5-oxo-7,8-dihydropyrimido[5,4-f][1,4]oxazepin-6(5H)-yl)-2,6-diethylphenyl)-2-oxoimidazolidin)-1-yl) acetic acid | white solid | 455.2 [M + 1] | ¹H NMR (400 MHz, DMSO-d₆) 8.18 (s, 1H), 7.64 (s, 4H), 7.15 (s, 2H), 4.61 (t, 2H ), 4.00 (t, 2H), 3.88 (s, 2H), 3.61 (s, 4H), 2.56-2.54 (m, 4H), 1.15 (t, 6H) |
| 20 | 3-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl) propanoic acid | white solid | 411.1 [M + 1] | ¹H NMR(400 MHz, DMSO-d₆) δ 12.40 (br, 1H), 8.15 (s, 1H), 7.23 (d, 2H), 7.62 (br., 2H), 7.32 (d, 2H), 7.04 (d, 1H), 6.74 (d, 1H), 4.59 (t, 2H), 3.97 (t, 2H), 3.77 (t, 2H), 2.62 (t, 2H) |
| 21 | 2-(3-(4-(4-amino-5-oxo-7,8-dihydropyrimido[5,4-f][1,4]oxazepin-6(5H)-yl)-2-(trifluoromethoxy)phenyl)-2-oxo-2,3-dihydro-1H-imidazol-1-yl) acetic acid | white solid | 481.1 [M + 1] | ¹H NMR (400 MHz, DMSO-d₆): 8.32 (s, 1H), 7.69 (s, 1H), 7.60 (d, 1H), 7.53 (dd, 1H), 6.70 (dd, 2H), 4.73 (t, 2H), 4.33 (s, 2H), 4.12 (t, 2H) |

| No | Structure | property | MS | HNMR |
|---|---|---|---|---|
| 22 | 2-(3-(4-(4-amino-5-oxo-7,8-dihydropyrimido [5,4-f][1,4]oxazepin-6(5H)-yl)phenyl)-2-oxo-2,3-dihydro-1H-imidazol-1-yl)propanoic acid | white solid | 411.2 [M + 1] | $^1$H NMR (400 MHz, DMSO-$d_6$) 8.32 (s, 1H), 7.76 (d, 2H), 7.44 (d, 2H), 7.09 (d, 1H), 6.86 (d, 1H), 4.74-4.72 (m, 3H), 3.60 (t, 2H), 1.52 (d, 1H) |
| 23 | 2-(3-(4-(4-amino-5-oxo-7,8-dihydropyrimido [5,4-f][1,4]oxazepin-6(5H)-yl)phenyl)-2-oxoimidazolidin-1-yl)butanoic acid | yellow solid | 427.0 [M + 1] | $^1$H NMR (400 MHz, CD$_3$OD) 8.44 (s, 1H), 7.68 (d, 2H), 7.36 (d, 3H), 5.01 (br.s, 3H), 4.40 (dd, 11.0 Hz, 1H), 4.25 (br. s., 2H), 4.03-3.91 (m, 2H), 3.77-3.67 (m, 1H), 3.65-3.56 (m, 1H), 2.18-1.99 (m, 1H), 1.90-1.74 (m, 1H), 1.05 (t, 3H) |
| 24 | 3-(3-(4-4-amino-5-oxo-7,8-dihydropyrimido [5,4-f][1,4]oxazepin-6(5H)-yl)phenyl)-2-oxoimidazolidin-1-yl)-2-methylpropanoic acid | yellow solid | 427.0 [M + 1] | $^1$H NMR (400 MHz, CD$_3$OD), 8.43 (s, 1H), 7.67 (d, 2H), 7.35 (d, 2H), 5.03-4.96 (m, 2H), 4.28-4.19 (m, 2H), 3.96-3.86 (m, 2H), 3.68-3.57 (m, 2H), 3.55-3.39 (m, 2H), 2.89-2.77 (m, 1H), 1.22 (d, 3H) |
| 25 | 2-(3-(4-(4-amino-5-oxo-7,8-dihydropyrimido [5,4-f][1,4]oxazepin-6(5H)-yl)-2-(trifluoromethyl) phenyl)-2-oxoimidazolidin-1-yl)acetic acid | white solid | 467.1 [M + 1] | $^1$H NMR (400 MHz, DMSO-$d_6$) 8.14 (s, 1H), 7.82 (d, 1H), 7.73 (dd, 1H), 7.65 (br. s, 2H), 7.51 (d, 1H), 4.61 (t, 2H), 4.03 (t, 2H), 3.89 (s, 2H), 3.67-3.63 (m, 2H), 3.58-3.54 (m, 2H) |

-continued

| No | Structure | property | MS | HNMR |
|---|---|---|---|---|
| 26 | 2-(3-(4-(4-amino-5-oxo-7,8-dihydropyrimido[5,4-f][1,4]oxazepin-6(5H)-yl)-2-fluoro-6-methylphenyl)-2-oxoimidazolidin-1-yl) acetic acid | white solid | 431.1 [M + 1] | $^1$H NMR (400 MHz, CD$_3$OD) 8.41 (s, 1H), 7.17 (d, 2H), 4.98 (t, 2H), 4.22 (t, 2H), 4.02 (d, 1H), 3.95 (d, 1H), 3.79-3.71 (m, 4H), 2.34 (s, 3H) |
| 27 | 2-(3-(4-(4-amino-5-oxo-7,8-dihydro)pyrimido[5,4-f][1,4]oxazepin-6(5H)-yl)-2-chloro-6-methylphenyl)-2-oxoimidazolidin-1-yl) acetic acid | whie solid | 447.0 [M + 1] | $^1$H NMR (400 MHz, CDCl$_3$) 12.73 (s, 1H), 8.17 (s, 1H), 7.65 (s, 1H), 7.51 (d, 1H), 7.33 (d, 1H), 4.62 (t, 2H), 4.0-3.5 (m, 8H), 2.25 (s, 3H) |
| 28 | 2-(3-(4-(4-amino-5-oxo-7,8-dihydropyrimido[5,4-f][1,4]oxazepin-6(5H)-yl)-2-chloro phenyl)-2-oxo-2,3-dihydro-1H-imidazol-1-yl)acetic acid | white solid | 431.1 [M + 1] | $^1$H NMR (400 MHz, DMSO-d$_6$) 12.96 (s, 1H), 8.14 (s, 1H), 7.74 (d, 1H), 7.64 (br, 2H), 7.50-7.44 (m, 2H), 6.69 (dd, 1H), 4.61 (t, 2H), 4.33 (s, 2H), 4.01 (t, 2H) |
| 29 | 4-amino-6-(3-chloro-4-(3-isobutyl-2-oxoimidazolidin-1-yl)phenyl)-7,8-dihydropyrimido[5,4-f][1,4]oxazepin-5(6H)-one | white solid | 431.1 [M + 1] | 1H NMR (400 MHz, CD$_3$OD) 8.37 (d, 1H), 7.60 (d, 1H), 7.46 (d, 1H), 7.38-7.35 (dd, 1H), 4.96-4.93 (m, 2H), 4.41 (t, 2H), 3.82 (dd, 2H), 3.1 (d, 2H), 1.99-1.94 (m, 1H), 0.95 (d, 6H) |

-continued

| No | Structure | property | MS | HNMR |
|---|---|---|---|---|
| 30 | 4-amino-6-(3-chloro-4-(3-(cyclopropylmethyl)-2-oxoimidazolidin-1-yl)phenyl)-7,8-dihydropyrimido[5,4-f][1,4]oxazepin-5(6H)-one | white solid | 429.1 [M + 1] | 1H NMR (400 MHz, CD$_3$OD) 8.39 (s, 1H), 7.60 (d, 2H), 7.47 (d, 1H), 7.36 (dd, 1H), 4.92 (q, 2H), 4.22 (t, 2H), 3.83 (q, 2H), 3.71 (q, 2H), 3.13 (d, 2H), 1.01-0.97 (m, 1H), 0.56 (dd, 2H), 0.25 (d, 2H) |
| 31 | 4-amino-6-(3-chloro-4-(3-(2-fluoro-2-methylpropyl)-2-oxoimidazolidin-1-yl)phenyl)-7,8-dihydropyrimido[5,4-f][1,4]oxazepin-5(6H)-one | white solid | 407.2 [M + 1] | $^1$H NMR (400 MHz, CD$_3$OD) δ 8.39 (s, 1H), 7.62 (d, 1H), 7.50 (d, 1H), 7.38 (dd, 1H), 5.00-4.92 (m, 2H), 4.35-4.27 (m, 2H), 3.87-3.79 (m, 2H), 3.78-3.68 (m, 2H), 3.42 (s, 1H), 3.36 (s, 1H), 1.41 (s, 3H), 1.36 (s, 3H) |

Example 32

2-(4-(4-(4-amino-5-oxo-7,8-dihydropyrimido[5,4-f][1,4]oxazepin-6(5H)-yl)phenyl)-3,5-dimethyl-1H-pyrazol-1-yl)acetic acid

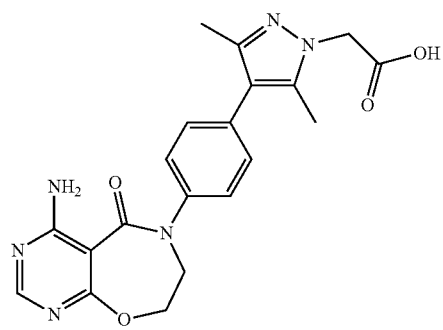

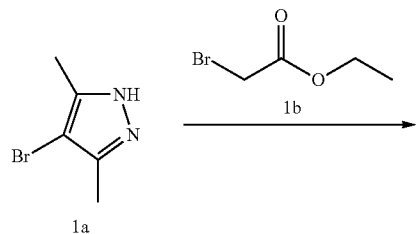

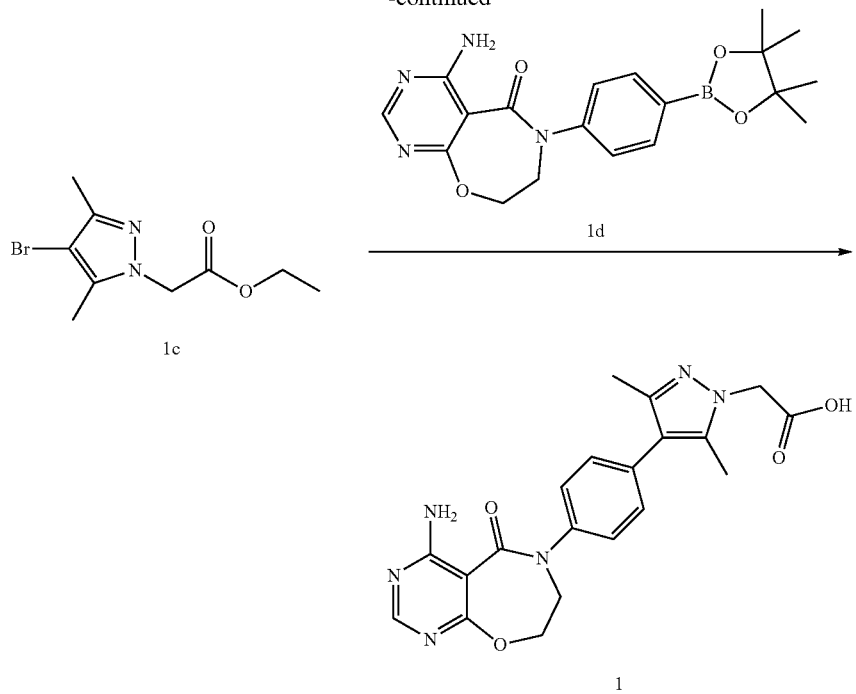

Step 1

Ethyl 2-(4-bromo-3,5-dimethyl-1H-pyrazol-1-yl)acetate

To a mixture of 4-bromo-3,5-dimethyl-1H-pyrazole (500 mg, 2.8 mmol) in DMF (8 mL) cooled to 0° C., was added 60% NaH (137 mg, 5.7 mmol) slowly. The solution was stirred for 1 h, then added ethyl 2-bromoacetate (524.8 mg. 3.1 mmol) and KI (450 mg, 2.7 mmol). Reaction mixture was stirred at 80° C. for 12 h. Reaction mixture was cooled to room temperature. Then added sat aq NH$_4$Cl (20 mL), extracted with EtOAc (20 mL*3), the organic layers were combined and washed with sat aq NaCl (20 mL*2), dried over Na$_2$SO$_4$, Filtered and filtrate was concentrated. The residue was purified by silica column (Eluent C) (PE: EA, 10:1-8:1) to afford ethyl 2-(4-bromo-3,5-dimethyl-1H-pyrazol-1-yl)acetate (552 mg, 74.0%) as a pale-yellow liquid.

MS m/z (ESI): 263 [M+1]

$^1$H NMR (400 MHz, CDCl$_3$) δ 4.78 (s, 2H), 4.23 (q, 2H), 2.21 (s, 6H), 1.28 (t, 3H)

Step 2

2-(4-(4-(4-amino-5-oxo-7,8-dihydropyrimido[5,4-f][1,4]oxazepin-6(5H)-yl)phenyl)-3,5-dimethyl-1H-pyrazol-1-yl)acetic acid To a solution of 2-(4-bromo-3,5-dimethyl-1H-pyrazol-1-yl)acetate (55 mg, 0.21 mmol) and 4-amino-6-(4-(4,4,5,5-tetramethyl-1,3,2-dioxaborolan-2-yl)phenyl)-7,8-dihydropyrimido[5,4-f][1,4]oxazepin-5(6H)-one (80 mg, 0.21 mmol, prepared by WO2011121250) in dioxane (4 mL) and H$_2$O (1.5 mL) was added K$_2$CO$_3$ (57 mg, 0.42 mmol) and Pd(dppf)Cl$_2$ (10 mg). The mixture was stirred for 12 h at 80° C. The mixture was cooled to room temperature. The mixture was filtered and filtrate was concentrated. The residue was purified by prep HPLC to afford 2-(4-(4-(4-amino-5-oxo-7,8-dihydropyrimido[5,4-f][1,4]oxazepin-6(5H)-yl)phenyl)-3,5-dimethyl-1H-pyrazol-1-yl)acetic acid (17 mg, yellow solid), yield: 20.4%.

MS m/z (ESI): 409.2 [M+1]

$^1$H NMR (400 MHz, CD$_3$OD) δ 8.39 (s, 1H), 7.45 (m, 4H), 5.21 (s, 2H), 4.98 (m, 2H), 4.26 (m, 2H), 2.37 (s, 3H), 2.34 (s, 3H)

Example 33

2-(4-(4-(4-amino-5-oxo-7,8-dihydropyrimido[5,4-f][1,4]oxazepin-6(5H)-yl)-2-chlorophenyl)-1H-pyrazol-1-yl)-2-methylpropanoic acid

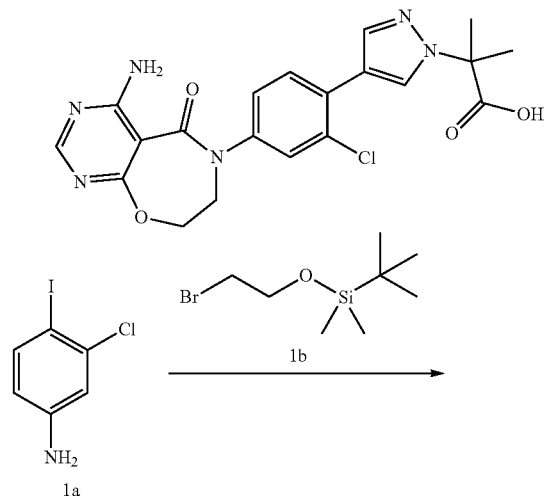

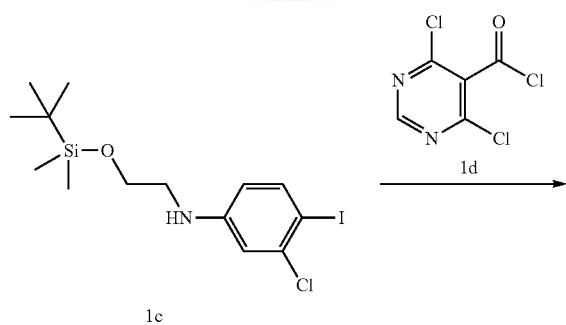
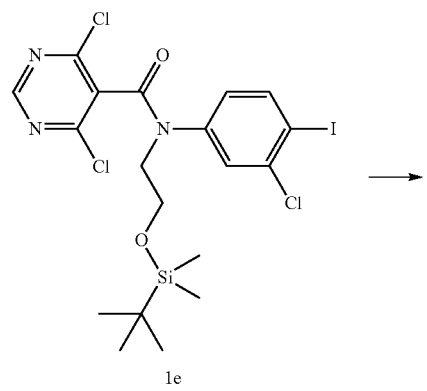
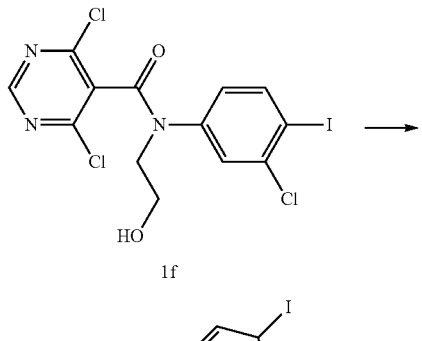
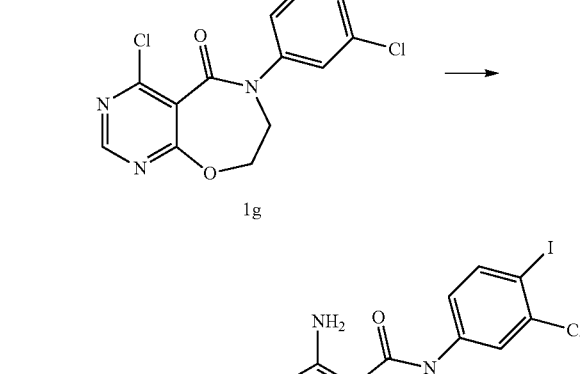
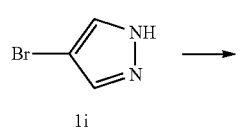
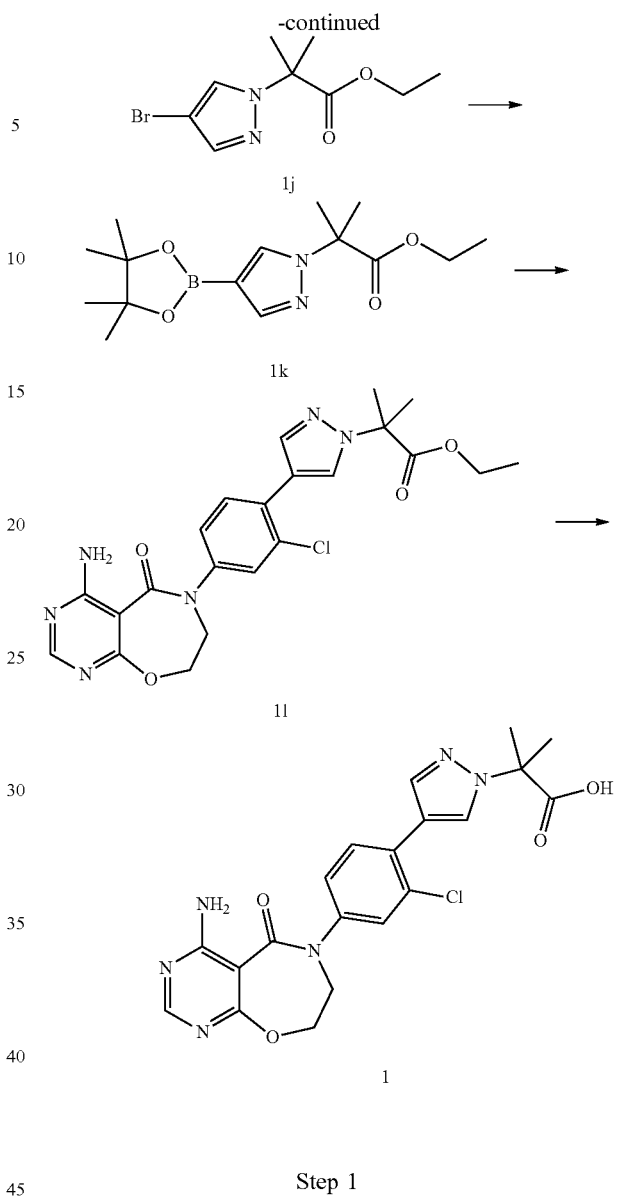

Step 1

N-(2-((tert-butyldimethylsilyl)oxy)ethyl)-3-chloro-4-iodoaniline

To a solution of 3-chloro-4-iodoaniline (3.0 g, 11.84 mmol) in THF (18 mL) was cooled to 0° C. 60% of NaH (1.16 g, 29.06 mmol) was added. The mixture was stirred for 1 h at room temperature. Then (2-bromoethoxy)(tert-butyl) dimethylsilane (3.48 g, 14.53 mmol) was added. The mixture was stirred for 12 h at 40° C. The reaction was quenched by sat aq (20 mL) and H₂O (50 mL). The mixture was extracted with EA (40 mL*3), the organic layers were combined and washed with brine (30 mL*2), dried over Na₂SO₄. Filtered and filtrate was concentrated. The residue was purified silica column (Eluent C) to afford N-(2-((tert-butyldimethylsilyl)oxy)ethyl)-3-chloro-4-iodoaniline (3.5 g, yellow solid), yield: 58.5%.

MS m/z (ESI): 412.0 [M+1]

$^1$H NMR (400 MHz, CDCl$_3$) δ 7.51 (d, 1H), 6.74 (d, 1H), 6.27 (dd, 1H), 4.12 (t, 2H), 3.17 (t, 2H), 0.90 (s, 9H), 0.07 (s, 6H)

Step 2

N-(2-((tert-butyldimethylsilyl)oxy)ethyl)-4,6-dichloro-N-(3-chloro-4-iodophenyl)pyrimidine-5-carboxamide To a solution of N-(2-((tert-butyldimethylsilyl)oxy) ethyl)-3-chloro-4-iodoaniline (2.9 mg, 7.03 mmol) in THF (30 mL) was added 4,6-dichloropyrimidine-5-carbonyl chloride (1.7 g, 8.06 mmol) and DIEA (1.6 mL). The mixture was stirred for 12 h. The reaction was diluted by ea (50 mL) and H$_2$O (50 mL). The organic layers were combined and washed with sat aq NaCl (100 mL), dried over Na$_2$SO$_4$. Filtered and filtrate was concentrated. The residue was purified silica column (Eluent C) to afford N-(2-((tert-butyldimethylsilyl)oxy)ethyl)-4,6-dichloro-N-(3-chloro-4-iodophenyl)pyrimidine-5-carboxamide (3.4 g, yellow solid), yield: 82.3%.

$^1$H NMR (400 MHz, CDCl$_3$) δ 8.89 (s, 1H), 7.92 (d, 1H), 6.65 (d, 1H), 7.07 (dd, 1H), 3.99 (t, 2H), 3.78 (t, 2H), 0.83 (s, 9H), 0.00 (s, 6H)

Step 3

4,6-dichloro-N-(3-chloro-4-iodophenyl)-N-(2-hydroxyethyl)pyrimidine-5-carboxamide To a mixture of N-(2-((tert-butyldimethylsilyl)oxy)ethyl)-4,6-dichloro-N-(3-chloro-4-iodophenyl)pyrimidine-5-carboxamide (3.4 g, 5.79 mmol) in EtOH (40 mL) and HCl (1.2 mL) was stirred for 3 h. The reaction was diluted with H$_2$O (50 mL). The mixture was extracted with EA (50 mL*3), the organic layers were combined and washed with sat aq NaCl (100 mL*2), dried over Na$_2$SO$_4$. Filtered and filtrate was concentrated to afford 4,6-dichloro-N-(3-chloro-4-iodophenyl)-N-(2-hydroxyethyl)pyrimidine-5-carboxamide (2.9 g, yellow liquid), yield: 105.8%.

$^1$H NMR (400 MHz, CDCl$_3$) δ 8.67 (s, 1H), 7.76 (d, 1H), 7.56 (d, 1H), 7.03 (dd, 1H), 4.06 (t, 2H), 3.93 (t, 2H)

Step 4

44-chloro-6-(3-chloro-4-iodophenyl)-7,8-dihydropyrimido[5,4-f][1,4]oxazepin-5(6H)-one To a solution of 4,6-dichloro-N-(3-chloro-4-iodophenyl)-N-(2-hydroxyethyl)pyrimidine-5-carboxamide (2.9 g, 6.14 mmol) in MeCN (30 mL) was added TEA (2.4 mL). The mixture was stirred for 12 h at 80° C. The mixture was cooled to room temperature. Then diluted with H$_2$O (50 mL). The mixture was extracted with DCM (50 mL*3), the organic layers were combined and washed with sat aq NaCl (100 mL*2), dried over Na$_2$SO$_4$. Filtered and filtrate was concentrated to afford 4-chloro-6-(3-chloro-4-iodophenyl)-7,8-dihydropyrimido-7,8-dihydropyrimido[5,4-f][1,4]oxazepin-5(6H)-one (1.0 g, 37.3% yield) as a yellow solid and crude product (1.2 g) as a yellow liquid.

Step 5

4-amino-6-(3-chloro-4-iodophenyl)-7,8-dihydropyrimido[5,4-f][1,4]oxazepin-5(6H)-one To a solution of 4-chloro-6-(3-chloro-4-iodophenyl)-7,8-dihydropyrimido[5,4-f][1,4]oxazepin-5(6H)-one (1 g, 2.29 mmol) in 0.5 M ammonia in dioxane (80 mL). The mixture was stirred for 12 h. Filtered to afford 1 h (300 mg, 31.4%) as a yellow solid.

$^1$H NMR (400 MHz, DMSO-d$_6$) δ 8.14 (s, 1H), 7.96 (d, 1H), 7.69 (d, 1H), 7.12 (dd, 1H), 4.57 (t, 2H), 3.96 (t, 2H)

Step 6

Ethyl 2-(4-bromo-1H-pyrazol-1-yl)-2-methylpropanoate

To a solution of 4-bromo-1H-pyrazole (2 g, 13.7 mmol) in DMF (40 mL) was added NaH (657 mg, 16.4 mmol) and ethyl 2-bromo-2-methylpropanoate (3.2 g, 16.4 mmol). The mixture was stirred for 12 h. The mixture was cooled to room temperature. Then H$_2$O (200 mL) was added and extracted with EA (80 ml*3), the organic layers were combined and washed with H$_2$O (100 mL*2), sat aq NaCl (100 mL*2), dried over Na$_2$SO$_4$. Filtered and filtrate was concentrated. The residue was purified by silica column (Eluent C) to afford ethyl 2-(4-bromo-1H-pyrazol-1-yl)-2-methylpropanoate (3.4 g, yellow liquid), yield: 95.5%.

$^1$H NMR (400 MHz, CDCl$_3$) δ 7.58 (s, 1H), 7.50 (s, 1H), 4.17 (q, 2H), 1.83 (s, 6H), 1.22 (t, 3H)

Step 7 ethyl 2-methyl-2-(4-(4,4,5,5-tetramethyl-1,3,2-dioxaborolan-2-yl)-1H-pyrazol-1-yl)propanoate To a solution of ethyl 2-(4-bromo-1H-pyrazol-1H-pyrazol-1-yl)-2-methylpropanoate (3.4 g, 13 mmol) in DMF (50 mL) was added 4,4,4',4',5,5,5',5'-octamethyl-2,2'-bi(1,3,2-dioxaborolane) (4 g, 15.6 mmol), KOAc (3.8 g, 39 mmol) and Pd(dppf)Cl$_2$ (1 g, 1.3 mmol). The mixture was stirred for 12 h at 90° C. The mixture was add H$_2$O (200 mL) and extracted with EA (80 mL*3), the organic layers were combined and washed with H$_2$O (100 mL*2), sat aq NaCl (100 mL*2), dried over Na$_2$SO$_4$. Filtered and filtrate was concentrated. The residue was purified by silica column (Eluent C) to afford ethyl 2-methyl-2-(4-(4,4,5,5-tetramethyl-1,3,2-dioxaborolan-2-yl)-1H-pyrazol-1-yl)propanoate (1.7 g, yellow liquid), yield: 42.5%.

$^1$H NMR (400 MHz, CDCl$_3$) δ 7.87 (s, 1H), 7.86 (s, 1H), 4.14 (q, 2H), 1.83 (s, 6H), 1.30 (s, 12H), 1.18 (t, 3H)

Step 8 ethyl-2-(4-(4-(4-amino-5-oxo-7,8-dihydropyrimido[5,4-f][1,4]oxazepin-6(5H)-yl)-2-chlorophenyl)-1H-pyrazol-1-yl)-2-methylpropanoate A mixture of 4-amino-6-(3-chloro-4-iodophenyl)-7,8-dihydropyrimido[5,4-f][1,4]oxazepin-5(6H)-one (80 mg, 192 umol) and 2-methyl-2-(4-(4,4,5,5-tetramethyl-1,3,2-dioxaborolan-2-yl)-1H-pyrazol-1-yl)propanoate (59 mg, 192 mmol) in a mixture solution of dioxane and H$_2$O (3 mL, v/v=2/1) was added K$_2$CO$_3$ (80 mg, 577 umol) and Pd(ddpf)Cl$_2$ (6 mg, 7.2 umol). The mixture was stirred for 12 h at 90° C. The mixture was cooled to RT and used for next step reaction directly.

Step 9

2-(4-(4-(4-amino-5-oxo-7,8-dihydropyrimido[5,4-f][1,4]oxazepin-6(5H)-yl)-2-chlorophenyl)-1H-pyrazol-1-yl)-2-methylpropanoic acid The above step reaction mixture was added LiOH (30 mg, 63 umol), the mixture was stirred for 3 h. The mixture was concentrated and residue was prep HPLC (Eluent B) to afford 2-(4-(4-(4-amino-5-oxo-7,8-dihydropyrimido[5,4-f][1,4]oxazepin-6(5H)-yl)-2-chlorophenyl)-1H-pyrazol-1-yl)-2-methylpropanoic acid (1.69 mg, white solid), yield: 2.0%.

MS m/z (ESI): 443.1 [M+1]

$^1$H NMR (400 MHz, CD$_3$OD) δ 8.45 (s, 1H), 8.26 (s, 1H), 7.95 (s, 1H), 7.70 (d, 1H), 7.60 (d, 1H), 7.36 (dd, 1H), 5.02 (t, 2H), 4.28 (t, 2H), 1.91 (s, 6H)

Example 34

2-(4-(4-(4-amino-5-oxo-7,8-dihydropyrimido[5,4-f][1,4]oxazepin-6(5H)-yl)-2-chlorophenyl)-1H-pyrazol-1-yl) propanoic acid

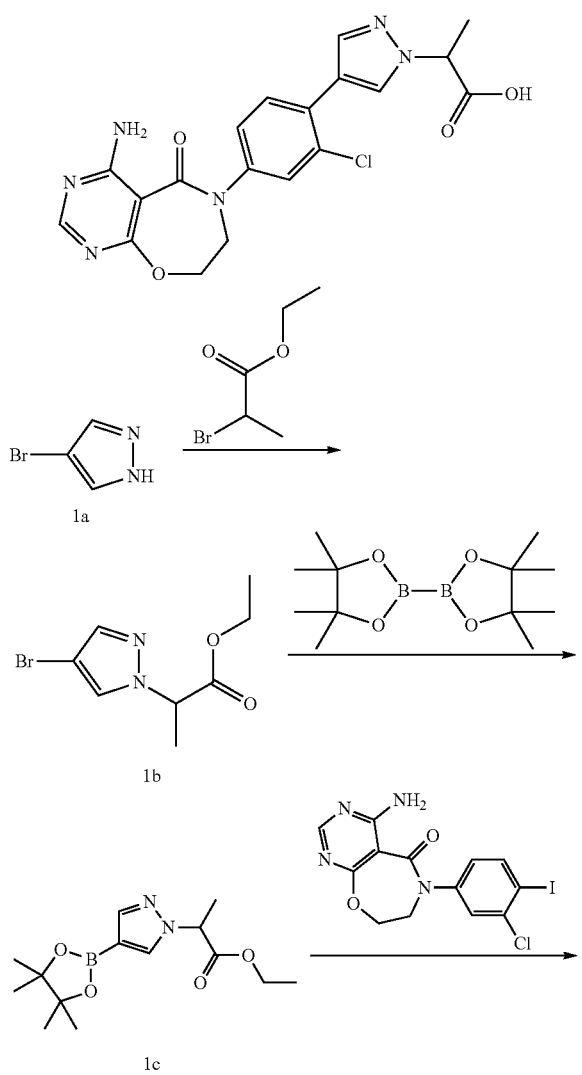

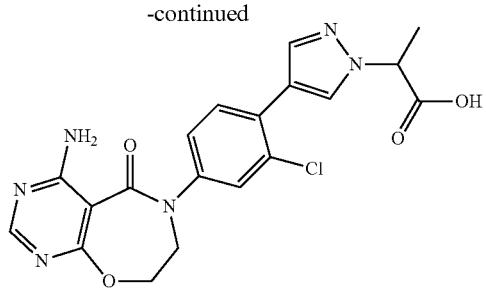

Step 1

Ethyl 2-(4-bromo-1H-pyrazol-1-yl)propanoate

To a solution of 4-bromo-1H-pyrazole (2 g, 13.7 mmol) in DMF (40 mL) was cooled to 0° C., 60% NaH (657 mg, 16.4 mmol) was added slowly. The mixture was stirred for 1 h, ethyl 2-bromopropanoate (3.0 g, 16.4 mmol) was added. The mixture was stirred 12 h. The mixture was quenched by sat aq NH$_4$Cl (200 mL), extracted with EA (80 mL*3), the organic layers were combined and washed with sat aq NaCl (50 mL*2), dried over Na$_2$SO$_4$. Filtered and filtrate was concentrated. The residue was purified by silica column (Eluent C) to afford ethyl 2-(4-bromo-1H-pyrazol-1-yl)propanoate (1.4 g, yellow liquid), yield: 42%.

$^1$H NMR (400 MHz, CDCl$_3$) δ 7.56 (s, 1H), 7.48 (s, 1H), 5.03 (q, 1H), 4.19 (q, 2H), 1.76 (d, 3H), 1.25 (t, 3H)

Step 2 ethyl 2-(4-(4,4,5,5-tetramethyl-1,3,2-dioxaborolan-2-yl)-1H-pyrazol-1-yl)propanoate To a solution of ethyl 2-(4-bromo-1H-pyrazol-1-yl)propanoate (50 mg, 0.1 mmol) and in dioxane (2 mL) was added 4,4,4',4',5,5,5',5'-octamethyl-2,2'-bi(1,3,2-dioxaborolane) (68 mg, 0.27 mmol), KOAc (53 mg, 0.54 mmol), Pd(dppf)Cl$_2$ (7.3 mg, 0.009 mmol). Reaction mixture was stirred at 110° C. for 12 h. The mixture was cooled to room temperature. Then the mixture was concentrated. The residue was diluted with (10 mL), extracted with DCM (20 mL*3), the organic layers were combined and dried over Na$_2$SO$_4$. Filtered and filtrate was concentrated. The residue was purified prep TLC (Eluent C) to afford ethyl 1-(4-(4,4,5,5-tetramethyl-1,3,2-dioxaborolan-2-yl)-1H-pyrazol-1-yl)propanoate (90 mg, white solid), yield: 100%.

Step 3

2-(4-(4-(4-amino-5-oxo-7,8-dihydropyrimido[5,4-f][1,4]oxazepin-6(5H)-yl)-2-chlorophenyl)-1H-pyrazol-1-yl) propanoic acid A mixture of 4-amino-6-(3-chloro-4-iodophenyl)-7,8-dihydropyrimido[5,4-f][1,4]oxazepin-5(6H)-one (80 mg, 192 mmol) and ethyl 2-(4-(4,4,5,5-tetramethyl-1,3,2-dioxaborolan-2-yl)-1H-pyrazol-1-yl)propanoate (59 mg, 192 umol) in dioxane and H₂O (v/v=2/1) (3 mL) was added K₂CO₃ (80 mg, 577 umol), Pd(dppf)Cl₂ (6 mg, 7.2 umol) under N₂. Reaction mixture was stirred at 90° C. for 12 h. The mixture was cooled to room temperature. Then the mixture was concentrated. The residue was purified prep HPLC (Eluent B) to afford 2-(4-(4-(4-amino-5-oxo-7,8-dihydropyrimido[5,4-f][1,4]oxazepin-6(5H)-yl)-2-chlorophenyl)-1H-pyrazol-1-yl) propanoic acid (20 mg, yellow solid), yield: 25.0%.

MS m/z (ESI): 443.1 [M+1]

¹H NMR (400 MHz, CD₃OD) δ 8.47 (s, 1H), 8.30 (br.s, 1H), 8.04 (br.s, 1H), 7.72 (d, 1H), 7.63 (d, 1H), 7.40 (dd, 1H), 5.28 (br.s, 1H), 5.04 (t, 2H), 4.30 (t, 2H) 1.86 (d, 3H)

Example 35

3-(4-(4-(4-amino-5-oxo-7,8-dihydropyrimido[5,4-f][1,4]oxazepin-6(5H)-yl)-2-chlorophenyl)-1H-pyrazol-1-yl)propanoic acid

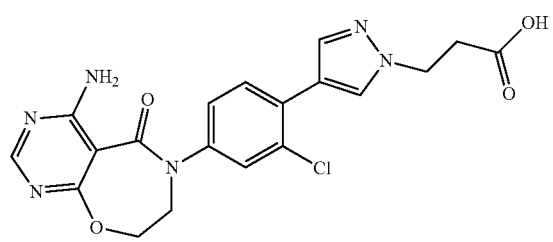

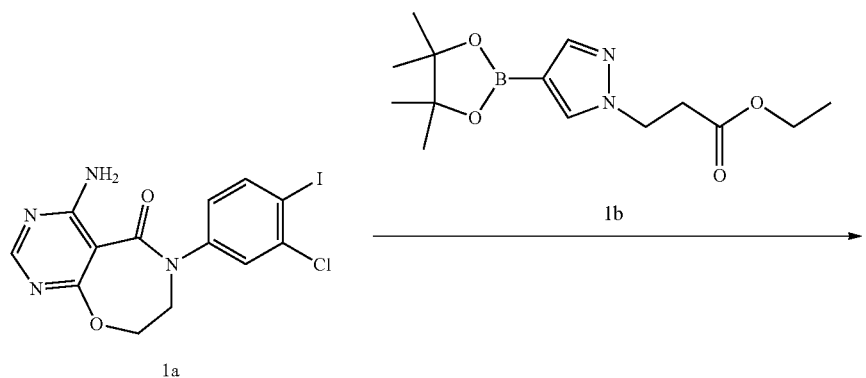

1a

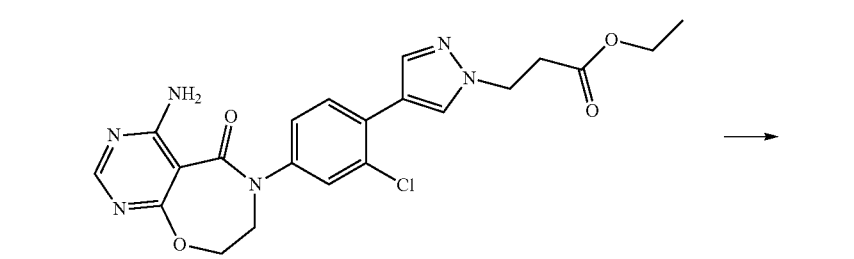

1c

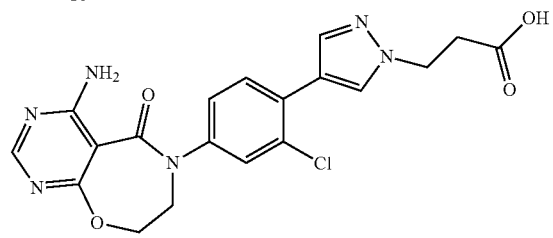

1

Step 1 ethyl-3-(4-(4-(4-amino-5-oxo-7,8-dihydropyrimido [5,4-f][1,4]oxazepin-6(5H)-yl)-2-chlorophenyl)-1H-pyrazol-1-yl)propanoate A mixture of compound 4-amino-6-(3-chloro-4-iodophenyl)-7,8-dihydropyrimido[5,4-f][1,4]oxazepin-5(6H)-one (80 mg, 192 umol, 1.0 eq), compound ethyl 3-(4-(4,4,5,5-tetramethyl-1,3,2-dioxaborolan-2-yl)-1H-pyrazol-1-yl)propanoate (56 mg, 192 umol, 1.0 eq), K$_2$CO$_3$ (80 mg, 577 umol), Pd (dppf) C12 (6 mg, 7.2 umol) in Dioxane/H$_2$O (3 mL) was stirred for 12 h at 90° C. under N$_2$. The mixture was used in next step directly.

Step 2

3-(4-(4-(4-amino-5-oxo-7,8-dihydropyrimido[5,4-f] [1,4]oxazepin-6(5H)-yl)-2-chlorophenyl)-1H-pyrazol-1-yl)propanoic acid The mixture of above reaction was added LiOH.H$_2$O (30 mg, 63 umol) in Dioxane/H$_2$O (2 mL) was stirred for 3 hours. The reaction mixture was concentrated, the residue was purified by prepare HPLC to give the desired compound 3-(4-(4-(4-amino-5-oxo-7,8-dihydropyrimido[5,4-f][1,4] oxazepin-6(5H)-yl)-2-chlorophenyl)-1H-pyrazol-1-yl)propanoic (11 mg, white solid), yield: 14.3%.

MS m/z (ESI): 429.1 [M+1]

$^1$H NMR (400 MHz, DMSO-d$_6$) δ 8.70 (br. s, 1H), 8.60 (br. s, 1H), 8.43 (d, 1H), 8.24 (s, 1H), 7.90 (s, 1H), 7.66 (d, 2H), 7.40 (dd, 1H), 7.36 (dd, 1H), 4.83 (t, 2H) 4.15 (s, 2H), 2.85 (t, 2H)

Example 36

2-(4-(4-(4-amino-5-oxo-7,8-dihydropyrimido[5,4-f] [1,4]oxazepin-6(5H)-yl)-2-chlorophenyl)-3-methyl-1H-pyrazol-1-yl)acetic acid

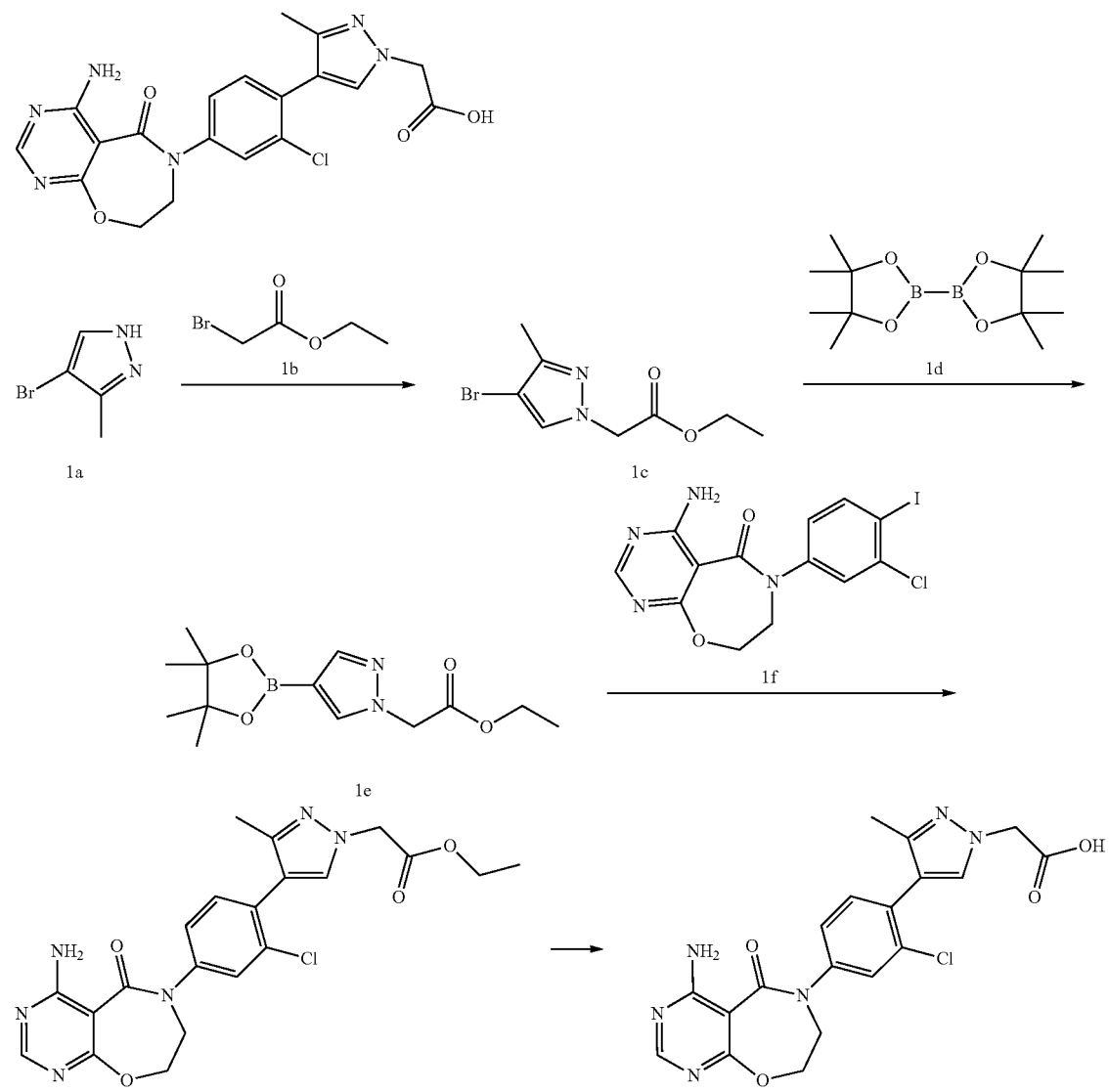

Step 1

Ethyl 2-(4-bromo-3-methyl-1H-pyrazol-1-yl)acetate

To a solution of 4-bromo-3-methyl-1H-pyrazole 1a (500 mg, 3.1 mmol) in 8 mL DMF was added NaH (60% purity, 149 mg, 6.2 mmol), ethyl 2-bromoacetate (570 mg, 3.4 mmol) and KI (489 mg, 2.9 mmol). The mixture was stirred at 80° C. for 12 h. To the reaction mixture was added $H_2O$ (20 mL), extracted with EA (20 ml*3), combined the organic phase, washed with $H_2O$ (20 mL*2), saturation NaCl solution (20 mL*2), dried over $Na_2SO_4$, filtered, the filtrate was concentrated under reduced pressure. The residue was purified by silica column chromatography (Eluent C) to give title product ethyl 2-(4-bromo-3-methyl-1H-pyrazol-1-yl)acetate 1b (522 mg, pale yellow liquid), yield: 68.0%.

$^1$H NMR (400 MHz, $CDCl_3$) δ 7.44 (d, 1H), 4.85 (s, 1H), 4.79 (s, 1H), 4.24 (q, 2H), 2.23 (s, 3H), 1.29 (t, 3H)

Step 2 ethyl 2-(4-(4,4,5,5-tetramethyl-1,3,2-dioxaborolan-2-yl)-1H-pyrazol-1-yl)acetate To a solution of ethyl 2-(4-bromo-3-methyl-1H-pyrazol-1-yl)acetate 1b (300 mg, 1.21 mmol) in 10 mL DMF was added 4,4,4',4',5,5,5',5'-octamethyl-2,2'-bi(1,3,2-dioxaborolane) (369 mg, 1.46 mmol), potassium acetate (178 mg, 1.82 mmol) and Pd(dppf)$Cl_2$ (10 mg, 130 umol). The mixture was stirred at 90° C. for 12 h. To the reaction mixture was added $H_2O$ (20 mL), extracted with EA (20 mL*3), combined the organic phase, washed with $H_2O$ (20 mL*2), saturation NaCl solution (20 mL*2), dried over $Na_2SO_4$, filtered, the filtrate was concentrated under reduced pressure. The residue was purified by silica column chromatography (Eluent C) to give title product ethyl 2-(4-(4,4,5,5-tetramethyl-1,3,2-dioxaborolan-2-yl)-1H-pyrazol-1-yl)acetate 1c (160 mg, pale yellow liquid), yield: 44.8%.

Step 3 ethyl 2-(4-(4-(4-amino-5-oxo-7,8-dihydropyrimido[5,4-f][1,4]oxazepin-6(5H)-yl)-2-chlorophenyl)-3-methyl-1H-pyrazol-1-yl)acetate To a solution of 4-amino-6-(3-chloro-4-iodophenyl)-7,8-dihydropyrimido[5,4-f][1,4]oxazepin-5(6H)-one (100 mg, 240 umol) and ethyl 2-(4-(4,4,5,5-tetramethyl-1,3,2-dioxaborolan-2-yl)-1H-pyrazol-1-yl)acetate (85 mg, 288 umol) in 1,4-dioxane/$H_2O$ (V/V=2:1, 3 mL) was added $K_2CO_3$ (100 mg, 821 umol) and Pd(dppf)$Cl_2$ (12 mg, 15 umol). The mixture was stirred at 90° C. for 12 h. The reaction mixture was cooled to room temperature then used into the next step directly.

Step 4

2-(4-(4-(4-amino-5-oxo-7,8-dihydropyrimido[5,4-f][1,4]oxazepin-6(5H)-yl)-2-chlorophenyl)-3-methyl-1H-pyrazol-1-yl)acetic acid To the previous step reaction mixture was added LiOH.$H_2O$ (30 mg, 63 umol), then stirred for 3 h. The mixture was concentrated under reduced pressure. The residue was purified by prep.HPLC (Eluent B) to give title product 2-(4-(4-(4-amino-5-oxo-7,8-dihydropyrimido[5,4-f][1,4]oxazepin-6(5H)-yl)-2-chlorophenyl)-3-methyl-1H-pyrazol-1-yl)acetic acid 1 (5 mg, white solid), yield: 5.6%.

MS m/z (ESI): 429.0 [M+1]

$^1$H NMR (400 MHz, $CD_3OD$) δ 8.41 (s, 1H), 7.82 (s, 0.4H), 7.62-7.60 (m, 1.5H), 7.48-7.42 (m, 1H), 7.38-7.35 (m, 1H), 5.00 (m, 1H), 5.00 (t, 4H), 4.26 (t, 2H), 2.23 (d, 3H)

Example 37

3-(4-(4-(4-amino-5-oxo-7,8-dihydropyrimido[5,4-f][1,4]oxazepin-6(5H)-yl)-2-fluorophenyl)-1H-pyrazol-1-yl) propanoic acid

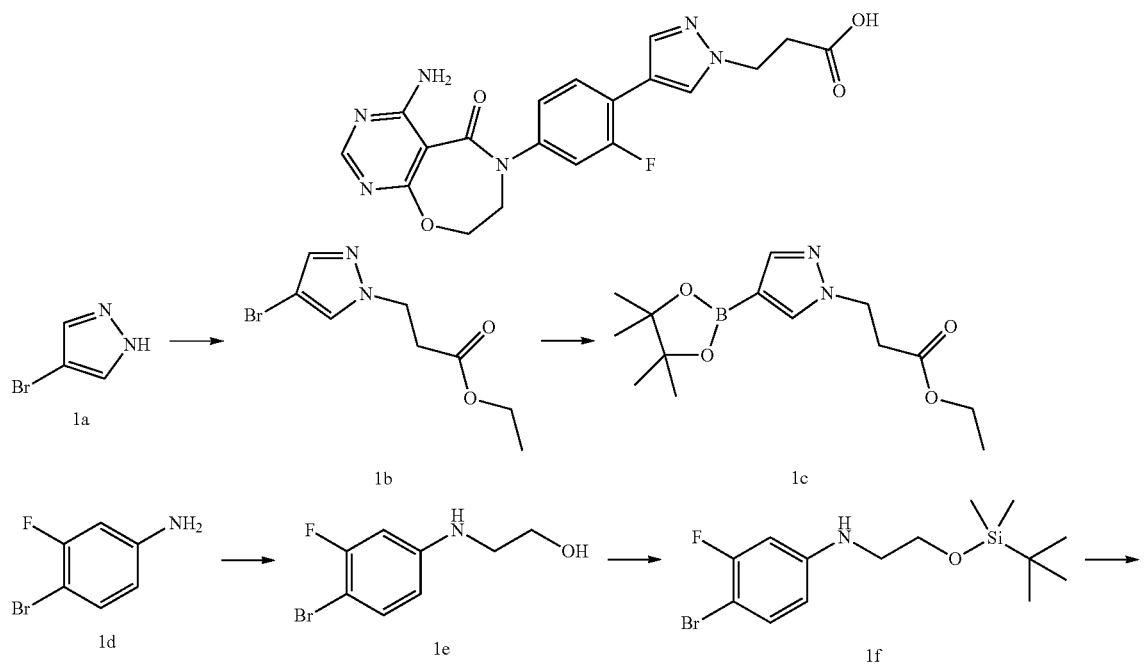

-continued

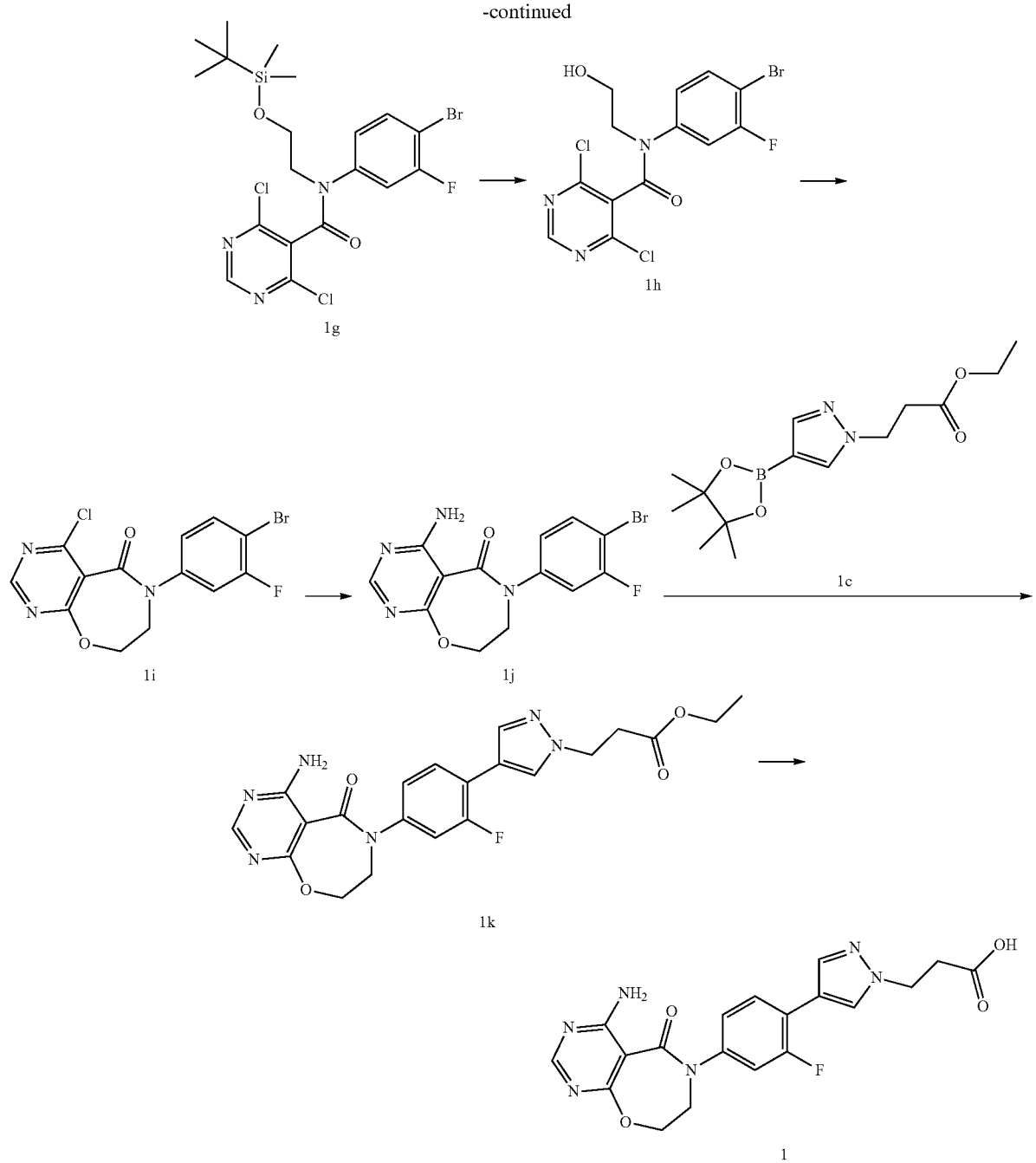

Step 1 ethyl 3-(4-bromo-1H-pyrazol-1-yl)propanoate

To a solution of 4-bromo-1H-pyrazole 1a (1.47 g, 10.00 mmol) in 20 mL DMF was added NaH (480 mg, 12.00 mmol) at ice-bath, stirred 1 h. To the reaction mixture was added ethyl 3-bromopropanoate (2.00 g, 11.05 mmol) and KI (1.74 g, 10.48 mmol). The mixture was stirred at 70° C. for 12 h. To the reaction mixture was added 100 mL sat. NH$_4$Cl solution, extracted with EA (100 mL*3), combined the organic phase, washed with H$_2$O (100 mL*2), saturation NaCl solution (100 mL*2), dried over Na$_2$SO$_4$, filtered, the filtrate was concentrated under reduced pressure to give crude title product ethyl 3-(4-bromo-1H-pyrazol-1-yl)propanoate 1b (2.2 g, yellow liquid), yield: 76.9%.

$^1$H NMR (400 MHz, CDCl$_3$) δ 7.46 (d, 2H), 4.39 (t, 2H), 4.14 (q, 2H), 2.86 (t, 2H), 1.24 (t, 3H)

Step 2 ethyl 3-(4-(4,4,5,5-tetramethyl-1,3,2-dioxaborolan-2-yl)-1H-pyrazol-1-yl)propanoate To a solution of ethyl 3-(4-bromo-1H-pyrazol-1-yl)propanoate 1b (1.8 g, 7.28 mmol) in 20 mL DMF was added 4,4,4',4',5,5,5',5'-octamethyl-2,2'-bi(1,3,2-dioxaborolane) (2.22 g, 8.74 mmol), KOAc (2.14 g, 21.84 mmol) and Pd(dppf)Cl$_2$ (297 mg, 0.36 mmol), stirred at 80° C. for 12 h. The reaction mixture was cooled to room temperature, added H$_2$O (50 mL), extracted with EA (40 mL*3), combined the organic phase, washed with saturation NaCl solution (30 mL*2), dried over Na$_2$SO$_4$, filtered, the filtrate was concentrated under reduced pressure. The residue was purified by silica column chromatography (Eluent C) to give title product ethyl 3-(4-(4,4,5,5-tetramethyl-1,3,2-dioxaborolan-2-yl)-1H-pyrazol-1-yl)propanoate 1c (1.2 g, colourless liquid), yield: 63.8%.

$^1$H NMR (400 MHz, CDCl$_3$) δ 7.75 (d, 2H), 4.42 (t, 2H), 4.13 (q, 2H), 2.89 (t, 2H), 1.31 (s, 12H), 1.26 (t, 3H).

Step 3

1-((4-bromo-3-fluorophenyl)amino)ethanol

To a solution or 4-bromo-3-fluoroaniline 1d (2.00 g, 10.53 mmol) in 20 mL DMF was added K$_2$CO$_3$ (7.26 g, 52.63 mmol), stirred at 100° C. for 12 h. The reaction mixture was cooled to room temperature, added H$_2$O (20 mL), extracted with EA (20 mL*3), combined the organic phase, washed with H$_2$O (100 mL*2), saturation NaCl solution (100 mL*2), dried over Na$_2$SO$_4$, filtered, the filtrate was concentrated under reduced pressure. The residue was purified by silica column chromatography (Eluent C) to give title product 2-((4-bromo-3-fluorophenyl)amino)ethanol 1e (630 mg, yellow oil), yield: 25.6%.

$^1$H NMR (400 MHz, DMSO-d$_6$) δ 7.44-7.43 (m, 1H), 7.36-7.33 (m, 1H), 7.14 (d, 1H), 6.70 (br. s, 1H), 3.69-3.65 (m, 2H), 3.40-3.36 (m, 2H), 2.17 (s, 3H)

Step 4

4-bromo-N-(2-((tert-butyldimethylsilyl)oxy)ethyl)-3-fluoroaniline

To a solution, of 2-((4-bromo-3-fluorophenyl)amino)ethanol 1e (630 mg, 2.96 mmol) in 15 mL (DCM was added TBSCl (470 mg, 11.76 mmol), stirred for 30 min. To the reaction mixture was added ethyl bromoacetate (1.96 g, 11.76 mmol), then stirred at room temperature for 12 h. To the mixture was added sat. NH$_4$Cl solution (50 mL), extracted with EA (50 mL*3), combined the organic phase, washed with H$_2$O (50 mL*2), saturation NaCl solution (50 mL*2), dried over Na$_2$SO$_4$, filtered, the filtrate was concentrated under reduced pressure. The residue was purified by silica column chromatography (Eluent C) to give title product 4-bromo-N-(2-((tert-butyldimethylsilyl)oxy)ethyl)-3-fluoroaniline 1f (530 mg, colourless liquid), yield: 49.6%, $^1$H NMR (400 MHz, CDCl$_3$) δ 7.24-7.22 (m, 1H), 6.40-6.37 (m, 1H), 6.31-6.28 (m, 1H), 4.19 (br. s, 1H), 3.80 (t, 2H), 3.17 (t, 2H), 0.90 (s, 9H), 0.07 (s, 6H).

Step 5

N-(4-bromo-3-fluorophenyl)-N-(2-((tert-butyldimethylsilyl)oxy)ethyl)-4,6-dichloropyrimidine-5-carboxamide To a solution of 4-bromo-N-(2-((tert-butyldimethylsilyl)oxy)ethyl)-3-fluoroaniline 1f (510 mg, 1.41 mmol) in 10 mL DCM was added TEA (445 mg, 4.41 mmol) and 4,6-dichloropyrimidine-5-carbonyl chloride (463 mg, 2.20 mmol), stirred for 12 h. To the mixture was added 10 mL H$_2$O, extracted with DCM (10 mL*3), combined the organic phase, washed with H$_2$O (10 mL*2), saturation NaCl solution (10 mL*2), dried over Na$_2$SO$_4$, filtered, the filtrate was concentrated under reduced pressure to give title product N-(4-bromo-3-fluorophenyl)-N-(2-((tert-butyldimethylsilyl)oxy)ethyl)-4,6-dichloropyrimidine-5-carboxamide 1g (730 mg, yellow solid). The product was used into the next step directly without further purification.

$^1$H NMR (400 MHz, CDCl$_3$) δ 8.86 (s, 1H), 7.37-7.33 (m, 1H), 7.27-7.19 (m, 1H), 7.04-7.01 (m, 1H), 3.94-3.91 (m, 2H), 3.87-3.85 (m, 2H), 0.81 (s, 9H), 0.00 (s, 6H)

Step 6

N-(4-bromo-3-fluorophenyl)-4,6-dichloro-N-(2-hydroxyethyl)pyrimidine-5-carboxamide To a solution of 1g (730 mg, 1.39 mmol) in 10 mL EtOH was added conc. HCl (0.3 mL), stirred for 1 h. To the mixture was added 10 mL H$_2$O, extracted with EA (10 mL*3), combined the organic phase, washed with H$_2$O (10 mL*2), saturation NaHCO$_3$ solution (10 mL*2), saturation NaCl solution (10 mL*2), dried over Na$_2$SO$_4$, filtered, the filtrate was concentrated under reduced pressure to give crude title product N-(4-bromo-3-fluorophenyl)-4,6-dichloro-N-(2-hydroxyethyl)pyrimidine-5-carboxamide 1h (560 mg, yellow solid). The product was used into the next step directly without further purification.

$^1$H NMR (400 MHz, CDCl$_3$) δ 8.65 (s, 1H), 7.48-7.44 (m, 1H), 7.29-7.24 (m, 1H), 7.13-7.10 (m, 1H), 4.06 (t, 2H), 3.93 (t, 2H)

Step 7

6-(4-bromo-3-fluorophenyl)-4-chloro-7,8-dihydropyrimido[5,4-f][1,4]oxazepin-5(6H)-one To a solution of N-(4-bromo-3-fluorophenyl)-4,6-dichloro-N-(2-hydroxyethyl)pyrimidine-5-carboxamide 1h (560 mg, 1.37 mmol) in 10 mL MeCN was added TEA (417 mg, 4.13 mmol), stirred at 80° C. for 12 h. The reaction mixture was cooled to room temperature, added 20 mL H$_2$O, extracted with EA (20 mL*3), combined the organic phase, washed with saturation NaCl solution (20 mL*2), dried over Na$_2$SO$_4$, filtered, the filtrate was concentrated under reduced pressure to give crude title product 6-(4-bromo-3-fluorophenyl)-4-chloro-7,8-dihydropyrimido[5,4-f][1,4]oxazepin-5(6H)-one 1i (480 mg, yellow solid). The product was used into the next step directly without further purification.

$^1$H NMR (400 MHz, CDCl$_3$) δ 8.79 (s, 1H), 7.67-7.63 (m, 1H), 7.27-7.24 (m, 1H), 7.11-7.08 (m, 1H), 4.76 (t, 2H), 4.06 (t, 2H)

Step 8

4-amino-6-(4-bromo-3-fluorophenyl)-7,8-dihydropyrimido[5,4-f][1,4]oxazepin-5(6H)-one A solution of 6-(4-bromo-3-fluorophenyl)-4-chloro-7,8-dihydropyrimido[5,4-f][1,4]oxazepin-5(6H)-one 1i (480 mg, 1.29 mmol) in 10 mL 0.5 M NH$_3$-dioxane was stirred for 12 h. The reaction mixture was concentrated under reduced pressure, added 20 mL H$_2$O, extracted with EA (20 ml*3), combined the organic phase, washed with H$_2$O (210 mL*2), saturation NaCl solution (20 mL*2), dried over Na$_2$SO$_4$, filtered, the filtrate was concentrated under reduced pressure to give crude title product 4-amino-6-(4-bromo-3-fluorophenyl)-7,8-dihydropyrimido[5,4-f][1,4]oxazepin-5(6H)-one 1j (340 mg, yellow solid). The product was used into the next step directly without further purification.

$^1$H NMR (400 MHz, DMSO-d$_6$) δ 8.18 (s, 1H), 7.77 (d, 1H), 7.64 (br, 2H), 7.58 (dd, 1H), 7.26 (dd, 1H), 4.62 (t, 2H), 4.01 (t, 2H)

Step 9

3-(4-(4-(4-amino-5-oxo-7,8-dihydropyrimido[5,4-f][1,4]oxazepin-6(5H)-yl)-2-fluorophenyl)-1H-pyrazol-1-yl)propanoate To a solution of 4-amino-6-(4-bromo-3-fluorophenyl)-7,8-dihydropyrimido[5,4-f][1,4]oxazepin-5(6H)-one 1j (80 mg, 0.23 mmol) in 5 mL 1,4-dioxane/H$_2$O (V/V=4:1) was added ethyl 3-(4-(4-(4-amino-5-oxo-7,8-dihydropyrimido[5,4-f][1,4]oxazepin-6(5H)-yl)-2-fluorophenyl)-1H-pyrazol-1-yl)propanoate 1c (64 mg, 0.23 mmol), Cs$_2$CO$_3$ (222 mg, 0.68 mmol) and Pd(dppf)Cl$_2$ (19 mg, 0.02 mmol). The mixture was irradiated in the microwave at 100° C. for 0.5 h. The reaction mixture was cooled to room temperature, filtered; the filtrate was used into the next step directly.

Step 10

3-(4-(4-(4-amino-5-oxo-7,8-dihydropyrimido[5,4-f][1,4]oxazepin-6(5H)-yl)-2-fluorophenyl)-1H-pyrazol-1-yl)propanoic acid To a solution of 3-(4-(4-(4-amino-5-oxo-7,8-dihydropyrimido[5,4-f][1,4]oxazepin-6(5H)-yl)-2-fluorophenyl)-1H-pyrazol-1-yl)propanoate 1k (90 mg, 0.20 mmol) in 8 mL 1,4-dioxane/H$_2$O (V/V=3:1) was added LiOH.H$_2$O (34 mg, 0.82 mmol), stirred for 12 h. To the mixture was added 1M HCl dropwise until pH:5~6, concentrated under reduced pressure the residue was purified by prep.HPLC to give title product 3-(4-(4-(4-amino-5-oxo-7,8-dihydropyrimido[5,4-f][1,4]oxazepin-6(5H)-yl)-2-fluorophenyl)-1H-pyrazol-1-yl)propanoic acid 1 (27 mg, white solid), yield: 33.2%.

MS m/z (ESI): 413.1 [M+1]

$^1$H NMR (400 MHz, DMSO-d$_6$) δ 8.55-8.43 (m, 3H), 8.16 (d, 1H), 7.92 (d, 1H), 7.74 (d, 1H), 7.41 (dd, 1H), 7.25 (dd, 1H), 4.77-4.75 (m, 2H), 4.34 (t, 2H), 4.10 (t, 2H), 2.81 (t, 2H)

Example 38

3-(4-(4-(4-amino-5-oxo-7,8-dihydropyrimido[5,4-f][1,4]oxazepin-6(5H)-yl)-2-chlorophenyl)-3,5-dimethyl-1H-pyrazol-1-yl)propanoic acid

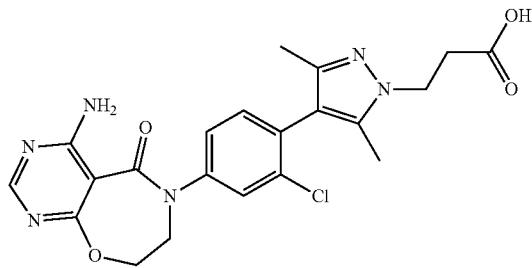

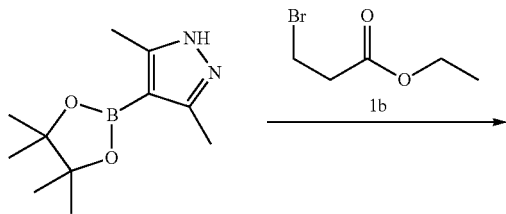

1a

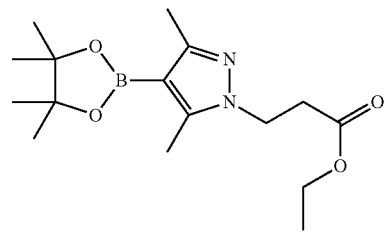

1c

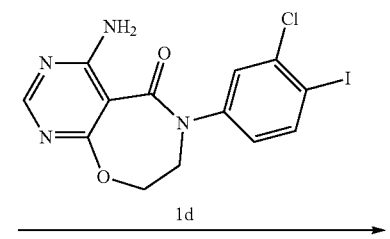

1d

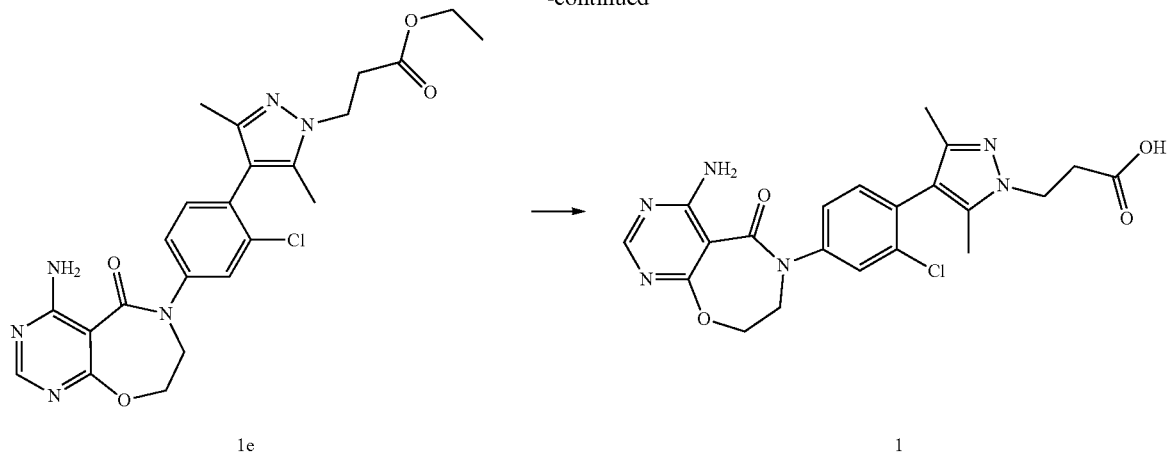

Step 1 ethyl 3-(3,5-dimethyl-4-(4,4,5,5-tetramethyl-1,3,2-dioxoaborolan-2-yl)-1H-pyrazol-1-yl)propanoate To a solution of 3,5-dimethyl-4-(4,4,5,5-tetramethyl-1,3,2-dioxaborolan-2-yl)-1H-pyrazole 1a (100 mg, 0.45 mmol) in 1 mL DMF was added $Cs_2CO_3$ (293 mg, 0.90 mmol) and ethyl 3-bromopropanoate (151 mg, 0.90 mmol) at ice-bath, stirred for 12 h. To the mixture was added 10 mL $H_2O$, extracted with EA (10 mL*3) combined the organic phase, washed with saturation NaCl solution (10 mL*2), dried over $Na_2SO_4$, filtered, the filtrate was concentrated under reduced pressure to give title product ethyl 3-(3,5-dimethyl-4-(4,4,5,5-tetramethyl-1,3,2-dioxaborolan-2-yl)-1H-pyrazol-1-yl)propanoate 1c (200 mg, pale yellow oil).

MS m/z (ESI): 309.1 [M+1]

Step 2 ethyl 3-(4-(4-(4-amino-5-oxo-7,8-dihydropyrimido[5,4-f][1,4]oxazepin-6(5H)-yl)-2-chlorophenyl)-3,5-dimethyl-1H-pyrazol-1-yl)propanoate To a solution of ethyl 3-(3,5-dimethyl-4-(4,4,5,5-tetramethyl-1,3,2-dioxaborolan-2-yl)-1H-pyrazol-1-yl)propanoate 1c (63 mg, 0.19 mmol), 4-amino-6-(3-chloro-4-iodophenyl)-7,8-dihydropyrimido[5,4-f][1,4]oxazepin-5(6H)-one 1d (80 mg, 0.19 mmol), $K_2CO_3$ (53.08 mg, 0.38 mmol) and Pd(dppf)$Cl_2$ (5 mg) in 2 mL 1,4-dioxane was added 0.6 mL $H_2O$. The mixture was stirred in the microwave at 100° C. for 0.5 h. The reaction mixture was cooled to room temperature, filtered; the filtrate was used into the next step directly.

Step 3

3-(4-(4-(4-amino-5-oxo-7,8-dihydropyrimido[5,4-f][1,4]oxazepin-6(5H)-yl)-2-chlorophenyl)-3,5-dimethyl-1H-pyrazol-1-yl)propanoic acid To the previous step reaction mixture was added LiOH.$H_2O$ (30 mg, 63 umol). The mixture was stirred for 3 h. The mixture was concentrated under reduced pressure. The residue was purified by prep. HPLC (Eluent B) to give title product 3-(4-(4-(4-amino-5-oxo-7,8-dihydropyrimido[5,4-f][1,4]oxazepin-6(5H)-yl)-2-chlorophenyl)-3,5-dimethyl-1H-pyrazol-1-yl)propanoic acid 1 (12 mg, white solid), yield: 42.3%.

MS m/z (ESI): 457.0 [M+1]

$^1$H NMR (400 MHz, $CD_3OD$) δ 8.18 (s, 1H), 7.66-7.68 (m, 3H), 7.41 (dd, 1H), 7.32 (d, 1H), 4.64 (t, 2H), 4.19 (t, 2H), 4.05 (t, 2H), 2.80 (t, 2H), 2.12 (s, 3H), 2.01 (s, 3H)

Example 39

2-(4-(4-(4-amino-5-oxo-7,8-dihydropyrimido[5,4-f][1,4]oxazepin-6(5H)-yl)phenyl)-3-(trifluoromethyl)-1H-pyrazol-1-yl)acetic acid

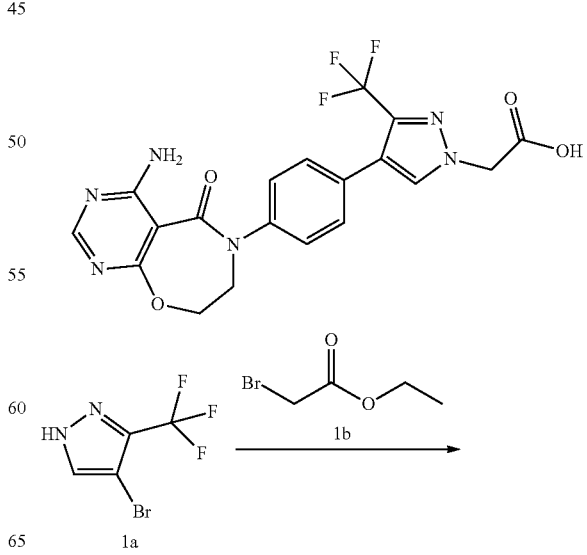

115
-continued

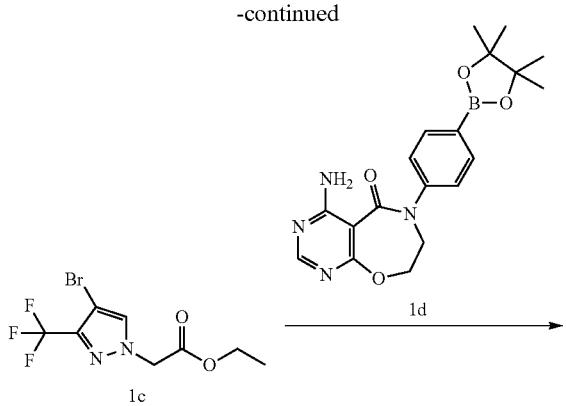

Step 1

Ethyl 2-(4-bromo-3-(trifluoromethyl)-1H-pyrazol-1-yl)acetate

To a solution of 4-bromo-3-(trifluoromethyl)-1H-pyrazole 1a (500 mg, 2.33 mmol) in 10 mL DMF was added NaH (140 mg, 3.49 mmol) at ice-bath. The mixture was stirred for 0.5 h. Ethyl 2-bromoacetate 1b (582 mg, 3.49 mmol) was added to above solution. Reaction mixture was stirred at room temperature for 12 h. To the mixture was added 30 mL H₂O, extracted with EA (20 mL*3), combined the organic phase, washed with H₂O (10 mL*2), saturation NaCl solution (10 mL*2), dried over filtered, the filtrate was concentrated under reduced pressure. The residue was purified by silica column chromatography (Eluent C) to give title product ethyl 2-(4-bromo-3-trifluoromethyl)-1H-pyrazol-1-yl)acetate 1b (450 mg, white solid), yield: 64.3%.

$^1$H NMR (400 MHz, CDCl₃) δ 7.60 (s, 1H), 4.90 (s, 2H), 4.25 (q, 2H), 1.29 (t, 3H)

Step 2

2-(4-(4-(4-amino-5-oxo-7,8-dihydropyrimido[5,4-f][1,4]oxazepin-6(5H)-yl)phenyl)-3-)trifluoromethyl)-1H-pyrazol-1-yl)acetic acid To a solution of ethyl 2-(4-bromo-3-(trifluoromethyl)-1H-pyrazol-1-yl)acetate 1b (50 mg, 170 umol) and 4-amino-6-(4-(4,4,5,5-tetramethyl-1,3,2-dioxaborolan-2-yl)phenyl)-7,8-dihydropyrimido[5,4-f][1,4]oxazepin-5(6H)-one (64 mg, 170 umol, prepared by WO2011121350) in 1,4-dioxane/H₂O (V/V=4:1, 5 mL) was added K₂CO₃ (70 mg, 510 umol)

116 and Pd(dppf)Cl₂ (6.2 mg, 8.5 umol)), stirred at 80° C. for 12 h. The mixture was cooled to room temperature, concentrated under reduced pressure. The residue was purified by prepare HPLC (Eluent B) to afford title product 2-(4-(4-(4-amino-5-oxo-7,8-dihydropyrimido[5,4-f][1,4]oxazepin-6(5H)-yl)phenyl)-3-(trifluoromethyl)-1H-pyrazol-1-yl)acetic acid 1 (16 mg, white solid), yield: 21.5%

MS m/z (ESI): 449.1 [M+1]

$^1$H NMR (400 MHz, DMSO-d₆) δ 8.20 (s, 1H), 8.18 (s, 1H), 7.71 (br. s, 2H), 7.47-7.41 (m, 4H), 5.10 (s, 2H), 4.62-4.60 (m, 2H), 4.03-4.01 (m, 2H)

Example 40

4-amino-6-(3-chloro-4-(3-methyl-1-(2,2,2-trifluoroethyl)-1H-pyrazol-4-yl)phenyl)-7,8-dihydropyrimido[5,4-f][1,4]oxazepin-5(6H)-one

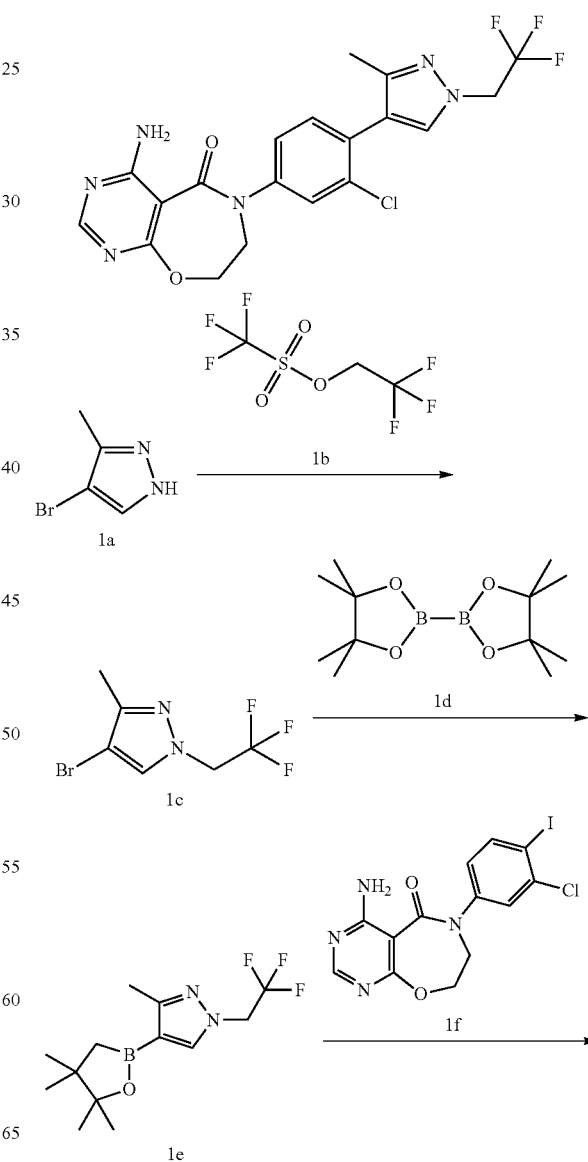

-continued

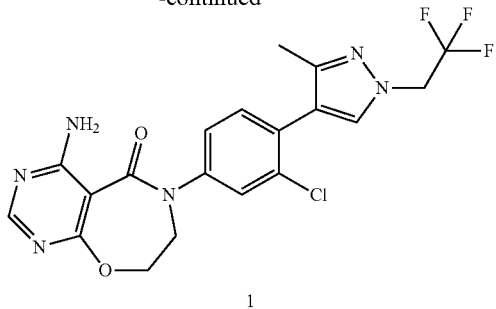

1

Step 1

4-bromo-3-methyl-1-(2,2,2-trifluoroethyl)-1H-pyrazole

To a solution of 4-bromo-3-methyl-1H-pyrazole 1a (500 mg, 3.11 mmol) in 10 mL DMF was added 2,2,2-trifluoroethyl trifluoromethanesulfonate 1b (756 mg, 3.26 mmol) and $Cs_2CO_3$ (2.02 g, 6.21 mmol). The mixture was heated at 100° C. in microwave for 30 min. The mixture cooled to room temperature, added 30 mL. $H_2O$, extracted with EA (30 mL*3), combined the organic phase, washed with $H_2O$ (30 mL*2), saturation NaCl solution (30 mL*2), dried over $Na_2SO_4$, filtered, the filtrate was concentrated under reduced pressure. The residue was purified by silica column chromatography (Eluent C) to give title product 4-bromo-3-methyl-1-(2,2,2-trifluoroethyl)-1H-pyrazole (516 mg, white solid), yield: 68.4%.

$^1$H NMR (400 MHz, $CDCl_3$) δ 7.99 (s, 1H), 5.11-5.02 (m, 2H), 2.43 (s, 3H)

Step 2

3-methyl-4-(4,4,5,5-tetramethyl-1,3,2-dioxaborolan-2-yl)-1-(2,2,2-trifluoroethyl)-1H-pyrazole To a solution of 4-bromo-3-methyl-1-(2,2,2-trifluoroethyl-1H-pyrazole (516 mg, 2.12 mmol) and 4,4,4',4',5,5,5',5'-octamethyl-2,2'-bi(1,3,2,-dioxaborolane) (647 mg, 2.55 mmol) in 3 mL 1,4-dioxane was added KOAc (625 mg, 6.37 mmol) and Pd(dppf)Cl$_2$ (86 mg, 106 umol), stirred at 90° C. for 12 h. To the mixture was added 20 mL $H_2O$, extracted with EA (20 mL*3), combined the organic phase, washed with $H_2O$ (20 mL*2), saturation NaCl solution (20 mL*2), dried over $Na_2SO_4$, filtered, the filtrate was concentrated under reduced pressure. The residue was purified by silica column chromatography (Eluent C) to give title product 3-methyl-4-(4,4,5,5-tetramethyl-1,3,2-dioxaborolan-3-yl)-1-(2,2,2-trifluoroethyl)-1H-pyrazole 1c (200 mg, white solid) yield: 32.5%.

Step 3

4-amino-6-(3-chloro-4-(3-methyl-1-(2,2,2-trifluoroethyl)-1H-pyrazol-4-yl)phenyl-7,8-dihydropyrimido[5,4-f][1,4]oxazepin-5(6H)-one To a solution of 3-methyl-4-(4,4,5,5-tetramethyl-1,3,2-dioxaborolan-2-yl)-1-(2,2,2-trifluoroethyl)-1H-pyrazole 1c (41 mg, 144 umol) and 4-amino-6-(3-chloro-4-iodophenyl)-7,8-dihydropyrimido[5,4-f][1,4]oxazepin-5(6H)-one (60 mg, 144 umol) in 3 mL 1,4-dioxane/$H_2O$ (V/V=2:1) was added $K_2CO_3$ (60 mg, 432 umol) and Pd(dppf)Cl$_2$ (6 mg, 7.2 umol), stirred in microwave at 90° C. for 30 min. The reaction mixture was cooled to room temperature, concentrated under reduced pressure. The residue was purified by prep.HPLC (Eluent B) to give title product 4-amino-6-(3-chloro-4-(3-methyl-1-(2,2,2-trifluoroethyl)-1H-pyrazol-4-yl)phenyl)-7,8-dihydropyrimido[5,4-f][1,4]oxazepin-5(6H)-one 1 (28 mg, white solid), yield: 43.5%.

MS m/z (ESI): 453.0 [M+1]

$^1$H NMR (400 MHz, DMSO-$d_6$) δ 8.31 (s, 1H), 7.97 (s, 1H), 7.71 (d, 1H), 7.48-7.41 (m, 2H), 5.18-5.07 (m, 2H), 4.75-4.73 (t, 2H), 4.12 (t, 2H) 2.27 (s, 3H)

Example 41

4-amino-6-(3,5-dimethyl-4-(3-methyl-1-(2,2,2-trifluoroethyl)-1H-pyrazol-4-yl)phenyl)-7,8-dihydropyrimido[5,4-f][1,4]oxazepin-5(6H)-one

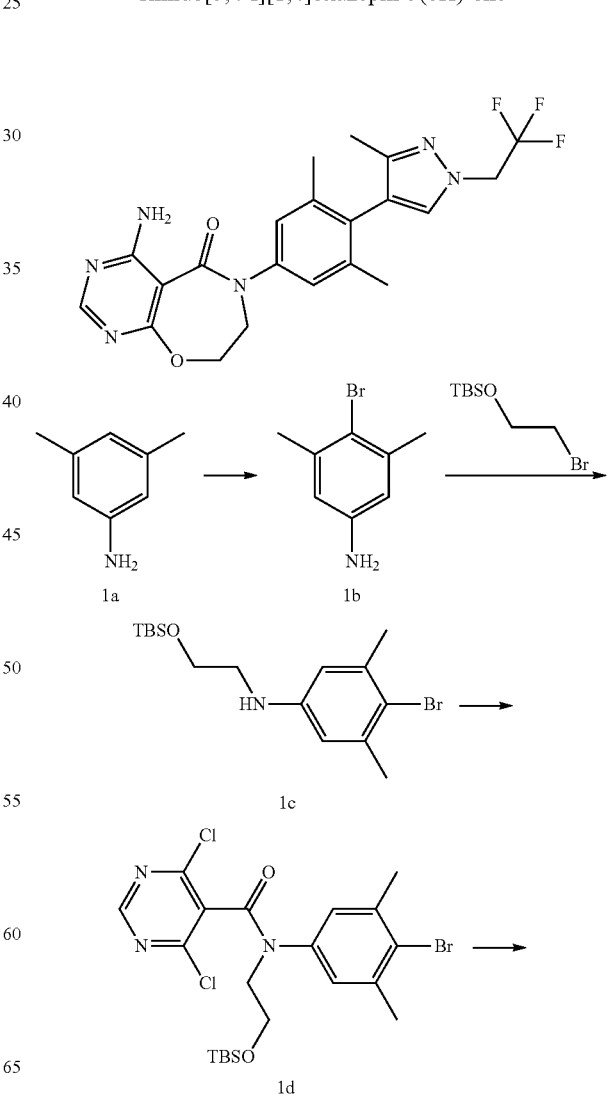

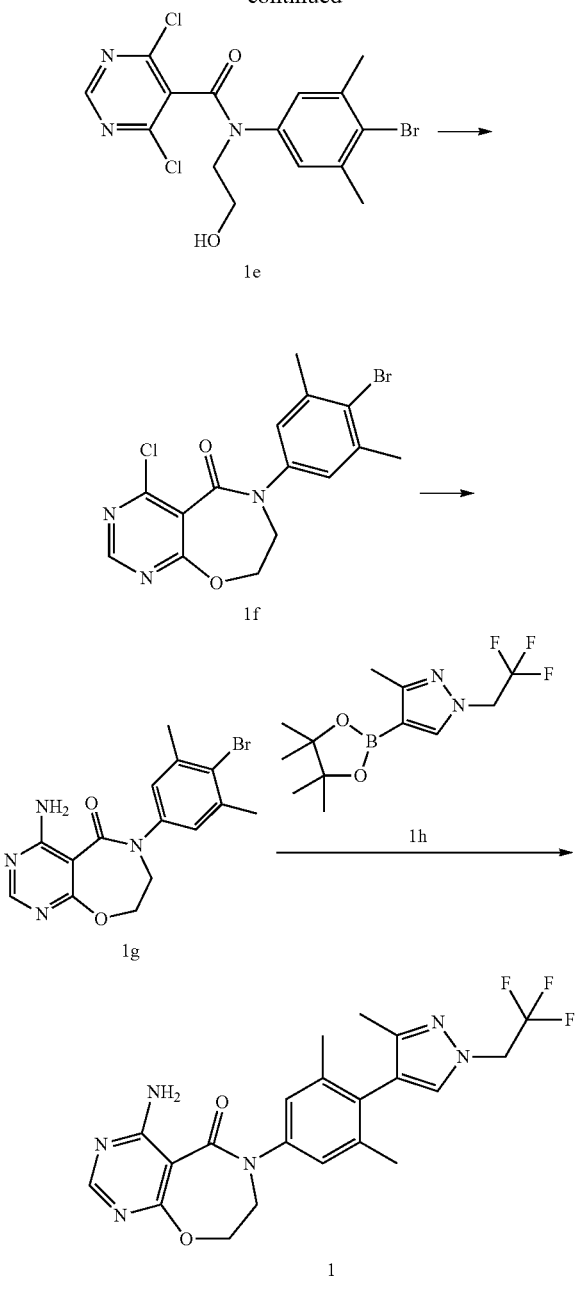

Step 2

4-bromo-N-(2-((tert-butyldimethylsilyl)oxy)ethyl)-3,5-dimethylaniline

To NaH (60% purity, 40 g, 1000 mmol) was added a solution of 4-bromo-3,5-dimethylaniline 1b (100 g, 500 mmol) in THF (1 L) at ice-bath. The mixture was stirred at room temperature for 1 h. To the mixture was added (2-bromoethoxy)(tert-butyl)dimethylsilane (179 g, 749 mmol), the mixture was stirred at 40° C. for 16 h. The reaction mixture was cooled to room temperature, quenched excess NaH by adding dropwise slowly sat. $NH_4Cl$ solution (50 mL) and $H_2O$ (100 mL), extracted with EA (500 mL*2) and $H_2O$ (500 mL*2), combined the organic phase, saturation NaCl solution (300 mL*2), dried over $Na_2SO_4$, filtered, the filtrate was concentrated under reduced pressure. The residue was purified by silica column chromatography (Eluent C) to give title product 4-bromo-N-(2-((tert-butyldimethylsilyl)oxy)ethyl)-3,5-dimethylaniline 1c (180 g, yellow solid), yield: 100%.

MS m/z (ESI): 358 [M+1]

Step 3

N-(4-bromo-3,5-dimethylphenyl)-N-(2-((tert-butyldimethylsilyl)oxy)ethyl)-4,6-dichloropyrimidine-5-carboxamide To a solution of 4-bromo-N-(2-((tert-butyldimethylsilyl)oxy)ethyl)-3,5-dimethylaniline 1c (180 g, 503 mmol) in DCM (2 L) was added 4,6-dichloropyrimidine-5-carbonyl chloride (138 g, 654 mmol) and TEA (210 mL), stirred for 16 h. The reaction mixture was diluted with DCM (1 L*2) and $H_2O$ (1L*2), combined the organic phase, washed with saturation NaCl solution (300 mL*2), dried over $Na_2SO_4$, filtered, the filtrate was concentrated under reduced pressure. The residue was purified by silica column chromatography (Eluent C) to give title product N-(4-bromo-3,5-dimethylphenyl)-N-(2-((tert-butyldimethylsilyl)oxy)ethyl)-4,6-dichloropyrimidine-5-carboxamide 1d (160 g, yellow oil), yield: 59.7%.

MS m/z (ESI): 533.9 [M+1]

1H NMR (400 MHz, $CDCl_3$): δ 8.61 (s, 1H), 7.13 (s, 2H), 7.27 (s, 1H), 3.97 (t, 2H), 3.89 (t, 2H), 2.30 (s, 6H), 0.87 (s, 9H), 0.06 (s, 6H)

Step 4

N-(4-bromo-3,5-dimethylphenyl)-4,6-dichloro-N-(2-hydroxyethyl)pyrimidine-5-carboxamide A solution of N-(4-bromo-3,5-dimethylphenyl)-N-(2-((tert-butyldimethylsilyl)oxy)ethyl)-4,6-dichloropyrimidine-5-carboxamide 1d (160 g, 299.6 mmol) in 1.5 L EtOH and 45 mL HCl was stirred for 3 h. The reaction mixture was extracted with EA (500 mL*3) and $H_2O$ (500 mL*2), combined the organic phase, washed with saturation NaCl solution (300 mL*2), dried over $Na_2SO_4$, filtered, the filtrate was concentrated under reduced pressure to give title product N-(4-bromo-3,5-dimethylphenyl)-4,6-dichloro-N-(2-hydroxyethyl)pyrimidine-5-carboxamide 1e (125 g, pale yellow solid), yield: 100%.

MS m/z (ESI): 419.9 [M+1]

1H NMR (400 MHz, $CDCl_3$) δ 8.62 (s, 1H), 7.13 (s, 2H), 7.27 (s, 1H), 4.06 (t, 2H), 3.91 (t, 2H), 2.32 (s, 6H)

Step 1

4-bromo-3,5-dimethylaniline

To a solution of 3,5-dimethylaniline 1a (80 g, 60 mmol) in 800 mL MeCN was added a solution of NBS (117 g, 660 mmol) in 400 ml MeCN at ice bath, stirred at room temperature for 16 h. The reaction mixture was concentrated under reduced pressure. The residue was purified by silica column chromatography (Eluent C) to give title product 4-bromo-3,5-dimethylaniline 1b (90 g, yellow solid), yield: 68.2%.

MS m/z (ESI): 200 [M+1]

Step 5

6-(4-bromo-3,5-dimethylphenyl)-4-chloro-7,8-dihydropyrimido[5,4-f][1,4]oxazepin-5(6H)-one To a solution of N-(4-bromo-3,5-dimethylphenyl)-4,6-dichloro-N-(2-hydroxyethyl)pyrimidine-5-carboxamide 1e (125 g, 298 mmol) in 1.5 L MeCN was added TEA (154.4 mL) at room temperature, stirred at 80° C. for 16 h. The reaction mixture was cooled to room temperature, extracted with DCM (500 mL*3) and H₂O (500 mL*2), combined the organic phase, washed with saturation NaCl solution (300 mL*2), dried over Na2SO4, filtered, the filtrate was concentrated under reduced pressure to give title product 6-(4-bromo-3,5-dimethylphenyl)-4-chloro-7,8-dihydropyrimido[5,4-f][1,4]oxazepin-5(6H)-one 1f (103 g, pale yellow solid), yield: 91%.

MS m/z (ESI): 383.9 [M+1]
$^1$H NMR (400 MHz, CDCl3) δ 8.76 (s, 1H), 6.98 (s, 2H), 7.27 (s, 1H), 4.74 (t, 2H), 4.01 (t, 2H), 2.45 (s, 6H)

Step 6

4-amino-6-(4-bromo-3,5-dimethylphenyl)-7,8-dihydropyrimido[5,4-f][1,4]oxazepin-5(6H)-one A solution of 6-(4-bromo-3,5-dimethylphenyl)-4-chloro-7,8-dihydropyrimido[5,4-f][1,4]oxazepin-5(6H)-one 1f (103 g, 268.9 mmol) in 0.5N NH₃/1,4-dioxane (1.2 L), stirred for 16 h. The reaction mixture was filtered to give the title product 4-amino-6-(4-bromo-3,5-dimethylphenyl)-7,8-dihydropyrimido[5,4-f][1,4]oxazepin-5(6H)-one 1g (90 g, white solid), yield: 92.4%.

MS m/z (ESI): 364.9 [M+1]
$^1$H NMR (400 MHz, DMSO) δ 8.17 (s, 1H), 7.62 (br. s, 2H), 7.31 (s, 6H), 7.24 (s, 2H), 4.60 (t, 2H), 3.95 (t, 2H), 2.40-2.34 (s, 6H)

Step 7

4-amino-6-(3,5-dimethyl-4-(3-methyl-1-(2,2,2-trifluoroethyl-1H-pyrazol-4-yl)phenyl-7,8-dihydropyrimido[5,4-f][1,4]oxazepin-5(6H)-one To a solution of 3-methyl-4-(4,4,5,5-tetramethyl-1,3,2-dioxaborolan-2-yl)-1-(2,2,2-trifluoroethyl)-1H-pyrazole 1h (57 mg, 290 umol) and 4-amino-6-(4-bromo-3,5-dimethylphenyl)-7,8-dihydropyrimido[5,4-f][1,4]oxazepin-5(6H)-one 1g (60 mg, 165 umol) in 3 mL 1,4-dioxane/H₂O (V/V=2:1) was added K₂CO₃ (68 mg, 495 umol) and Pd(dppf)Cl₂ (6 mg, 7.2 umol). The mixture was stirred at 90° C. for 30 min under microwave irradiation. The reaction mixture was cooled to room temperature, concentrated under reduced pressure. The residue was purified by prep.HPLC (Eluent B) to give title product 4-amino-6-(3,5-dimethyl-4-(3-methyl-1-(2,2,2-trifluoroethyl)-1H-pyrazol-4-yl)phenyl)-7,8-dihydropyrimido[5,4-f][1,4]oxazepin-5(6H)-one 1 (30 mg, white solid), yield: 40.7%.

MS m/z (ESI): 446.1 [M+1]
$^1$H NMR (400 MHz, DMSO-d6) δ 8.35 (s, 1H), 7.68 (s, 1H), 7.16 (s, 1H), 5.07 (q, 2H), 4.75 (t, 2H), 4.09 (t, 2H), 2.01 (s, 6H), 1.94 (s, 3H)

Example 42

4-amino-6-(3-chloro-4-(1-(2-hydroxy-2-methylpropyl)-1H-pyrazol-4-yl)phenyl)-7,8-dihydropyrimido[5,4-f][1,4]oxazepin-5(6H)-one

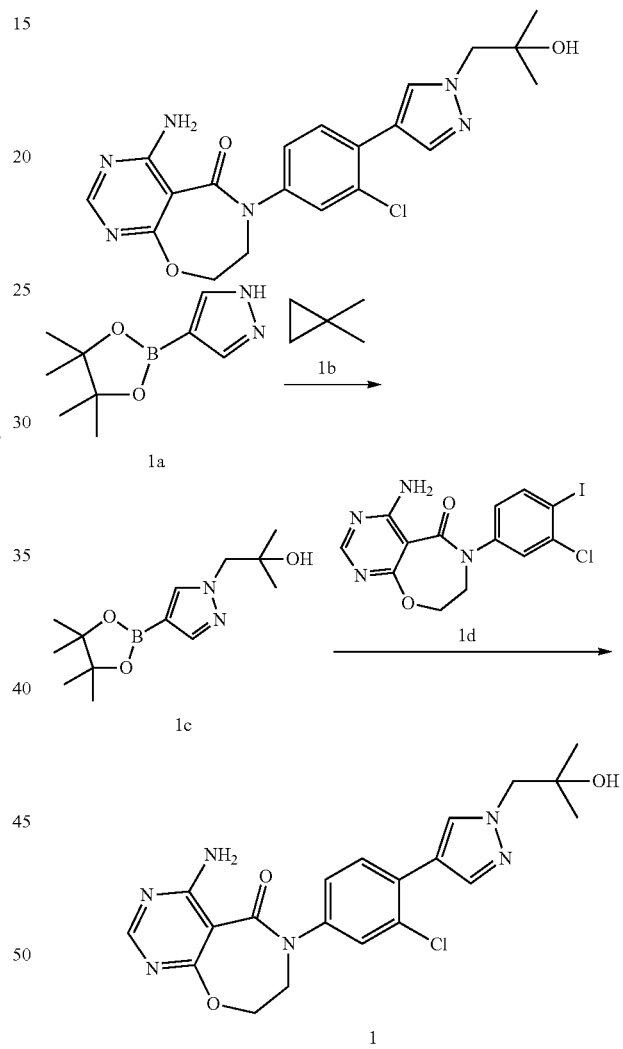

Step 1

2-methyl-1-(4-(4,4,5,5-tetramethyl-1,3,2-dioxaborolan-2-yl)-1H-pyrazol-1-yl)propan-2-ol To a solution of 4-(4,4,5,5-tetramethyl-1,3,2-dioxaborolan-2-yl)-1H-pyrazole 1a (100 mg, 0.52 mmol) in 2 mL DMF was added 2,2-dimethyloxirane 1b (190 mg, 1.55 mmol) and Cs₂CO₃ (251 mg, 0.77 mmol) at room temperature. Reaction mixture was stirred at 110° C. for 1 h under microwave irradiation. After cooling at room temperature, to the mixture was added 20 mL H₂O, extracted with EA (30 mL*3), combined the organic phase, dried over Na₂SO₄, filtered, the filtrate was concentrated under reduced pressure to give title product 2-methyl-1-(4-(4,4,5,5-tetramethyl-1,3,2-dioxaborolan-2-yl)-1H-pyrazol-1H-propan-2-ol 1c (90 mg, white solid), yield: 65.2%.

MS m/z (ESI): 239.2 [M+1]

¹H NMR (400 MHz, CDCl₃) δ 1.15 (s, 6H), 1.32 (s, 12H), 4.07 (s, 2H), 7.69 (s, 1H), 7.82 (s, 1H)

Step 2

4-amino-6-(3-chloro-4-(1-(2-hydroxy-2-methylpropyl)-1H-pyrazol-4-yl)phenyl-7,8-dihydropyrimido[5,4-f][1,4]oxazepin-5(6H)-one To a solution of 2-methyl-1-(4-(4,4,5,5-tetramethyl-1,3,2-dioxaborolan-2-yl)-1H-pyrazol-1-yl)propan-2-ol 1c (100 mg, 0.52 mmol), 4-amino-6-(3-chloro-4-iodophenyl)-7,8-dihydropyrimido[5,4-f][1,4]oxazepin-5(6H)-one (45 mg, 0.17 mmol), Cs₂CO₃ (110 mg, 0.34 mmol) and Pd(dppf)Cl₂ (5 mg, 0.006 mmol) in 1.5 mL 1,4-dioxane was added 0.5 mL H₂O at room temperature. Reaction mixture was stirred 110° C. for 30 min under microwave irradiation. After cooling at room temperature, the mixture was filtered and the filtrate was concentrated under reduced pressure. The reside was purified by prep HPLC to afford 4-amino-6-(3-chloro-4-(1-(2-hydroxy-2-methylpropyl)-1H-pyrazol-4-yl)phenyl)-7,8-dihydropyrimido[5,4-f][1,4]oxazepin-5(6H)-one 1 (4 mg, white solid), yield: 8.3%.

MS m/z (ESI): 429.1 [M+1]

¹H NMR (400 MHz, CD₃OD) δ 1.25 (s, 6H), 4.24 (s, 2H), 4.27-4.33 (m, 2H), 4.99-5.07 (m, 2H), 7.40 (dd, 1H), 7.64 (d, 1H), 7.72 (d, 1H), 8.09 (s, 1H), 8.29 (s, 1H), 8.46 (s, 1H)

Example 43

4-amino-6-(4-(1-(2,2-difluoroethyl)-3-methyl-1H-pyrazol-4-yl)-3,5-dimethylphenyl)-7,8-dihydropyrimido[5,4-f][1,4]oxazepin-5(6H)-one

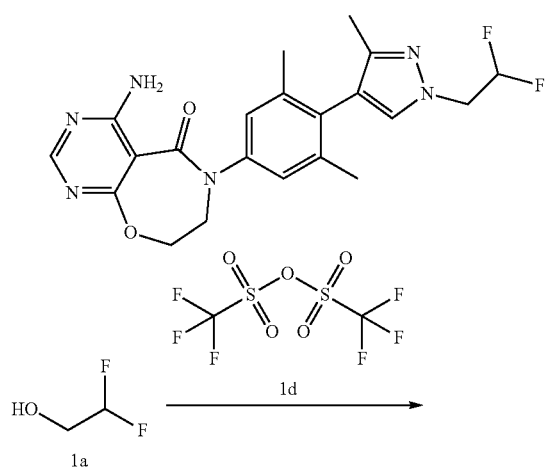

-continued

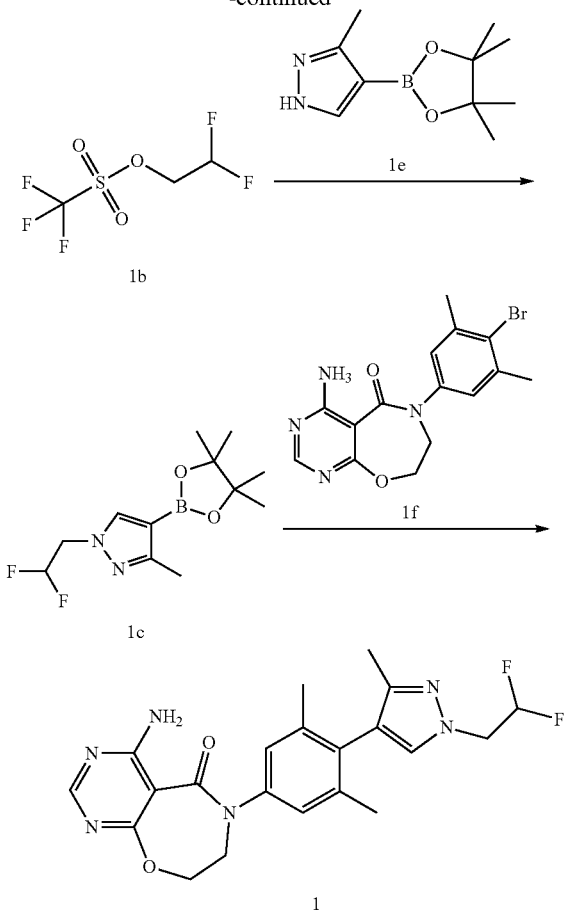

Step 1

2,2-difluoroethyl trifluoromethanesulfonate

To a solution of trifluoromethanesulfonic anhydride (34.39 g, 0.12 mol) in DCM (20 mL) was cooled to −78° C. then added 2,2-difluoroethanol 1a (10 g, 0.12 mol) and TEA (12 g, 0.12 mol) in DCM (10 mL) slowly. The mixture was warmed to rt then concentrated to afford crude 2,2-difluoroethyl trifluoromethanesulfonate 1b (53.00 g) as a yellow oil. It was used in the next step without further purification.

Step 2

1-(2,2-difluoroethyl)-3-methyl-4-(4,4,5,5-tetramethyl-1,3,2-dioxaborolan-2-yl)-1H-pyrazole A mixture of 2,2-difluoroethyl trifluoromethanesulfonate 1b (8.23 g, 0.38 mol), 3-methyl-4-(4,4,5,5-tetramethyl-1,3,2-dioxaborolan-2-yl)-1H-pyrazole (500 mg, 1.92 mmol) and Cs₂CO₃ (1.25 g, 3.84 mmol) in DMF (10 mL) was heated in microwave at 100° C. for 1 h. The reaction mixture was cooled to room temperature quenched with H₂O (30 mL) and extracted with EA (20 mL*3), the organic layers were combined and washed with water (10 mL*2) and brine (10 mL*2), dried over Na₂SO₄, evaporated. The residue was purified by silica column to afford 1-(2,2-difluoroethyl)-3-methyl-4-(4,4,5,5-tetramethyl-1,3,2-dioxoborolan-2-yl)-1H-pyrazole (117 mg, white solid), yield: 17.8%.

¹H NMR (400 MHz, CDCl₃) δ 7.63 (s, 1H), 6.23-5.89 (m, 1H), 4.41-4.43 (m, 1H), 2.36 (s, 3H), 1.28 (s, 12H)

Step 3

4-amino-6-(4-(1-(2,2-difluoroethyl)-3-methyl-1H-pyrazol-4-yl)-3,5-dimethylphenyl)-7,8-dihydropyrimido[5,4-f][1,4]oxazepin-5(6H)-one A mixture of 1-(2,2-difluoroethyl)-3-methyl-4-(4,4,5,5-tetramethyl-1,3,2-dioxaborolan-2-yl)-1H-pyrazole 1c (62 mg, 172 umol) and 4-amino-6-(4-bromo-3,5-dimethylphenyl)-7,8-dihydropyrimido[5,4-f][1,4]oxazepin-5(6H)-one (117 mg, 343 umol) in dioxane/H₂O (4/1, 2.5 mL) was added K₂CO₃ (71 mg, 516 umol) and Pd(dppf)Cl₂ (6.2 mg, 8.5 umol). The mixture was heated in microwave at 90° C. for 40 min. The mixture was concentrated to give the crude product. The residue was purified by prepare HPLC to afford 4-amino-6-(4-(1-(2,2-difluoroethyl)-3-methyl-1H-pyrazol-4-yl)-3,5-dimethylphenyl)-7,8-dihydropyrimido[5,4-f][1,4] oxazepin-5(6H)-one (30 mg, white solid), yield: 40.9%.

MS m/z (ESI): 429.0 [M+1]

¹H NMR (400 MHz, DMSO-d6) δ 8.71 (br. s, 1H), 8.58 (br. s, 1H), 8.41 (s, 1H), 7.58 (s, 1H), 7.12 (s, 1H), 6.50-6.20 (m, 1H), 4.79 (t, 2H) 4.59-4.50 (m, 2H), 4.10 (t, 2H), 1.99 (s, 6H), 1.90 (s, 3H)

Example 44

4-amino-6-(3-chloro-4-(1-(3-hydroxy-2,2-dimethylpropyl)-1H-pyrazol-4-yl)phenyl)-7,8-dihydropyrimido[5,4-f][1,4]oxazepin-5(6H)-one

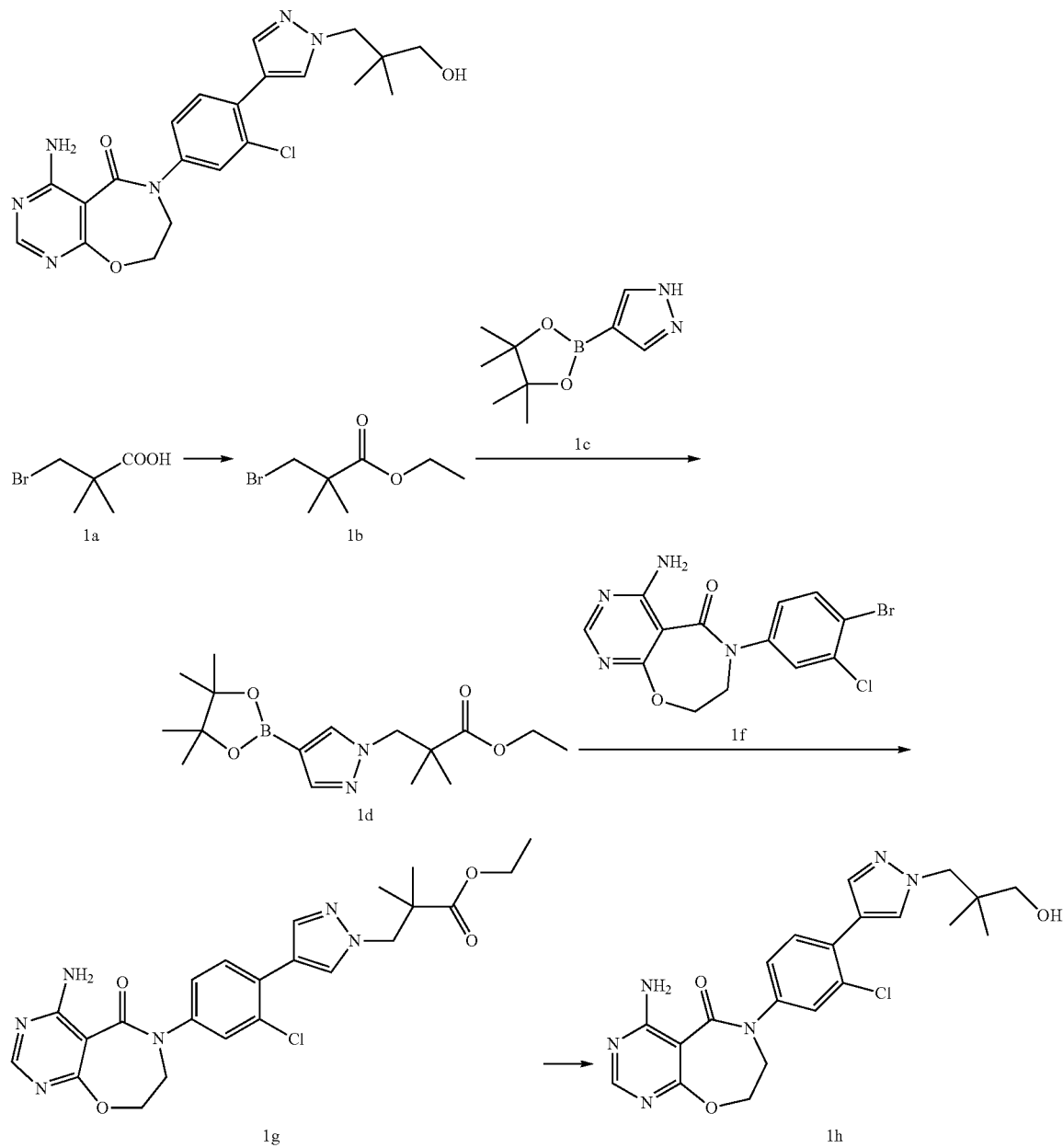

Step 1 ethyl 3-bromo-2,2-dimethylpropanoate

To a solution of 3-bromo-2,2-dimethylpropanoic acid 1a (500 mg, 2.76 mmol) in ethyl alcohol (5 mL) was added concentrated sulfuric acid (0.5 mL). It was stirred at 100° C. for 2 h. The reaction solution was cooled to room temperature, neutralized by $NaHCO_3$ and extracted with EA (30 mL*3). The combined organic phases was dried over $Na_2SO_4$, filtrated and evaporated to afford ethyl 3-bromo-2,2-dimethylpropanoate 1b (430 mg, yield 74.5%) as a yellow solid. It was used in the next step without further purification.

$^1$H NMR (400 MHz, $CDCl_3$) 4.18 (q, 2H), 3.5 (s, 1H), 1.57 (s, 6H), 1.30 (q, 3H)

Step 2 ethyl 2,2-dimethyl-3-(4-(4,4,5,5-tetramethyl-1,3,2-dioxaborolan-2-yl)-1H-pyrazol-1-yl)propanoate

To a mixture of ethyl 3-bromo-2,2-dimethylpropanoate 1b (400 mg, 1.91 mmol), 4-(4,4,5,5-tetramethyl-1,3,2-dioxaborolan-2-yl)-1H-pyrazole 1c (330 mg, 1.73 mmol) and $Cs_2CO_3$ (1.2 g, 3.45 mmol) in DMF (10 mL) was heated in microwave at 100° C. for 25 min. It was cooled to room temperature. EA (30 mL) was added to the mixture and washed with water (30 mL*3). The organic phase was dried over $Na_2SO_4$, filtrated and evaporated to afford ethyl 2,2-dimethyl-3-(4-(4,4,5,5-tetramethyl-1,3,2-dioxaborolan-2-yl)-1H-pyrazol-1-yl)propanoate (170 mg, yield: 30.5%) as a yellow solid. It was used in the next step without further purification.

$^1$H NMR (400 MHz, $CDCl_3$) 7.74 (s, 1H), 7.66 (s, 1H), 4.28 (s, 2H), 4.16 (q, 2H), 1.30 (s, 9H), 1.24 (t, 3H)

Step 3 ethyl-3-(4-(4-(4-amino-5-oxo-7,8-dihydropyrimido[5,4-f][1,4]oxazepin-6(5H)-yl)-2-chlorophenyl)-1H-pyrazol-1-yl)-2,2-dimethylpropanoate

A solution of ethyl 2,2-dimethyl-3-(4-(4,4,5,5-tetramethyl-1,3,2-dioxoaborolan-2-yl)-1H-pyrazol-1-yl)propanoate 1d (94 mg, 0.29 mmol), 4-amino-6-(4-bromo-3-chlorophenyl)-7,8-dihydropyrimido[5,4-f][1,4]oxazepin-5(6H)-one 1f (100 mg, 0.24 mmol), $Cs_2CO_3$ (156 mg, 0.48 mmol and Pd(dppf)$Cl_2$ (10 mg, 0.012 mmol) in dioxane/$H_2O$ (8 mL, V/V=3:1) was heated in microwave at 100° C. for 30 min. It was cooled to room temperature. EA (30 mL) was added to the mixture and washed with water (30 mL*3). The organic phase was dried over $Na_2SO_4$, filtrated and evaporated, the residue was purified by p-TLC to afford ethyl 3-(4-(4-(4-amino-5-oxo-7,8-dihydropyrimido[5,4-f][1,4]oxazepin-6(5H)-yl)-2-chlorophenyl)-1H-pyrazol-1-yl)-2,2-dimethylpropanoate 1g (60 mg, yield 42.7%) as a light yellow liquid.

$^1$H NMR (400 MHz, $CDCl_3$) δ 8.30 (s, 1H), 7.83 (s, 1H), 7.76 (s, 1H), 7.52 (d, 1H), 7.39 (d, 1H), 7.21 (dd, 12H), 4.74-4.69 (m, 2H) 4.34 (s, 2H), 4.22-4.14 (m, 2H), 4.05-4.01 (m, 2H), 1.57 (s, 9H)

Step 4

4-amino-6-(3-chloro-4-(1-(3-hydroxy-2,2-dimethylpropyl)-1H-pyrazol-4-yl)phenyl)-7,8-dihydropyrimido[5,4-f][1,4]oxazepin-5(6H)-one

To a solution of ethyl 3-(4-(4-(4-amino-5-oxo-7,8-dihydropyrimido[5,4-f][1,4]oxazepin-6(5H)-yl)-2-chlorophenyl)-1H-pyrazol-1-yl)-2,2-dimethylpropanoate 1g (80 mg, 0.16 mmol) in THF (2 mL) was added $CaCl_2$ (36 mg, 0.32 mmol) and $NaBH_4$ (31 mg, 0.82 mmol) at 0° C. It was stirred at room temperature for 12 h. The reaction solution was concentrated and the residue was purified by p-HPLC to afford 4-amino-6-(3-chloro-4-(1-(3-hydroxy-2,2-dimethylpropyl)-1H-pyrazol-4-yl)phenyl)-7,8-dihydropyrimido[5,4-f][1,4]oxazepin-5(6H)-one (6 mg, 8.1%) as a white solid.

MS m/z (ESI): 443.1 [M+1]

$^1$H NMR (400 MHz, $CD_3OD$) δ 8.45 (s, 1H), 8.20 (s, 1H), 8.01 (s, 1H), 7.70 (d, 1H), 7.62 (d, 1H), 7.39 (dd, 1H), 5.00-5.07 (m, 2H), 4.26-4.33 (m, 2H), 4.18 (s, 2H) 0.97 (s, 6H)

Example 45

(R)-4-amino-6-(3-chloro-4-(1-isobutyl-1H-pyrazol-4-yl)phenyl)-8-methyl-7,8-dihydropyrimido[5,4-f][1,4]oxazepin-5(6H)-one

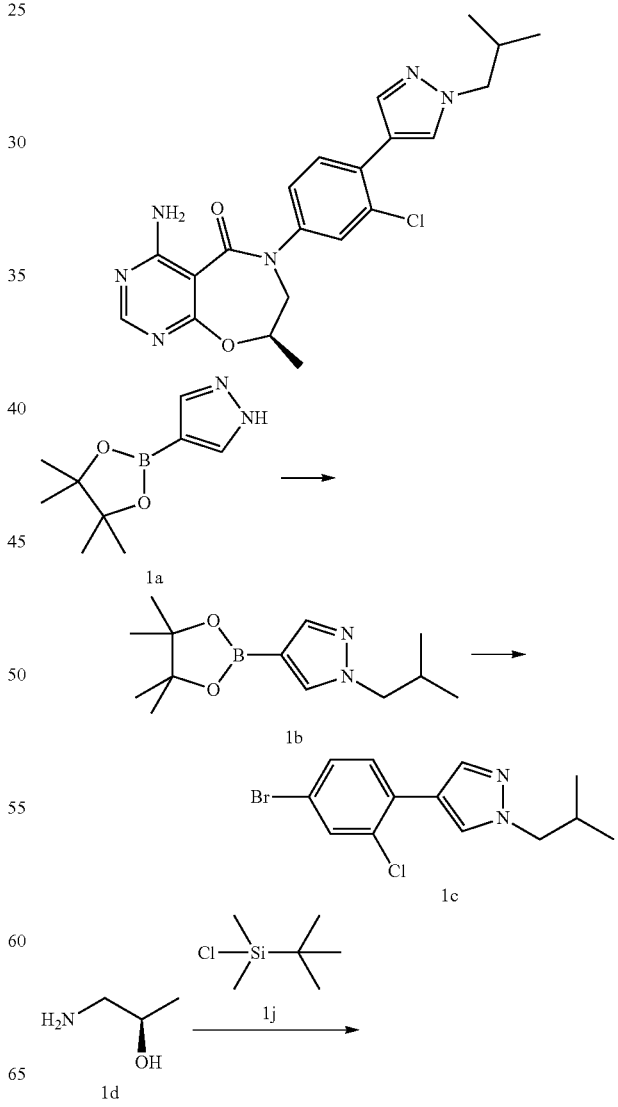

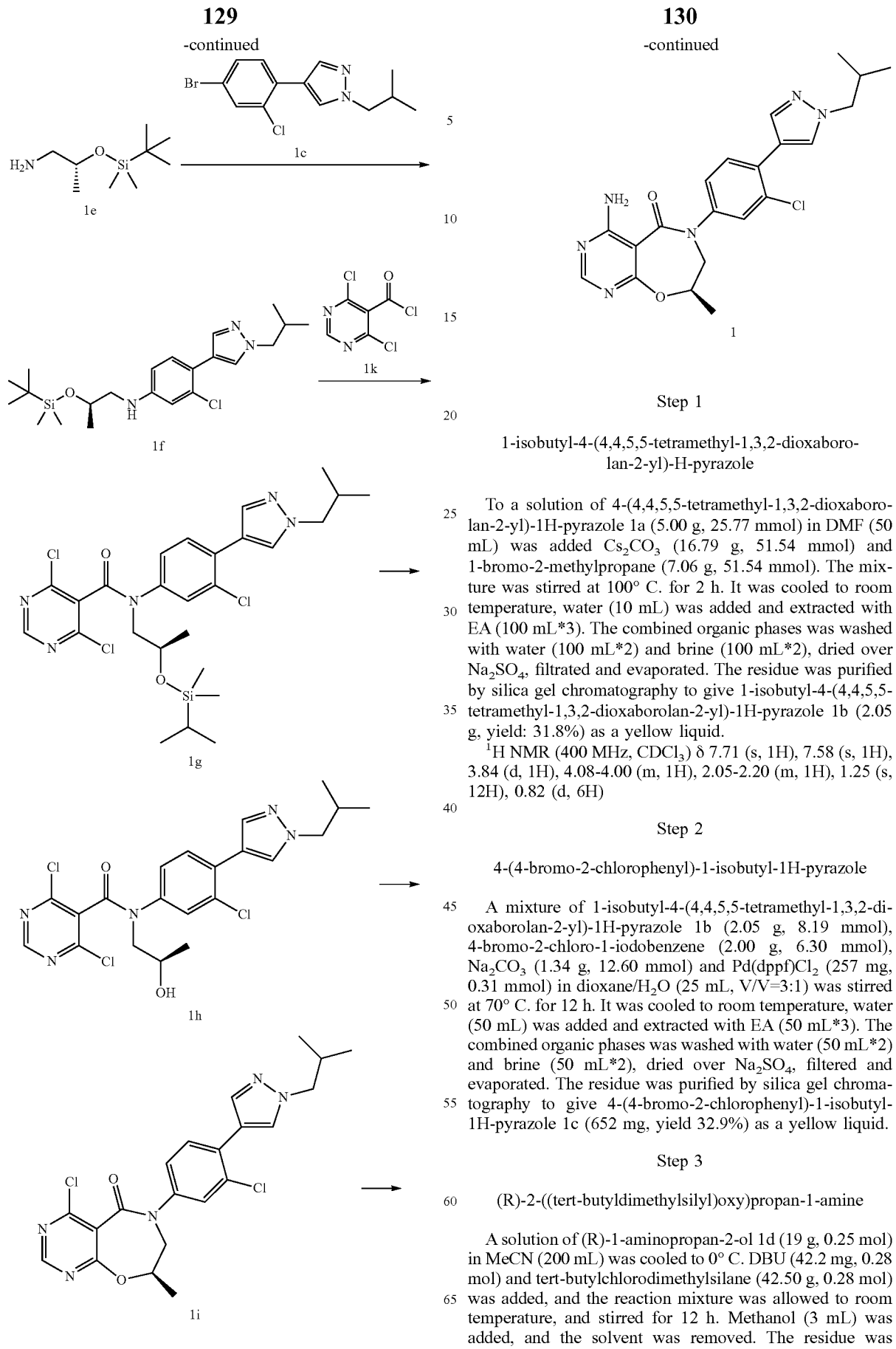

Step 1

1-isobutyl-4-(4,4,5,5-tetramethyl-1,3,2-dioxaborolan-2-yl)-H-pyrazole

To a solution of 4-(4,4,5,5-tetramethyl-1,3,2-dioxaborolan-2-yl)-1H-pyrazole 1a (5.00 g, 25.77 mmol) in DMF (50 mL) was added $Cs_2CO_3$ (16.79 g, 51.54 mmol) and 1-bromo-2-methylpropane (7.06 g, 51.54 mmol). The mixture was stirred at 100° C. for 2 h. It was cooled to room temperature, water (10 mL) was added and extracted with EA (100 mL*3). The combined organic phases was washed with water (100 mL*2) and brine (100 mL*2), dried over $Na_2SO_4$, filtrated and evaporated. The residue was purified by silica gel chromatography to give 1-isobutyl-4-(4,4,5,5-tetramethyl-1,3,2-dioxaborolan-2-yl)-1H-pyrazole 1b (2.05 g, yield: 31.8%) as a yellow liquid.

$^1$H NMR (400 MHz, $CDCl_3$) δ 7.71 (s, 1H), 7.58 (s, 1H), 3.84 (d, 1H), 4.08-4.00 (m, 1H), 2.05-2.20 (m, 1H), 1.25 (s, 12H), 0.82 (d, 6H)

Step 2

4-(4-bromo-2-chlorophenyl)-1-isobutyl-1H-pyrazole

A mixture of 1-isobutyl-4-(4,4,5,5-tetramethyl-1,3,2-dioxaborolan-2-yl)-1H-pyrazole 1b (2.05 g, 8.19 mmol), 4-bromo-2-chloro-1-iodobenzene (2.00 g, 6.30 mmol), $Na_2CO_3$ (1.34 g, 12.60 mmol) and Pd(dppf)$Cl_2$ (257 mg, 0.31 mmol) in dioxane/$H_2O$ (25 mL, V/V=3:1) was stirred at 70° C. for 12 h. It was cooled to room temperature, water (50 mL) was added and extracted with EA (50 mL*3). The combined organic phases was washed with water (50 mL*2) and brine (50 mL*2), dried over $Na_2SO_4$, filtered and evaporated. The residue was purified by silica gel chromatography to give 4-(4-bromo-2-chlorophenyl)-1-isobutyl-1H-pyrazole 1c (652 mg, yield 32.9%) as a yellow liquid.

Step 3

(R)-2-((tert-butyldimethylsilyl)oxy)propan-1-amine

A solution of (R)-1-aminopropan-2-ol 1d (19 g, 0.25 mol) in MeCN (200 mL) was cooled to 0° C. DBU (42.2 mg, 0.28 mol) and tert-butylchlorodimethylsilane (42.50 g, 0.28 mol) was added, and the reaction mixture was allowed to room temperature, and stirred for 12 h. Methanol (3 mL) was added, and the solvent was removed. The residue was dissolved in EA (100 mL), washed with water (50 mL*2) and brine (50 mL*2), dried over Na₂SO₄ and concentrated to give the crude (R)-2-((tert-butyldimethylsilyl)oxy)propan-1-amine 1e (40 g) as a yellow liquid. It was used in the next step without further purification.

Step 4

(R)—N-(2-((tert-butyldimethylsilyl)oxy)propyl)-3-chloro-4-(1-isobutyl)-1H-pyrazol-4-yl)aniline A mixture of (R)-2-((tert-butyldimethylsilyl)oxy)propan-1-amine 1e (900 mg, 2.87 mmol), 4-(4-bromo-2-chlorophenyl)-1-isobutyl-1H-pyrazole (652 mg, 3.44 mmol), Cs₂CO₃ (2.81 g, 8.61 mmol), x-Phos (138 mg, 0.29 mmol) and Pd₂(dba)₃ (265 mg, 0.29 mmol) in toluene (10 mL) was stirred at 100° C. under N₂ for 12 h. The mixture cooled to room temperature. It was quenched with water (20 mL) and extracted with EA (20 mL*3). The organic layer was washed with water (20 mL*2) and brine (20 mL*2), dried over Na₂SO₄, filtrated and concentrated. The residue was purified by silica gel chromatography to give (R)—N-(2-((tert-butyldimethylsilyl)oxy)propyl)-3-chloro-4-(1-isobutyl-1H-pyrazol-4-yl)aniline 1f (1 g, 83.3%) as a yellow oil.

Step 5

(R)-4,6-dichloro-N-(3-chloro-4-(1-isobutyl-1H-pyrazol-4-yl)phenyl)-N-(2-((isobutyldimethylsilyl)oxy)propyl)pyrimidine-5-carboxamide To a solution of (R)—N-(2-((tert-butyldimethylsilyl)oxy)propyl-3-chloro-4-(1-isobutyl-1H-pyrazol-4-yl)aniline 1f (1.0 g, 2.37 mmol) in DCM (15 mL) was added Et₃N (1.0 ml, 7.11 mmol) and 4,6-dichloropyrimidine-5-carbonyl chloride (1.0 g, 4.74 mmol). The mixture was stirred at room temperature for 12 h. The reaction was quenched with water (30 mL) and extracted with DCM (20 mL*3). The organic phase was washed with water (20 mL*2) and brine (20 mL*2), dried over Na₂SO₄ and concentrated to afford crude (R)-4,6-dichloro-N-(3-chloro-4-(1-isobutyl-1H-pyrazol-4-yl)phenyl)-N-(2-((isopropyldimethylsilyl)oxy)propyl)pyrimidine-5-carboxamide 1g (500 mg) as a yellow solid. It was used in the next step without further purification.

¹H NMR (400 MHz, CDCl₃) δ 8.63 (s, 1H), 7.75 (d, 2H), 7.45 (d, 1H), 7.33 (d, 1H), 7.24-7.19 (m, 1H), 4.21 (d, 1H), 4.08-4.00 (m, 1H), 3.97-3.86 (m, 3H), 1.33 (d, 3H), 0.94 (d, 7H), 0.77 (s, 10H), 0.02 (s, 3H), −0.01 (s, 3H)

Step 6

(R)-4,6-dichloro-N-(3-chloro-4-(1-isobutyl-1H-pyrazol-4-yl)phenyl)-N-(2-hydroxypropyl)pyrimidine-5-carboxamide To a mixture of (R)-4,6-dichloro-N-(3-chloro-4-(1-isobutyl-1H-pyrazol-4-yl)phenyl)-N-(2-((isopropyldimethylsilyl)oxy)propyl)pyrimidine-5-carboxamide 1g (500 mg, 0.84 mmol) in EtOH (10 mL) was added HCl (conc. 0.3 mL). It was stirred at room temperature for 1 h. Water (10 mL) was added to the mixture and extracted with EA (10 mL*3). The organic phase was washed with water (10 mL*2), sat. NaHCO₃ (10 mL*2) and brined (10 mL*2), dried over Na₂SO₄ and concentrated to afford crude (R)-4,6-dichloro-N-(3-chloro-4-(1-isobutyl-1H-pyrazol-4-yl)phenyl)-N-(2-hydroxypropyl)pyrimidine-5-carboxamide 1h (400 mg) as a yellow solid. It was used in the next step without further purification.

Step 7

(R)-4-chloro-6-(3-chloro-4-(1-isobutyl-1H-pyrazol-4-yl)phenyl)-8-methyl-7,8-dihydropyrimido[5,4-f][1,4]oxazepin-5(6H)-one To a solution of (R)-4,6-dichloro-N-(3-chloro-4-(1-isobutyl-1H-pyrazol-4-yl)phenyl)-N-(2-hydroxypropyl)pyrimidine-5-carboxamide 1h (100 mg, 0.21 mmol) in MeCN (5 mL) was added K₂CO₃ (86 mg, 0.62 mmol) and 5 Angstrom molecular sieves (30 mg). The mixture was stirred at 80° C. for 12 h. Water (10 mL) was added to the mixture and extracted with EA (10 mL*3). The organic phase was washed with brine (10 mL*2), dried over Na₂SO₄ and concentrated to afford crude (R)-4-chloro-6-(3-chloro-4-(1-isobutyl-1H-pyrazol-4-yl)phenyl)-8-methyl-7,8-dihydropyrimido[5,4-f][1,4]oxazepin-5(6H)-one (40 mg) as a yellow solid. It was used in the next step without further purification.

Step 8

(R)-4-amino-6-(3-chloro-4-(1-isobutyl-1H-pyrazol-4-yl)phenyl)-8-methyl-7,8-dihydropyrimido[5,4-f][1,4]oxazepin-5(6H)-one A mixture of (R)-4-chloro-6-(3-chloro-4-(1-isobutyl-1H-pyrazol-4-yl)phenyl)-8-methyl-7,8-dihydropyrimido[5,4-f][1,4]oxazepin-5(6H)-one (40 mg, 0.089 mmol) in NH₃/dioxane (0.5M, 5 mL) was stirred at room temperature for 12 h. The dioxane was removed, the residue was purified by prepare HPLC to give (R)-4-amino-6-(3-chloro-4-(1-isobutyl-1H-pyrazol-4-yl)phenyl)-8-methyl-7,8-dihydropyrimido[5,4-f][1,4]oxazepin-5(6H)-one 1 (17.5 mg, 46.0%) as a white solid.

MS m/z (ESI): 427.2 [M+1]

¹H NMR (400 MHz, CD3OD) δ 8.42 (s, 1H), 8.12 (s, 1H), 7.90 (s, 1H), 7.68 (d, 1H), 7.59 (d, 1H), 7.38-7.35 (dd, 1H), 5.34-5.30 (m, 1H), 4.26-4.12 (m, 2H), 4.08-4.05 (m, 2H), 2.28-2.19 (m, 1H), 0.96 (s, 6H)

Example 46

2-(4-(4-(4-amino-5-oxo-7,8-dihydropyrimido[5,4-f][1,4]oxazepin-6(5H)-yl)-2-chlorophenyl)-1H-pyrazol-1-yl)acetamide

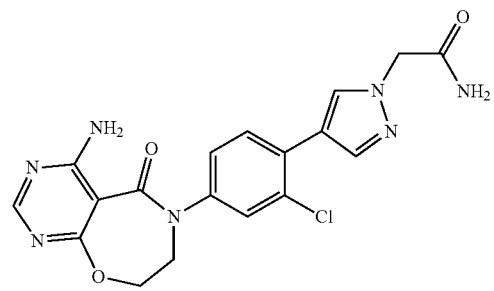

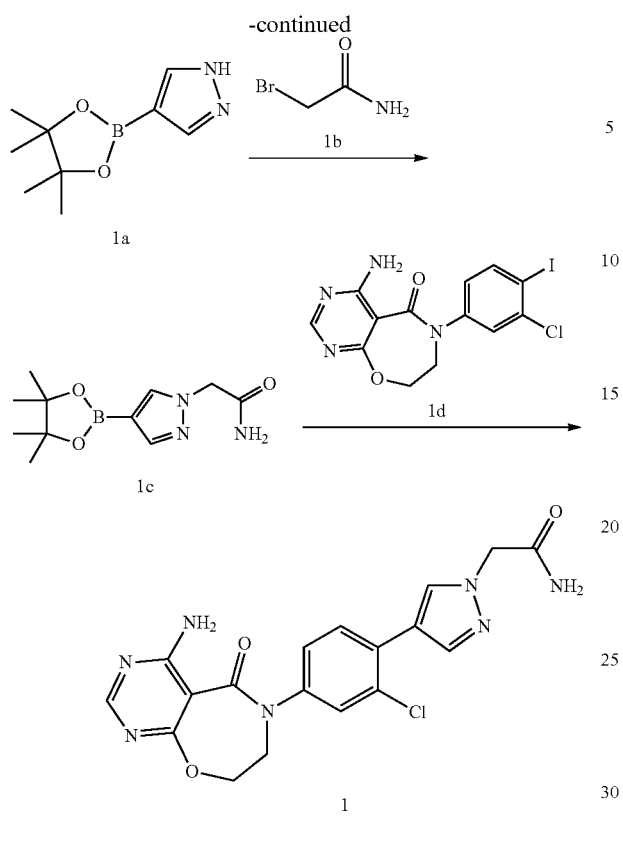

Step 1

2-(4-(4,4,5,5-tetramethyl-1,3,2-dioxaborolan-2-yl)-1H-pyrazol-1-yl)acetamide

To a solution of 4-(4,4,5,5-tetramethyl-1,3,2-dioxaborolan-2-yl)-1H-pyrazole 1a (100 mg, 0.52 mmol) in DMF (3 mL) was added 2-bromoacetamide 1b (143.5 mg, 1.04 mmol) and $Cs_2CO_3$ (253.5 mg, 0.78 mmol) in a sealed tube at RT. Reaction mixture was stirred at 100° C. for 35 min under microwave irradiation. After cooling at room temperature, the mixture was diluted with EA (10 mL) and water (10 mL), extracted with EA (10 mL*3), and the organic layers were combined and washed with water (30 mL*3) and brine (50 mL), dried over $Na_2SO_4$, filtrated and evaporated to afford 2-(4-(4,4,5,5-tetramethyl-1,3,2-dioxaborolan-2-yl)-1H-pyrazol-1-yl)acetamide 1c (70 mg) as a yellow oil and used in the next step directly.

MS m/z (ESI): 252.2 [M+1]

$^1$H NMR (400 MHz, $CDCl_3$) δ 7.9 (d, 2H), 2.05 (s, 2H), 1.32 (s, 12H)

Step 2

2-(4-(4-(4-amino-5-oxo-7,8-dihydropyrimido[5,4-f][1,4]oxazepin-6(5H)-yl)-2-chlorophenyl)-1H-pyrazol-1-yl)acetamide A mixture of 2-(4-(4,4,5,5-tetramethyl-1,3,2-dioxaborolan-2-yl)-1H-pyrazol-1-yl)acetamide 1c (70 mg, 0.28 mmol), 4-amino-6-(3-chloro-4-iodophenyl)-7,8-dihydropyrimido[5,4-f][1,4]oxazepin-5(6H)-one 1d (80 mg, 0.19 mmol), $Cs_2CO_3$ (1.2 g, 0.38 mmol) and $Pd(dppf)Cl_2$ (10 mg, 0.01 mmol) in a sealed tube was added Dioxane/$H_2O$ (4 mL, 3:1) at RT. Reaction mixture was stirred at 100° C. for 30 min under microwave irradiation. After cooling at room temperature, the mixture was filtered and the filtrate was purified by prep HPLC to afford 2-(4-(4-(4-amino-5-oxo-7,8-dihydropyrimido[5,4-f][1,4]oxazepin-6(5H)-yl)-2-chlorophenyl)-1H-pyrazol-1-yl)acetamide 1 (6 mg, 7.6%) as a white solid.

MS m/z (ESI): 414.4 [M+1]

$^1$H NMR (400 MHz, DMSO-$d_6$) δ 8.38 (s, 1H), 8.23 (s, 1H), 7.91 (s, 1H), 7.67-7.55 (m, 2H), 7.60 (s, 1H), 7.40 (q, 1H), 7.30 (s, 1H), 4.85-4.80 (m, 2H), 4.14 (t, 2H)

Example 47

4-amino-6-(3,5-dimethyl-4-(3-methyl-1-((3-methyl-oxetan-3-yl)methyl)-1H-pyrazol-4-yl)phenyl)-7,8-dihydropyrimido[5,4-f][1,4]oxazepin-5(6H)-one

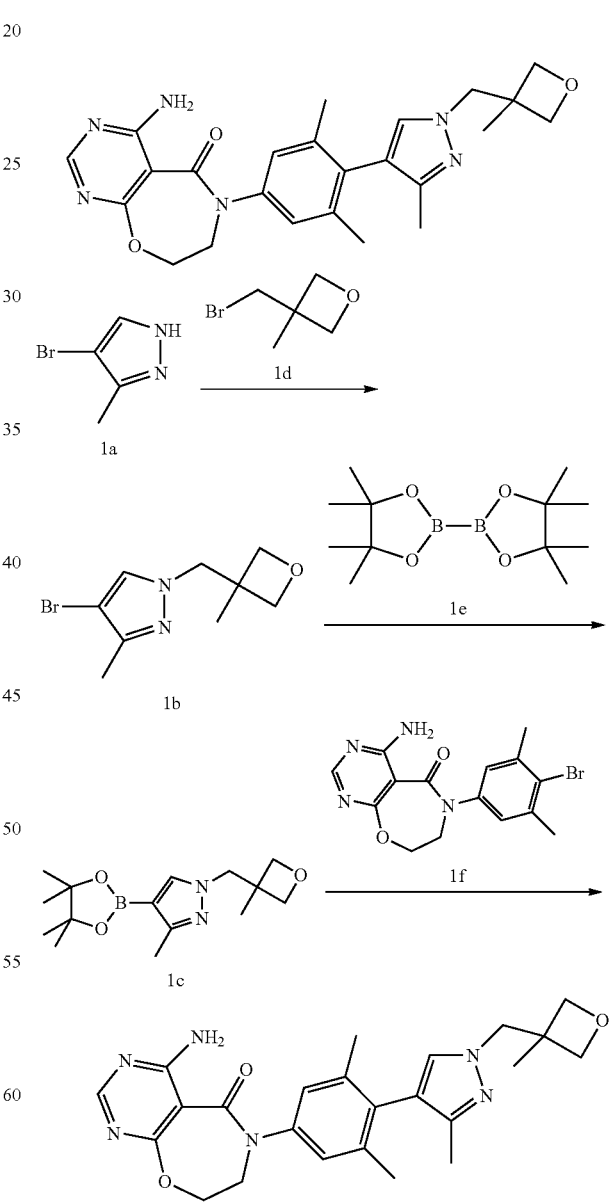

Step 1

4-bromo-3-methyl-1-((3-methyloxetan-3-yl)methyl)-1H-pyrazole

A solution of 4-bromo-3-methyl-1H-pyrazole 1a (350 mg, 2.19 mmol), 3-(bromomethyl)-3-methyloxetane (400 mg, 2.44 mmol) and $Cs_2CO_3$ (1.44 g, 4.44 mmol) in DMF (10 mL) was stirred at 100° C. under MW for 1.5 h. After filtration, the filtrate was concentrated to give 4-bromo-3-methyl-1-((3-methyloxetan-3-yl)methyl)-1H-pyrazole 1b (400 mg, 74.9%) as a light yellow solid.

Step 2

3-methyl-1-((3-methyloxetan-3-yl)methyl)-4-(4,4,5,5-tetramethyl-1,3,2,-dioxaborolan-2-yl)-1H-pyrazole To a mixture of 4-bromo-3-methyl-1-((3-methyloxetan-3-yl)methyl)-1H-pyrazole 1b (1.53 g, 6.25 mmol), 4,4,4',4',5,5,5',5'-octamethyl-2,2'-bi(1,3,2-dioxaborolane) (2.38 g, 9.38 mmol) and KOAc (1.23 g, 12.5 mmol) in dioxane (10 mL) was added $Pd(dppf)Cl_2$ (229 mg, 0.342 mmol) under $N_2$. The mixture was at 90° C. for 16 h. The reaction mixture was evaporated, the residue was purified by column to give 3-methyl-1-((3-methyloxetan-3-yl)methyl)-4-(4,4,5,5-tetramethyl-1,3,2-dioxaborolan-2-yl)-1H-pyrazole 1c (500 mg, yield: 28.0%) as a light yellow solid.

$^1$H NMR (400 MHz, $CDCl_3$) δ 7.56 (s, 1H), 4.69-4.67 (d, 2H), 4.37-4.36 (d, 2H), 4.23 (s, 2H), 1.30 (s, 6H), 1.26-1.23 (t, 12H)

Step 3

4-amino-6-(3,5-dimethyl-4-(3-methyl-1-((3-methyloxetan-3-yl)methyl)-1H-pyrazol-4-yl)phenyl)-7,8-dihydropyrimido[5,4-f][1,4]oxazepin-5(6H)-one A mixture of 3-methyl-1-((3-methyloxetan-3-yl)methyl)-4-(4,4,5,5-tetramethyl-1,3,2-dioxaborolan-2-yl)-1H-pyrazole 1c (80 mg, 0.27 mmol), 4-amino-6-(4-bromo-3,5-dimethylphenyl)-7,8-dihydropyrimido[5,4-f][1,4]oxazepin-5(6H)-one (66 mg, 0.18 mmol), $K_2CO_3$ (54 mg, 0.55 mmol) and $Pd(dppf)Cl_2$ (7 mg, 0.01 mmol) in dioxane/$H_2O$ (3 ml/0.3 mL) was stirred at 100° C. for 12 h under MW. The reaction mixture was cooled to room temperature and water (5 mL) was added. It was extracted with DCM (10 mL*3), and the organic layers were combined and washed with brine (5 mL*2), dried over $Na_2SO_4$, filtrated and evaporated. The residue was purified by prep-HPLC to give 4-amino-6-(3,5-dimethyl-4-(3-methyl-1-((3-methyloxetan-3-yl)methyl)-1H-pyrazol-4-yl)phenyl)-7,8-dihydropyrimido[5,4-f][1,4]oxazepin-5(6H)-one 1 (2.59 mg, yield: 2.1%) as a brown solid.

MS m/z (ESI): 449.2 [M+1]

$^1$H NMR (400 MHz, DMSO-d6) δ 8.18 (s, 1H), 7.62 (s, 2H), 7.56 (s, 1H), 7.13 (s, 2H), 4.62 (s, 4H), 4.29 (s, 2H), 4.25 (d, 2H) 3.99 (s, 2H), 2.02 (s, 6H), 1.92 (s, 3H), 1.14 (d, 3H)

Example 48

4-amino-6-(4-(1-(2,2-difluoropropyl)-3-methyl-1H-pyrazol-4-yl)-3,5-dimethylphenyl)-7,8-dihydropyrimido[5,4-f][1,4]oxazepin-5(6H)-one

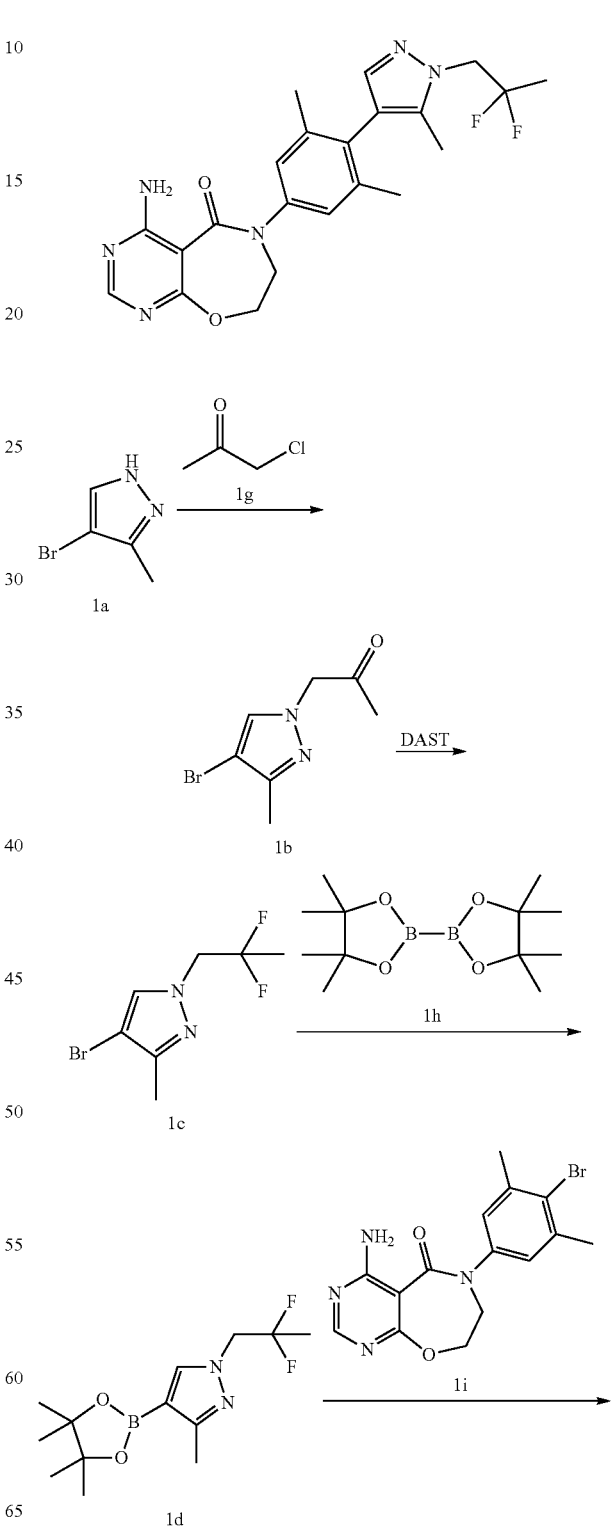

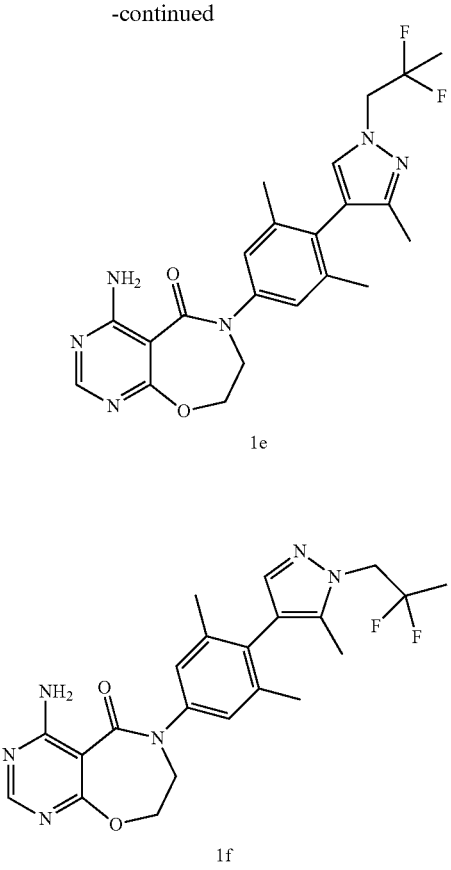

Step 1

1-(4-bromo-3-methyl-1H-pyrazol-1-yl)propan-2-one

A solution of 4-bromo-3-methyl-1H-pyrazole 1a (590 mg, 3.13 mmol), $Cs_2CO_3$ (2.04 g, 6.25 mmol) and 1-chloropropan-2-one (862 mg, 9.38 mmol) in DMF (3 mL) was stirred at 90° C. under MW for 1.5 h. The reaction mixture was cooled to room temperature and water (15 mL) was added. It was extracted with DCM (30 mL*3), and the organic layers were combined and washed with water (15 mL*2) and brine (15 mL*2), dried over $Na_2SO_4$, filtrated and evaporated. The residue was purified by column to give 1-(4-bromo-3-methyl-1H-pyrazol-1-yl)propan-2-one 1b (700 mg, crude) as a yellow oil.

$^1$H NMR (400 MHz, $CDCl_3$) δ 7.50 (d, 1H), 4.86 (d, 2H), 2.31-2.15 (m, 6H)

Step 2

4-bromo-1-(2,2-difluoropropyl)-3-methyl-1H-pyrazole

To a solution of 1-(4-bromo-3-methyl-1H-pyrazol-1-yl)propan-2-one 1b (700 mg, 3.24 mmol) in DCM (10 mL) was added DAST (1.57 g, 9.72 mmol) dropwise at −78° C. under $N_2$. The reaction mixture was stirred at rt for 12 h. The mixture was quenched with water (10 mL) and extracted with DCM (20 mL*3). The organic layer was washed with saturated $NaHCO_3$, (10 mL*2) and brine (10 mL*2), dried over $Na_2SO_4$, filtrated and concentrated. The residue was purified by column to give the 4-bromo-2-(2,2-difluoropropyl)-3-methyl-1H-pyrazole 1c (220 mg) as a yellow oil. It was used in the next step directly.

Step 3

1-(2,2-difluoropropyl)-3-methyl-4-(4,4,5,5-tetramethyl-1,3,2-dioxaborolan-2-yl)-1H-pyrazole To a solution of 4-bromo-(2,2-difluoropropyl)-3-methyl-1H-pyrazole 1c (200 mg, 0.84 mmol), $Pin_2B_2$ (360 mg, 1.26 mmol) and KOAc (247 mg, 2.52 mmol) in dioxane (10 ml) was added Pd(dppf)$Cl_2$ (62 mg, 0.08 mmol) under $N_2$. Then the mixture was stirred at 90° C. for 12 h. Water (5 mL) was added to the mixture and it was extracted with EA (10 mL*3). The organic layers were combined and washed with water (5 mL*2) and brine (5 mL*2), dried over $Na_2SO_4$, filtrated and evaporated. The residue was purified by p-TLC to give 1-(2,2-difluoropropyl)-3-methyl-4-(4,4,5,5-tetramethyl-1,3,2-dioxaborolan-2-yl)-1H-pyrazole 1d (80 mg, 31%) as a yellow oil.

$^1$H NMR (400 MHz, $CDCl_3$) δ 7.62 (d, 1H), 4.35-4.26 (m, 2H), 1.18 (d, 12H)

Step 4

4-amino-6-(4-(1-(2,2-difluoropropyl)-3-methyl-1H-pyrazol-4-yl)-3,5-dimethylphenyl)-7,8-dihydropyrimido[5,4-f][1,4]oxazepin-5(6H)-one To a solution of 1-(2,2-difluoropropyl)-3-methyl-4-(4,4,5,5-tetramethyl-1,3,2-dioxaborolan-2-yl)-1H-pyrazole 1d (60 mg, 0.21 mmol), 4-amino-6-(4-bromo-3,5-dimethylphenyl)-7,8-dihydropyrimido[5,4-f][1,4]oxazepin-5(6H)-one (50 mg, 0.14 mmol) and $K_2CO_3$ (38 mg, 0.28 mmol) in dioxane/$H_2O$ (3 mL, V/V=5:1) was added Pd(dppf)$Cl_2$ (5 mg, 0.007 mmol) under $N_2$. Then the mixture was stirred at 90° C. for 12 h. The reaction mixture was cooled to room temperature and water (5 mL) was added. It was extracted with EA (10 mL*3), and the organic layers were combined and washed with brine (5 mL*2), dried over $Na_2SO_4$, filtrated and evaporated. The residue was purified by prep-HPLC to give 4-amino-6-(4-(1-(2,2-difluoropropyl)-3-methyl-1H-pyrazol-4-yl)-3,5-dimethylphenyl)-7,8-dihydropyrimido[5,4-f][1,4]oxazepin-5(6H)-one 1e and 4-amino-6-(4-(1-(2,2-difluoropropyl)-5-methyl-1H-pyrazol-4-yl)-3,5-dimethylphenyl)-7,8-dihydropyrimido[5,4-f][1,4]oxazepin-5(6H)-one 1f (6.55 mg, 11% yield) as a white solid.

MS m/z (ESI): 443.2 [M+1]

$^1$H NMR (400 MHz, DMSO-d6) δ 8.17 (s, 1H), 7.34 (s, 1H), 7.13 (s, 2H), 4.74-4.72 (t, 2H), 4.58-4.55 (t, 2H), 4.08-4.05 (t, 2H), 2.09-2.07 (d, 9H), 1.69-1.60 (t, 3H)

Following 47 compounds were prepared referring to the preparation of examples 46~48:

| NO | Structure | property | MS | HNMR |
|---|---|---|---|---|
| 49 | 2-(4-(4-(4-amino-5-oxo-7,8-dihydropyrimido[5,4-f][1,4]oxazepin-6(5H)-yl)phenyl)-1H-pyrazol-1-yl)acetic acid | white solid | 381.0 [M + 1] | $^1$H NMR (400 MHz, CD$_3$OD) 8.44 (s, 1H), 8.13 (s, 1H), 7.97 (s, 1H), 7.90 (s, 1H), 7.70 (d, 2H), 7.39 (d, 2H), 5.05 (s, 2H), 5.03 (t, 2H), 4.27 (t, 2H), 2.68 (s, 2H). |
| 50 | 3-(4-(4-(4-amino-5-oxo-7,8-dihydropyrimido[5,4-f][1,4]oxazepin-6(5H)-yl)phenyl)-1H-pyrazol-1-yl)propanoic acid | white solid | 395.1 [M + 1] | $^1$H NMR (400 MHz, DMSO-d6) δ 8.18 (d, 2H), 7.9 (s, 1H), 7.62-7.60 (m, 4H), 7.37-7.35 (m, 2H), 4.62 (t, 2H), 4.32 (t, 2H), 3.99 (t, 2H), 2.77 (t, 2H) |
| 51 | 2-(4-(4-(4-amino-5-oxo-7,8-dihydropyrimido[5,4-f][1,4]oxazepin-6(5H)-yl)phenyl)-1H-pyrazol-1-yl)propanoic acid | yellow solid | 395.1 [M + 1] | $^1$H NMR (400 MHz, CD$_3$OD) 8.40 (s, 1H), 8.16 (s, 1H), 7.89 (s, 1H), 7.67 (d, 1H), 7.35 (d, 1H), 5.17 (q, 1H), 4.98 (t, 2H), 4.23 (d, 2H), 1.81 (d, 3H). |
| 52 | 2-(4-(4-(4-amino-5-oxo-7,8-dihydropyrimido[5,4-f][1,4]oxazepin-6(5H)-yl)phenyl)-1H-pyrazol-1-yl)butanoic acid | yellow solid | 408.9 [M + 1] | $^1$H NMR (400 MHz, CD$_3$OD) 8.42 (s, 1H), 8.36 (s, 1H), 8.15 (s, 1H), 7.58 (d, 2H), 7.38 (d, 2H), 4,99-5.08 (m, 3H), 4.25 (s, 2H), 2.24-2-33 (m, 2H), 0.93 (t, 3H). |

-continued

| NO | Structure | property | MS | HNMR |
|----|-----------|----------|-----|------|
| 53 | 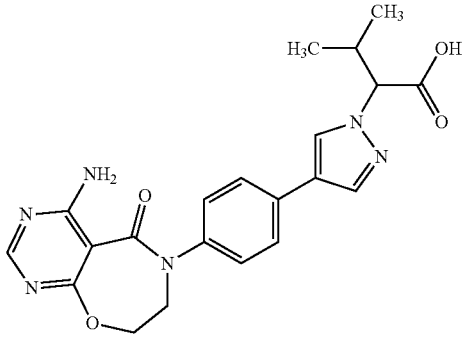 [SMILES: CC(C)C(C(=O)O)n1cc(-c2ccc(N3CCOc4ncnc(N)c4C3=O)cc2)cn1]<br>2-(4-(4-(4-amino-5-oxo-7,8-dihydropyrimido[5,4-f][1,4]oxazepin-6(5H)-yl)phenyl)-1H-pyrazol)-yl)-3-methylbutanoic acid | yellow solid | 423.0 [M + 1] | $^1$H NMR (400 MHz, CD$_3$OD) 8.42 (s, 1H), 8.29 (d, 1H), 8.03 (d, 1H), 7.70 (d, 2H), 7.38 (d, 1H), 4.99 (s, 2H), 4.72 (m, 1H), 4.25 (s, 2H), 2.65-2.56 (m, 1H), 1.09 (d, 3H), 0.87 (d, 3H). |
| 54 | 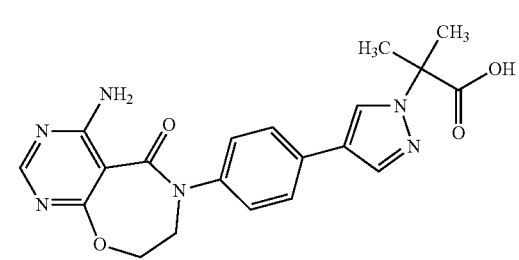 [SMILES: CC(C)(C(=O)O)n1cc(-c2ccc(N3CCOc4ncnc(N)c4C3=O)cc2)cn1]<br>2-(4-(4-(4-amino-5-oxo-7,8-dihydropyrimido[5,4-f][1,4]oxazepin-6(5H)-yl)phenyl)-1H-pyrazol-1-yl)-2-methylpropanoic acid | yellow solid | 408.9 [M + 1] | $^1$H NMR (400 MHz, CD$_3$OD) 8.41 (s, 1H), 8.22 (s, 1H), 7.89 (s, 1H), 7.68 (d, 2H), 7.35 (d, 2H), 4.98 (t, 2H), 4.24 (t, 2H), 1.87 (s, 3H). |
| 55 | 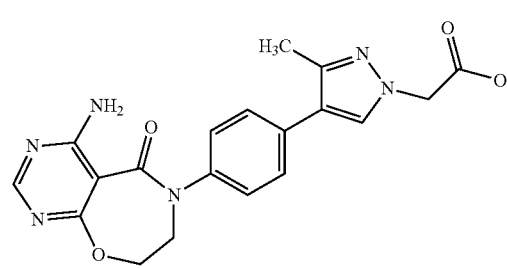<br>2-(4-(4-(4-amino-5-oxo-7,8-dihydropyrimido[5,4-f][1,4]oxazepin-6(5H)-yl)phenyl)-3-methyl-1H-pyrazol-1-yl)acetic acid | yellow solid | 395.2 [M + 1] | $^1$H NMR (400 MHz, CD$_3$OD) 8.39 (s, 1H), 8.0 (d, 1H), 7.54 (m, 2H), 7.42 (d, 2H), 5.08 (s, 2H), 4.97 (m, 2H), 4.21 (m, 2H), 2.40 (d, 3H) |
| 56 | 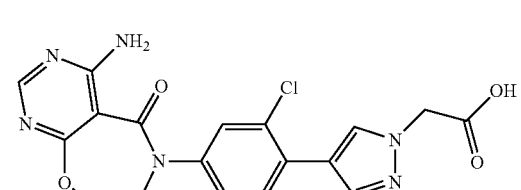<br>2-(4-(4-(4-amino-5-oxo-7,8-dihydropyrimido[5,4-f][1,4]oxaxepin-6(5H)-yl)-2-chlorophenyl)-1H-pyrazol-1-yl)acetic acid | white solid | 415.2 [M + 1] | $^1$H NMR (400 MHz, DMSO-d$_6$) 8.57 (s, 1H),, 8.33 (s, 1H), 8.04 (s, 1H), 7.80 (d, 1H), 7.72 (s, 1H), 7.47 (d, 1H), 5.14 (s, 2H), 5.07 (s, 2H), 4.34 (s, 2H). |

| NO | Structure | property | MS | HNMR |
|---|---|---|---|---|
| 57 | 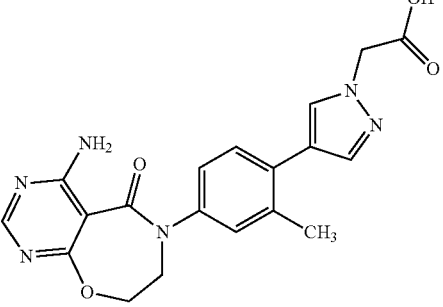<br>2-(4-(4-(4-amino-5-oxo-7,8-dihydropyrimido[5,4-f][1,4]oxazepin-6(5H)-yl)-2-methylphenyl)-1H-pyrazol-1-yl)acetic acid | white solid | 395.0 [M + 1] | $^1$H NMR (400 MHz, DMSO-d$_6$) 8.45 (s, 1H), 8.03 (s, 1H), 7.75 (s, 1H), 7.30 (d, 1H), 7.25-7.22 (m, 1H), 5.00 (s, 2H), 4.84 (t, 2H), 4.13 (t, 2H), 2.39 (s, 3H). |
| 58 | 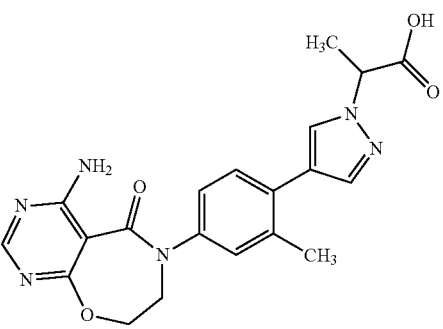 [SMILES: Cc1cc(N2CCOc3ncnc(N)c3C2=O)ccc1-c1cnn(C(C)C(=O)O)c1]<br>2-(4-(4-(4-amino-5-oxo-7,8-dihydropyrimido[5,4-f][1,4]oxazepin-6(5H)-yl)-2-methylphenyl)-1H-pyrazol-1-yl)propanoic acid | white solid | 409.2 [M + 1] | $^1$H NMR (400 MHz, DMSO-d$_6$) 8.35 (s, 1H), 8.09 (s, 1H), 7.74 (s, 1H), 7.45 (d, 1H), 7.24 (s, 1H), 7.22-7.20 (m, 1H), 5.18 (q, 1H), 4.75 (t, 2H), 4.08 (t, 2H), 2.40 (s, 3H), 1.70 (d, 3H). |
| 59 | 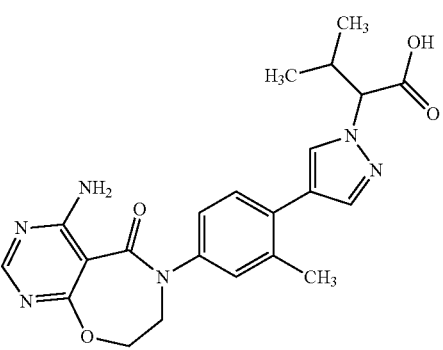 [SMILES: Cc1cc(N2CCOc3ncnc(N)c3C2=O)ccc1-c1cnn(C(C(=O)O)C(C)C)c1]<br>2-(4-(4-(4-amino-5-oxo-7,8-dihydropyrimido[5,4-f][1,4]oxazepin-6(5H)-yl)-2-methylphenyl)-1H-pyrazol-1-yl)-3-methylbutanoic acid | white solid | 437.2 [M + 1] | $^1$H NMR (400 MHz, DMSO-d$_6$) 8.36 (s, 1H), 8.07 (s, 1H), 7.74 (s, 1H), 7.43 (d, 1H), 7.24 (s, 1H), 7.22-7.20 (m, 1H), 4.77-4.68 (m, 3H), 4.08 (t, 2H), 2.39 (s, 3H), 1.01 (d, 3H), 0.80 (d, 3H). |

| NO | Structure | property | MS | HNMR |
|---|---|---|---|---|
| 60 | 3-(4-(4-(4-amino-5-oxo-7,8-dihydropyrimido[5,4-f][1,4]oxazepin-6(5H)-yl)-2-methylphenyl)-1H-pyrazol-1-yl)propanoic acid | white solid | 437.2 [M + 1] | $^1$H NMR (400 MHz, DMSO-d$_6$) 8.45 (s, 1H), 8.01 (s, 1H), 7.72 (s, 1H), 7.42 (d, 1H), 7.24 (s, 1H), 7.22-7.20 (m, 1H), 4.82 (t, 2H), 4.36 (q, 2H), 4.13 (t, 2H), 2.85 (t, 2H), 2.38 (s, 3H). |
| 61 | 2-(4-(4-(4-amino-5-oxo-7,8-dihydropyrimido[5,4-f][1,4]oxazepin-6(5H)-yl)-2-chlorophenyl)-1H-pyrazol-1-yl)butanoic acid | yellow solid | 443.1 [M + 1] | $^1$H NMR (400 MHz, DMSO-d6) 8.45 (br. 1H), 8.33 (s, 1H), 7.95 (s, 1H), 7.72-7.67 (m, 2H), 7.42 (dd, 1H), 5.01 (t, 1H), 4.84 (m, 2H), 4.16-4.12 (m, 2H), 2.18-2.14 (m, 2H), 0.84-0.80 (m, 3H) |
| 62 | 3-(4-(4-(4-amino-5-oxo-7,8-dihydropyrimido[5,4-f][1,4]oxazepin-6(5H)-yl)-phenyl-3-(trifluoromethyl)-1H-pyrazol-1-yl)propanoic acid | whie solid | 463.0 [M + 1] | $^1$H NMR (400 MHz, DMSO-d$_6$) 8.28 (s, 1H), 8.25 (s, 1H), 8.07-7.96 (br, 2H), 7.46 (s, 4H), 4.70 (s, 2H), 4.44 (s, 2H), 4.08 (s, 2H), 2.92-2.89 (m, 2H) |
| 63 | 2-(4-(4-(4-amino-5-oxo-7,8-dihydropyrimido[5,4-f][1,4]oxazepin-6(5H)-yl)-2-methylphenyl)-1H-pyrazol-1-yl)-2-methylpropanoic acid | white solid | 423.2 [M + 1] | $^1$H NMR (400 MHz, DMSO-d$_6$) 8.43 (s, 1H), 8.13 (s, 1H), 7.74 (s, 1H), 7.46 (d, 1H), 7.29 (d, 1H), 7.23-7.22 (m, 1H), 4.82 (t, 2H), 4.13 (t, 2H), 2.41 (s, 3H), 1.79 (s, 6H). |

| NO | Structure | property | MS | HNMR |
|---|---|---|---|---|
| 64 | 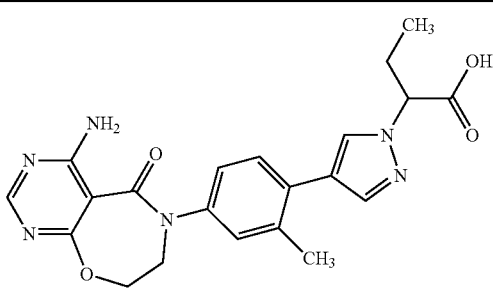<br>2-(4-(4-(4-amino-5-oxo-7,8-dihydropyrimido[5,4-f][1,4]oxazepin-6(5H)-yl)-2-methylphenyl)-1H-pyrazol-1-yl)butanoic acid | whtie solid | 423.2 [M + 1] | $^1$H NMR (400 MHz, DMSO-d$_6$) 8.54 (s, 1H), 8.10 (s, 1H), 7.75 (s, 1H), 7.47 (d, 1H), 7.31 (s, 1H), 7.30 (d, 2H), 4.98-4.88 (m, 3H), 4.18 [t, 2H), 2.20-2.10 (m, 2H). 0.82 (t, 3H). |
| 65 | 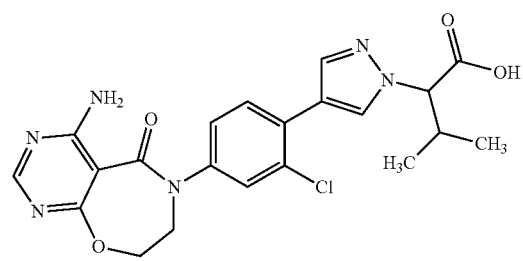 [SMILES: CC(C)C(C(=O)O)n1cc(-c2ccc(N3CCOc4ncnc(N)c4C3=O)cc2Cl)cn1]<br>2-(4-(4-(4-amino-5-oxo-7,8-dihydropyrimido[5,4-f][1,4]oxazepin-6(5H)-yl)-2-chlorophenyl)-1H-pyrazol-1-yl)-3-methylbutanoic acid | white solid | 457.0 [M + 1] | $^1$H NMR (400 MHz, DMSO-d6) 8.28 (s, 1H), 8.15 (s, 1H), 7.89 (s, 1H),7.70-7.60 (m, 4H), 7.37 (q, 1H), 4.71 (d, 1H), 4.61 (t, 2H), 3.99 (t, 2H), 0.96 (d, 3H), 0.77 (d, 3H). |
| 66 | 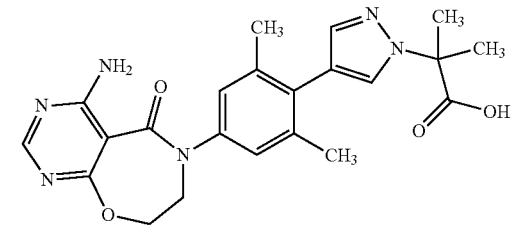 [SMILES: Cc1cc(N2CCOc3ncnc(N)c3C2=O)cc(C)c1-c1cnn(C(C)(C)C(=O)O)c1]<br>2-(4-(4-(4-amino-5-oxo-7,8-dihydropyrimido[5,4-f][1,4]oxazepin-6(5H)-yl)-2,6-dimethylphenyl)-1H-pyrazol-1-yl)-2-methylpropanoic acid | white solid | 437.1 [M + 1] | $^1$H NMR (400 MHz, DMSO-d6) 12.94 (br, 1H), 8.18 (s, 1H), 7.90 (s, 1H), 7.64 (s, 2H), 7.44 (s, 1H), 7.12 (s, 2H), 4.62 (t, 2H), 3.98 (t, 2H), 2.14 (s, 6H), 1.79 (s, 6H). |
| 67 | 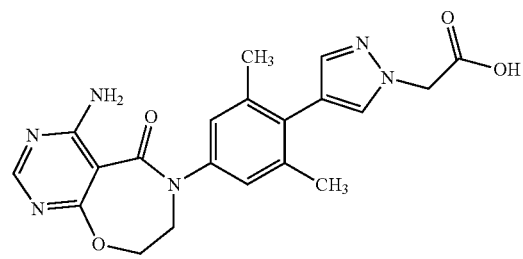 [SMILES: Cc1cc(N2CCOc3ncnc(N)c3C2=O)cc(C)c1-c1cnn(CC(=O)O)c1]<br>2-(4-(4-(4-amino-5-oxo-7,8-dihydropyrimido[5,4-f][1,4]oxazepin-6(5H)-yl)-2,6-dimethylphenyl)-1H-pyrazol-1-yl)acetic acid | white solid | 409.1 [M + 1] | $^1$H NMR (400 MHz, CD$_3$OD) 8.45 (s, 1H), 7.77 (s, 2H), 7.60 (s, 2H), 7.15 (s, 2H), 5.15 (s, 2H), 5.03 (t, 2H), 4.26 (t, 2H), 2.17 (s, 6H) |

| NO | Structure | property | MS | HNMR |
|---|---|---|---|---|
| 68 | 4-amino-6-(3-chloro-4-(1-(2,2,2-trifluoroethyl)-1H-pyrazol-4-yl)phenyl)-7,8-dihydropyrimido[5,4-f][1,4]oxazepin-5(6H)-one | white solid | 439.0 [M + 1] | $^1$H NMR (400 MHz, MeOD) δ 8.35 (s, 1H), 8.18 (s, 1H), 7.89 (s, 1H), 7.59 (d, 1H), 7.53 (s, 1H), 7.29 (d, 1H), 4.95 (t, 2H), 4.89 (s, 2H), 4.18 (t, 2H) |
| 69 | 2-(4-(4-(4-amino-5-oxo-7,8-dihydropyrimido[5,4-f][1,4]oxazepin-6(5H)-yl)-2-methoxyphenyl)-1H-pyrazol-1-yl)acetic acid | white solid | 411.1 [M + 1] | $^1$H NMR (400 MHz, DMSO-d6) δ 8.18 (s, 1H), 8.00 (s, 1H), 7.78 (s, 1H), 7.62-7.60 (m, 3H), 7.07 (s, 1H), 6.95-6.93 (m, 1H), 4.63 (s, 3H), 4.36 (s, 3H), 4.01 (s, 3H), 3.88 (s, 3H) |
| 70 | 3-(4-(4-(4-amino-5-oxo-7,8-dihydropyrimido[5,4-f][1,4]oxazepin-6(5H)-yl)-2,6-dimethylphenyl)-1H-pyrazol-1-yl)propanoic acid | white solid | 423.0 [M + 1] | $^1$H NMR (400 MHz, DMSO-d6) 8.18 (s, 1H), 7.71 (s, 1H), 7.62 (d, 1H), 7.48-7.43 (m, 1H), 7.38-7.35 (m, 1H), 5.01-4.98 (m, 4H), 4.26 (t, 2H), 3.23 (d, 3H). |
| 71 | 3-(4-(4-(4-amino-5-oxo-7,8-dihydropyrimido[5,4-f][1,4]oxazepin-6(5H)-yl)-2-chlorophenyl)-1H-pyrazol-1-yl)-2,2-dimethylpropanoic acid | white solid | 457.0 [M + 1] | $^1$H NMR (400 MHz, DMSO-d$_6$) 8.14 (s, 1H), 8.12 (s, 1H), 7.84 (s, 1H), 7.60 (m, 4H), 7.37 (d, 1H), 4.60 (t, 2H), 4.28 (s, 2H), 3.98 (t, 2H), 1.08 (s, 6H). |
| 72 | 2-(4-(4-(4-amino-5-oxo-7,8-dihydropyrimido[5,4-f][1,4]oxazepin-6(5H)-yl)-2-chlorophenyl)-3,5-dimethyl-1H-pyrazol-1-yl)acetic acid | white solid | 443.0 [M + 1] | $^1$H NMR (400 MHz, DMSO-d6) 8.15 (s, 1H), 7.89 (s, 1H), 7.66-7.64 (m, 3H), 7.40 (dd, 1H), 7.31 (d, 1H), 4.85 (d, 1H), 4.61 (t, 2H), 4.03 (t, 2H), 2.03 (d, 6H). |

| NO | Structure | property | MS | HNMR |
|---|---|---|---|---|
| 73 | 2-(4-(4-(4-amino-5-oxo-7,8-dihydropyrimido[5,4-f][1,4]oxazepin-6(5H)-yl)-2,6-dimethylphenyl)-3-methyl-1H-pyrazol-1-yl)acetic acid | white solid | 423.3 [M + 1] | $^1$H NMR (400 MHz, DMSO-d6) 8.29 (s, 1H), 8.23-8.11 (m, 1H), 7.51 (s, 1H), 7.11 (s, 2H), 4.87 (s, 2H), 4.70 (t, 2H), 4.04 (t, 2H), 2.00 (s, 6H), 1.94 (s, 3H) |
| 74 | 3-(4-(4-(4-amino-5-oxo-7,8-dihydropyrimido[5,4-f][1,4]oxazepin-6(5H)-yl)-2-methoxyphenyl)-1H-pyrazol-1-yl)propanoic acid | white solid | 425.1 [M + 1] | $^1$H NMR (400 MHz, DMSO-d6) δ 8.17-8.13 (m, 2H), 7.88 (s, 1H), 7.67-7.63 (m, 3H), 4.62 (s, 2H), 4.28 (s, 2H), 4.00 (s, 2H), 3.87 (s, 3H), 2.61 (s, 2H) |
| 75 | 2-(4-(4-(4-amino-5-oxo-7,8-dihydropyrimido[5,4-f][1,4]oxazepin-6(5H)-yl)-2-fluorophenyl)-1H-pyrazol-1-yl)acetic acid | white solid | 399.1 [M + 1] | $^1$H NMR (400 MHz, DMSO-d6) δ 8.50-8.29 (m, 3H), 8.18 (d, 1H), 7.96 (s, 1H) 7.76 (d, 1H), 7.43 (dd, 1H), 7.26 (dd, 1H), 5.00 (s, 2H), 4.76 (t, 2H), 4.10 (t, 2H). |
| 76 | 3-4-(4-(4-amino-5-oxo-7,8-dihydropyrimido[5,4-f][1,4]oxazepin-6(5H)-yl)phenyl)-3,5-dimethyl-1H-pyrazol-1-yl)propanoic acid | white solid | 423.1 [M + 1] | $^1$H NMR (400 MHz, CD$_3$OD) 2.37 (s, 3H), 2.44 (s, 3H), 2.97 (t, 2H), 4.29 (t, 2H), 4.55 (t, 2H), 5.01 (t, 2H), 7.44 (m, 2 H), 7.52 (m, 2H), 8.43 (s, 1H) |

-continued

| NO | Structure | property | MS | HNMR |
|---|---|---|---|---|
| 77 | 3-(4-(4-(4-amino-5-oxo-7,8-dihydropyrimido [5,4-f][1,4]oxazepin-6(5H)-yl)-2-methylphenyl)-3,5-dimethyl-1H-pyrazol-1-yl)propanoic acid | white solid | 437.1 [M + 1] | $^1$H NMR (400 MHz, CD$_3$OD) 2.01 (s, 3H), 2.11 (s, 6H), 2.87 (t, 2H), 4.06-4.12 (m, 2H), 4.71-4.77 (m, 2H), 7.13-7.23 (m, 2H), 7.31 (s, 1H), 8.18 (s, 1H) |
| 78 | 3-(4-(4-(4-amino-5-oxo-7,8-dihydropyrimido [5,4-f][1,4]oxazepin-6(5H)-yl)-2-chlorophenyl)-3-methyl-1H-pyrazol-1-yl)propanoic acid | white solid | 453.0 [M + 1] | $^1$H NMR (400 MHz, DMSO-d6) 8.15 (s, 1H), 7.80 (s, 1H), 7.64-7.62 (m, 2H), 7.39-7.32 (,, 2H), 4.17-4.59 (t, 2H), 4.27-4.22 (q, 2H), 4.02-3.99 (t, 2H), 2.83-2.77 (m, 2H), 2.22-2.11 (s, 3H) |
| 79 | 4-amino-6-(3-chloro-4-(1-ethyl-1H-pyrazol-4-yl)phenyl)-7,8-dihydropyrimido [5,4-f][1,4]oxazepin-5(6H)-one | white solid | 385.1 [M + 1] | $^1$H NMR (400 MHz, DMSO-d$_6$) 8.38 (s, 1H, 8.22 (s, 1H), 7.85 (s, 1H), 7.62 (dd, 2H), 7.37 (d, 1H), 4.78 (t, 2H), 4.18-4.08 (m, 4H), 1.39 (t, 3H). |
| 80 | 4-amino-6-(3-chloro-4-(1-isobutyl-1H-pyrazol-4-yl)phenyl)-7,8-dihydropyrimido [5,4-f][1,4]oxazepin-5(6H)-one | white solid | 413.2 [M + 1] | $^1$H NMR (400 MHz, DMSO-d$_6$) 8.39 (s, 1H), 8.19 (s, 1H), 7.86 (s, 1H), 7.65-7.62 (m, 2H), 7.38 (d, 1H), 4.79 (t, 2H). 4.11 (t, 2H). 3.94 (d, 2H), 2.15 (m, 1H), 0.84 (t, 6H). |

-continued

| NO | Structure | property | MS | HNMR |
|---|---|---|---|---|
| 81 | 4-amino-6-(3-chloro-4-(1-isopropyl-1H-pyrazol-4-yl)phenyl)-7,8-dihydropyrimido[5,4-f][1,4]oxazepin-5(6H)-one | white solid | 399.0 [M + 1] | ¹H NMR (400 MHz, DMSO-d₆) 8.42 (s, 1H), 8.21 (s, 1H), 7.99 (s, 1H), 7.66 (d, 1H), 7.58 (d, 1H), 7.35 (dd, 1H), 4.99 (t, 2H), 4.60-4.67 (m, 1H), 4.25 (t, 2H), 1.55 (d, 6H). |
| 82 | 4-amino-6-(3-chloro-4-(1-(2-hydroxyethyl)-1H-pyrazol-4-yl)phenyl)-7,8-dihydropyrimido[5,4-f][1,4]oxazepin-5(6H)-one | yellow solid | 401.0 [M + 1] | ¹H NMR (400 MHz, CD₃OD) 3.17 (s, 1H), 3.80 (br. s., 2H), 4.11 (br. s., 2H), 4.21 (t, 2H), 4.76 (br. s., 2H), 7.40 (dd, 1H), 7.61-7.70 (m, 2H), 7.90 (s, 1H), 8.22 (s, 1H), 8.34 (s, 1H) |
| 83 | 3-(4-(4-(4-amino-5-oxo-7,8-dihydropyrimido[5,4-f][1,4]oxazepin-6(5H)-yl)-2,6-dimethylphenyl)-3-methyl-1H-pyrazol-1-yl)propanoic acid | white solid | 437.1 [M + 1] | ¹H NMR (400 MHz, CD₃OD) 8.19 (s, 1H), 7.44 (s, 1H), 7.13 (s, 2H), 4.40 (t, 2H), 4.75 (t, 2H), 4.42 (t, 2H), 4.09 (t, 2H), 2.90 (q, 2H), 2.18 (s, 1H), 2.10 (d, 6H), 2.02 (s, 2H) |
| 84 | 2(-4-(4-(4-amino-5-oxo-7,8-dihydropyrimido[5,4-f][1,4]oxazepin-6(5H)-yl)-2-chlorophenyl)-1H-pyrazol-1-yl)acetonitrile | white solid | 414.0 [M + 1] | ¹H NMR (400 MHz, DMSO-d₆) 8.33 (s, 1H), 8.02 (s, 1H), 7.66 (d, 1H), 7.40 (d, 1H), 4.55 (s, 2H), 4.74 (s, 2H), 4.08 (s, 2H). |

| NO | Structure | property | MS | HNMR |
|---|---|---|---|---|
| 85 | 4-amino-6-(3-chloro-4-(1-(2,2-dimethyl-3-oxo-3-(pyrrolidin-1-yl)propyl-1H-pyrazol-4-yl)phenyl)-7,8-dihydropyrimido[5,4-f][1,4]oxazepin-5(6H)-one | white solid | 510.0 [M + 1] | $^1$H NMR (400 MHz, DMSO-$d_6$) 8.14 (s, 1H), 8.09 (s, 1H), 7.84 (s, 1H), 7.60 (m, 4H), 7.34 (d, 1H), 4.59 (t, 2H), 4.30 (s, 2H), 3.98 (t, 2H), 2.42 (s, 8H), 1.18 (s, 6H). |
| 86 | 4-amino-6-(3-chloro-4-(1-isobutyl-1H-pyrazol-4-yl)phenyl)-8,8-dimethyl-7,8-dihydropyrimido[5,4-f][1,4]oxazepin-5(6H)-one | white solid | 441.1 [M + 1] | $^1$H NMR (400 MHz. CD$_3$OD) 8.46 (s, 1H), 8.28 (br. s., 1H), 8.09 (br. s., 1H), 7.69 (d, 1H), 7.62 (d, 1H), 7.42 (dd, 1H), 4.23 (s, 2H), 4.11 (d, 2H), 2.26 (m, 1H), 1.60 (s, 6H), 0.98 (s, 3H), 0.97 (s, 3H) |
| 87 | 4-amino-6-(3-chloro-4-(1-(cyclopropyl methyl)-1H-pyrazol-4-yl)phenyl)-7,8-dihydropyrimido[5,4-f][1,4]oxazepin-5(6H)-one | yellow solid | 411.1 [M + 1] | 1H NMR (400 MHz, CDCl3) δ 8.30 (s, 1H), 8.19 (brs, 1H), 7.93 (d, 1H), 7.81 (d, 1H), 7.56-7.54 (m, 1H) 7.40 (t, 1H), 7.26-7.21 (m, 1H), 5.68 (brs, 1H), 4.72 (t, 2H), 4.06 (t, 2H), 1.37-1.34 (m, 1H), (d, 2H), 0.43 (s, 2H) |
| 88 | 4-amino-6-(3-chloro-4-(1-(neopentyl-1H-pyrazol-4-yl)phenyl)-7,8-dihydropyrimido[5,4-f][1,4]oxazepin-5(6H)-one | white solid | 427.2 [M + 1] | 1H NMR (400 MHz, DMSO-d6) δ 8.24 (s, 1H), 8.14 (s, 1H), 7.90 (brs, 1H), 7.85 (s, 1H), 7.64-7.61 (m, 2H), 7.36 (d, 1H), 4.67 (d, 2H), 4.04 (s, 2H), 3.95 (s, 2H), 0.91 (s, 6H) |

-continued

| NO | Structure | property | MS | HNMR |
|---|---|---|---|---|
| 89 | 3-(4-(4-(4-amino-5-oxo-7,8-dihydropyrimido[5,4-f][1,4]oxazepin-6(5H)-yl)-2-chlorophenyl)-1H-pyrazol-1-yl)-N,N,2,2-tetramethylpropanamide | white solid | 484.0 [M + 1] | $^1$H NMR (400 MHz, DMSO-d$_6$) 8.28 (s, 1H), 8.00 (s, 1H), 7.76 (s, 1H), 7.51 (d, 1H), 7.37 (s, 1H), 7.18 (d, 1H), 4.70 (s, 2H), 4.41 (s, 2H), 4.01 (s, 2H), 3.01 (s, 6H), 1.34 (s, 6H). |
| 90 | 4-amino-6-(3-ethyl-4-(1-isobutyl-1H-pyrazol-4-yl)phenyl)-7,8-dihydropyrimido[5,4-f][1,4]oxazepin-5(6H)-one | white solid | 407.0 [M + 1] | $^1$H NMR (400 MHz, DMSO-d$_6$) 8.28 (s, 1H), 7.57 (s, 1H), 7.41 (s, 1H), 7.36 (d, 1H), 7.16 (d, 1H), 7.10 (dd, 1H), 4.71 (t, 2H), 4.03 (t, 2H), 3.94 (d, 2H), 2.75 (t, 2H), 2.25 (m, 1H), 1.19 (t, 3H), 0.94 (s, 3H), 0.93 (s, 3H). |
| 91 | 4-amino-6-(3-chloro-4-(1-(2-fluoro-2-methylpropyl)-1H-pyrazol-4-yl)phenyl)-7,8-dihydropyrimido[5,4-f][1,4]oxazepin-5(6H)-one | yellow solid | 431.1 [M + 1] | 1H NMR (400 MHz, MeOD) δ 8.40 (s, 1H), 8.10 (s, 1H), 7.89 (s, 1H), 7.68-7.66 (dd, 1H), 7.58 (d, 1H), 7.66-7.61 (dd, 1H), 7.35 (d, 1H), 4.97 (s, 2H), 4.37 (d, 2H), 4.24 (t, 2H), 1.38 (s, 3H), 1.32 (s, 3H) |
| 92 | 4-amino-6-(3-chloro-4-(1-isobutyl-1H-pyrazol-4-yl)phenyl)-7,7-dimethyl-7,8-dihydropyrimido[5,4-f][1,4]oxazepin-5(6H)-one | Off-white solid | 441.0 [M + 1] | $^1$H NMR (400 MHz, CD3OD) 8.09 (d, 2H), 7.95-7.82 (m, 1H), 7.63 (d, 1H), 7.36 (d, 1H), 7.16 (dd, 1H), 4.66-4.51 (m, 2H), 4.02 (d, 2H), 2.34-2.16 (m, 1H), 1.30 (s, 6H), 1.00-0.90 (m, 6H) |

| NO | Structure | property | MS | HNMR |
|---|---|---|---|---|
| 93 | 4-amino-6-(4-(3,5-dimethyl-1-(2,2,2-trifluoroethyl)-1H-pyrazol-4-yl)-3,5-dimethylphenyl)-7,8-dihydropyrimido[5,4-f][1,4]oxazepin-5(6H)-one | white solid | 461.1 [M + 1] | $^1$H NMR (400 MHz, DMSO-d6) 8.18 (s, 1H), 7.63 (s, 2H), 7.17 (s, 2H), 5.09 (q, 2H), 4.62 (t, 2H), 4.01 (t, 2H), 2.0 (s, 3H), 1.97 (s, 6H), 1.89 (s, 3H) |
| 94 | 4-amino-6-(3-chloro-4-(1-(2-methoxy-2-methylpropyl)-1H-pyrazol-4-yl)phenyl)-7,8-dihydropyrimido[5,4-f][1,4]oxazepin-5(6H)-one | whtie solid | 433.1.0 [M + 1] | $^1$H NMR (400 MHz, CD$_3$OD) 8.40 (s, 1H), 8.10 (s, 1H), 7.85 (s, 1H), 7.66 (d, 1H), 7.57 (s, 1H), 7.34 (d, 1H), 4.98 (t, 2H), 4.24 (t, 2H), 4,21 (s, 2H), 3.28 (s, 3H), 1.18 (s, 6H). |
| 95 | 4-amino-6-(3-chloro-4-(1-(2-fluoro-2-methylpropyl)-1H-pyrazol-3-yl)phenyl)-7,8-dihydropyrimido[5,4-f][1,4]oxazepin-5(6H)-one | white solid | 431.0 [M + 1] | $^1$H NMR (400 MHz, CD$_3$OD) 8.41 (s, 1H), 7.81 (d, 1H), 7.71 (s, 1H), 7.38 (d, 1H), 5.00 (t, 2H), 4.36 (d, 2H), 4.26 (t, 2H), 1.36 (d, 6H) |
| 96 | (R)-4-amino-6-(3-chloro-4-(1-isobutyl-1H-pyrazol-4-yl)phenyl)-7-methyl-7,8-dihydropyrimido[5,4-f][1,4]oxazepin-5-(6H)-one | white solid | 427.0 [M + 1] | $^1$H NMR (400 MHz, DMSO-d$_6$) 8.22 (s, 1H), 7.80 (s, 1H), 7.79 (s, 1H), 7.55 (d, 1H), 7.30 (d, 1H), 7.12 (dd, 1H), 4.62 (d, 2H), 4.08 (m, 1H), 3.97 (d, 2H), 2.25 (m, 1H), 1.36 (d, 3H), 0.95 (s, 3H). 0.93 (s, 3H). |

-continued

| NO | Structure | property | MS | HNMR |
|---|---|---|---|---|
| 97 | 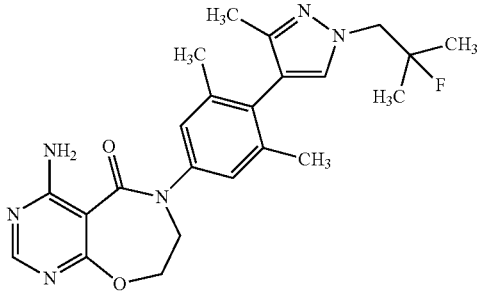 [SMILES: Cc1cc(N2CCOc3ncnc(N)c3C2=O)cc(C)c1-c1cn(CC(C)(C)F)nc1C]<br>4-amino-6-(4-(1-(2-fluoro-2-methylpropyl)-3-methyl-1H-pyrazol-4-yl)-3,5-dimethylphenyl)-7,8-dihydropyrimido[5,4-f][1,4]oxazepin-5(6H)-one | white solid | 439.2 [M + 1] | $^1$H NMR (400 MHz, DMSO-d6) 8.40 (d, 1H), 7.46 (s, 1H), 7.12 (s, 1H), 4.76 (t, 2H), 4.25 (d, 2H), 4.08 (t, 2H), 2.0 (s, 6H), 1.90 (s, 3H), 1.30 (s, 3H), 1.25 (s, 3H) |
| 98 | 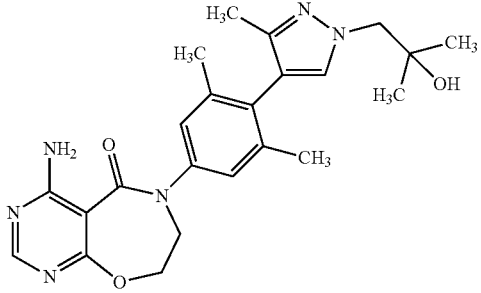 [SMILES: Cc1cc(N2CCOc3ncnc(N)c3C2=O)cc(C)c1-c1cn(CC(C)(C)O)nc1C]<br>4-amino-6-(4-(1-(2-hydroxy-2-methylpropyl)-3-methyl-1H-pyrazol-4-yl)-3,5-dimethylphenyl)-7,8-dihydropyrimido[5,4-f][1,4]oxazepin-5(6H)-one | white solid | 437.2 [M + 1] | $^1$H NMR (400 MHz, DMSO-d6) 8.72 (s, 1H), 8.66 (s, 1H), 8.40 (s, 1H), 7.49 (s, 1H), 7.12 (s, 2H), 4.72 (t, 2H), 4.09 (t, 2H), 3.97 (s, 2H), 2.0 (s, 6H), 1.89 (s, 3H), 1.05 (s, 6H) |
| 99 | 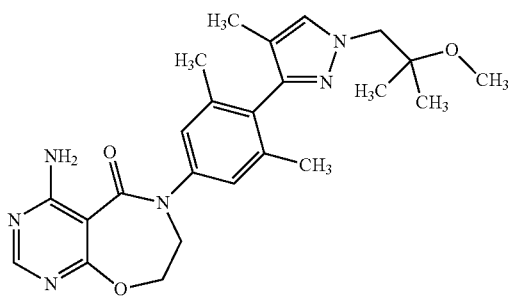 [SMILES: COC(C)(C)Cn1cc(C)c(-c2c(C)cc(N3CCOc4ncnc(N)c4C3=O)cc2C)n1]<br>4-amino-6-(4-(1-(2-methoxy-2-methylpropyl)-3-methyl-1H-pyrazol-4-yl)-3,5-dimethylphenyl)-7,8-dihydropyrimido[5,4-f][1,4]oxazepin-5(6H)-one | white solid | 451.2 [M + 1] | $^1$H NMR (400 MHz, DMSO-d6) 9.08 (s, 1H), 8.82 (s, 2H), 8.49 (s, 1H), 7.47 (s, 1H), 7.13 (s, 2H), 4.85 (t, 2H), 4.14 (t, 2H), 4.07 (s, 3H), 3.14 (s, H), 1.90 (s, 6H), 1.90 (s, 3H), 1.06 (s, 3H) |

Example 100

4-amino-6-(4-(2-oxo-1-(2,2,2-trifluoroethyl)-1,2-dihydropyridin-3-yl)phenyl)-7,8-dihydropyrimido[5,4-f][1,4]oxazepin-5-(6H)-one

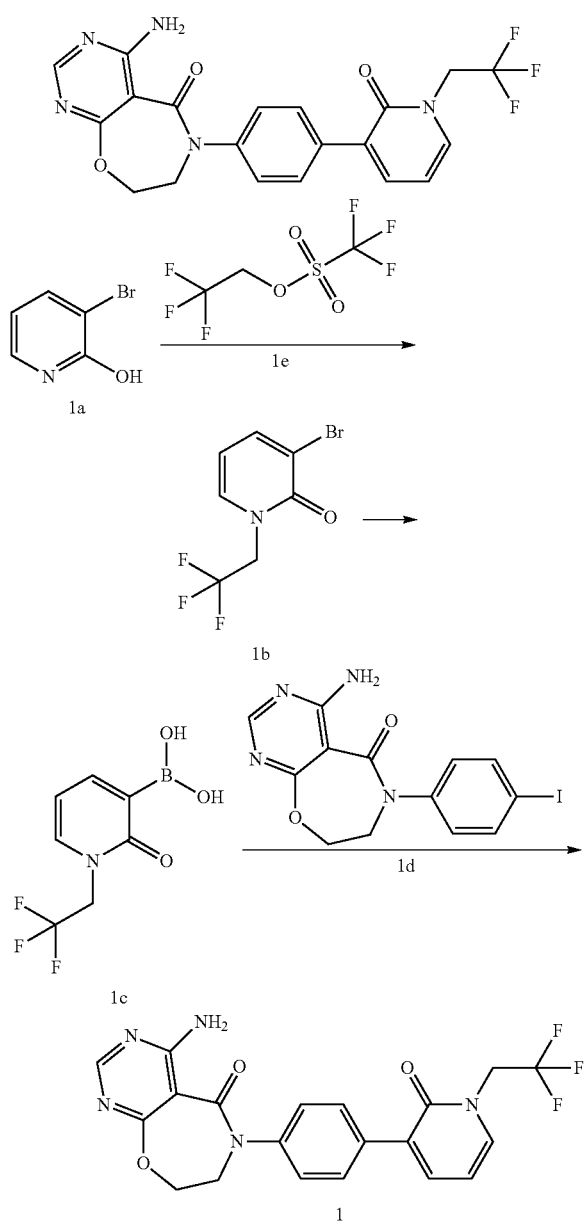

Step 1

3-bromo-1-(2,2,2-trifluoroethyl)pyridin-2(1H)-one

To a solution of 3-bromopyridin-2-ol 1a (600 mg, 3.45 mmol) in DMF (10 mL) was added K₂CO₃ (950 mg, 6.9 mmol) and 2,2,2-trifluoroethyl trifluoromethanesulfonate (1.6 g, 6.9 mmol). The mixture was stirred at room temperature for 12 h, then diluted with water (150 mL) and extracted with EA (50 mL*3). The organic layers were combined and washed with water (50 mL*2) and brine (50 mL*2), dried over Na₂SO₄, filtrated and evaporated. The residue was purified by column chromatography on silica gel to give 3-bromo-1-(2,2,2-trifluoroethyl)pyridine-2(1H)-one 1b (515 mg, 58.6%) as a light yellow liquid.

$^1$H NMR (400 MHz, (CDCl₃) δ 7.77 (d, 1H), 7.27 (d, 1H), 6.13 (t, 1H), 4.65 (q, 2H)

Step 2

2-oxo-1-(2,2,2-trifluoroethyl)-1,2-dihydropyridin-3-yl)boronic acid

To a solution of 3-bromo-1-(2,2,2-trifluoroethyl)pyridin-2(1H)-one 1b (250 mg, 1 mmol) in Toluene (20 mL) was added Pin₂B₂ (300 mg, 1.2 mmol), KOAc (300 mg, 3 mmol) and Pd(dppf)Cl₂ (40 mg, 0.05 mmol). The mixture was stirred at 120° C. for 30 min in a microwave reactor. Then it was filtrated and concentrated under reduced pressure. The residue was purified by cp-TLC to give (2-oxo-1-(2,2,2-trifluoroethyl)-1,2-dihydropyridin-3-yl)boronic acid 1c (120 mg, 55.6%) as a white solid.

$^1$H NMR (400 MHz, DMSO-d₆) δ 8.55 (s, 2H), 7.98 (dd, 1H), 7.84 (d, 1H), 6.48 (t, 1H), 4.91 (q, 2H).

Step 3

4-amino-6-(4-(2-oxo-1-(2,2,2-trifluoroethyl)-1,2-dihydropyridin-3-yl)phenyl)-7,8-dihydropyrimido[5,4-f][1,4]oxazepin-5-(6H)-one To a solution of (2-oxo-1-(2,2,2-trifluoroethyl)-1,2-dihydropyridin-3-yl)boronic acid 1c (50 mg, 0.13 mmol) in dioxane/H₂O (1 mL/0.2 mL) was added 4-amino-6-(4-iodophenyl)-7,8-dihydropyrimido[5,4-f][1,4]oxazepin-5-(6H)-one (50 mg, 0.13 mmol, prepared according to patent WO2009016462), K₂CO₃ (40 mg, 0.26 mmol), and Pd(dppf)Cl₂ (5 mg, 0.004 mmol). The mixture was stirred at 100° C. for 30 min in a microwave reactor, then diluted with water (20 mL) and extracted with EA (50 mL*3). The combined organic layers was washed with brine (30 mL), dried over Na₂SO₄, concentrated under reduced pressure and purified by p-HPLC to give 4-amino-6-(4-(2-oxo-1-(2,2,2-trifluoroethyl)-1,2-dihydropyridin-3-yl)phenyl)-7,8-dihydropyrimido[5,4-f][1,4]oxazepin-5-(6H)-one as a white solid.

$^1$H NMR (400 MHz, CD₃OD) δ 8.40 (s, 1H), 7.70-7.76 (m, 3H), 7.65 (d, 1H), 7.40 (d, 2H), 6.51 (t, 1H), 4.99 (s, 2H), 4.89-4.95 (m, 2H), 4.25 (s, 2H)

Example 101

4-amino-6-(3,5-dimethyl-4-(6-oxo-1-(2,2,2-trifluoroethyl)-1,6-dihydropyridin-3-yl)phenyl)-7,8-dihydropyrimido[5,4-f][1,4]oxazepin-5-(6H)-one

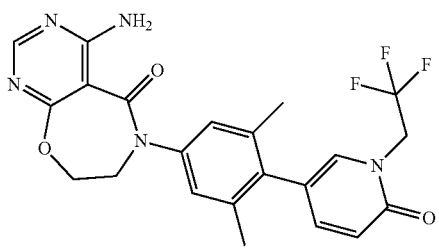

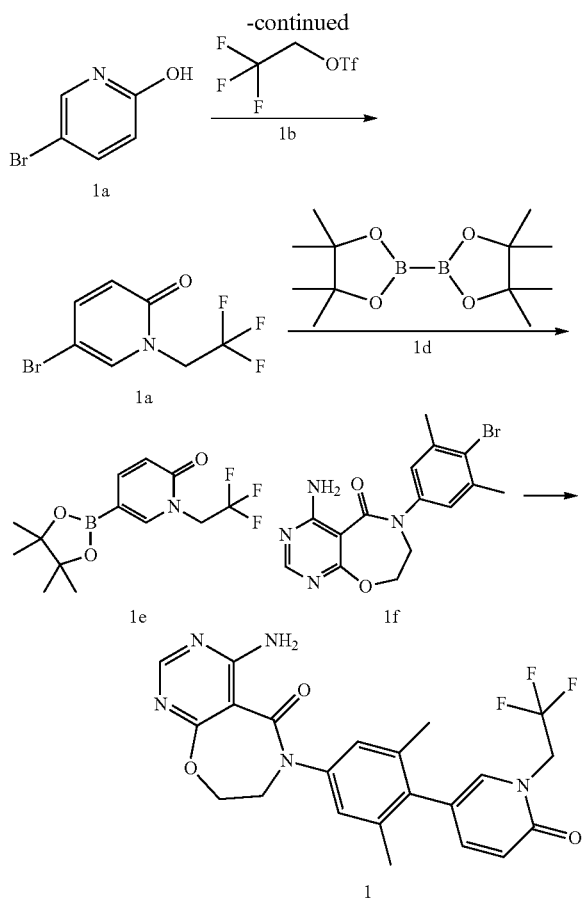

Step 1

5-bromo-1-(2,2,2-trifluoroethyl)pyridin-2(1H)-one

To a mixture of 5-bromopyridin-2-ol 1a (300 mg, 1.72 mmol) in DMF (10 mL) was added 2,2,2-trifluoroethyl trifluoromethanesulfonate 1b (800 mg, 3.45 mmol) and $Cs_2CO_3$ (476 mg, 3.45 mmol) at 0° C. Reaction mixture was stirred at RT for 4 h. The mixture was poured into water, extracted with EtOAc (30 mL*3). The organic layers were combined and washed with water (100 mL*3), sat. NaCl aqueous solution (100 mL), dried over $Na_2SO_4$, filtered and concentrated to give a crude product. The crude was then purified by silica column (eluent system C) to give 5-bromo-4-(2,2,2-trifluoroethyl)pyridin-2(1H)-one 1c (430 mg, yield: 36.4%) as a white solid.

$^1$H NMR (400 MHz, $CDCl_3$) δ 7.90 (d, 1H), 7.64 (dd, 1H), 6.56 (d, 1H), 4.80 (q, 2H).

Step 2

5-(4,4,5,5-tetramethyl-1,3,2-dioxaborolan-2-yl)-1-(2,2,2-trifluoroethyl)pyridin-2(1H)-one To a stirred solution of 5-bromo-1-(2,2,2-trifluoroethyl) pyridin-2(1H)-one 1c (400 mg, 1.56 mmol) in dioxane (5 mL) was added 4,4,4',4',5,5,5',5'-octamethyl-2,2'-bi(1,3,2-dioxaborolane) 1d (595 mg, 2.34 mmol), KOAc (458 mg, 4.63 mmol) and Pd(dppf)$Cl_2$ (63.6 mg, 0.08 mmol) at RT. Reaction mixture was stirred at 100° C. for 0.5 h under microwave irradiation. The mixture was cooled to RT and concentrated. The residue was diluted with water (10 mL), extracted with DCM (20 mL*3). The organic layers were combined and dried over $Na_2SO_4$, filtered and concentrated. The residue was purified by prep TLC (eluent system C) to give 5-(4,4,5,5-tetramethyl-1,3,2-dioxaborolan-2-yl)-1-(2,2,2-trifluoroethyl)pyridin-2(1H)-one 1e (800 mg, yield; 100%) as a white solid.

Step 3

4-amino-6-(3,5-dimethyl-4-(6-oxo-1-(2,2,2-trifluoroethyl)-1,6-dihydropyridin-3-yl)phenyl)-7,8-dihydropyrimido[5,4-f][1,4]oxazepin-5-(6H)-one A mixture 5-(4,4,5,5-tetramethyl-1,3,2-dioxaborolan-2-yl)-1-(2,2,2-trifluoroethyl)pyridin-2(1H)-one 1e (167 mg, 0.55 mmol), 4-amino-6-(4-bromo-3,5-dimethylphenyl)-7,8-dihydropyrimido[5,4-f][1,4]oxazepin-5-(6H)-one 1f (100 mg, 0.28 mmol), $K_2CO_3$ (76 mg, 0.55 mmol) and Pd(dppf)$Cl_2$ (22 mg, 0.0275 mmol) in Dioxane/$H_2O$ (2 mL, 3:1) was stirred at 100° C. for 30 min under microwave irradiation. The mixture was cooled to RT and diluted with water and DCM, extracted with DCM (20 mL*3). The organic layers were combined and dried over $Na_2SO_4$, filtered and concentrated. The residue was purified by prep HPLC to afford 4-amino-6-(3,5-dimethyl-4-(6-oxo-1-(2,2,2-trifluoroethyl)-1,6-dihydropyridin-3-yl)phenyl)-7,8-dihydropyrimido[5,4-f][1,4]oxazepin-5-(6H)-one (37 mg, yield: 28.2%) as a white solid.

$^1$H NMR (400 MHz, $CD_3OD$) δ 8.43 (s, 1H), 7.50 (s, 1H), 7.41 (d, 1H), 7.20-7.09 (m, 2H), 6.76-6.65 (m, 1H), 5.00 (br,s, 2H), 4.93-4.88 (m, 2H), 4.23 (br,s, 2H), 2.18 (s, 6H)

Example 102

4-amino-6-(3-chloro-4-(1-(2-fluoro-2-methylpropyl)-1H-imidazol-4-yl)phenyl)-7,8-dihydropyrimido[5,4-f][1,4]oxazepin-5-(6H)-one

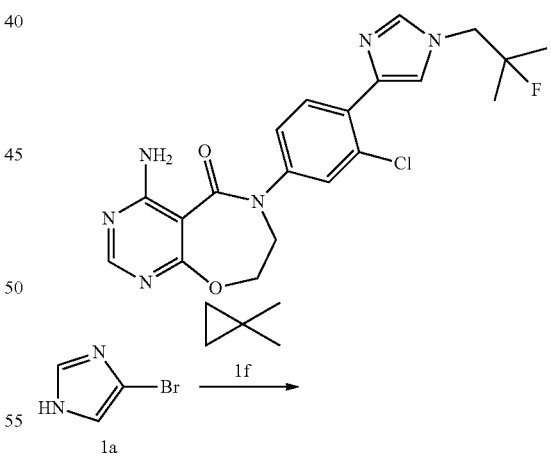

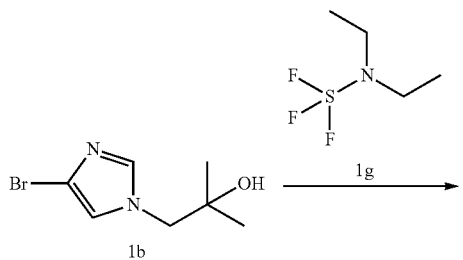

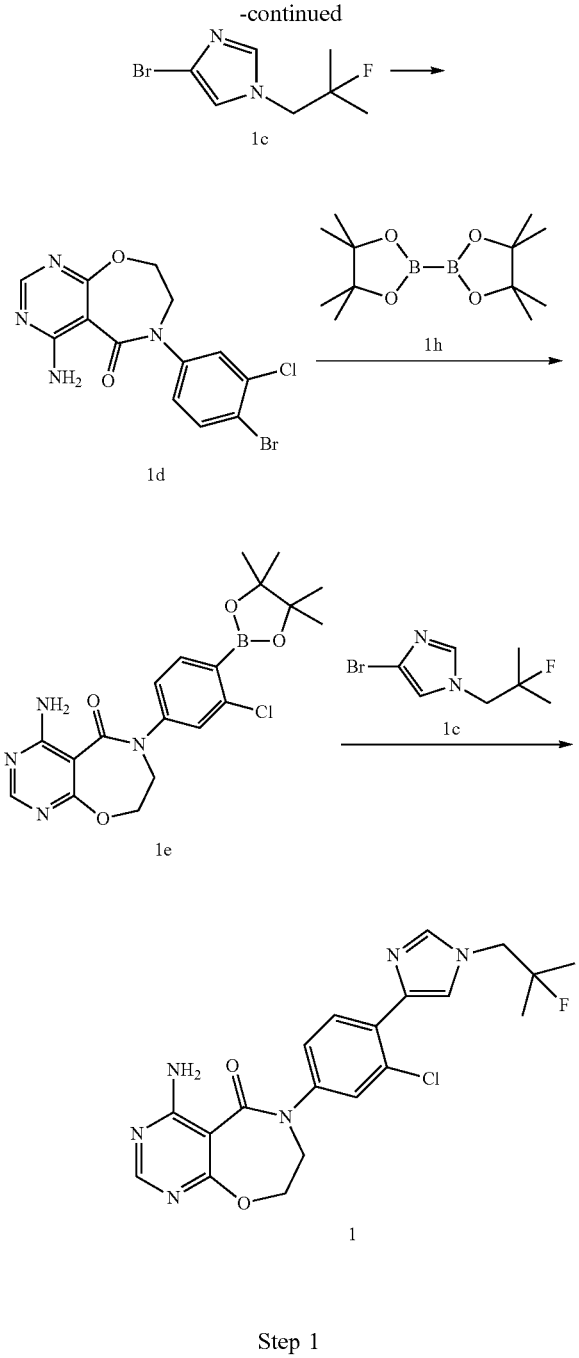

Step 2

4-bromo-1-(2-fluoro-2-methylpropyl)-1H-imidazole

To a solution of 1-(4-bromo-1H-imidazol-1-yl)-2-methylpropan-2-ol 1b (2.7 g, 12.33 mmol) in DCM (30 ml) was added dropwise DAST 1g (4.96 g, 30.83 mmol) at −70° C. under $N_2$. Then the mixture was stirred for 12 h. The reaction mixture was washed with water (10 mL*2), saturated $NaHCO_3$ (5 mL*2) and saturated NaCl aqueous solution (5 mL*2), dried over $Na_2SO_4$, filtered and concentrated. The residue was purified by column to give the target compound 4-bromo-1-(2-fluoro-2-methylpropyl)-1H-imidazole 1c (1g, yellow oil), yield: 36.8%.

$^1$H NMR (400 MHz, $CDCl_3$) δ 7.37 (s, 1H), 6.95 (s, 1H), 4.00 (d, 2H), 1.33 (d, 6H)

Step 3

4-amino-6-(3-chloro-4-(4,4,5,5-tetramethyl-1,3,2-dioxaborolan-2-yl)phenyl)-7,8-dihydropyrimido[5,4-f][1,4]oxazepin-5-(6H)-one To a solution of 4-amino-6-(4-bromo-3-chlorophenyl)-7,8-dihydropyrimido[5,4-f][1,4]oxazepin-5-(6H)-one 1d (100 mg, 0.27 mmol) in dioxane (3 mL) was added 1h (103 mg, 0.41 mmol) and KOAc (79.38 mg, 0.81 mmol) and Pd(dppf)$Cl_2$ (20 mg, 0.027 mmol) under $N_2$. The mixture was stirred at 80° C. under N2 for 12 h. The reaction mixture was evaporated and the residue was purified by prep-TLC to give the crude product 4-amino-6-(3-chloro-4-(4,4,5,5-tetramethyl-1,3,2-dioxaborolan-2-yl)phenyl)-7,8-dihydropyrimido[5,4-f][1,4]oxazepin-5-(6H)-one 1e (40 mg, crude). The crude was a mixture of 1e and de_bromo product of 1d and used in the next step directly.

Step 4

4-amino-6-(3-chloro-4-(1-(2-fluoro-2-methylpropyl)-1H-imidazol-4-yl)phenyl)-7,8-dihydropyrimido[5,4-f][1,4]oxazepin-5-(6H)-one To a solution of 4-amino-6-(3-chloro-4(4,4,5,5-tetramethyl-1,3,2-dioxaborolan-2-yl)phenyl)-7,8-dihydropyrimido[5,4-f][1,4]oxazepin-5-(6H)-one 1d (40 mg, 0.096 mmol) in dioxane/$H_2O$ (1.2 mL, V/V=4:1) was added 4-bromo-1-(2-fluoro-2-methylpropyl)-1H-imidazole 1c (21.22 mg. 0.096 mmol), $K_2CO_3$ (26.50 mg, 0.192 mmol) and Pd(dppf)$Cl_2$ (7 mg, 0.0096 mmol) under $N_2$. Then the mixture was stirred at 90° C. for 12 h. The reaction mixture was cooled to RT. To the mixture was added water (5 mL) and then extracted with EA (5 mL*3). The organic layers were combined and washed with saturated NaCl aqueous solution (5 mL*2), dried over $Na_2SO_4$, filtered and concentrated. The residue was purified by prep-HPLC to give the target compound 4-amino-6-(3-chloro-4-(1-(2-fluoro-2-methylpropyl)-1H-imidazol-4-yl)phenyl)-7,8-dihydropyrimido[5,4-f][1,4]oxazepin-5-(6H)-one a (2.08 mg, white solid), yield; 5%.

MS m/z (ESI): 431.1 [M+1]

$^1$H NMR (400 MHz, $CD_3OD$) δ 9.15 (s, 1H), 8.40 (s, 1H), 8.02 (s, 1H), 7.76 (d, 2H), 7.55 (d, 1H), 4.98 (t, 2H), 4.52 (d, 2H), 4.29 (t, 2H), 1.42 (d, 6H)

Step 1

1-(4-bromo-1H-imidazol-1-yl)-2-methylpropan-2-ol

To a solution of 4-bromo-1H-imidazole 1a (2 g, 13.70 mmol) in DMF (30 mL) was added 2,2-dimethyloxirane 1f (20 mL) and $Cs_2CO_3$ (8 g, 24.62 mmol). The mixture was stirred at 90° C. overnight. Then the mixture was evaporated to dryness. The residue was dissolved in DCM (30 mL), washed with water (10 mL*2) and brine (10 mL), dried over $Na_2SO_4$, filtered and concentrated to give the target compound 1-(4-bromo-1H-imidazol-1-yl)-2-methylpropan-2-ol 1b (2.7 g, pale yellow solid), yield: 90.6%.

$^1$H NMR (400 MHz, $CDCl_3$) δ 7.33 (s, 1H), 6.94 (s, 1H), 3.82 (s, 2H), 1.22 (s, 6H)

Example 103

2-(4-(4-(4-amino-5-oxo-7,8-dihydropyrimido[5,4-f][1,4]oxazepin-6-(5H)yl)phenyl)piperidinyl)acetic acid

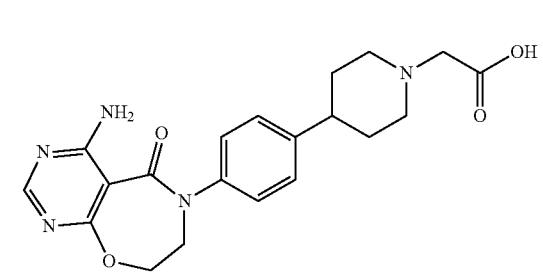

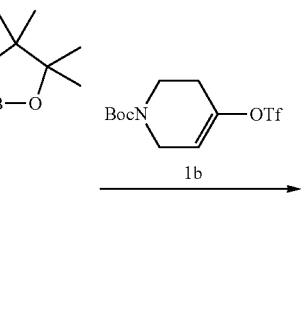

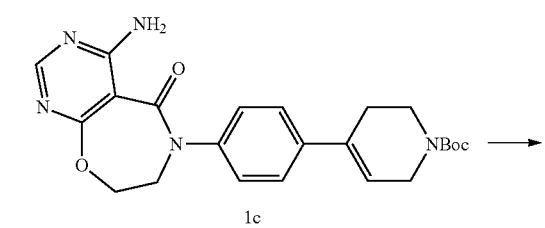

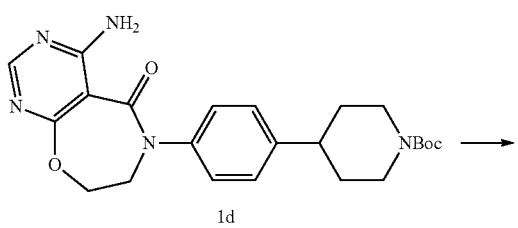

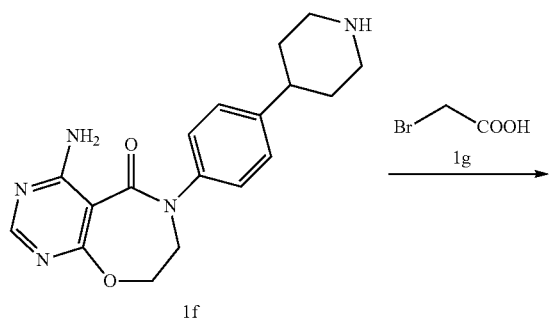

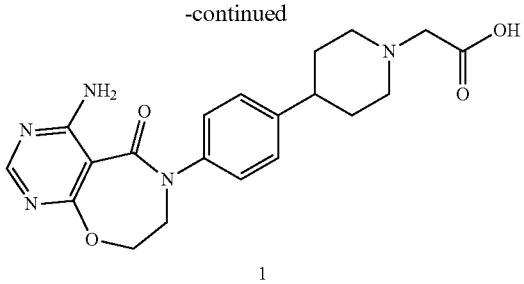

Step 1

Tertiary butyl 4-(4-(4-amino-5-oxo-7,8-dihydropyrimido[5,4-f][1,4]oxazepin-6-(5H)yl-phenyl)-5,6-dihydroxypyridine-1-(2H)-carboxylic ester To a mixture solvents of 7.5 mL THF and water (V/V=2:1) was added tert-butyl 4-(((trifluoromethyl)sulfonyl)oxy)-5,6-dihydropyridine-1(2H)-carboxylate 1b (325 mg, 0.98 mmol), prepared by the common method "Patent WO 2005037826"), 1a (250 mg, 0.65 mmol, prepared by the common method "Patent WO2011121350"), sodium carbonate (138 mg, 1.3 mmol), 1,1'-bis(diphenylphosphorus) ferrocene palladium chloride (24 mg, 0.033 mmol). The mixture was stirred at 80° C. for 12 h. 10 mL water was added into the mixture and it was extracted with ethyl acetate (20 mL*3), the organic layer was combined and washed with saturated sodium chloride solution (10 mL), then it was dried over anhydrous sodium sulfate. The mixture was filtered, and the filtrate was concentrated under pressure. The residue was purified by thin layer chromatography with eluent system C to obtain the title product tertiary butyl 4-(4-(4-amino-5-oxo-7,8-dihydropyrimido[5,4-f][1,4]oxazepin-6-(5H)yl-phenyl)-5,6-dihydroxypyridine-1(2H)-carboxylic ester 1c (220 mg, white solid), yield: 76.9%.

MS m/z (ESI): 438.3 [M+1]

$^1$H NMR (400 MHz, CDCl$_3$) δ 8.29 (s, 1H), 7.45 (d, 2H), 7.25 (d, 2H), 6.05 (s, 1H), 4.70 (t, 2H), 4.08 (m, 2H), 4.03 (t, 2H), 3.64 (t, 2H), 2.52 (m, 2H), 1.50 (s, 9H)

Step 2

Tertiary butyl 4-(4-(4-amino-5-oxo-7,8-dihydropyrimido[5,4-f][1,4]oxazepin-6-(5H)yl-phenyl)pyridine-1-carboxylic ester To a solution of tertiary butyl 4-(4-(4-amino-5-oxo-7,8-dihydropyrimido[5,4-f][1,4]oxazepin-6-(5H)yl-phenyl)-5,6-dihydroxypyridine-1(2H)-carboxylic ester 1c (220 mg, 0.50 mmol) in 10 mL methanol was added sodium acetate (410 mg, 5.0 mmol) and 10% wet Pd/C (100 mg). The mixture was vacuum pumped and filled with hydrogen for 3 times, and then it was stirred at room temperature for 12 hours. The mixture was filtered, and the filtrate was concentrated under pressure to obtain the title product tertiary butyl 4-(4-(4-amino-5-oxo-7,8-dihydropyrimido[5,4-f][1,4]oxazepin-6-(5H)yl-phenyl)pyridine-1-carboxylic ester 1d (200 mg, white solid). The product was used in the next step directly without purification.

MS m/z (ESI): 440.3 [M+1]

Step 3

4-amino-6-(4-(piperidine-4-)phenyl-7,8-dihydropyrimido[5,4-f][1,4]oxazepin-5-(6H)-one To a solution of tertiary butyl 4-(4-(4-amino-5-oxo-7,8-dihydropyrimido[5,4-f][1,4]oxazepin-6-(5H)yl-phenyl)pyridine-1-carboxylic ester 1d (200 mg, 0.45 mmol) in 4 mL 1,4-dioxane was 1 mL 2 M HCl 1,4-dioxane solution. The mixture was stirred at room temperature for 1 hour and then was concentrated under pressure to give the title product 4-amino-6-(4-(piperidine-4-yl)phenyl)-7,8-dihydropyrimido[5,4-f][1,4]oxazepin-5-(6H)-one 1f (140 mg, light yellow solid), yield: 83.0%.

$^{1}$H NMR (400 MHz, DMSO-$d_6$) δ 8.32 (s, 1H), 7.40-7.25 (m, 4H), 4.72 (t, 2H), 4.04 (t, 2H), 3.10-2.80 (m, 4H), 2.70-2.50 (m, 1H), 1.95-1.80 (m, 4H)

Step 4

2-(4-(4-(4-amino-5-oxo-7,8-dihydropyrimido[5,4-f][1,4]oxazepin-6-(5H)yl)phenyl)piperidinyl)acetic acid To a solution of 4-amino-6-(4-(piperidine-4-yl)phenyl)-7,8-dihydropyrimido[5,4-f][1,4]oxazepin-5-(6H)-one (80 mg, 0.21 mmol) in 3 mL DCM was added triethylamine (0.15 mL, 1.06 mmol) and bromoacetic acid 1g (44 mg, 0.32 mmol). The mixture was stirred at room temperature for 2 hours and then was concentrated under pressure. It was purified by prep-HPLC to give the title product 2-(4-(4-(4-amino-5-oxo-7,8-dihydropyrimido[5,4-f][1,4]oxazepin-6-(5H)yl)phenyl)piperidinyl)acetic acid 1 (13 mg, white solid), yield: 15.8%.

$^{1}$H NMR (400 MHz, CD$_3$OD) δ 8.43 (s, 1H), 7.45-7.30 (m, 4H), 5.00 (t, 2H), 4.23 (t, 2H), 3.79 (d, 1H), 3.51 (d, 1H), 3.30-3.10 (m, 2H), 3.05-2.90 (m, 1H), 2.18-1.90 (m, 4H)

Example 104

2-(3-(4-(4-amino-5-oxo-7,8-dihydropyrimido[5,4-f][1,4]oxazepin-6-(5H)yl)phenyl)pyrrole-1-yl)acetic acid

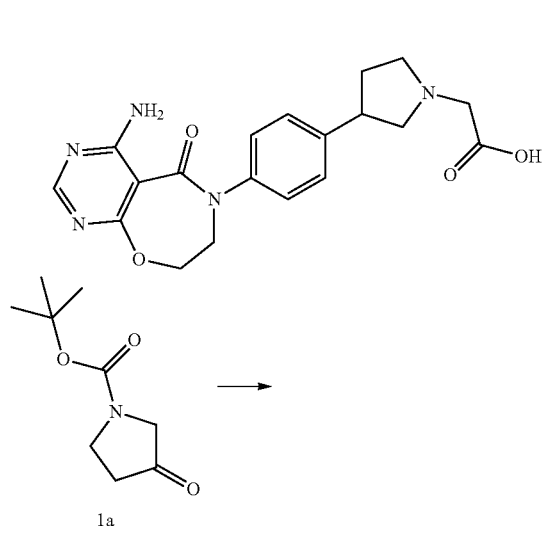

1a

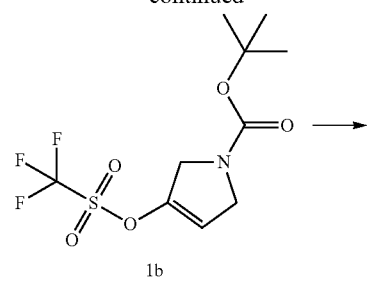

1b

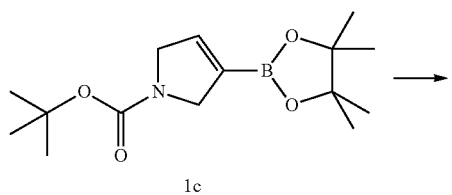

1c

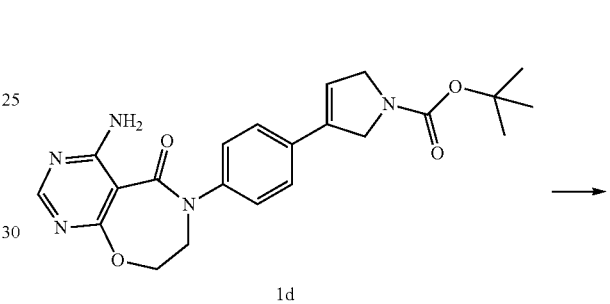

1d

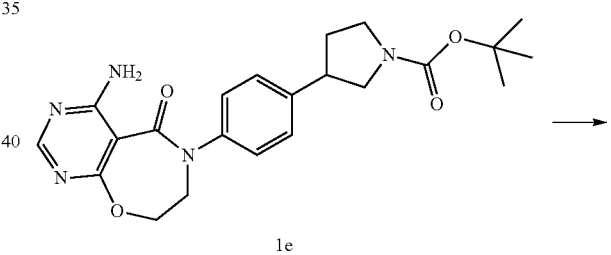

1e

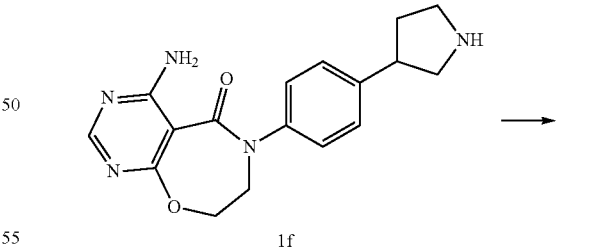

1f

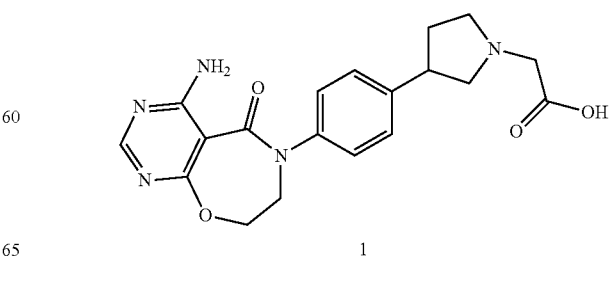

1

Step 1 tert-butyl 3-(((trifluoromethyl)sulfonyl)oxy)-2,5-dihydro-1H-pyrrole-1-carboxylate To a solution of tert-butyl 3-oxopyrrolidine-1-carboxylate 1a (3 g, 16.2 mmol) in 30 mL THF on ice bath was added LHMDS (19.5 mL, 19.5 mmol) and N-Phenylbis(trifluoromethanesulfon)imide (6.36 g, 18 mmol). The mixture was stirred on ice bath for 2 h. Then 50 mL water was added, and it was extracted with EA (30 mL*3). The organic layer was combined and washed with saturated sodium chloride solution (50 mL), dried over anhydrous sodium sulfate. The mixture was filtered and the filtrate was concentrated under pressure to obtain the crude title product tert-butyl 3-(((trifluoromethyl)sulfonyl)oxy)-2,5-dihydro-1H-pyrrole-1-carboxylate 1b (9 g, light yellow oil). The product was used in the next step directly without purification.

$^1$H NMR (400 MHz, CDCl$_3$) δ 5.73 (d, 1H), 4.25-4.15 (m, 2H), 3.78-3.68 (m, 2H), 1.46 (s, 9H)

Step 2 tert-butyl 3-(4,4,5,5-tetramethyl-1,3,2-dioxaborolan-2-yl)-2,5-dihydro-1H-pyrrole-1-carboxylate To a solution of tert-butyl 3-(((trifluoromethyl)sulfonyl)oxy-2,5-dihydro-1H-pyrrole-1-carboxylate 1b (9 g, 16.2 mmol) in 100 mL dioxane was added 4,4,4',4',5,5,5',5'-octamethyl-2,2'-bis(1,3,2-dioxoborane) 4.11 g, 16.2 mmol), potassium acetate (4.72 g, 48.6 mmol) and Pd(dppf)$_2$ (660 mg, 0.8 mmol). The mixture was stirred at 90° C. for 12 h. Then 100 mL water was added into the mixture and extracted with EA (80 mL*3). The organic layer was combined and washed with saturated sodium chloride solution (100 mL), dried over anhydrous sodium sulfate. The mixture was filtered; the filtrate was concentrated under pressure. The residue was purified by silica column chromatography with eluent system C to obtain the crude title product 3-(4,4,5,5-tetramethyl-1,3,2-dioxaborolan-2-yl)-2,5-dihydro-1H-pyrrole-1-carboxylate 1c (4.5 g, yellow oil).

$^1$H NMR (400 MHz, CDCl$_3$) δ 6.50-6.40 (m, 1H), 4.25-4.15 (m, 4H), 1.46 (s, 9H), 1.26 (s, 12H)

Step 3 tert-butyl 3-(4-(4-amino-5-oxo-7,8-dihydropyrimido[5,4-f][1,4]oxazepin-6-(5H)-yl)phenyl)-2,5-dihydro-1H-pyrrole-1-carboxylate To a solution of 3-(4,4,5,5-tetramethyl-1,3,2-dioxaborolan-2-yl)-2,5-dihydro-1H-pyrrole-1-carboxylate 1c (1.15 g, 0.78 mmol) in 25 mL dioxane and water (V/V=5/1) was added 4-amino-6-(4-iodobenzene)-7,8-dihydropyrimido[5,4-f][1,4]oxazepin-5-(6H)-one (300 mg, 0.78 mmol, prepared by the common method "Patent WO2009016462"), potassium carbonate (216 mg, 1.57 mmol) and Pd(dppf)Cl$_2$ (64 mg, 0.08 mmol). The mixture was stirred at 90° C. for 12 h. Then 100 mL water was added into the mixture and extracted with EA (60 mL*3). The organic layer was combined and washed with saturated sodium chloride solution (100 mL), dried over anhydrous sodium sulfate. The mixture was filtered, and the filtrate was concentrated under pressure. The residue was purified by silica column chromatography with eluent system C to obtain the title product 3-(4-(4-amino-5-oxo-7,8-dihydropyrimido[5,4-f][1,4]oxazepin-6-(5H)-yl)phenyl)-2,5-dihydro-1H-pyrrole-1-carboxylate 1d (160 mg, white solid), yield: 48.19%.

$^1$H NMR (400 MHz, CDCl$_3$) δ 8.30 (s, 1H), 7.47 (d, 2H), 7.26 (d, 2H), 6.17 (d, 1H), 4.71 (t, 2H), 4.31-4.52 (m, 4H), 4.04 (t, 2H), 1.53 (s, 9H).

Step 4 tert-butyl-3-(4-(4-amino-5-oxo-7,8-dihydropyrimido[5,4-f][1,4]oxazepin-6-(5H)-yl)phenyl)pyrrolidine-1-carboxylate To a solution of 3-(4-(4-amino-5-oxo-7,8-dihydropyrimido[5,4-f][1,4]oxazepin-6-(5H)-yl)phenyl)-2,5-dihydro-1H-pyrrole-1-carboxylate 1d (160 mg, 0.37 mmol) in 5 mL methanol was added sodium acetate (320 mg) and Pd/C (100 mg). The mixture was vacuum pumping and filled with hydrogen for 3 times, and it was stirred at room temperature under hydrogen for 1 hour. The mixture was filtered, the filtrate was concentrated under pressure to obtain the crude title product 3-(4-(4-amino-5-oxo-7,8-dihydropyrimido[5,4-f][1,4]oxazepin-6-(5H)-yl)phenyl)pyrrolidine-1-carboxylate 1e (100 mg, white solid). The product was used in the next step directly without purification.

$^1$H NMR (400 MHz, CDCl$_3$) δ 8.29 (s, 1H), 8.18 (br. s, 1H), 7.34 (d, 2H), 7.24 (d, 2H), 5.68 (br. s., 1H), 4.70 (t, 2H), 4.01 (t, 2H), 3.08-3.70 (m, 1H), 3.65-3.52 (m, 1H), 3.50-3.25 (m, 3H), 2.35-2.20 (m, 1H), 2.05-1.95 (m, 1H), 1.49 (s, 9H)

Step 5

4-amino-6-(4-(pyrrolidin-3-yl)phenyl)-7,8-dihydropyrimido[5,4-f][1,4]oxazepin-5-(6H)-one To a solution of 3-(4-(4-amino-5-oxo-7,8-dihydropyrimido[5,4-f][1,4]oxazepin-6-(5H)-yl)phenyl)pyrrolidine-1-carboxylate 1d (100 mg, 0.23 mmol) in 3 mL DCM was added 1 mL hydrochloric 1,4-dioxane (V/V=1/1). The mixture was stirred for 1 hour. The mixture was concentrated under pressure to obtain the crude title product 4-amino-6-(4-(pyrrolidin-3-yl)phenyl-7,8-dihydropyrimido[5,4-f][1,4]oxazepin-5-(6H)-one 1f (50 mg, yellow oil). The product was used in the next step directly without purification.

Step 6

2-(3-(4-(4-amino-5-oxo-7,8-dihydropyrimido[5,4-f][1,4]oxazepin-6-(5H)yl)phenyl)pyrrole-1-yl)acetic acid To a solution of 4-amino-6-(4-(pyrrolidin-3-yl)phenyl)-7,8-dihydropyrimido[5,4-f][1,4]oxazepin-5-(6H)-one 1e (50 mg, 0.15 mmol) in 3 mL DCM was added triethylamine (78 mg, 0.77 mmol) and bromoacetic acid (32 mg, 0.23 mmol). The mixture was stirred for 2 hours. Then it was concentrated under pressure, the residue was purified by prep-HPLC to obtain the title product 2-(3-(4-(4-amino-5-oxo-7,8-dihydropyrimido[5,4-f][1,4]oxazepin-6-(5H)yl)phenyl)pyrrole-1-yl)acetic acid 1 (5 mg, white solid), yield: 8.52%.

¹H NMR (400 MHz, CD₃OD) δ 8.42 (s, 1H), 7.44-7.52 (m, 2H), 7.39 (d, 2H), 4.99 (br. s., 2H), 4.28-4.35 (m, 2H), 4.23 (br s., 2H), 3.32-4.14 (m, 5H), 2.43-2.61 (m, 1H), 2.07-2.38 (m, 1H)

Example 105

4-amino-6-(3,5-dimethyl-4-(1-oxo-2-(2,2,2-trifluoroethyl)-1,2-dihydroisoquinolin-7-yl)phenyl)-7,8-dihydropyrimido[5,4-f][1,4]oxazepin-5-(6H)-one

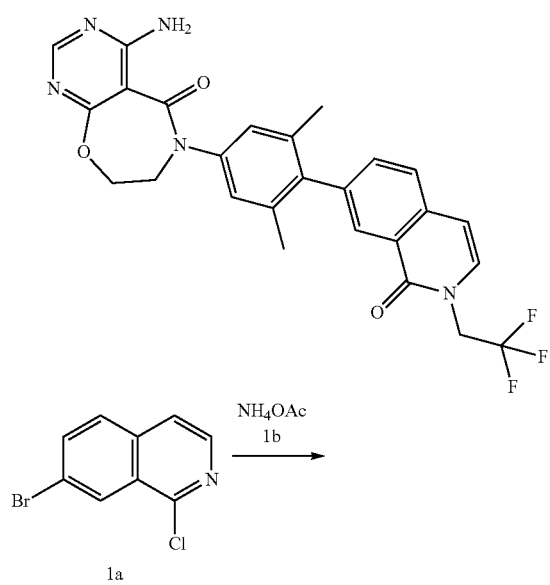

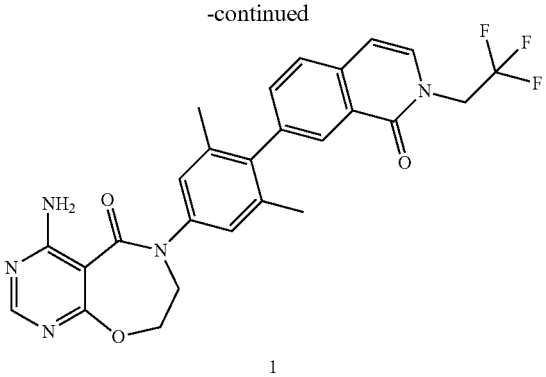

Step 1

7-bromoisoquinolin-1(2H)-one

To a solution of 7-bromo-1-chloroisoquinoline 1a (2.70 g, 11.10 mmol) in acetic acid (50 mL) was added ammonium acetate 1b (8.50 g, 111.10 mmol). Reaction mixture was stirred at 100° C. for 4 h. The reaction mixture was concentrated in vacuo, and to the residue was added water. The precipitate was collected by filtration and washed with water to give 7-bromoisoquinolin-1(2H)-one 1c (2.7 g, white solid). The product was used in the next step directly without purification.

MS m/z (ESI): 225.9 [M+1]

¹H NMR (400 MHz, CDCl₃) δ 8.55 (d, J=1.8 Hz, 1H), 7.75 (dd, J=2.1, 8.5 Hz, 1H), 7.43 (d, J=8.6 Hz, 1H), 7.14 (d, J=6.2 Hz, 1H), 6.52 (d, J=7.3 Hz, 1H)

Step 2

7-bromo-2-(2,2,2-trifluoroethyl)isoquinolin-1(2H)-one

To a solution of 7-bromoisoquinolin-1(2H)-one 1c (2.70 g, 12.05 mmol) in DMF (40 mL) was added Cs₂CO₃ (7.80 g, 24.10 mmol) and 2,2,2-trifluoroethyl trifluoromethanesulfonate 1d (3.35 g, 14.46 mmol). Reaction mixture was stirred for 12 h. The mixture was poured into 200 mL water; the precipitate was filtered and washed with water. The filter cake was dissolved in EA (200 mL), dried over Na₂SO₄, filtered and concentrated in vacuum. The residue was purified by silic gel column (eluent system C) to afford 7-bromo-2-(2,2,2-trifluoroethyl)isoquinolin-1(2H)-one 1e (2.5 g, white solid), yield: 68.1%.

¹H NMR (400 MHz, CDCl₃) δ 8.58 (d, J=1.8 Hz, 1H), 7.78 (dd, J=2.0, 8.4 Hz, 1H), 7.42 (d, J=8.4 Hz, 1H), 7.09 (d, J=7.3 Hz, 1H), 6.52 (d, J=7.3 Hz, 1H), 4.67 (q, J=8.6 Hz, 2H)

Step 3

7-(4,4,5,5-tetramethyl-1,3,2-dioxaborolan-2-yl)-2-(2,2,2-trifluoroethyl)isoquinolin-1(2H)-one To a solution of 7-bromo-2-(2,2,2-trifluoroethyl)isoquinolin-1(2H)-one 1e (2.50 g, 8.17 mmol) in dioxane (30 mL) was added Pin₂B₂ (3.10 g, 12.25 mmol), KOAc (2.40 g, 24.50 mmol) and Pd(dppf)Cl₂ (333 mg, 0.41 mmol). Reaction mixture was stirred at 100° C. for 24 h. The mixture was cooled to RT and concentrated. To the residue was added water (40 mL), extracted with DCM (40 mL*3). The organic layers were combined and dried over $Na_2SO_4$, filtered and concentrated. The residue was purified by silic gel column (eluent system C) to give 7-(4,4,5,5-tetramethyl-1,3,2-dioxaborolan-2-yl)-2-(2,2,2-trifluoroethyl)isoquinolin-1(2H)-one 1f (3.3 g, yellow oil), yield: 100%.

$^1$H NMR (400 MHz, $CDCl_3$) δ 8.92 (s, 1H), 8.05 (d, J=7.7 Hz, 1H), 7.50 (d, J=7.9 Hz, 1H), 7.09 (d, J=7.5 Hz, 1H), 6.53 (d, J=7.5 Hz, 1H), 4.68 (q, J=8.7 Hz, 2H), 1.37 (s, 12H).

Step 4

4-amino-6-(3,5-dimethyl-4-(1-(oxo-2-(2,2,2-trifluoroethyl)-1,2-dihydroisoquinolin-7-yl)phenyl)-7,8-dihydropyrimido[5,4-f][1,4]oxazepin-5-(6H)-one To a mixture of 7-(4,4,5,5-tetramethyl-1,3,2-dioxaborolan-2-yl)-2-(2,2,2-trifluoroethyl)isoquinolin-1(2H)-one 1f (3.12 g, 9.09 mmol), 4-amino-6-(4-bromo-3,5-dimethylphenyl)-7,8-dihydropyrimido[5,4-f][1,4]oxazepin-5-(6H)-one 1g (3.0 g, 8.62 mmol), $K_2CO_3$ (3.42 g, 24.78 mmol) and $Pd(dppf)Cl_2$ (337 mg, 0.41 mmol) in dioxane (30 mL) was added $H_2O$ (10 mL). Reaction mixture was stirred at 100° C. for 12 h. The mixture was cooled to RT concentrated, filtered and the filtrate was concentrated. The residue was purified by silic gel column (eluent system C) to give the crude. The crude was recrystallized in DCM to afford 4-amino-6-(3,5-dimethyl-4-(1-oxo-2-(2,2,2-trifluoroethyl)-1,2-dihydroisoquinolin-7-yl)phenyl)-7,8-dihydropyrimido[5,4-f][1,4]oxazepin-5-(6H)-one 1 (1.5 g, white solid), yield: 44.9%.

MS m/z (ESI): 510.2 [M+1]

$^1$H NMR (400 MHz, DMSO-$d_6$) δ 8.16 (s, 1H), 7.95 (s, 1H), 7.79 (d, J=8.2 Hz, 1H), 7.66-7.54 (m, 3H), 7.49 (d, J=7.5 Hz, 1H), 7.18 (s, 2H), 6.78 (d, J=7.5 Hz, 1H), 4.92 (q, J=9.4 Hz, 2H), 4.61 (t, J=4.5 Hz, 2H), 4.00 (t, J=4.5 Hz, 2H), 1.97 (s, 6H)

Example 106

(E)-4-amino-6-(6-((2,2,2-trifluoroethoxy)imino)-5,6,7,8-tetrahydronaphthalen-2-yl)-7,8-dihydropyrimido[5,4-f][1,4]oxazepin-5-(6H)-one

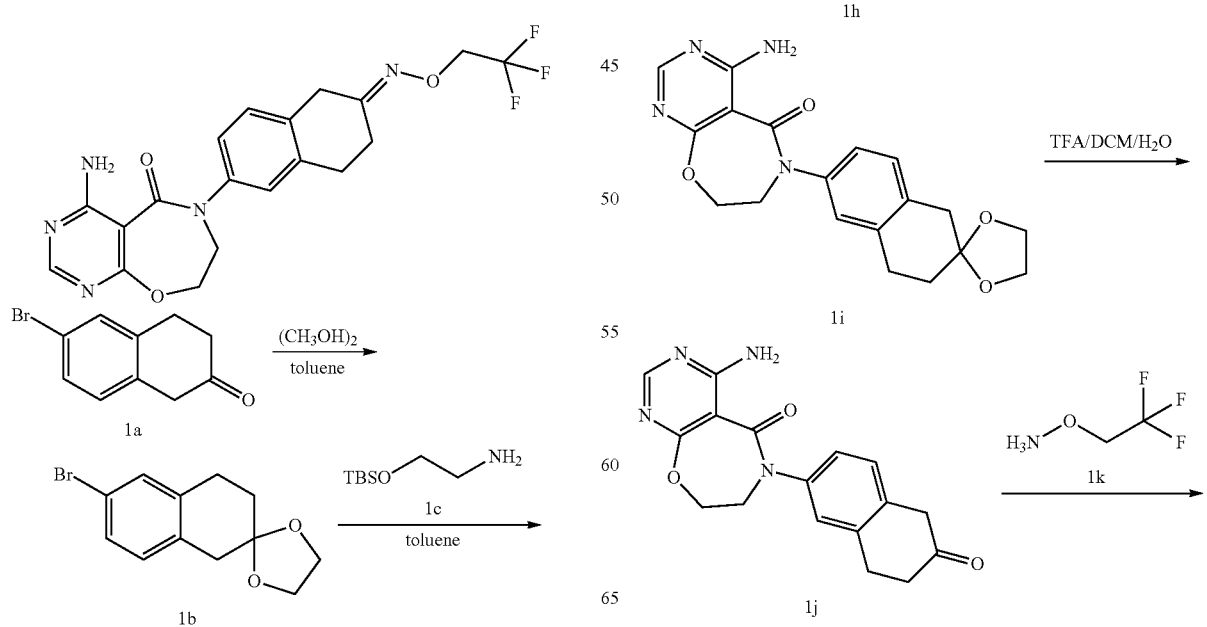

-continued

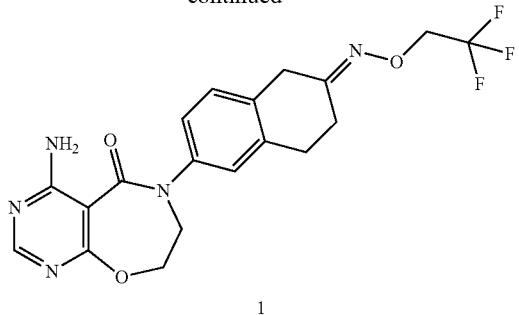

1

Step 1

6'-bromo-3',4'-dihydro-1'H-spiro[[1,3]dioxolane-2,2'-naphthalene]

To a solution of 6-bromo-3,4-dihydronaphthalen-2(1H)-one 1a (10 g, 44.40 mmol) in dry toluene (100 mL) was added $(CH_2OH)_2$ (2.7 mL, 48.30 mmol) and TsOH (3 mg). The reaction was heated at 110° C. under $N_2$ for 6 h and a Dean-Stark was used to collect the water produced. After cooled, the mixture was washed with 10% aqueous NaOH (4 mL) and $H_2O$ (20 mL). The organic layer was dried over $Na_2SO_4$, filtered and concentrated in vacuo. The mixture was purified by silica gel column (eluent system C) to afford 6'-bromo-3',4'-dihydro-1'H-spiro[[1,3]-dioxolane-2,2'-naphthalene]1b (10 g, yellow oil), yield: 84.03%

MS m/z (ESI): 270.9 [M+1]

$^1$H NMR (400 MHz, $CDCl_3$) δ 7.27 (s, 1H), 7.23 (d, 1H), 6.91 (d, 1H), 4.01-4.04 (m, 4H), 2.96 (t, 2H), 2.92 (s, 2H), 1.93 (t, 2H)

Step 2

N-(2-((tert-butyldimethylsilyl)oxy)ethyl)-3',4'-dihydro-1'H-spiro[[1,3]dioxolane-2,2'-naphthalen]-6'-amine To a mixture of 6'-bromo-3',4'-dihydro-1'H-spiro[[1,3]dioxolane-2,2'-naphthalen]1b (10 g, 37.17 mmol), 2-((tert-butyldimethylsilyl)oxy)ethanamine 1c (7.8 g, 44.60 mmol) and $Cs_2CO_3$ (36 g, 110.40 mmol) in dry toluene (100 mL) was added $Pd_2(dba)_3$ (700 mg) and X-PhOS (700 mg). The reaction was heated at 110° C. under $N_2$ for 18 h. The resulting mixture was cooled to RT, dilute with DCM and washed with water. The organic layer was separated, dried over $Na_2SO_4$, filtered and concentrated in vacuum. The residue was purified by silica gel column (eluent system C) to afford N-(2-((tert-butyldimethylsilyl)oxy)ethyl)-3',4'-dihydro-1'H-spiro[[1,3]dioxolane-2,2'-naphthalen]-6'-amine 1d (1.53 g, yellow oil), yield: 11.3%.

MS m/z (ESI): 364.1 [M+1]

$^1$H NMR (400 MHz, $CDCl_3$) δ 6.7 (d, 1H), 6.3 (d, 1H), 6.26 (s, 1H), 3.87 (m, 4H), 2.77 (t, 2H), 2.72 (s, 2H), 1.77 (t, 2H), 0.79 (s, 9H), 0.07 (s 6H)

Step 3

N-(2-((tert-butyldimethylsilyl)oxy)ethyl)-4,6-dichloro-N-(3',4'-dihydro-1'H-spiro[[1,3]dioxolane-2,2'-naphthalen]-6'-yl)pyrimidine-5-carboxamide To a solution of N-(2-((tert-butyldimethylsilyl)oxy)ethyl)-3',4'-dihydro-1'H-spiro[[1,3]dioxolane-2,2'-naphthalen]-6'-amine 1d (1.53 g, 4.20 mmol) and 4,6-dichloropyrimidine-5-carbonyl chloride 1e (1.15 g, 5.40 mmol) in 15 mL of DCM was added TEA (1.6 mL). The reaction was stirred for 18 h. The resulting mixture was dilute with DCM and washed with water. The organic layer was dried over $Na_2SO_4$, filtered and concentrated in vacou. The residue was purified by silica gel column (eluent system C) to afford N-(2-((tert-butyldimethylsilyl)oxy)ethyl)-4,6-dichloro-N-(3',4'-dihdyro-1'H-spiro[[1,3]dioxolane-2,2'-naphthalen]-6'-yl)pyrimidine-5-carboxamide 1f (2.1 g, yellow oil), yield: 92.9%

MS m/z (ESI): 538.0 [M+1]

Step 4

4,6-dichloro-N-(3',4'-dihydro-1'H-spiro[[1,3]dioxolane-2,2'-naphthalen]-6'-yl)-N-(2-hydroxyethyl)pyrimidine-5-carboxamide A mixture of N-(2-((tert-butyldimethylsilyl)oxy)ethyl)-4,6-dichloro-N-(3',4'-dihydro-1'H-spiro[[1,3]dioxolane-2,2'-naphthalen]-6'-yl)pyrimidine-5-carboxamide 1f (1.7 g, 3.17 mmol) in HCl/EtOH (0.6 mL/20 mL) was stirred for 30 min. The mixture was adjusted pH to 8 by $NaHCO_3$ (aqueous sat. solution). Then the mixture was dilute with DCM and then washed with water. The organic layer was dried over $Na_2SO_4$, filtered and concentrated in vacuum. The residue was purified by silica gel column (eluent system C) to afford 4,6-dichloro-N-(3',4'-dihydro-1'H-spiro[[1,3]dioxolane-2,2'-naphthalen]-6'-yl)-N-(2-hydroxyethyl)pyrimidine-5-carboxamide 1g (450 mg, yellow oil), yield: 33%.

MS m/z (ESI): 424.0 [M+1]

Step 5

4-chloro-6-(3',4'-dihydro-1'H-spiro[[1,3]dioxolane-2,2'-naphthalen]-6'-yl)-7,8-dihydropyrimido[5,4-f][1,4]oxazepin-5-(6H)-one A mixture of 4,6-dichloro-N-(3',4'-dihydro-1'H-spiro[[1,3]dioxolane-2,2'-naphthalen]-6'-yl)-N-(2-hydroxyethyl)pyrimidine-5-carboxamide 1g (450 mg, 1.06 mmol) and $K_2CO_3$ (439 mg, 3.18 mmol) in MeCN (10 mL) was stirred at 80° C. for 16 h. The reaction mixture cooled to RT, dilute with DCM and washed with water. The organic layer was dried over $Na_2SO_4$, filtered and concentrated in vacuum. The residue was purified by silica gel column (eluent system C) to afford 4-chloro-6-(3',4'-dihydro-1'H-spiro[[1,3]dioxolane-2,2'-naphthalen]-6'-yl)-7,8-dihydropyrimido[5,4-f][1,4]oxazepin-5-(6H)-one 1h (410 mg, yellow solid), yield: 100%

MS m/z (ESI): 388.0 [M+1]

$^1$H NMR (400 MHz, DMSO-$d_6$) δ 8.82 (s, 1H), 7.22-7.10 (m, 3H), 4.71 (t, 2H), 4.11 (t, 2H), 3.95 (s, 4H), 2.91 (br. s., 4H), 1.87 (t, H)

Step 6

4-amino-6-(3',4'-dihydro-1'H-spiro[[1,3]dioxolane-2,2'-naphthalen]-6'-yl)-7,8-dihydropyrimido[5,4-f][1,4]oxazepin-5-(6H)-one A mixture of 4-chloro-6-(3',4'-dihydro-1'H-spiro[[1,3]dioxolane-2,2'-naphthalen]-6'-yl)-7,8-dihydropyrimido[5,4-f][1,4]oxazepin-5-(6H)-one 1h (410 mg, 1.11 mmol) in $NH_3$/dioxane (0.5 M, 5 mL) was stirred for 16 h. The resulting mixture was evaporated to afford 4-amino-6-(3',4'-dihydro- 1'H-spiro[[1,3]dioxolane-2,2'-naphthalen]-6'-yl)-7,8-dihydropyrimido[5,4-f][1,4]oxazepin-5-(6H)-one 1i (370 mg, yellow solid), yield: 100%.

MS m/z (ESI): 369 [M+1]

Step 7

4-amino-6-(6-oxo-5,6,7,8-tetrahydronaphthalen-2-yl)-7,8-dihydropyrimido[5,4-f][1,4]oxazepin-5-(6H)-one To mixture of 4-amino-6-(3',4'-dihydro-1'H-spiro[[1,3]dioxolane-2,2'-naphthalen]-6'-yl)-7,8-dihydropyrimido[5,4-f][1,4]oxazepin-5-(6H)-one 1i (150 mg, 0.41 mmol) in TFA/DCM (1 mL/4 mL) was added H$_2$O (0.12 mL). The reaction was stirred for 16 h. The resulting mixture was dilute with DCM and washed with water. The organic layer was dried over Na$_2$SO$_4$, filtered and concentrated in vacuum to afford 4-amino-6-(6-oxo-5,6,7,8-tetrahydronaphthalen-2-yl)-7,8-dihydropyrimido[5,4-f][1,4]oxazepin-5-(6H)-one 1j (120 mg, yellow oil), yield: 90.9%.

Step 8

(E)-4-amino-6-(6-((2,2,2-trifluoroethoxy)imino)-5,6,7,8-tetrahydronaphthalen-2-yl)-7,8-dihydropyrimido[5,4-f][1,4]oxazepin-5-(6H)-one A mixture of 4-amino-6-(6-oxo-5,6,7,8-tetrahydronaphthalen-2-yl)-7,8-dihydropyrimido[5,4-f][1,4]oxazepin-5-(6H)-one 1j (90 mg, 0.278 mmol), O-(2,2,2-trifluoroethyl) hydoxylamine 1k (42 mg, 0.305 mmol), NaOAc (68.3 mg, 0.833 mmol) in EtOH/H$_2$O (4 mL/1 mL) was stirred at 80° C. for 3 h. The reaction mixture was cooled to RT and filtered. The filtrate was concentrated in vacuum. The residue was purified by pre.HPLC to afford (E)-4-amino-6-(6-((2,2,2-trifluoroethoxy)imino)-5,6,7,8-tetrahydronaphthalen-2-yl)-7,8-dihydropyrimido[5,4-f][1,4]oxazepin-5-(6H)-one 1 (7.15 mg, yellow solid), yield: 7.15%

MS m/z (ESI): 422.1 [M+1]

$^1$H NMR (400 MHz, DMSO-d$_6$) δ 8.30 (s, 1H), 7.34-7.17 (m, 3H), 4.74-4.58 (m, 4H), 4.03 (br. s., 2H), 3.79 (s, 1H), 3.55 (s, 1H), 2.86 (d, J=6.0 Hz, 2H), 2.61 (m, 1H), 2.54 (br. s., 1H)

Example 107

(Z)-4-amino-6-(5-((2,2,2-trifluoroethoxy)imino)-5,6,7,8-tetrahydronaphthalen-2-yl)-7,8-dihydropyrimido[5,4-f][1,4]oxazepin-5-(6H)-one

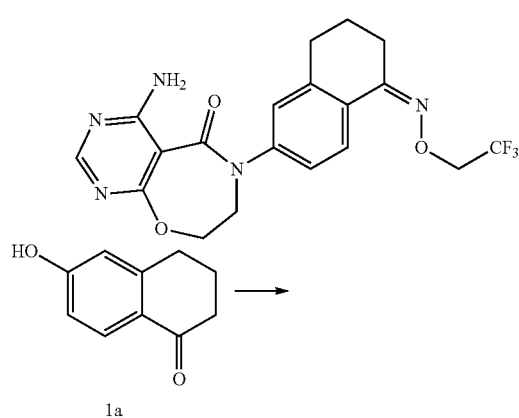

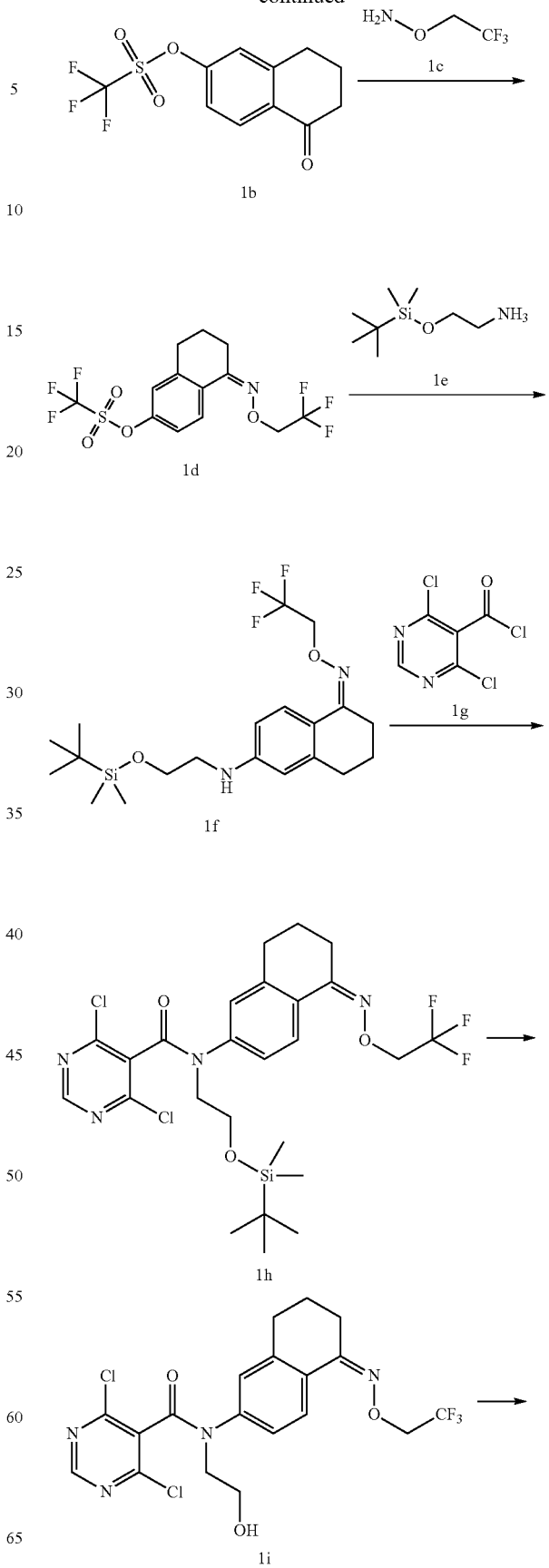

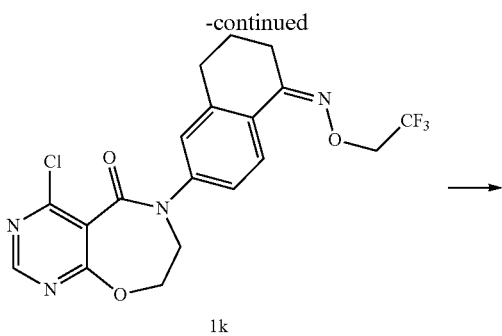

Step 1

5-oxo-5,6,7,8-tetrahydronaphthalen-2-yl trifluoromethanesulfonate

To a solution of 6-hydroxy-3,4-dihydronaphthalen-1(2H)-one 1a (5 g, 30.8 mmol) and TEA (3.1 g, 30.8 mmol) in DCM (50 mL) was added Tf$_2$O (8.7 g, 30.8 mmol) at 0° C. The mixture was then stirred at RT for 18 h. The reaction mixture was washed with water and sat. NaHCO$_3$. The organic layer was dried over Na$_2$SO$_4$ filtered and concentrated. The residue was purified by silica gel column (eluent system B) to afford 5-oxo-5,6,7,8-tetrahydronaphthalen-2-yl trifluoromethanesulfonate 1b (2.0 g, colorless liquid), yield: 24.0%

$^1$H NMR (400 MHz, CDCl$_3$) δ 8.13 (d, 2H), 7.20-7.15 (m, 2H), 3.05-2.95 (m, 2H), 2.70-2.62 (m, 2H), 2.20-2.10 (m, 2H).

Step 2

(Z)-5-((2,2,2-trifluoroethoxy)imino)-5,6,7,8-tetrahydronaphthalen-2-yl trifluoromethanesulfonate A mixture of 5-oxo-5,6,7,8-tetrahydronaphthalen-2-yl trifluoromethanesulfonate 1b (2.0 g, 6.8 mmol), O-(2,2,2-trifluoroethyl)hydroxylamine 1c (1.54 g, 10.2 mmol) and NaOAc (1.67 g, 20.4 mmol) in EtOH/H$_2$O (25 mL, V:V=4:1) was stirred at reflux for 6 h. The reaction mixture was cooled to RT, dilute with EA (50 mL) and washed with water. The organic layer was dried over Na$_2$SO$_4$, filtered and concentrated in vacuum. The residue was purified by silica gel column (eluent system B) to afford (Z)-5-((2,2,2-trifluoroethoxy)imino)-5,6,7,8-tetrahydronaphthalen-2-yl trifluoromethanesulfonate 1d (1.6 g, light yellow solid), yield: 61.0%.

$^1$H NMR (400 MHz, CDCl$_3$) δ 8.02 (d, 2H), 7.10-7.05 (m, 2H), 4.58-4.50 (m, 2H), 2.70-2.65 (m, 4H), 1.90-1.82 (m, 2H)

Step 3

(Z)-6-((2-((tert-butyldimethylsilyl)oxy)ethyl)amino)-3,4-dihydronaphthalen-1(2H)-one O-(2,2,2-trifluoroethyl)oxime A mixture of (Z)-5-((2,2,2-trifluoroethoxy)imino)-5,6,7,8-tetrahydronaphthalen-2-yl trifluoromethanesulfonate 1d (1.6 g, 4.09 mmol), 2-((tert-butyldimethylsilyl)oxy)ethanamine 1e (1.07 g, 6.4 mmol), Cs$_2$CO$_3$ (2.66 g, 8.18 mmol), Pd$_2$(dba)$_3$ (100 mg) and x-phos (100 mg) in toluene (15 mL) was stirred at 110° C. under N$_2$ for 18 h. The reaction mixture was cooled to RT and concentrated in vacuum. The residue was purified by silica gel column (eluent system B) to afford (Z)-6-((2-((tert-butyldimethylsilyl)oxy)ethyl)amino)-3,4-dihydronaphthalen-1(2H)-one O-(2,2,2-trifluoroethyl)oxime 1f (440 mg, light yellow liquid), yield: 26.0%

$^1$H NMR (400 MHz, CDCl$_3$) δ 6.60 (q, 1H), 6.53 (d, 1H), 6.38 (q, 1H), 4.45-4.35 (d, 2H), 3.70 (t, 2H), 3.15-3.11 (m, 2H), 2.70-2.55 (m, 4H), 1.80-1.70 (m, 2H), 0.86 (s, 6H), 0.82 (s, 9H)

Step 4

(Z)—N-(2-((tert-butyldimethylsilyl)oxy)ethyl)-4,6-dichloro-N-(5-((2,2,2-trifluoroethoxy)imino)-5,6,7,8-tetrahydronaphthalen-2-yl)pyrimidine-5-carboxamide To a solution of (Z)-6-((2-((tert-butyldimethylsilyl)oxy)ethyl)amino)-3,4-dihydronaphthalen-1(2H)-one O-(2,2,2-trifluoroethyl)oxime 1f (440 mg, 1.06 mmol) and TEA (440 umL, 1.38 mmol) in DCM (6 mL) was added 4,6-dichloropyrimidine-5-carbonyl chloride 1g (336 mg, 1.59 mmol) at 0° C. The mixture was stirred at RT for 1 h. The reaction mixture was concentrated in vacuum. The residue was purified by silica gel column (eluent system B) to afford (Z)—N-(2-((tert-butyldimethylsilyl)oxy)ethyl)-4,6-dichloro-N-(5-((2,2,2-trifluoroethoxy)imino)-5,6,7,8-tetrahydronaphthalen-2-yl)pyrimidine-5-carboxamide 1h (320 mg, light yellow solid), yield: 51.0%

$^1$H NMR (400 MHz, CDCl$_3$) δ 8.59 (s, 1H), 8.20 (s, 1H), 7.25-7.17 (m, 2H), 4.51 (q, 2H), 4.05-3.90 (m, 4H), 2.72-2.62 (m, 4H), 1.80-1.70 (m, 2H), 0.87 (s, 9H), 0.06 (s, 6H)

Step 5

(Z)-4,6-dichloro-N-(2-hydroxyethyl)-N-(5-((2,2,2-trifluoroethoxy)imino)-5,6,7,8-tetrahydronaphthalen-2-yl)pyrimidine-5-carboxamide To a solution of (Z)—N-(2-((tert-butyldimethylsilyl)oxy)ethyl)-4,6-dichloro-N-(5-(2,2,2-trifluoroethoxy)imino)-5,6,7,8-tetrahydronaphthalen-2-yl)pyrimidine-5-carboxamide 1h (270 mg, 0.46 mmol) in EtOH (5 mL) was added HCl (0.15 mL). The mixture was stirred at Rt for 1.5 h. The reaction mixture was dilute with EA (50 mL) and washed with sat. NaHCO$_3$. The organic layer was dried over Na₂SO₄, filtered and concentrated in vacuum to afford (Z)-4,6-dichloro-N-(2-hydroxyethyl)-N-(5-((2,2,2-trifluoroethoxy)imino)-5,6,7,8-tetrahydronaphthalen-2-yl)pyrimidine-5-carboxamide 1i (150 mg, light yellow solid), yield: 69.0%

¹H NMR (400 MHz, CDCl₃) δ 8.61 (s, 1H), 7.81-7.92 (m, 1H), 7.21 (s, 2H), 4.51 (q, 2H), 4.06-4.13 (m, 2H), 3.88-3.97 (m, 2H), 2.57-2.83 (m, 4H), 2.11-2.23 (m, 1H), 1.72-1.89 (m, 2H)

Step 6

(Z)-4-chloro-6-(5-((2,2,2-trifluoroethyl)imino)-5,6,7,8-tetrahydronaphthalen-2-yl)-7,8-dihydropyrimido[5,4-f][1,4]oxazepin-5-(6H)-one A solution of (Z)-4,6-dichloro-N-(2-hydroxyethyl)-N-(5-((2,2,2-trifluoroethoxy)imino)-5,6,7,8-tetrahydronaphthalen-2-yl)pyrimidine-5-carboxamide 1j (100 mg, 0.20 mmol) and TEA (0.084 mL, 0.60 mmol) in MECN (4 mL) was stirred at 80° C. for 18 h. The reaction mixture was cooled to RT, dilute with EA (30 mL) and washed with water. The organic layer was dried over Na₂SO₄, filtered and concentrated in vacuum to afford (Z)-4-chloro-6-(5-((2,2,2-trifluoroethoxy)imino)-5,6,7,8-tetrahydronaphthalen-2-yl)-7,8-dihydropyrimido[5,4-f][1,4]oxazepin-5-(6H)-one 1k (80 mg, light yellow solid), yield: 91.0%

MS m/z (ESI): 441.1 [M+1]

Step 7

(Z)-4-amino-6-(5-((2,2,2-trifluoroethoxy)imino)-5,6,7,8-tetrahydronaphthalen-2-yl)-7,8-dihydropyrimido[5,4-f][1,4]oxazepin-5-(6H)-one A mixture of (Z)-4-chloro-6-(5-((2,2,2-trifluoroethoxy)imino)-5,6,7,8-tetrahydronaphthalen-2-yl)-7,8-dihydropyrimido[5,4-f][1,4]oxazepin-5-(6H)-one 1k (80 mg, 0.18 mmol) and MN₃/1,4-dioxane (0.5 M, 5 mL) was stirred at RT for 18 h. The reaction mixture was concentrated in vacuum. The residue was purified by prep. TLC (eluent system C) to afford (Z)-4-amino-6-(5-((2,2,2-trifluoroethoxy)imino)-5,6,7,8-tetrahydropyrimido[5,4-f][1,4]oxazepin-5-(6H)-one 1 (58.94 mg, white solid), yield: 78.0%.

¹H NMR (400 MHz, MeOD) δ 8.19 (s, 1H), 8.03 (d, 1H), 7.24 (d, 2H), 4.74 (q, 2H), 4.65 (q, 2H), 4.07-4.12 (m, 2H), 2.83 (t, 4H), 1.90 (q, 2H)

Example 108

4-amino-6-(6-(2,2,2-trifluoroethoxy)-5,6,7,8-tetrahydonaphthalen-2-yl)-7,8-dihydropyrimido[5,4-f][1,4]oxazepin-5-(6H)-one

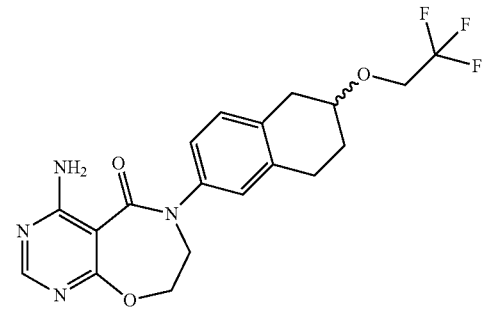

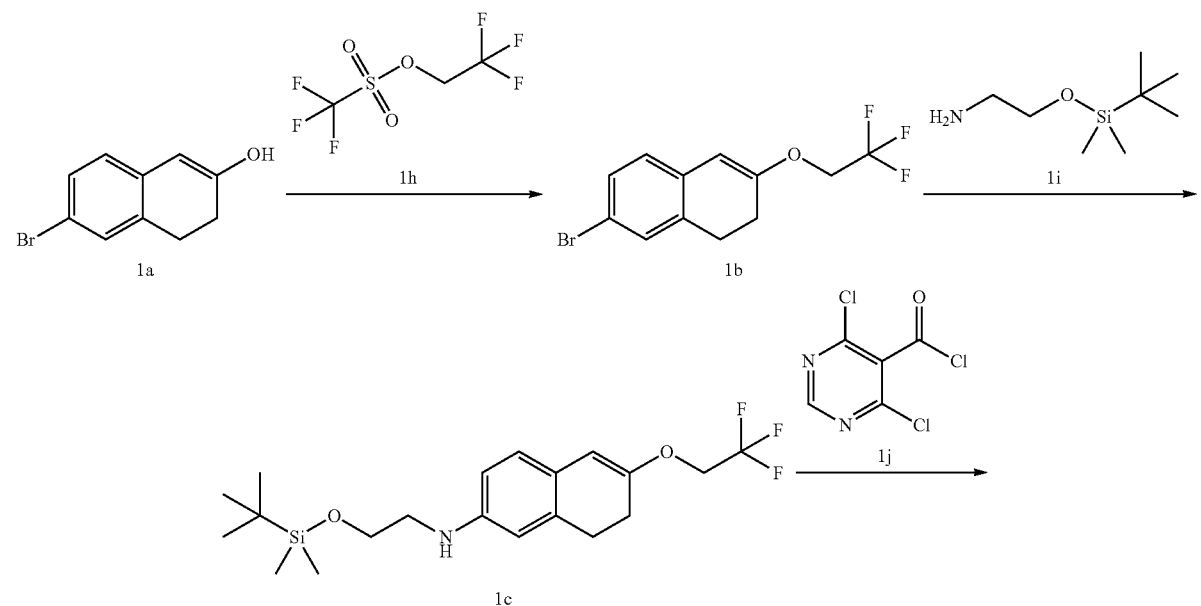

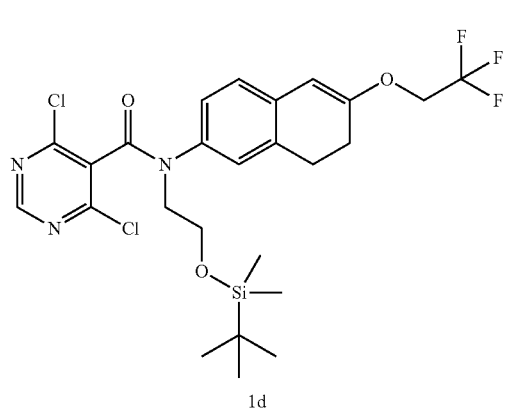

1d

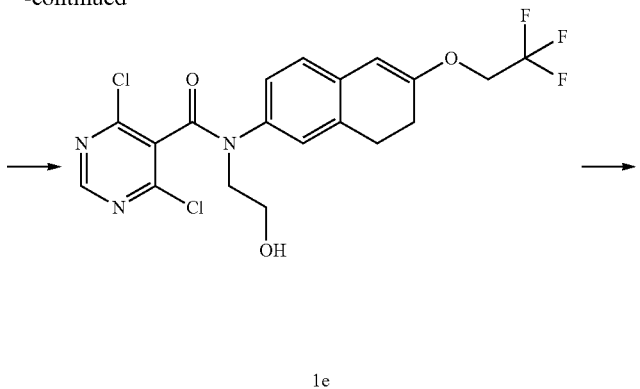

1e

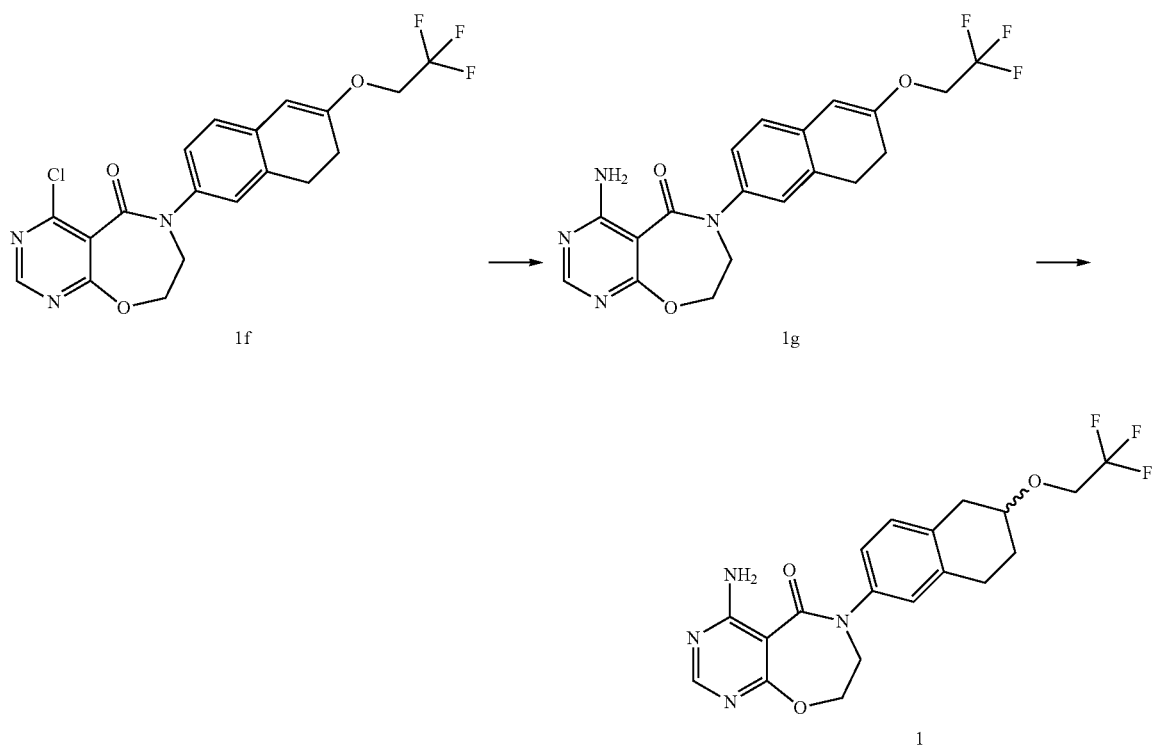

Step 1

7-bromo-3-(2,2,2-trifluoroethoxy)-1,2-dihydronaphthalene

To a solution of 6-bromo-3,4-dihydronaphthalen-2-ol 1a (2.0 g, 8.9 mmol) in DMF (30 mL) was added 2,2,2-trifluoroethyl trifluoromethanesulfonate 1h (792 mg, 19.8 mmol) and CsCO$_3$ (5.80 g, 17.8 mmol). The mixture was stirred at room temperature for 12 h. To the reaction mixture was added water (90 mL) and then extracted with EA (40 mL*3). The organic layers were combined and washed with water (20 mL*2) and brine (20 mL*2), dried over Na$_2$SO$_4$, filtered and concentrated to give the crude product 7-bromo-3-(2,2,2-trifluoroethoxy)-1,2-dihydronaphthalene 1b (2.7 g, brown solid). The product was used in the next step directly without purification.

$^1$H NMR (400 MHz, CDCl$_3$) δ 7.23-7.19 (m, 2H), 6.79-6.77 (dd, 2H), 5.45 (s, 1H), 4.22-4.15 (m, 2H), 2.89-2.84 (m, 2H), 2.47-2.41 (m, 2H)

Step 2

N-(2-((tert-butyldimethylsilyl)oxy)ethyl-6-(2,2,2-trifluoroethoxy)-7,8-dihydronaphthalen-2-amine To a mixture of 7-bromo-3-(2,2,2-trifluoroethoxy)-1,2-dihydronaphthalene 1b (2.7 g, 8.9 mmol) in toluene (30 mL) was added 2-((tert-butyldimethylsilyl)oxy)ethanamine 1i (1.87 g, 10.7 mmol), Cs$_2$CO$_3$ (5.80 g, 17.8 mmol), x-Phos (212 mg, 0.45 mmol) and Pd$_2$(dba)$_3$ (412 mg, 0.45 mmol). The mixture was stirred at 90° C. under N$_2$ for 12 h. The reaction mixture was cooled to RT, quenched with water (30 mL) and extracted with EA (20 mL*3). The organic layers were combined and washed with water (20 mL*2) and brine (20 mL*2), dried over Na$_2$SO$_4$, filtered and concentrated.

The residue was purified by silica gel chromatography (eluent system C) to give N-(2-((tert-butyldimethylsilyl)oxy)ethyl)-6-(2,2,2-trifluoroethoxy)-7,8-dihydronaphthalen-2-amine 1c (800 mg, yellow oil), yield: 22.4%

Step 3

N-(2-((tert-butyldimethylsilyl)oxy)ethyl)-4,6-dichloro-N-(6-(2,2,2-trifluoroethoxy)-7,8-dihydronaphthalen-2-yl)pyrimidine-5-carboxamide To a solution of N-(2-((tert-butyldimethylsilyl)oxy)ethyl)-6-(2,2,2-trifluoroethoxy)-7,8-dihydronaphthalen-2-amine 1c (800 mg, 1.99 mmol) in DCM (15 mL) was added Et$_3$N (0.83 mL, 6.0 mmol) and 4,6-dichloropyrimidine-5-carbonyl chloride 1j (506 mg, 2.39 mmol). The mixture was stirred for 12 h. The reaction was quenched with water (30 mL) and extracted with DCM (20 mL*3). The organic layers were combined and washed with water (20 mL*2) and brine (20 mL*2), dried over Na$_2$SO$_4$, filtered and concentrated to give the crude product N-(2-((tert-butyldimethylsilyl)oxy)ethyl)-4,6-dichloro-N-(6-(2,2,2-trifluoroethoxy)-7,8-dihydronaphthalen-2-yl)pyrimidine-5-carboxamide 1d (570 mg, yellow solid). The product was used in the next step directly without purification.

$^1$H NMR (400 MHz, CDCl$_3$) δ 8.51 (s, 6H), 7.07-7.03 (m, 2H), 6.70 (d, 1H), 5.36 (s, 6H), 4.16-4.09 (q, 2H), 3.92 (t, 2H), 3.92 (t, 2H), 2.74 (t, 2H), 2.35 (t, 2H), 0.81 (s, 9H), 0.00 (s, 6H).

Step 4

4,6-dichloro-N-(2-hydroxyethyl)-N-(6-(2,2,2-trifluoroethoxy)-7,8-dihydronaphthalen-2-yl)pryimidine-5-carboxamide To a solution of N-(2-((tert-butyldimethylsilyl)oxy)ethyl)-4,6-dichloro-N-(6-(2,2,2-trifluoroethoxy)-7,8-dihydronaphthalen-2-yl)pyrimidine-5-carboxamide 1d (570 mg, 0.99 mmol) in EtOH (10 mL) was added conc. HCl (0.3 mL). The mixture was stirred for 1 h. To the reaction was added water (10 mL) and extracted with EA (10 mL*2). The organic layers were combined and washed with water (10 mL*2), sat. NaHCO$_3$ (10 mL*2) and brine (10 mL*2), dried over Na$_2$SO$_4$, filtered and concentrated to give the crude product 4,6-dichloro-N-(2-hydroxyethyl)-N-(6-(2,2,2-trifluoroethoxy)-7,8-dihydronaphthalen-2-yl)pyrimidine-5-carboxamide 1e (460 mg, yellow solid). The product was used in the next step directly without purification.

Step 5

4-chloro-6-(6-(2,2,2-trifluoroethoxy)-7,8-dihydronaphthalen-2-yl)-7,8-dihydropyrimido[5,4-f][1,4]oxazepin-5(6H)-one To a solution of 4,6-dichloro-N-(2-hydroxyethyl)-N-(6-(2,2,2-trifluoroethoxy)-7,8-dihydronaphthalen-2-yl)pyrimidine-5-carboxamide 1e (460 mg, 1.00 mmol) in MeCN (10 mL) was added Et$_3$N (0.42 mL, 3.02 mmol). The mixture was stirred at 80° C. for 12 h. The reaction mixture was cooled to RT, diluted with water (20 mL) and extracted with EA (20 mL*3). The organic layers were combined and washed with brine (20 mL*2), dried over Na$_2$SO$_4$, filtered and concentrated to give 4-chloro-6-(6-(2,2,2-trifluoroethoxy)-7,8-dihydronaphthalen-2-yl)-7,8-dihydropyrimido[5,4-f][1,4]oxazepin-5-(6H)-one 1f (350 mg, yellow solid). The product was used in the next step directly without purification.

Step 6

4-amino-6-(6-(2,2,2-trifluoroethoxy)-7,8-dihydronaphthalen-2-yl)-7,8-dihydropyrimido[5,4-f][1,4]oxazepin-5(6H)-one A mixture of 4-chloro-6-(6-(2,2,2-trifluoroethoxy)-7,8-dihydronaphthalen-2-yl)-7,8-dihydropyrimido[5,4-f][1,4]oxazepin-5-(6H)-one 1f (350 mg, 0.82 mmol) in NH$_3$/dioxane (0.5 M, 10 mL) was stirred for 12 h. The mixture was concentrated to give the crude product 4-amino-6-(6-(2,2,2-trifluoroethoxy)-7,8-dihydronaphthalen-2-yl)-7,8-dihydropyrimido[5,4-f][1,4]oxazepin-5-(6H)-one 1g (300 mg, yellow solid). The product was used in the next step directly without purification.

Step 7

4-amino-6-(6-(2,2,2-trifluoroethoxy)-5,6,7,8-tetrahydronaphthalen-2-yl)-7,8-dihydropyrimido[5,4-f][1,4]oxazepin-5-(6H)-one To a solution of 4-amino-6-(6-(2,2,2-trifluoroethoxy)-7,8-dihydronaphthalen-2-yl)-7,8-dihydropyrimido[5,4-f][1,4]oxazepin-5-(6H)-one 1g (300 mg, 0.74 mmol) in MeOH (10 ml) was added wet Pd/C (10%, 60 mg). The mixture was stirred at 70° C. under H$_2$ (50 psi) for 12 h. The reaction mixture was cooled to RT and filtered. The filtrate was concentrated. The residue was purified by prep. HPLC and SFC separation to give two isomers: the forward peak (26.71 mg, white solid) and the backward peak (52.85 mg, white solid), yield: 26.3%.

MS m/z (ESI): 409.1 [M+1]

$^1$H NMR (400 MHz, Methanol-d$_4$) δ 8.16 (s, 1H), 7.18-7.07 (m, 3H), 4.71-4.69 (m, 2H), 4.07-3.96 (m, 5H), 3.31-2.77 (m, 4H), 2.10-1.88 (m, 2H)

$^1$H NMR (400 MHz, Methanol-d$_4$) δ 8.16 (s, 1H), 7.19-7.07 (m, 3H), 4.71-4.69 (m, 2H), 4.07-3.96 (m, 5H), 3.31-2.77 (m, 4H), 2.08-1.89 (m, 2H)

Example 109

4-amino-6-(3,5-dimethyl-4-(3-methyl-2-(2,2,2-trifluoroethyl)-2H-indazol-5-yl)phenyl)-7,8-dihydropyrimido[5,4-f][1,4]oxazepin-5-(6H)-one

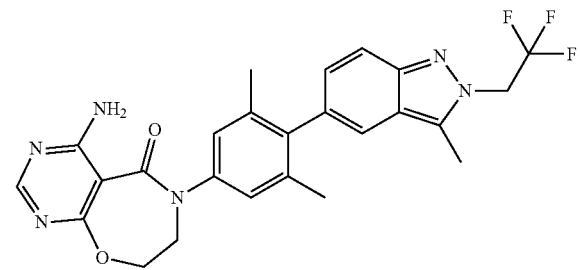

193
-continued

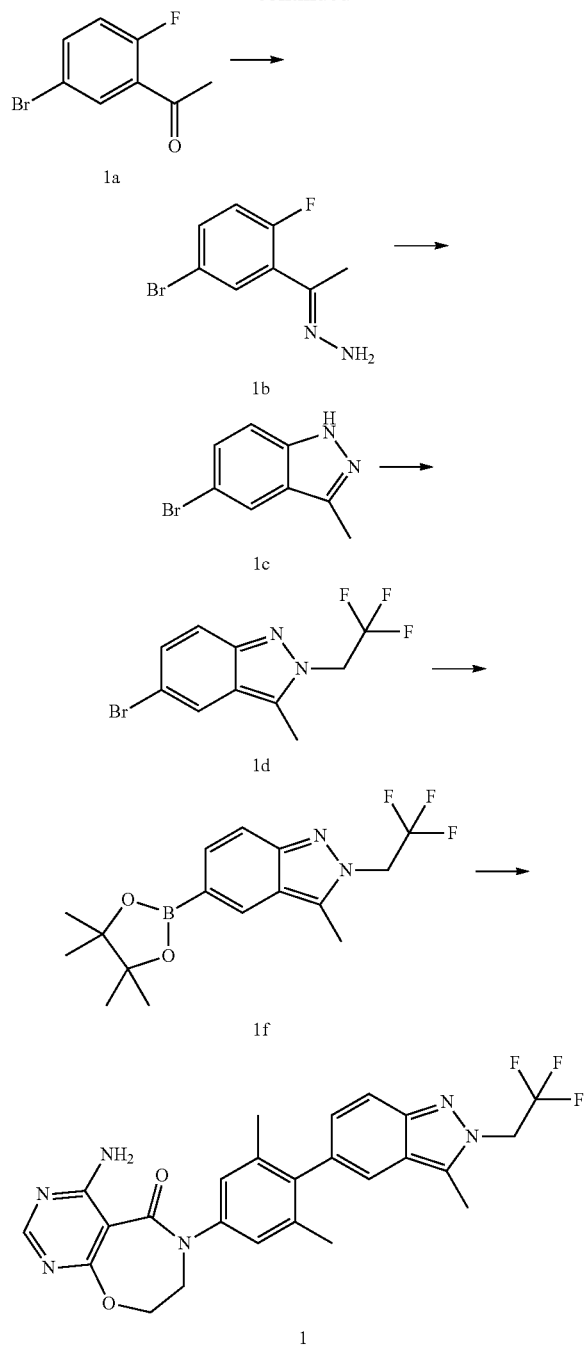

Step 1

(E)-(1-(5-bromo-2-fluorophenyl)ethylidene)hydrazine

The mixture of 1-(5-bromo-2-fluorophenyl)ethanone 1 (2 g, 9.2 mmol) and hydrazine (7.8 g, 7.6 mL, 16 mmol) was stirred at 100° C. for 12 h. The reaction mixture was diluted with water (150 mL) and extracted with EA (50 ml*3). The organic layers were combined, washed with water (50 ml), and brine (50 mL), dried over Na$_2$SO$_4$, filtered and concentrated to give the product (E)-(1-(5-bromo-2-fluorophenyl) ethylidene)hydrazine 1b (2.48 g, white solid), yield: 100%.

194

Step 2

5-bromo-3-methyl-1H-indazole

The mixture of (E)-(1-(5-bromo-2-fluorophenyl)ethylidene)hydrazine 1b (2.48 g, 10.8 mmol) and ethane-1,2-diol (24 mL) was stirred at 165° C. for 1.5 h in a microwave reactor, then diluted with water (100 mL) and extracted with EA (50 mL*3). The organic layers were combined, washed with water (50 mL), and brine (50 mL), dried over Na$_2$SO$_4$, filtered and concentrated under reduced pressure and purified by flash chromatography on silica gel to give the product 5-bromo-3-methyl-1H-indazole 1c (1.26 g, white solid), yield: 55.50%.

$^1$H NMR (400 MHz, CDCl$_3$) δ 7.82 (d, J=1.6 Hz, 1H), 7.44 (dd, J$_1$=8.8 Hz, J$_2$=1.6 Hz, 1H), 7.32 (d, J=8.4 Hz, 1H), 4.73 (br, s, 1H), 2.55 (s, 3H)

Step 3

5-bromo-3-methyl-2-(2,2,2-trifluoroethyl-2H-indazole

To a solution of 5-bromo-3-methyl-1H-indazole 1c (1.26 g, 6 mmol) in DMF (10 mL) was added Cs$_2$CO$_3$ (3.9 g, 12 mmol) and 2,2,2-trifluoroethyl trifluoromethanesulfonate (2.1 g, 9 mmol). The mixture was stirred at room temperature for 12 h, then diluted with water (100 mL) and extracted with EA (50 mL*3). The organic layers wee combined, washed with water (50 mL) and brine (50 mL), dried over Na$_2$SO$_4$, filtered and concentrated under reduced pressure. The residue was purified by column chromatography on silica gel (eluent system A) to give the product 5-bromo-3-methyl-2-(2,2,2-trifluoroethyl)-2H-indazole 1d (260 mg, white solid), yield: 14.80%

$^1$H NMR (400 MHz, CDCl$_3$) δ 7.73 (d, J=1.2 Hz, 1H), 7.53 (d, J=9.2 Hz, 1H), 7.35 (dd, J$_1$=9.2 Hz, J$_2$2.0 Hz, 1H), 4.93 (q, J$_1$=16.4 Hz, J$_2$=8.4 Hz, 2H), 2.63 (s, 3H)

Step 4

3-methyl-5-(4,4,5,5-tetramethyl-1,3,2-dioxaborolan-2-yl)-2-(2,2,2-trifluoroethyl)-2H-indazole To a solution of 5-bromo-3-methyl-2-(2,2,2-trifluoroethyl-2H-indazole 1d (260 mg, 0.9 mmol) in dioxane (5 mL) was added Pin$_2$B$_2$ (250 mg, 0.98 mmol), KOAc (260 mg, 2.7 mmol) and Pd(dppf)Cl$_2$ (36 mg. 0.04 mmol) The mixture was stirred at 90° C. for 12 h, then diluted with water (30 mL) and extracted with EA (20 mL*3). The organic layers were combined, washed with water (30 mL), brine (30 mL), dried over Na$_2$SO$_4$, filtered and concentrated under reduced pressure. The residue was purified by column chromatography on silic gel (eluent system A) to give the product 3-methyl-5-(4,4,5,5-tetramethyl-1,3,2-dioxaborolan-2-yl)-2-(2,2,2-trifluoroethyl)-2H-(indazole 1e (200 mg, white solid), yield: 66.67%

$^1$H NMR (400 MHz, CDCl$_3$) δ 8.15 (s, 1H), 7.65 (d, J=8.8 Hz, 1H), 7.59 (d, J=8.8 Hz, 1H), 4.93 (q, J$_1$=16.8 Hz, J$_2$=8.4 Hz, 2H), 2.67 (s, 3H), 1.36 (s, 12H)

Step 5

4-amino-6-(3,5-dimethyl-4-(3-methyl-2-(2,2,2-trifluoroethyl)-2H-indazol-5-yl)phenyl)-7,8-dihydropyrimido[5,4-f][1,4]oxazepin-5-(6H)-one To a solution of compound 3-methyl-5-(4,4,5,5-tetramethyl-1,3,2-dioxaborolan-2-yl)-2-(2,2,2-trifluoroethyl)-2H- indazole 1e (94 mg, 0.27 mmol) in dioxane/H$_2$O (2 mL/0.4 mL) was added 4-amino-6-(4-bromo-3,5-dimethylphenyl)-7,8-dihydropyrimido[5,4-f][1,4]oxazepin-5-(6H)-one (80 mg, 0.22 mmol), K$_2$CO$_3$ (61 mg, 0.44 mmol), and Pd(dppf)Cl$_2$ (9 mg, 0.011 mmol). The mixture was stirred at 100° C. for 40 min in a microwave reactor, then diluted with water (20 mL) and extracted with EA (10 mL*3). The organic layers were combined, washed with brine (30 mL), dried over Na$_2$SO$_4$, filtered and concentrated under reduced pressure. The residue was purified by prep-HPLC to give the product 4-amino-6-(3,5-dimethyl-4-(3-methyl-2-(2,2,2-trifluoroethyl)-2H-indazol-5-yl)phenyl)-7,8-dihydropyrimido[5,4-f][1,4]oxazepin-5(6H)-one 1 (52 mg, white solid), yield: 47.70%.

$^1$H NMR (400 MHz, DMSO-d$_6$) δ 8.48 (s, 1H), 7.61 (d, J=8.8 Hz, 1H), 7.46 (s, 1H), 7.15 (s, 2H), 7.00 (d, J=9.6 Hz, 1H), 5.41 (q, J$_1$=18.0 Hz, J$_2$=8.8 Hz, 2H), 4.86 (s, 2H), 4.15 (s, 2H), 2.65 (s, 3H) 2.00 (s, 6H)

1. In Vitro Assay for DGAT-1 Enzyme Inhibition:

The ability of compounds to inhibit DGAT enzyme activity is determined by calculating IC50 values of test compounds. Ki values of DGAT1 are calculated as follows:

Cheng-Prusoff equation: Ki=IC50/(1+[S]/Km)

(1) Human DGAT1 IC50 (nM) Experiment

Samples: Samples for human DGAT1 IC50 (nM) experiment were selected from some representative compounds that prepared by example 1 to 109.

Human DGAT1 activity was determined as follows:

Expressing human DGAT1 enzyme, used diacylglycerol and 14C-labeled acyl-CoA as the substrate, choose PE Company Flashplate testing board to build DGAT1 enzyme reaction system. 14C-labeled acyl-CoA binds to diacylglycerol by covalent bonding after enzymology reaction, and generates the product of 14C-labeled triglyceride. 14C-labeled acyl-CoA substrate is dissolved in reaction solution and 14C-labeled triglyceride product combine with phospholipids of Flashplate plate bottom layer, thus effectively separate labeled substrates and products. The radioactive of 14C-labeled triglyceride which is combined with phospholipid layer is counted, and the potencies of DGAT-1 inhibition for the compounds are determined by calculating the IC50 values.

The experiment results are shown in table 1:

TABLE 1

| | hDGAT 1 IC50 (nM) | | |
|---|---|---|---|
| | hDGAT1 IC50(nM) | | |
| Compound | First | Second | Average |
| PF-04620110 | 23.7 | 28.65 | 25.73 |
| Pradigastat | 68.19 | 29.71 | 48.95 |
| Compound 1 | 53.28 | 43.02 | 48.15 |
| Compound 2 | 64.11 | 41.6 | 52.86 |
| Compound 3 | 60.9 | 69.53 | 65.22 |
| Compound 4 | 46.19 | 32.88 | 39.54 |
| Compound 5 | 51.56 | 69.01 | 60.29 |
| Compound 6 | 24.42 | 38.51 | 31.47 |
| Compound 7 | 43.47 | 30.37 | 36.92 |
| Compound 8 | 41.88 | 35.91 | 38.90 |
| Compound 19 | 136 | 66.52 | 101.26 |
| Compound 25 | 57.18 | 60.68 | 58.93 |
| Compound 26 | 41.29 | 59.98 | 50.64 |
| Compound 27 | 69 | 55.69 | 62.35 |
| Compound 28 | 45.64 | 37.91 | 41.78 |

TABLE 1-continued

| | hDGAT 1 IC50 (nM) | | |
|---|---|---|---|
| | hDGAT1 IC50(nM) | | |
| Compound | First | Second | Average |
| Compound 29 | 37.41 | 32.95 | 35.18 |
| Compound 30 | 25.37 | 23.36 | 24.37 |
| Compound 31 | 23.62 | 23.39 | 23.51 |
| Compound 33 | 26.92 | 46.72 | 36.82 |
| Compound 34 | 77.97 | 33.63 | 55.80 |
| Compound 35 | 24.78 | 26.73 | 25.76 |
| Compound 36 | 37.67 | 21.03 | 29.35 |
| Compound 37 | 84.56 | 74.54 | 79.55 |
| Compound 38 | 46.46 | 54.95 | 50.71 |
| Compound 39 | 72.87 | 124 | 98.44 |
| Compound 41 | 37.7 | 29.97 | 31.34 |
| Compound 42 | 75.01 | 44.21 | 59.61 |
| Compound 43 | 18.50 | 16.73 | 17.62 |
| Compound 44 | 59.51 | 30.50 | 45.01 |
| Compound 45 | 17.35 | 14.59 | 15.97 |
| Compound 46 | 89.03 | 102.2 | 95.62 |
| Compound 47 | 65.44 | 108.6 | 87.02 |
| Compound 48 | 46.14 | 29.83 | 37.99 |
| Compound 56 | 65.82 | 37.75 | 51.79 |
| Compound 57 | 81.31 | 102.4 | 91.86 |
| Compound 59 | 54.87 | 105.8 | 80.34 |
| Compound 61 | 28.19 | 47.36 | 37.78 |
| Compound 62 | 57.92 | 78.55 | 68.24 |
| Compound 64 | 38.7 | 76.53 | 57.62 |
| Compound 65 | 38.97 | 44.07 | 41.52 |
| Compound 66 | 47.08 | 38.21 | 42.65 |
| Compound 67 | 56.12 | 50.27 | 53.20 |
| Compound 70 | 27.59 | 13.19 | 20.39 |
| Compound 71 | 35.94 | 25.3 | 30.62 |
| Compound 73 | 24.54 | 44.25 | 34.40 |
| Compound 76 | 14.62 | 32.36 | 23.49 |
| Compound 78 | 69.23 | 40.3 | 54.77 |
| Compound 79 | 46.41 | 57.82 | 52.12 |
| Compound 83 | 52.75 | 38.43 | 45.59 |
| Compound 85 | 59.62 | 63.69 | 61.66 |
| Compound 87 | 49.26 | 44.2 | 46.73 |
| Compound 88 | 26.99 | 24.39 | 25.69 |
| Compound 89 | 71.18 | 90.13 | 80.66 |
| Compound 90 | 61.98 | 57.99 | 59.99 |
| Compound 91 | 12.46 | 27.49 | 19.98 |
| Compound 93 | 64.51 | 74.20 | 69.36 |
| Compound 94 | 63.06 | 55.12 | 59.09 |
| Compound 95 | 32.18 | 52.85 | 42.52 |
| Compound 96 | 69.35 | 71.72 | 70.54 |
| Compound 97 | 30.28 | 23.41 | 26.85 |
| Compound 99 | 104.30 | 79.10 | 91.70 |
| Compound 105 | 27.05 | 36.43 | 31.74 |
| Compound 105 (peak1) | 103.20 | 43.32 | 73.26 |
| Compound 108 (peak2) | 56.38 | 48.78 | 52.58 |

Notes: hDGAT1 IC50<100 nM that is shown to have a high biological activity in vitro; Positive compound PF-04620110 was prepared by the methods disclosed in "Discovery of PF-04620110: A Potent, Orally-Bioavailable Inhibitor of DGAT-1, ACS Med. Chem. Lett. 2011, 2, 407-412"; Positive compound Pradigastat was prepared by the methods disclosed in "WO2007126957".

Conclusion: Compared with the prior art, the compounds of the presents invention have stronger or equivalent activity for inhibiting human DGAT1.

(2) Other In Vitro Assays

Samples: On the base of the Human DGAT1 IC50 (nM) experiment, some compounds that had high activity, representative structures were selected for further experiment.

Mouse DGAT1 activity was determined as follows:

Mouse DGAT1 IC50 determination method: in addition to expression of mouse DGAT1, experiment method with human DGAT1 enzymatic assay is the same.

In Vitro Assay in HEK-293 Cells:

We treated HEK293 cells with stable isotope $^{13}$C-labeled oleic acid and endogenous DGAT1-expressing catalytic $^{13}$C-labeled oleic acid incorporate to TG. The extraction and separation of cell suspension is to obtain the triglycerides composition. A LC/MS/MS method is used to measure the concentration of $^{13}$C in TG to determine catalytic reaction rate of DGAT1, then determine the compound of DGAT1 inhibition (IC50).

The experiment results are shown in table 2:

TABLE 2

| other in vitro assays | | | | |
|---|---|---|---|---|
| | Pradigastat | PF-04620110 | Compound 41 | Compound 105 |
| cLogP | 6.8 | 2.61 | 1.6 | 2.6 |
| Sol pH 7.4 (uM) | 22 | | 187 | 70 |
| mouse DGAT1 IC50 (nM) | 30.23 | 38.46 | 12.51 | 33.58 |
| EC50/HEK293 (nM) | 3.65 | 20.16 | 22.06 | 3.64 |

Conclusion: Compared with Pradigastat, the cLogP of compounds of the present invention are significantly closer to the ideal value, the solubility of compounds of the present invention have obvious advantages and have considerably activity for inhibiting mouse DGAT1; Compared with Pradigastat, compound 105 has better cell activity.

(3) Pharmacokinetics of Test Compounds

The purpose of this study is to determine the plasma pharmacokinetics of male SD rats. Two animals will receive a solution of test article in vehicle by single intravenous bolus via tail vein; the dosage is 2 mg/kg. Blood samples are taken at specified time points (0, 0.0833, 0.25, 0.5, 1, 2, 4, 7, 24 h) after dosing. Another two animals will receive a solution or suspension of TA in vehicle by oral gavage at 10 mg/kg. The schedule for sample collection is 0.5, 1, 2, 3, 4, 6, 24 h after dosing. A LC/MS/MS method is used to measure the concentration of test compound in plasma. Non-compartmental pharmacokinetic analysis is performed on the plasma concentration-time data. PK parameters of calculations are done using Phoenix WinNonlin. 6.2.1 software program.

PK results are shown in table 3:

Conclusion: Compared with Pradigastat, compounds of the present invention have better bioavailability and longer half-life period.

2. In Vivo Assay

On the base of the in vitro assay, some compounds that had high activity, representative structures were selected for in vivo assay.

(1) Lipid Tolerance Test in Mice:

Samples: On the base of the aforesaid experiment, some compounds that had high activity, representative structures were selected for further experiment.

CDI mice (30 g or so) were individually housed in hanging wire cages at 20-25° C. with a 12:12 hour light:dark cycle (Humidity: 40~70%). The mice had ad libitum access to water. On the day of experimentation, food jars were removed from each cage 16 hours prior to rate received either vehicle or test article based on a randomization plan generated by randomization. After sixty minutes, oral administration (gavage) of corn oil at a dose volume of 6 mL/kg (time=0). Blood samples were obtained from each mouse via tail snip procedure at −0.5, 0.5, 1, 2 and 4 hours. 20 ul of blood sampling will be rapidly collected, and then is centrifuged at 7000 rpm for 10 min to determine plasma triacylglycerol levels. Triglyceride was quantitated using TG ELISA kit. All data will be analyzed using SPSS. $p<0.05$ is considered to be statistically significant.

The experiment results are shown in table 4:

TABLE 4

| Lipid Tolerance Test (LTT) in the mice | |
|---|---|
| Compound | Inhibtion % @ 2 h 1 MPK PO |
| Pradigastat | 34% inh |
| Compound 41 | 83% inh |
| Compound 105 | 118% inh |

Conclusion: Compared with Pradigastat, compounds of the present invention have significantly even unexpected progress, in terms of in vivo efficacy.

TABLE 3

| PK results | | | | | |
|---|---|---|---|---|---|
| | Ideal value | Pradigastat | PF-04620110 | Example 41 | Example 105 |
| Cmax (ng/mL) | >300 | 5735 (rat, po, 8.94 mg/kg) | 7105 (rat, po, 9.57 mg/kg, suspension) | 3110 (rat, po, 9.11 mg/kg) | 5811 (rat, po, 9.33 mg/kg) |
| Cl mL/min/kg | <20 | 0.70 | | 14.4 | 1.96 |
| $V_{dss}$ (L/kg) | <3 | 0.15 | | 1.49 | 0.54 |
| $T_{1/2}$ (b) | >2 | 2.33 (rat, po, 8.94 mg/kg) 2.19 (rat, iv, 1.78 mg/kg) | ND (rat, po, 9.57 mg/kg, suspension) ND (rat, iv, 2 mg/kg) 6.8 (rat, po, 5 mg/kg) | 3.2 (rat, po, 9.11 mg/kg) ND (rat, iv, 1.84 mg/kg) | 2.93 (rat, po, 9.33 mg/kg) 3.81 (rat, iv, 2.06 mg/kg) |
| $AUC_{0-1}$ (ng · n/mL) | >500 | 32075 (rat, po, 8.94 mg/kg) 42934 (rat, iv, 1.78 mg/kg) | 15750 (rat, po, 9.57 mg/kg, suspension) 2920 (rat, iv, 2 mg/kg) | 14500 (rat, po, 9.11 mg/kg) 2125 (rat, iv, 1.84 mg/kg) | 45575 (rat, po, 9.33 mg/kg) 17725 (rat, iv, 2.06 mg/kg) |
| F(%) | >30 | 14.9 | 109 (rat) | ~100 | 56.8 |

(2) Diet Induced Obesity in Mice

Samples: On the base of the aforesaid experiment, some compounds that had high activity, representative structures were selected for further experiment.

DIO Mice Creation:

Male C57bl/6J mice (6 weeks) were individually housed in hanging wire cages at 20-25° C. with a 12:12 hour light:dark cycle (Humidity: 40~70%). After one week acclimation, the mice are fed with high fat pelleted diet (D12492i, Research Diets, Inc) and fresh water, ad libitum. Typically; C57BL/6J male mice become obese, and reach 40-50 g after 12-14 weeks of high fat diet treatment.

Experimental Design:

Animals accept oral gavages acclimation for two weeks. Then next, they are dosed with test articles or vehicle (bid) accordingly for 7 day. Food intake and body weight are recorded every day. Data are graphed by Graph Pad Prism 5.0 and evaluated using SPSS, p<0.05 is considered to be statistically significant.

The experiment results are shown in table 5 and 6:

TABLE 5

7 day Cumulative Body Weight Change

| Compound | 7 days Cumulative Body Weight Change (%) |
| --- | --- |
| Pradigastatt 30mpk BID | 1.72 |
| Compound 41 10mpk BID | −3.32 |
| Compound 105 10mpk BID | −1.06 |

TABLE 6

7 day Cumulative Food Intake Change

| Compound | 7 days Cumulative Food Intake Change (%) |
| --- | --- |
| Pradigastatt 30mpk BID | 5.85 |
| Compound 41 10mpk BID | −16.35 |
| Compound 105 10mpk BID | −8.56 |

Conclusion: Mice dosed with compounds of the present invention 10 mpk BID can effectively reduce body weight and greatly reduce food intake, while body weight and food intake of the mice increased slight even though the mice are dosed with Pradigastatt 30 mpk BID.

It will thus be seen that the objects of the present invention have been fully and effectively accomplished. Its embodiments have been shown and described for the purposes of illustrating the functional and structural principles of the present invention and is subject to change without departure from such principles. Therefore, this invention includes all modifications encompassed within the spirit and scope of the following claims.

We claim:

1. A compound represented by formula (I)

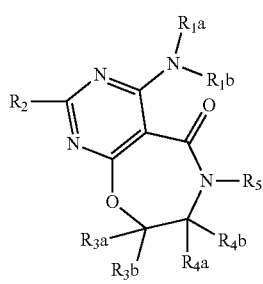

(I)

wherein $R_1a$, $R_1b$, $R_2$, $R_3a$, $R_3b$, $R_4a$, and $R_4b$ are each independently selected from the group consisting of H, $C_{1-10}$ alkyl, $C_{1-10}$ alkoxy, $C_{3-10}$ cycloalkyl, and $C_{3-10}$ cycloalkoxy, wherein each of the $C_{1-10}$ alkyl, $C_{1-10}$ alkoxy, $C_{3-10}$ cycloalkyl, or $C_{3-10}$ cycloalkoxy is optionally substituted by one or more substituents, each independently selected from the group consisting of halogen, OH, SH, $NH_2$, and $PH_2$, $R_5$ is

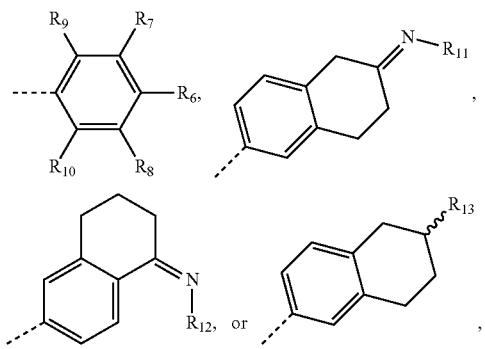

wherein $R_6$ is selected from the group consisting of

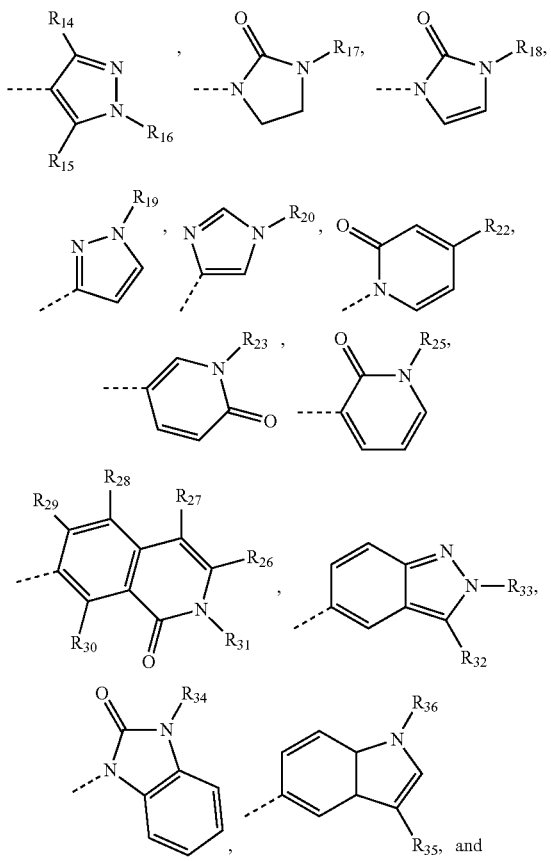

-continued

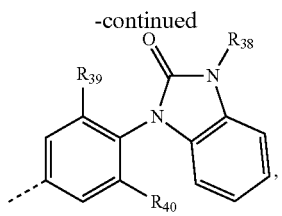

and R$_6$ is optionally protected by a protecting group, wherein

R$_{14}$ and R$_{15}$ are each independently selected from the group consisting of H, C$_{1-6}$ alkyl, and C$_{1-6}$ alkoxy, wherein each of the C$_{1-6}$ alkyl or C$_{1-6}$ alkoxy is optionally substituted by one to three substituents, each independently selected from the group consisting of halogen, OH, SH, NH$_2$, and PH$_2$; and R$_{16}$, R$_{17}$, R$_{18}$, R$_{19}$, R$_{20}$, R$_{22}$, R$_{23}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{38}$, R$_{39}$, and R$_{40}$ are each independently selected from the group consisting of H, halogen, OH, SH, NH$_2$, PH$_2$, C$_{1-6}$ alkyl, C$_{1-6}$ alkoxy, —C$_{1-6}$OH, —COOH, —C$_{1-6}$COOH, —OC$_{1-6}$COOH, —C$_{1-6}$OC$_{1-6}$, —C$_{1-6}$COOC$_{1-6}$, —C$_{1-6}$CN, —C$_{1-6}$CONH$_2$, and

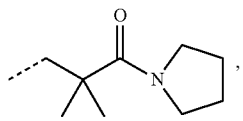

wherein said C$_{1-6}$ alkyl, C$_{1-6}$ alkoxy, —C$_{1-6}$OH, —C$_{1-6}$COOH, —OC$_{1-6}$COOH, —C$_{1-6}$OC$_{1-6}$, —C$_{1-6}$COOC$_{1-6}$, —C$_{1-6}$CN, and —C$_{1-6}$CONH$_2$ are optionally substituted by one to three substituents, each independently selected from the group consisting of halogen, OH, SH, NH$_2$, PH$_2$, and C$_{1-6}$ cycloalkyl, the carbon atoms, located on both sides or on the same side of each oxygen or carbonyl in said —C$_{1-6}$OC$_{1-6}$ or —C$_{1-6}$COOC$_{1-6}$, are optionally joined together to form a ring, and the H atom, connected with the N atom of —C$_{1-6}$NH$_2$, is optionally replaced by C$_{1-6}$ alkyl singly or bothly;

R$_7$, R$_8$, R$_9$, and R$_{10}$ are each independently selected from the group consisting of C$_{1-10}$ alkyl, C$_{1-10}$ alkoxy, C$_{3-10}$ cycloalkyl, C$_{3-10}$ cycloalkoxy, H, halogen, OH, SH, NH$_2$, PH$_2$, and CN, wherein each of the C$_{1-10}$ alkyl, C$_{1-10}$ alkoxy, C$_{3-10}$ cycloalkyl, and C$_{3-10}$ cycloalkoxy is optionally substituted by one or more substituents, each independently selected from the group consisting of halogen, OH, SH, NH$_2$, PH$_2$, CN, CH$_3$, and CF$_3$;

R$_{11}$, R$_{12}$, and R$_{13}$ are each independently selected from the group consisting of C$_{1-10}$ alkyl, C$_{1-10}$ alkoxy, C$_{3-10}$ cycloalkyl, and C$_{3-10}$ cycloalkoxy, wherein each of the C$_{1-10}$ alkyl, C$_{1-10}$ alkoxy, C$_{3-10}$ cycloalkyl, and C$_{3-10}$ cycloalkoxy is optionally substituted by one to three substituents, each independently selected from the group consisting of halogen, OH, SH, NH$_2$, PH$_2$, CN, CF$_3$, —OCF$_3$, and —OCH$_3$, or a pharmaceutically acceptable salt thereof.

2. The compound of claim 1, wherein R$_1$a, R$_1$b, or R$_2$ is H.

3. The compound of claim 1, wherein R$_3$a, R$_3$b, R$_4$a, or R$_4$b is H or methyl.

4. The compound of claim 1, wherein R$_{14}$ and R$_{15}$ are each independently selected from the group consisting of H, methyl, and CF$_3$.

5. The compound of claim 1, wherein R$_{26}$, R$_{27}$, R$_{28}$, R$_{29}$, and R$_{30}$ are H.

6. The compound of claim 1, wherein R$_{16}$, R$_{17}$, R$_{18}$, R$_{19}$, R$_{20}$, R$_{22}$, R$_{23}$, R$_{25}$, R$_{26}$, R$_{27}$, R$_{28}$, R$_{29}$, R$_{30}$, R$_{31}$, R$_{32}$, R$_{33}$, R$_{34}$, R$_{35}$, R$_{36}$, R$_{38}$, R$_{39}$, and R$_{40}$ are each independently selected from the group consisting of 1) halogen;
2) —CH$_3$, —CH$_2$CH(CH$_3$)$_2$, —C(CH$_3$)$_3$, —CH$_2$CH(CH$_3$)$_2$, —CH(CH$_3$)$_2$,

3) —CH$_2$CF$_3$, —CH$_2$C(CH$_3$)$_2$F, —CH$_2$C(CH$_3$)F$_2$, —CH$_2$CHF$_2$, —OCH$_2$CF$_3$;
4) —CH$_2$CH$_2$OH, —CH$_2$C(CH$_3$)$_2$CH$_2$OH, —CH$_2$C(CH$_3$)$_2$OH;
5) —COOH, —CH$_2$COOH, —CH$_2$CH$_2$COOH, —CH$_2$C(CH$_3$)$_2$COOH, —CH$_2$CH(CH$_3$)COOH, —CH(CH$_3$)COOH, —C(CH$_3$)$_2$COOH, —CH(CH$_2$CH$_3$)COOH,

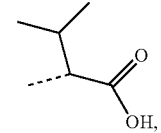

—OCH(CH$_3$)COOH;
6) —CH$_2$C(CH$_3$)$_2$OCH$_3$,

7) —CH$_2$COOC$_2$CH$_5$;
8) —CH$_2$CN; and
9) —CH$_2$CONH$_2$,

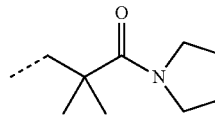 and 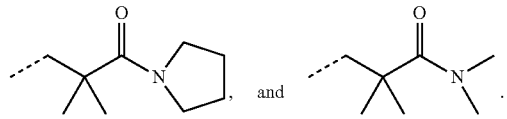

7. The compound of claim 1, wherein R$_7$ and R$_8$ are each independently selected from the group consisting of —CH$_3$, —CH$_2$CH$_3$, —CF$_3$, —OCH$_3$, —OCF$_3$, halogen, OH, and H.

8. The compound of claim 1, wherein R$_9$ and R$_{10}$ are H.

9. The compound of claim 1, wherein R$_{11}$, R$_{12}$, R$_{13}$ are each independently selected from the group consisting of —OCH$_3$, —OCF$_3$, —OCH$_2$CF$_3$, and —CF$_3$.

10. A compound selected from the group consisting of:
1) 2-(3-(4-(4-amino-5-oxo-7,8-dihydropyrimido[5,4-f][1,4]oxazepin-6(5H)-yl)-2-chlorophenyl)-2-oxoimidazolidin-1-yl)acetic acid;
2) 2-(3-(4-(4-amino-5-oxo-7,8-dihydropyrimido[5,4-f][1,4]oxazepin-6(5H)-yl)-2-fluorophenyl)-2-oxoimidazolidin-1-yl)acetic acid;

3) 2-(3-(4-(4-amino-5-oxo-7,8-dihydropyrimido[5,4-f][1,4]oxazepin-6(5H)-yl)-2-methylphenyl)-2-oxoimidazolidin-1-yl)acetic acid;
4) 2-(3-(4-(4-amino-5-oxo-7,8-dihydropyrimido[5,4-f][1,4]oxazepin-6(5H)-yl)-2-ethyl-6-methylphenyl)-2-oxoimidazolidin-1-yl)acetic acid;
5) 2-(3-(4-(4-amino-5-oxo-7,8-dihydropyrimido[5,4-f][1,4]oxazepin-6(5H)-yl)-2-ethylphenyl)-2-oxoimidazolidin-1-yl)acetic acid;
6) 3-(3-(4-(4-amino-5-oxo-7,8-dihydropyrimido[5,4-f][1,4]oxazepin-6(5H)-yl)-2-chlorophenyl)-2-oxoimidazolidin-1-yl)propanoic acid;
7) 2-(3-(4-(4-amino-5-oxo-7,8-dihydropyrimido[5,4-f][1,4]oxazepin-6(5H)-yl)-2-(trifluoromethoxy)phenyl)-2-oxoimidazolidin-1-yl)acetic acid;
8) 4-amino-6-(3-chloro-4-(2-oxo-3-(2,2,2-trifluoroethyl)imidazolidin-1-yl)phenyl)-7,8-dihydropyrimido[5,4-f][1,4]oxazepin-5(6H)-one;
9) 4-amino-6-(3,5-dimethyl-4-(2-oxo-3-(2,2,2-trifluoroethyl)-2,3-dihydro-1H-benzo[d]imidazol-1-yl)phenyl)-7,8-dihydropyrimido[5,4-f][1,4]oxazepin-5(6H)-one;
10) 2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)acetic acid;
11) 2-(3-(4-(4-amino-5-oxo-7,8-dihydropyrimido[5,4-f][1,4]oxazepin-6(5H)-yl)phenyl)-2-oxoimidazolidin-1-yl)acetic acid;
12) Ethyl-2-(3-(4-(4-amino-5-oxo-7,8-dihydropyrimido[5,4-f][1,4]oxazepin-6(5H)-yl)phenyl)-2-oxoimidazolidin-1-yl)acetate;
13) 3-(3-(4-(4-amino-5-oxo-7,8-dihydropyrimido[5,4-f][1,4]oxazepin-6(5H)-yl)phenyl)-2-oxoimidazolidin-1-yl)propanoic acid;
14) 2-(3-(4-(4-amino-5-oxo-7,8-dihydropyrimido[5,4-f][1,4]oxazepin-6(5H)-yl)-2-methoxyphenyl)-2-oxoimidazolidin-1-yl)acetic acid;
15) 2-(3-(4-(4-amino-5-oxo-7,8-dihydropyrimido[5,4-f][1,4]oxazepin-6(5H)-yl)phenyl)-2-oxoimidazolidin-1-yl)propanoic acid;
16) 2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)acetic acid;
17) 2-(3-(4-(4-amino-5-oxo-7,8-dihydropyrimido[5,4-f][1,4]oxazepin-6(5H)-yl)phenyl)-2-oxoimidazolidin-1-yl)-3-methylbutanoic acid;
18) 2-(3-(4-(4-amino-5-oxo-7,8-dihydropyrimido[5,4-f][1,4]oxazepin-6(5H)-yl)-2,6-dimethylphenyl)-2-oxoimidazolidin-1-yl)acetic acid;
19) 2-(3-(4-(4-amino-5-oxo-7,8-dihydropyrimido[5,4-f][1,4]oxazepin-6(5H)-yl)-2,6-diethylphenyl)-2-oxoimidazolidin-1-yl)acetic acid;
20) 3-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)propanoic acid;
21) 2-(3-(4-(4-amino-5-oxo-7,8-dihydropyrimido[5,4-f][1,4]oxazepin-6(5H)-yl)-2-(trifluoromethoxy)phenyl)-2-oxo-2,3-dihydro-1H-imidazol-1-yl)acetic acid;
22) 2-(3-(4-(4-amino-5-oxo-7,8-dihydropyrimido[5,4-f][1,4]oxazepin-6(5H)-yl)phenyl)-2-oxo-2,3-dihydro-1H-imidazol-1-yl)propanoic acid;
23) 2-(3-(4-(4-amino-5-oxo-7,8-dihydropyrimido[5,4-f][1,4]oxazepin-6(5H)-yl)phenyl)-2-oxoimidazolidin-1-yl)butanoic acid;
24) 3-(3-(4-(4-amino-5-oxo-7,8-dihydropyrimido[5,4-f][1,4]oxazepin-6(5H)-yl)phenyl)-2-oxoimidazolidin-1-yl)-2-methylpropanoic acid;
25) 2-(3-(4-(4-amino-5-oxo-7,8-dihydropyrimido[5,4-f][1,4]oxazepin-6(5H)-yl)-2-(trifluoromethyl)phenyl)-2-oxoimidazolidin-1-yl)acetic acid;
26) 2-(3-(4-(4-amino-5-oxo-7,8-dihydropyrimido[5,4-f][1,4]oxazepin-6(5H)-yl)-2-fluoro-6-methylphenyl)-2-oxoimidazolidin-1-yl)acetic acid;
27) 2-(3-(4-(4-amino-5-oxo-7,8-dihydropyrimido[5,4-f][1,4]oxazepin-6(5H)-yl)-2-chloro-6-methylphenyl)-2-oxoimidazolidin-1-yl)acetic acid;
28) 2-(3-(4-(4-amino-5-oxo-7,8-dihydropyrimido[5,4-f][1,4]oxazepin-6(5H)-yl)-2-chlorophenyl)-2-oxo-2,3-dihydro-1H-imidazol-1-yl)acetic acid;
29) 4-amino-6-(3-chloro-4-(3-isobutyl-2-oxoimidazolidin-1-yl)phenyl)-7,8-dihydropyrimido[5,4-f][1,4]oxazepin-5(6H)-one;
30) 4-amino-6-(3-chloro-4-(3-(cyclopropylmethyl)-2-oxoimidazolidin-1-yl)phenyl)-7,8-dihydropyrimido[5,4-f][1,4]oxazepin-5(6H)-one;
31) 4-amino-6-(3-chloro-4-(3-(2-fluoro-2-methylpropyl)-2-oxoimidazolidin-1-yl)phenyl)-7,8-dihydropyrimido[5,4-f][1,4]oxazepin-5(6H)-one;
32) 2-(4-(4-(4-amino-5-oxo-7,8-dihydropyrimido[5,4-f][1,4]oxazepin-6(5H)-yl)phenyl)-3,5-dimethyl-1H-pyrazol-1-yl)acetic acid;
33) 2-(4-(4-(4-amino-5-oxo-7,8-dihydropyrimido[5,4-f][1,4]oxazepin-6(5H)-yl)-2-chlorophenyl)-1H-pyrazol-1-yl)-2-methylpropanoic acid;
34) 2-(4-(4-(4-amino-5-oxo-7,8-dihydropyrimido[5,4-f][1,4]oxazepin-6(5H)-yl)-2-chlorophenyl)-1H-pyrazol-1-yl)propanoic acid;
35) 3-(4-(4-(4-amino-5-oxo-7,8-dihydropyrimido[5,4-f][1,4]oxazepin-6(5H)-yl)-2-chlorophenyl)-1H-pyrazol-1-yl)propanoic acid;
36) 2-(4-(4-(4-amino-5-oxo-7,8-dihydropyrimido[5,4-f][1,4]oxazepin-6(5H)-yl)-2-chlorophenyl)-3-methyl-1H-pyrazol-1-yl)acetic acid;
37) 3-(4-(4-(4-amino-5-oxo-7,8-dihydropyrimido[5,4-f][1,4]oxazepin-6(5H)-yl)-2-fluorophenyl)-1H-pyrazol-1-yl)propanoic acid;
38) 3-(4-(4-(4-amino-5-oxo-7,8-dihydropyrimido[5,4-f][1,4]oxazepin-6(5H)-yl)-2-chlorophenyl)-3,5-dimethyl-1H-pyrazol-1-yl)propanoic acid;
39) 2-(4-(4-(4-amino-5-oxo-7,8-dihydropyrimido[5,4-f][1,4]oxazepin-6(5H)-yl)phenyl)-3-(trifluoromethyl)-1H-pyrazol-1-yl)acetic acid;
40) 4-amino-6-(3-chloro-4-(3-methyl-1-(2,2,2-trifluoroethyl)-1H-pyrazol-4-yl)phenyl)-7,8-dihydropyrimido[5,4-f][1,4]oxazepin-5(6H)-one;
41) 4-amino-6-(3,5-dimethyl-4-(3-methyl-1-(2,2,2-trifluoroethyl)-1H-pyrazol-4-yl)phenyl)-7,8-dihydropyrimido[5,4-f][1,4]oxazepin-5(6H)-one;
42) 4-amino-6-(3-chloro-4-(1-(2-hydroxy-2-methylpropyl)-1H-pyrazol-4-yl)phenyl)-7,8-dihydropyrimido[5,4-f][1,4]oxazepin-5(6H)-one;
43) 4-amino-6-(4-(1-(2,2-difluoroethyl)-3-methyl-1H-pyrazol-4-yl)-3,5-dimethylphenyl)-7,8-dihydropyrimido[5,4-f][1,4]oxazepin-5(6H)-one;

44) 4-amino-6-(3-chloro-4-(1-(3-hydroxy-2,2-dimethylpropyl)-1H-pyrazol-4-yl)phenyl)-7,8-dihydropyrimido[5,4-f][1,4]oxazepin-5(6H)-one;
45) (R)-4-amino-6-(3-chloro-4-(1-isobutyl-1H-pyrazol-4-yl)phenyl)-8-methyl-7,8-dihydropyrimido[5,4-f][1,4]oxazepin-5(6H)-one;
46) 2-(4-(4-(4-amino-5-oxo-7,8-dihydropyrimido[5,4-f][1,4]oxazepin-6(5H)-yl)-2-chlorophenyl)-1H-pyrazol-1-yl)acetamide;
47) 4-amino-6-(3,5-dimethyl-4-(3-methyl-1-((3-methyloxetan-3-yl)methyl)-1H-pyrazol-4-yl)phenyl)-7,8-dihydropyrimido[5,4-f][1,4]oxazepin-5(6H)-one;
48) 4-amino-6-(4-(1-(2,2-difluoropropyl)-3-methyl-1H-pyrazol-4-yl)-3,5-dimethylphenyl)-7,8-dihydropyrimido[5,4-f][1,4]oxazepin-5(6H)-one;
49) 2-(4-(4-(4-amino-5-oxo-7,8-dihydropyrimido[5,4-f][1,4]oxazepin-6(5H)-yl)phenyl)-1H-pyrazol-1-yl)acetic acid;
50) 3-(4-(4-(4-amino-5-oxo-7,8-dihydropyrimido[5,4-f][1,4]oxazepin-6(5H)-yl)phenyl)-1H-pyrazol-1-yl)propanoic acid;
51) 2-(4-(4-(4-amino-5-oxo-7,8-dihydropyrimido[5,4-f][1,4]oxazepin-6(5H)-yl)phenyl)-1H-pyrazol-1-yl)propanoic acid;
52) 2-(4-(4-(4-amino-5-oxo-7,8-dihydropyrimido[5,4-f][1,4]oxazepin-6(5H)-yl)phenyl)-1H-pyrazol-1-yl)butanoic acid;
53) 2-(4-(4-(4-amino-5-oxo-7,8-dihydropyrimido[5,4-f][1,4]oxazepin-6(5H)-yl)phenyl)-1H-pyrazol-1-yl)-3-methylbutanoic acid;
54) 2-(4-(4-(4-amino-5-oxo-7,8-dihydropyrimido[5,4-f][1,4]oxazepin-6(5H)-yl)phenyl)-1H-pyrazol-1-yl)-2-methylpropanoic acid;
55) 2-(4-(4-(4-amino-5-oxo-7,8-dihydropyrimido[5,4-f][1,4]oxazepin-6(5H)-yl)phenyl)-3-methyl-1H-pyrazol-1-yl)acetic acid;
56) 2-(4-(4-(4-amino-5-oxo-7,8-dihydropyrimido[5,4-f][1,4]oxazepin-6(5H)-yl)-2-chlorophenyl)-1H-pyrazol-1-yl)acetic acid;
57) 2-(4-(4-(4-amino-5-oxo-7,8-dihydropyrimido[5,4-f][1,4]oxazepin-6(5H)-yl)-2-methylphenyl)-1H-pyrazol-1-yl)acetic acid;
58) 2-(4-(4-(4-amino-5-oxo-7,8-dihydropyrimido[5,4-f][1,4]oxazepin-6(5H)-yl)-2-methylphenyl)-1H-pyrazol-1-yl)propanoic acid;
59) 2-(4-(4-(4-amino-5-oxo-7,8-dihydropyrimido[5,4-f][1,4]oxazepin-6(5H)-yl)-2-methylphenyl)-1H-pyrazol-1-yl)-3-methylbutanoic acid;
60) 3-(4-(4-(4-amino-5-oxo-7,8-dihydropyrimido[5,4-f][1,4]oxazepin-6(5H)-yl)-2-methylphenyl)-1H-pyrazol-1-yl)propanoic acid;
61) 2-(4-(4-(4-amino-5-oxo-7,8-dihydropyrimido[5,4-f][1,4]oxazepin-6(5H)-yl)-2-chlorophenyl)-1H-pyrazol-1-yl)butanoic acid;
62) 3-(4-(4-(4-amino-5-oxo-7,8-dihydropyrimido[5,4-f][1,4]oxazepin-6(5H)-yl)phenyl)-3-(trifluoromethyl)-1H-pyrazol-1-yl)propanoic acid;
63) 2-(4-(4-(4-amino-5-oxo-7,8-dihydropyrimido[5,4-f][1,4]oxazepin-6(5H)-yl)-2-methylphenyl)-1H-pyrazol-1-yl)-2-methylpropanoic acid;
64) 2-(4-(4-(4-amino-5-oxo-7,8-dihydropyrimido[5,4-f][1,4]oxazepin-6(5H)-yl)-2-methylphenyl)-1H-pyrazol-1-yl)butanoic acid;
65) 2-(4-(4-(4-amino-5-oxo-7,8-dihydropyrimido[5,4-f][1,4]oxazepin-6(5H)-yl)-2-chlorophenyl)-1H-pyrazol-1-yl)-3-methylbutanoic acid;
66) 2-(4-(4-(4-amino-5-oxo-7,8-dihydropyrimido[5,4-f][1,4]oxazepin-6(5H)-yl)-2,6-dimethylphenyl)-1H-pyrazol-1-yl)-2-methylpropanoic acid;
67) 2-(4-(4-(4-amino-5-oxo-7,8-dihydropyrimido[5,4-f][1,4]oxazepin-6(5H)-yl)-2,6-dimethylphenyl)-1H-pyrazol-1-yl)acetic acid;
68) 4-amino-6-(3-chloro-4-(1-(2,2,2-trifluoroethyl)-1H-pyrazol-4-yl)phenyl)-7,8-dihydropyrimido[5,4-f][1,4]oxazepin-5(6H)-one;
69) 2-(4-(4-(4-amino-5-oxo-7,8-dihydropyrimido[5,4-f][1,4]oxazepin-6(5H)-yl)-2-methoxyphenyl)-1H-pyrazol-1-yl)acetic acid;
70) 3-(4-(4-(4-amino-5-oxo-7,8-dihydropyrimido[5,4-f][1,4]oxazepin-6(5H)-yl)-2,6-dimethylphenyl)-1H-pyrazol-1-yl)propanoic acid;
71) 3-(4-(4-(4-amino-5-oxo-7,8-dihydropyrimido[5,4-f][1,4]oxazepin-6(5H)-yl)-2-chlorophenyl)-1H-pyrazol-1-yl)-2,2-dimethylpropanoic acid;
72) 2-(4-(4-(4-amino-5-oxo-7,8-dihydropyrimido[5,4-f][1,4]oxazepin-6(5H)-yl)-2-chlorophenyl)-3,5-dimethyl-1H-pyrazol-1-yl)acetic acid;
73) 2-(4-(4-(4-amino-5-oxo-7,8-dihydropyrimido[5,4-f][1,4]oxazepin-6(5H)-yl)-2,6-dimethylphenyl)-3-methyl-1H-pyrazol-1-yl)acetic acid;
74) 3-(4-(4-(4-amino-5-oxo-7,8-dihydropyrimido[5,4-f][1,4]oxazepin-6(5H)-yl)-2-methoxyphenyl)-1H-pyrazol-1-yl)propanoic acid;
75) 2-(4-(4-(4-amino-5-oxo-7,8-dihydropyrimido[5,4-f][1,4]oxazepin-6(5H)-yl)-2-fluorophenyl)-1H-pyrazol-1-yl)acetic acid;
76) 3-(4-(4-(4-amino-5-oxo-7,8-dihydropyrimido[5,4-f][1,4]oxazepin-6(5H)-yl)phenyl)-3,5-dimethyl-1H-pyrazol-1-yl)propanoic acid;
77) 3-(4-(4-(4-amino-5-oxo-7,8-dihydropyrimido[5,4-f][1,4]oxazepin-6(5H)-yl)-2-methylphenyl)-3,5-dimethyl-1H-pyrazol-1-yl)propanoic acid;
78) 3-(4-(4-(4-amino-5-oxo-7,8-dihydropyrimido[5,4-f][1,4]oxazepin-6(5H)-yl)-2-chlorophenyl)-3-methyl-1H-pyrazol-1-yl)propanoic acid;
79) 4-amino-6-(3-chloro-4-(1-ethyl-1H-pyrazol-4-yl)phenyl)-7,8-dihydropyrimido[5,4-f][1,4]oxazepin-5(6H)-one;
80) 4-amino-6-(3-chloro-4-(1-isobutyl-1H-pyrazol-4-yl)phenyl)-7,8-dihydropyrimido[5,4-f][1,4]oxazepin-5(6H)-one;
81) 4-amino-6-(3-chloro-4-(1-isopropyl-1H-pyrazol-4-yl)phenyl)-7,8-dihydropyrimido[5,4-f][1,4]oxazepin-5(6H)-one;
82) 4-amino-6-(3-chloro-4-(1-(2-hydroxyethyl)-1H-pyrazol-4-yl)phenyl)-7,8-dihydropyrimido[5,4-f][1,4]oxazepin-5(6H)-one;
83) 3-(4-(4-(4-amino-5-oxo-7,8-dihydropyrimido[5,4-f][1,4]oxazepin-6(5H)-yl)-2,6-dimethylphenyl)-3-methyl-1H-pyrazol-1-yl)propanoic acid;
84) 2-(4-(4-(4-amino-5-oxo-7,8-dihydropyrimido[5,4-f][1,4]oxazepin-6(5H)-yl)-2-chlorophenyl)-1H-pyrazol-1-yl)acetonitrile;
85) 4-amino-6-(3-chloro-4-(1-(2,2-dimethyl-3-oxo-3-(pyrrolidin-1-yl)propyl)-1H-pyrazol-4-yl)phenyl)-7,8-dihydropyrimido[5,4-f][1,4]oxazepin-5(6H)-one;
86) 4-amino-6-(3-chloro-4-(1-isobutyl-1H-pyrazol-4-yl)phenyl)-8,8-dimethyl-7,8-dihydropyrimido[5,4-f][1,4]oxazepin-5(6H)-one;
87) 4-amino-6-(3-chloro-4-(1-(cyclopropylmethyl)-1H-pyrazol-4-yl)phenyl)-7,8-dihydropyrimido[5,4-f][1,4]oxazepin-5(6H)-one;

88) 4-amino-6-(3-chloro-4-(1-neopentyl-1H-pyrazol-4-yl)phenyl)-7,8-dihydropyrimido[5,4-f][1,4]oxazepin-5(6H)-one;
89) 3-(4-(4-(4-amino-5-oxo-7,8-dihydropyrimido[5,4-f][1,4]oxazepin-6(5H)-yl)-2-chlorophenyl)-1H-pyrazol-1-yl)-N,N,2,2-tetramethylpropanamide;
90) 4-amino-6-(3-ethyl-4-(1-isobutyl-1H-pyrazol-4-yl)phenyl)-7,8-dihydropyrimido[5,4-f][1,4]oxazepin-5(6H)-one;
91) 4-amino-6-(3-chloro-4-(1-(2-fluoro-2-methylpropyl)-1H-pyrazol-4-yl)phenyl)-7,8-dihydropyrimido[5,4-f][1,4]oxazepin-5(6H)-one;
92) 4-amino-6-(3-chloro-4-(1-isobutyl-1H-pyrazol-4-yl)phenyl)-7,7-dimethyl-7,8-dihydropyrimido[5,4-f][1,4]oxazepin-5(6H)-one;
93) 4-amino-6-(4-(3,5-dimethyl-1-(2,2,2-trifluoroethyl)-1H-pyrazol-4-yl)-3,5-dimethylphenyl)-7,8-dihydropyrimido[5,4-f][1,4]oxazepin-5(6H)-one;
94) 4-amino-6-(3-chloro-4-(1-(2-methoxy-2-methylpropyl)-1H-pyrazol-4-yl)phenyl)-7,8-dihydropyrimido[5,4-f][1,4]oxazepin-5(6H)-one;
95) 4-amino-6-(3-chloro-4-(1-(2-fluoro-2-methylpropyl)-1H-pyrazol-3-yl)phenyl)-7,8-dihydropyrimido[5,4-f][1,4]oxazepin-5(6H)-one;
96) (R)-4-amino-6-(3-chloro-4-(1-isobutyl-1H-pyrazol-4-yl)phenyl)-7-methyl-7,8-dihydropyrimido[5,4-f][1,4]oxazepin-5(6H)-one;
97) 4-amino-6-(4-(1-(2-fluoro-2-methylpropyl)-3-methyl-1H-pyrazol-4-yl)-3,5-dimethylphenyl)-7,8-dihydropyrimido[5,4-f][1,4]oxazepin-5(6H)-one;
98) 4-amino-6-(4-(1-(2-hydroxy-2-methylpropyl)-3-methyl-1H-pyrazol-4-yl)-3,5-dimethylphenyl)-7,8-dihydropyrimido[5,4-f][1,4]oxazepin-5(6H)-one;
99) 4-amino-6-(4-(1-(2-methoxy-2-methylpropyl)-3-methyl-1H-pyrazol-4-yl)-3,5-dimethylphenyl)-7,8-dihydropyrimido[5,4-f][1,4]oxazepin-5(6H)-one;
100) 4-amino-6-(4-(2-oxo-1-(2,2,2-trifluoroethyl)-1,2-dihydropyridin-3-yl)phenyl)-7,8-dihydropyrimido[5,4-f][1,4]oxazepin-5(6H)-one;
101) 4-amino-6-(3,5-dimethyl-4-(6-oxo-1-(2,2,2-trifluoroethyl)-1,6-dihydropyridin-3-yl)phenyl)-7,8-dihydropyrimido[5,4-f][1,4]oxazepin-5(6H)-one;
102) 4-amino-6-(3-chloro-4-(1-(2-fluoro-2-methylpropyl)-1H-imidazol-4-yl)phenyl)-7,8-dihydropyrimido[5,4-f][1,4]oxazepin-5(6H)-one;
105) 4-amino-6-(3,5-dimethyl-4-(1-oxo-2-(2,2,2-trifluoroethyl)-1,2-dihydroisoquinolin-7-yl)phenyl)-7,8-dihydropyrimido[5,4-f][1,4]oxazepin-5(6H)-one;
106) (E)-4-amino-6-(6-((2,2,2-trifluoroethoxy)imino)-5,6,7,8-tetrahydronaphthalen-2-yl)-7,8-dihydropyrimido[5,4-f][1,4]oxazepin-5(6H)-one;
107) (Z)-4-amino-6-(5-((2,2,2-trifluoroethoxy)imino)-5,6,7,8-tetrahydronaphthalen-2-yl)-7,8-dihydropyrimido[5,4-f][1,4]oxazepin-5(6H)-one;
108) 4-amino-6-(6-(2,2,2-trifluoroethoxy)-5,6,7,8-tetrahydronaphthalen-2-yl)-7,8-dihydropyrimido[5,4-f][1,4]oxazepin-5(6H)-one; and
109) 4-amino-6-(3,5-dimethyl-4-(3-methyl-2-(2,2,2-trifluoroethyl)-2H-indazol-5-yl)phenyl)-7,8-dihydropyrimido[5,4-f][1,4]oxazepin-5(6H)-one.

11. A method for preparing the compound of claim 1, wherein $R_5$ is

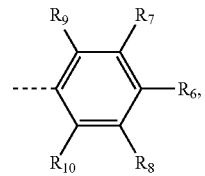

comprising the following step,

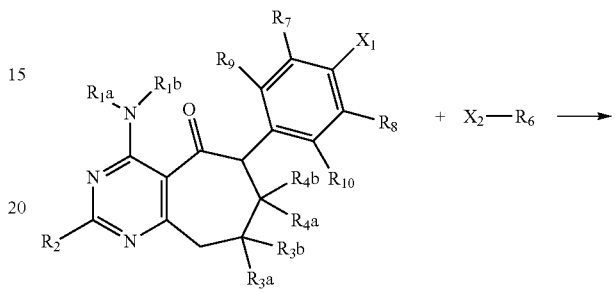

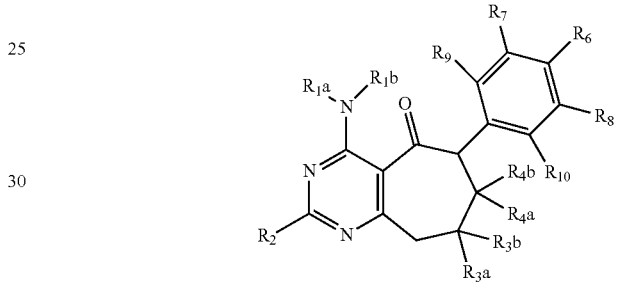

wherein
$X_1$ and $X_2$ are each independently selected from the group consisting of $CF_3$,

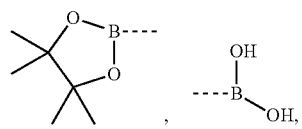

halogen, OH, SH, $NH_2$, $PH_2$, and $C_{1-6}$ alkyl, wherein the $C_{1-6}$ alkyl is optionally substituted by one to three substituents, each independently selected from the group consisting of halogen, OH, SH, $NH_2$, and $PH_2$.

12. A method for preparing a compound represented by formula (I)

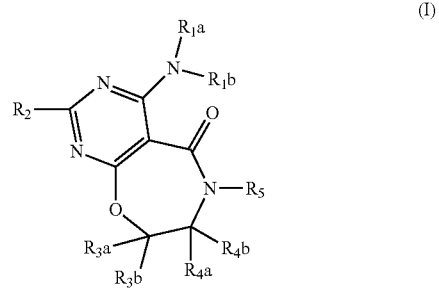

(I)

wherein
  $R_1a$, $R_1b$, $R_2$, $R_3a$, $R_3b$, $R_4a$, and $R_4b$ are each independently selected from the group consisting of H, $C_{1-10}$ alkyl, $C_{1-10}$ alkoxy, $C_{3-10}$ cycloalkyl, and $C_{3-10}$ cycloalkoxy, wherein each of the $C_{1-10}$ alkyl, $C_{1-10}$ alkoxy, $C_{3-10}$ cycloalkyl, or $C_{3-10}$ cycloalkoxy is optionally substituted by one or more substituents, each independently selected from the group consisting of halogen, OH, SH, $NH_2$, and $PH_2$, $R_5$ is

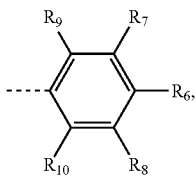

wherein
$R_6$ is selected from the group consisting of

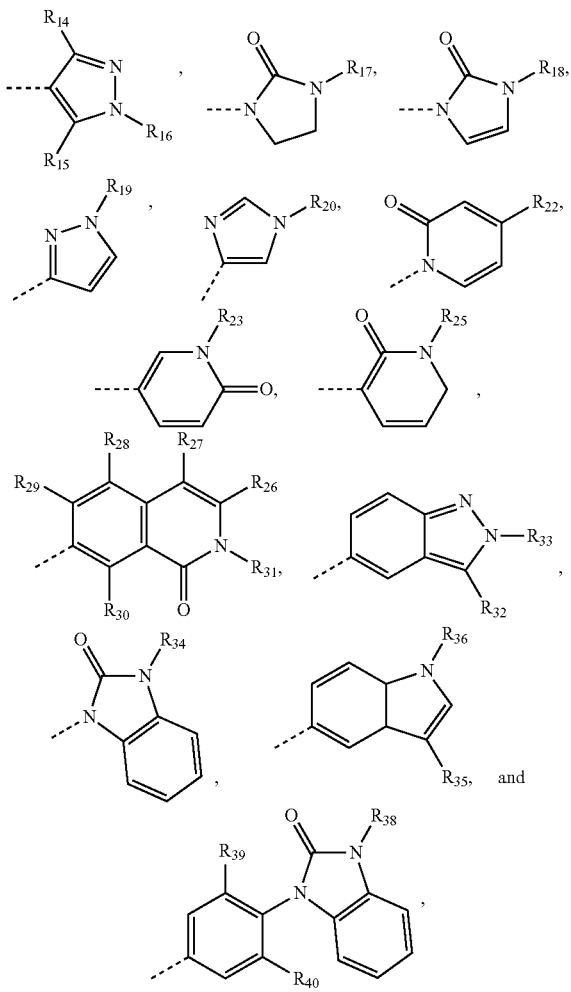

and $R_6$ is optionally protected by a protecting group,
wherein
$R_{14}$ and $R_{15}$ are each independently selected from the group consisting of H, $C_{1-6}$ alkyl, and $C_{1-6}$ alkoxy, wherein each of the $C_{1-6}$ alkyl or $C_{1-6}$ alkoxy is optionally substituted by one to three substituents, each independently selected from the group consisting of halogen, OH, SH, $NH_2$, and $PH_2$; and $R_{16}$, $R_{17}$, $R_{18}$, $R_{19}$, $R_{20}$, $R_{22}$, $R_{23}$, $R_{25}$, $R_{26}$, $R_{27}$, $R_{28}$, $R_{29}$, $R_{30}$, $R_{31}$, $R_{32}$, $R_{33}$, $R_{34}$, $R_{35}$, $R_{36}$, $R_{38}$, $R_{39}$, and $R_{40}$ are each independently selected from the group consisting of H, halogen, OH, SH, $NH_2$, $PH_2$, $C_{1-6}$ alkyl, $C_{1-6}$ alkoxy, —$C_{1-6}$OH, —COOH, —$C_{1-6}$COOH, —$OC_{1-6}$COOH, —$C_{1-6}OC_{1-6}$, —$C_{1-6}COOC_{1-6}$, —$C_{1-6}$CN, —$C_{1-6}CONH_2$, and

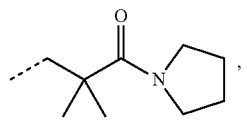

wherein said $C_{1-6}$ alkyl, $C_{1-6}$ alkoxy, —$C_{1-6}$OH, —$C_{1-6}$COOH, —$OC_{1-6}$COOH, —$C_{1-6}OC_{1-6}$, —$C_{1-6}COOC_{1-6}$, —$C_{1-6}$CN, and —$C_{1-6}CONH_2$ are optionally substituted by one to three substituents, each independently selected from the group consisting of halogen, OH, SH, $NH_2$, $PH_2$, and $C_{1-6}$ cycloalkyl, the carbon atoms, located on both sides or on the same side of each oxygen or carbonyl in said —$C_{1-6}OC_{1-6}$ or —$C_{1-6}COOC_{1-6}$, are optionally joined together to form a ring, and the H atom, connected with the N atom of —$C_{1-6}NH_2$, is optionally replaced by $C_{1-6}$ alkyl singly or bothly, $R_7$, $R_8$, $R_9$, and $R_{10}$ are each independently selected from the group consisting of $C_{1-10}$ alkyl, $C_{1-10}$ alkoxy, $C_{3-10}$ cycloalkyl, $C_{3-10}$ cycloalkoxy, H, halogen, OH, SH, $NH_2$, $PH_2$, and CN, wherein each of the $C_{1-10}$ alkyl, $C_{1-10}$ alkoxy, $C_{3-10}$ cycloalkyl, and $C_{3-10}$ cycloalkoxy is optionally substituted by one or more substituents, each independently selected from the group consisting of halogen, OH, SH, $NH_2$, $PH_2$, CN, $CH_3$, and $CF_3$;

$R_{11}$, $R_{12}$, and $R_{13}$ are each independently selected from the group consisting of $C_{1-10}$ alkyl, $C_{1-10}$ alkoxy, $C_{3-10}$ cycloalkyl, and $C_{3-10}$ cycloalkoxy, wherein each of the $C_{1-10}$ alkyl, $C_{1-10}$ alkoxy, $C_{3-10}$ cycloalkyl, and $C_{3-10}$ cycloalkoxy is optionally substituted by one to three substituents, each independently selected from the group consisting of halogen, OH, SH, $NH_2$, $PH_2$, CN, $CF_3$, —$OCF_3$, and —$OCH_3$ or a pharmaceutically acceptable salt thereof, comprising the following step,

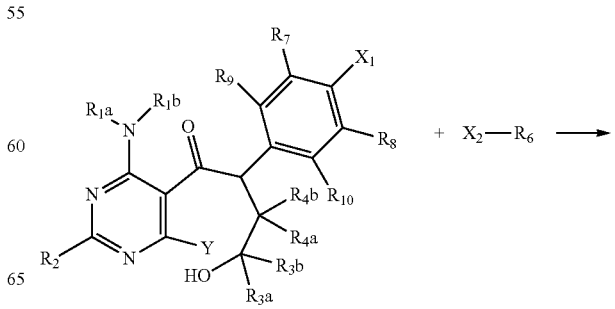

-continued

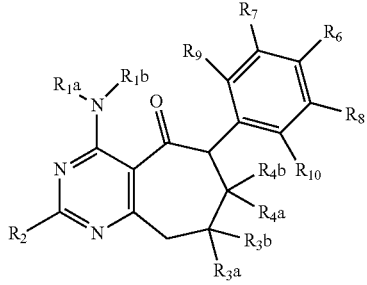

wherein
Y is selected from the group consisting of $CF_3$, halogen, OH, SH, $NH_2$, $PH_2$, and $C_{1-6}$ alkyl, wherein the $C_{1-6}$ alkyl is optionally substituted by one or more substituents selected from the group consisting of halogen, OH, SH, $NH_2$, and $PH_2$.

13. A method for preparing the compound of claim 11, wherein the protecting group is an amino-protecting group or a hydroxy-protecting group.

14. A method for preparing the compound of claim 12, wherein the protecting group is an amino-protecting group or a hydroxy-protecting group.

15. The method of claim 13, wherein the amino-protecting group is selected from the group consisting of BOC, Cbz, Fmoc, Bn, PMB, Pht, Ac, Trt, $CF_3CO$, Alloc, methyl ester, Troc, and PMP; and the hydroxy-protecting group is selected from the group consisting of ethyl, TBS, TBDPS, TMS, Ac, Me, MOM, MEM, THP, Bn, PMB, MTM, and Piv.

16. The method of claim 14, wherein the amino-protecting group is selected from the group consisting of BOC, Cbz, Fmoc, Bn, PMB, Pht, Ac, Trt, $CF_3CO$, Alloc, methyl ester, Troc, and PMP; and the hydroxy-protecting group is selected from the group consisting of ethyl, TBS, TBDPS, TMS, Ac, Me, MOM, MEM, THP, Bn, PMB, MTM, and Piv.

17. A pharmaceutical composition comprising a therapeutically effective amount of the compound of claim 1 and a pharmaceutical acceptable carrier.

18. A method of inhibiting or relieving a subject suffering from Familial hyperchylomicronemia (FCS), obesity, hyperlipoproteinemia, or hypertriglyceridemia, which comprises administering to the subject a therapeutically effective amount of the compound of claim 1.

19. A pharmaceutical composition comprising a therapeutically effective amount of the compound of claim 10 and a pharmaceutical acceptable carrier.

20. A method of inhibiting or relieving a subject suffering from Familial hyperchylomicronemia (FCS), obesity, hyperlipoproteinemia, or hypertriglyceridemia, which comprises administering to the subject a therapeutically effective amount of the compound of claim 10.

* * * * *